(12) United States Patent
Stahler et al.

(10) Patent No.: US 8,409,234 B2
(45) Date of Patent: Apr. 2, 2013

(54) ROTATIONAL APPARATUS SYSTEM AND METHOD FOR A ROBOTIC INSTRUMENT SYSTEM

(75) Inventors: Gregory J. Stahler, San Jose, CA (US); Christopher R. Carlson, Menlo Park, CA (US); Robert G. Younge, Portola Valley, CA (US)

(73) Assignee: Hansen Medical, Inc., Mountain View, CA (US)

( * ) Notice: Subject to any disclaimer, the term of this patent is extended or adjusted under 35 U.S.C. 154(b) by 619 days.

(21) Appl. No.: 12/126,814

(22) Filed: May 23, 2008

(65) Prior Publication Data

US 2009/0024141 A1 Jan. 22, 2009

Related U.S. Application Data

(60) Provisional application No. 60/931,827, filed on May 25, 2007, provisional application No. 60/934,639, filed on Jun. 15, 2007.

(51) Int. Cl.
*A61B 17/32* (2006.01)
(52) U.S. Cl. .......................................... 606/170
(58) Field of Classification Search .................. 600/101, 600/104, 106; 606/1, 167, 170–171
See application file for complete search history.

(56) References Cited

U.S. PATENT DOCUMENTS

| | | | |
|---|---|---|---|
| 2005/0137478 A1 | 6/2005 | Younge et al. | |
| 2005/0197530 A1 | 9/2005 | Wallace et al. | |
| 2005/0222554 A1 | 10/2005 | Wallace et al. | |
| 2006/0057560 A1 | 3/2006 | Hlavka et al. | |
| 2006/0084945 A1 | 4/2006 | Moll et al. | |
| 2006/0095022 A1 | 5/2006 | Moll et al. | |
| 2006/0100610 A1 | 5/2006 | Wallace et al. | |
| 2006/0111692 A1 | 5/2006 | Hlavka et al. | |
| 2006/0200026 A1 | 9/2006 | Wallace et al. | |
| 2006/0253108 A1 | 11/2006 | Yu et al. | |
| 2006/0276775 A1 | 12/2006 | Rosenberg et al. | |
| 2007/0043338 A1 | 2/2007 | Moll et al. | |
| 2007/0156123 A1 | 7/2007 | Moll et al. | |
| 2007/0197896 A1 | 8/2007 | Moll et al. | |
| 2008/0234693 A1* | 9/2008 | Stefanchik .................... 606/108 |
| 2008/0243064 A1 | 10/2008 | Stahler et al. | |
| 2008/0249536 A1 | 10/2008 | Stahler et al. | |
| 2008/0262480 A1 | 10/2008 | Stahler et al. | |
| 2008/0262513 A1 | 10/2008 | Stahler et al. | |

* cited by examiner

*Primary Examiner* — Ryan Severson
*Assistant Examiner* — Ashley Cronin
(74) *Attorney, Agent, or Firm* — Vista IP Law Group LLP

(57) ABSTRACT

Robotic instrument systems, apparatus, and methods for controllably rotating a tool or adapter coupled to a distal portion of a medical instrument such as a catheter. An interface, which may be integral with the medical instrument or a component of a separate rotatable apparatus or adapter, is operably coupled, e.g. fixedly coupled, to the distal end of the instrument. A tool, such as a rotatable portion of a collar or tool base, or a working instrument operably coupled thereto, is rotatable relative to the interface. The interface and collar have guide channels. A control element extends through the medical instrument and respective guide channels such that the tool or collar is controllably rotatable about the instrument axis by axial movement of the control element relative to the instrument.

30 Claims, 144 Drawing Sheets

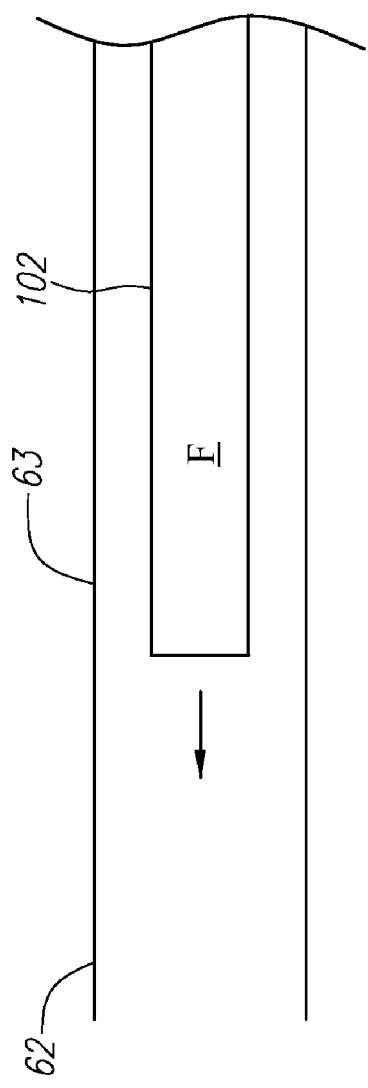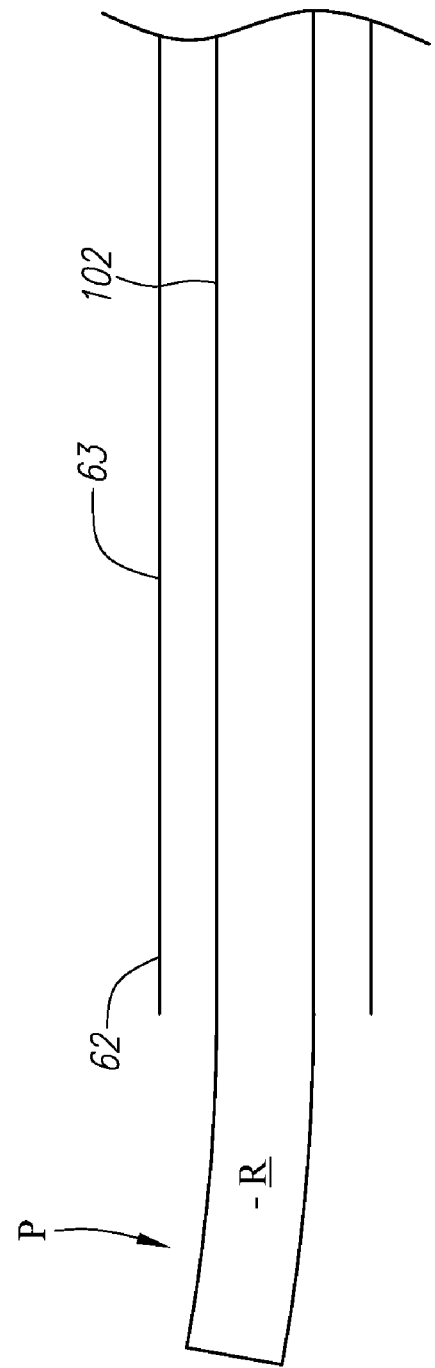

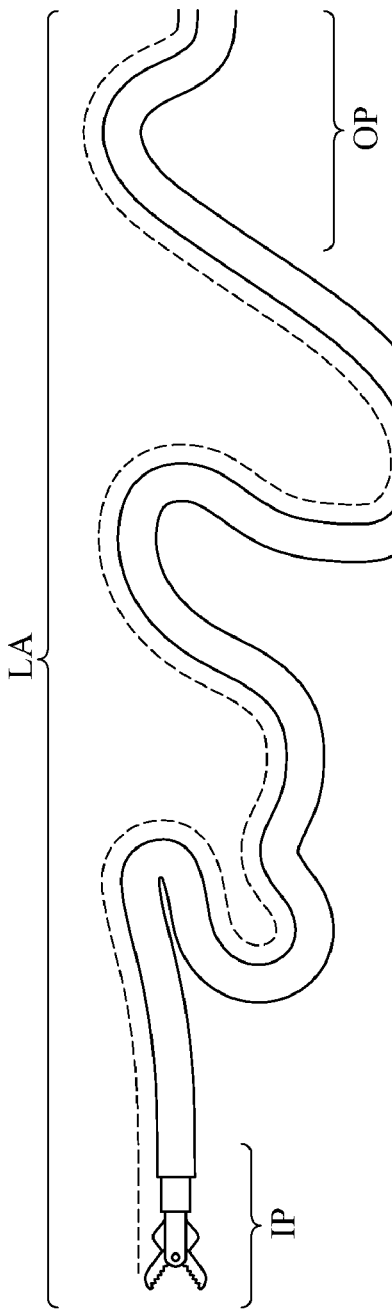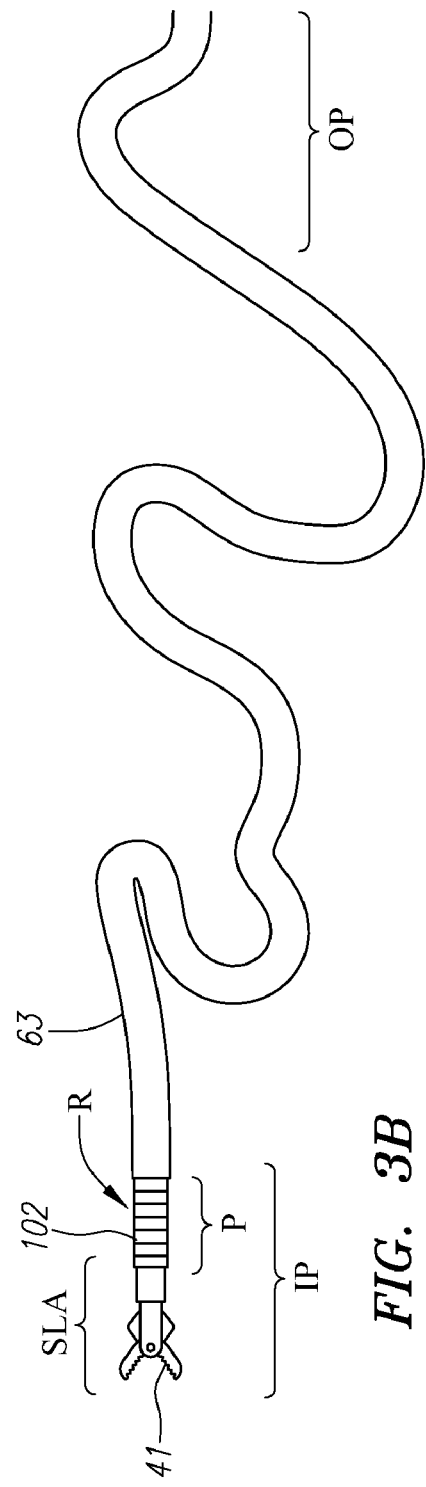
FIG. 3A (Prior Art)
FIG. 3B

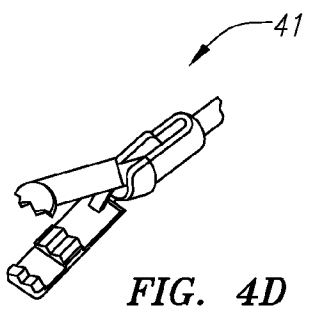
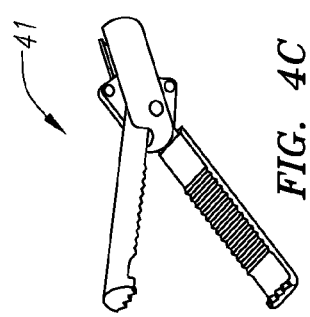
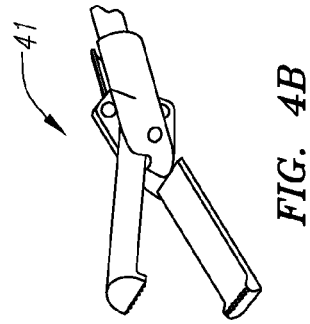
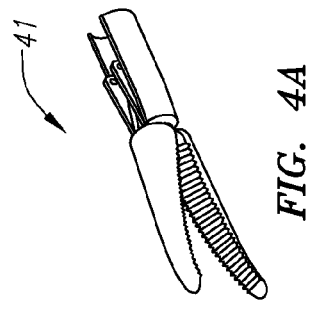
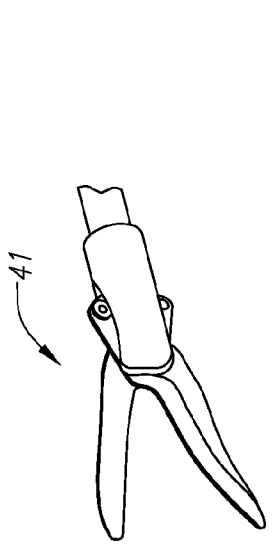
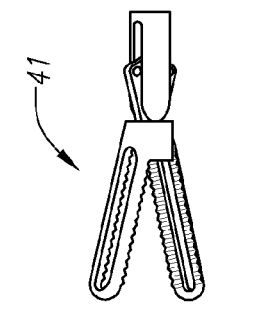
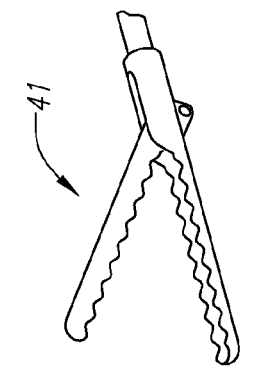
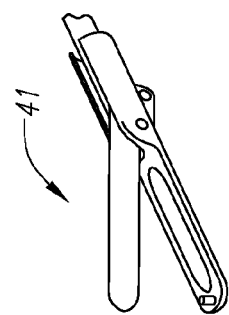
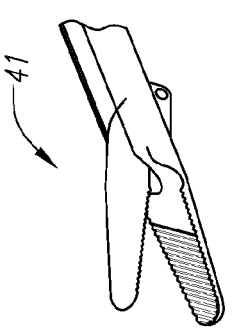
FIG. 4A, FIG. 4B, FIG. 4C, FIG. 4D, FIG. 4E, FIG. 4F, FIG. 4G, FIG. 4H, FIG. 4I, FIG. 4J, FIG. 4K

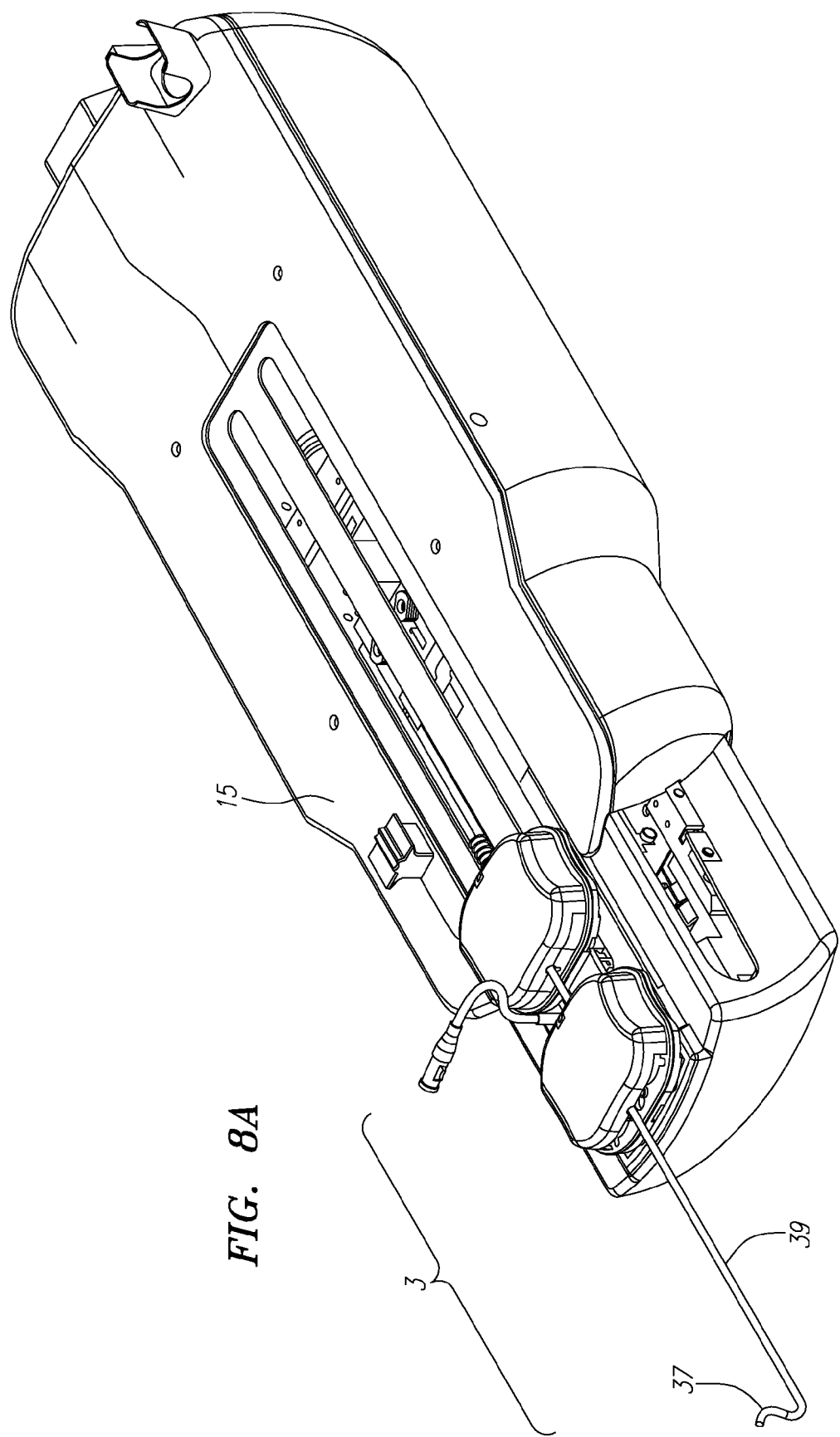

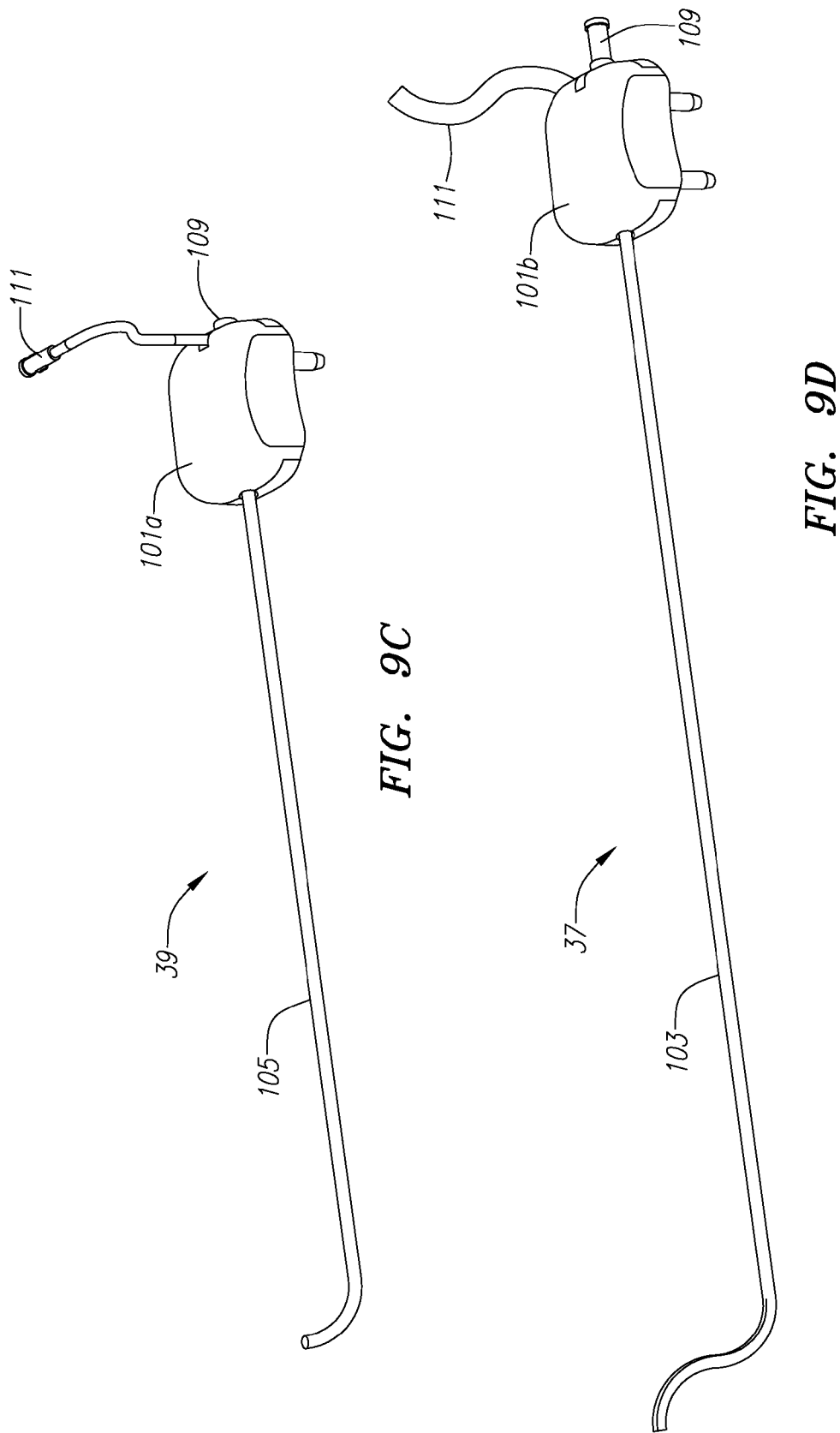

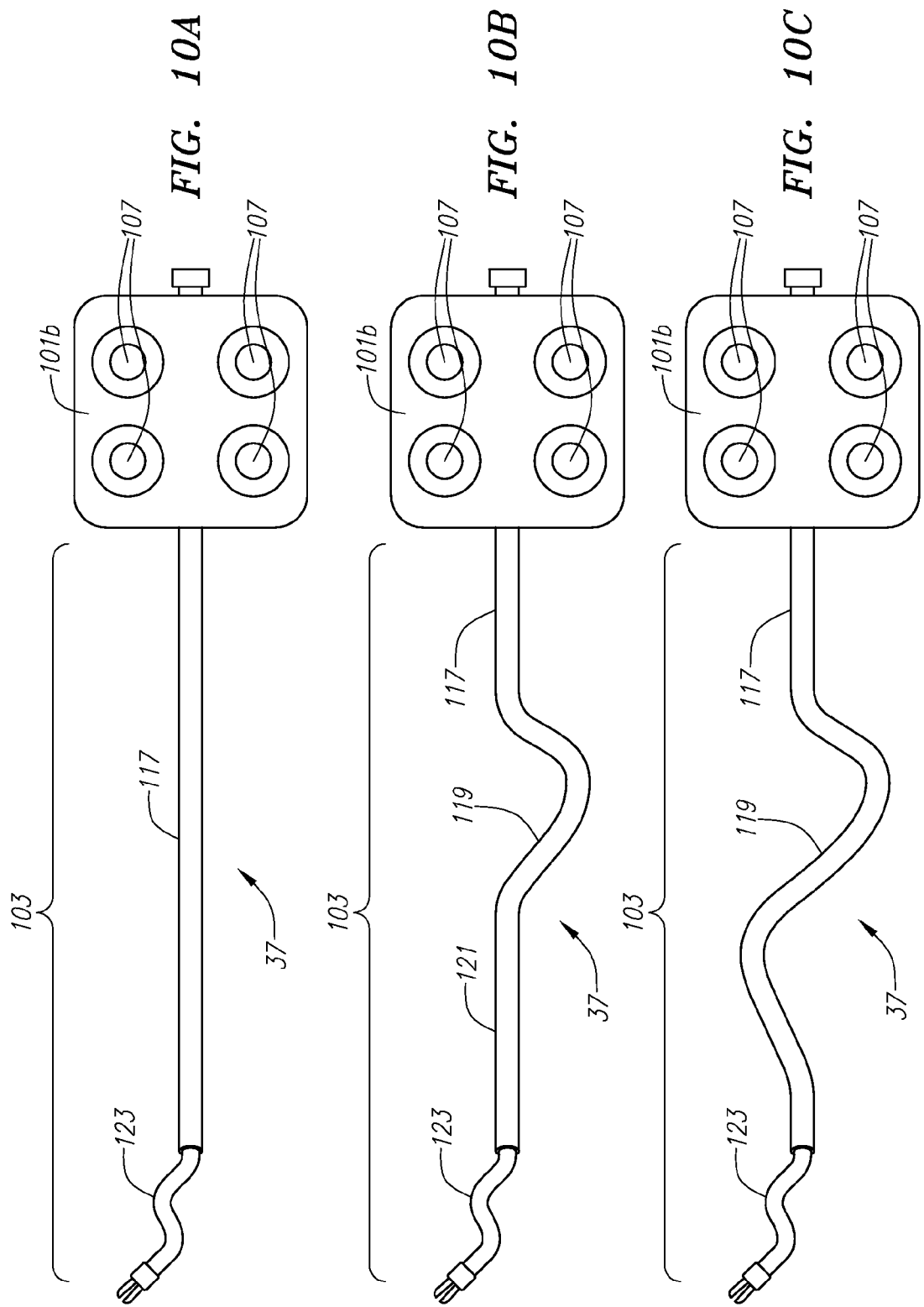

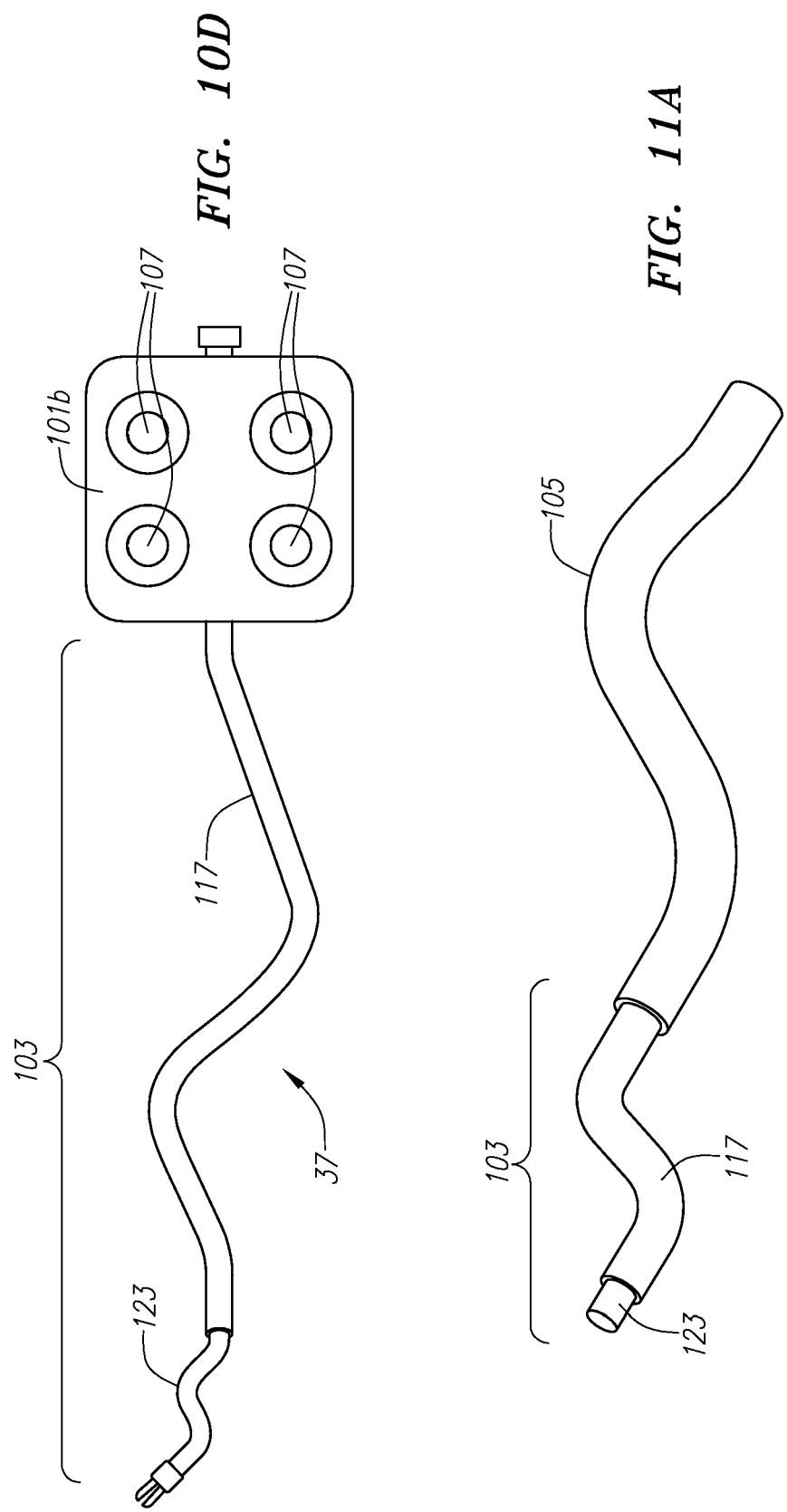

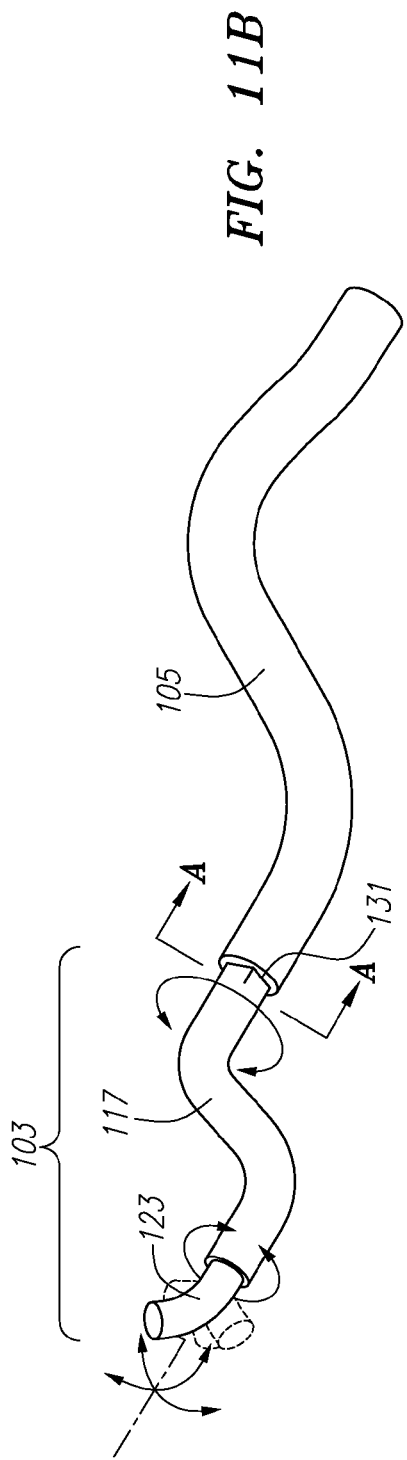
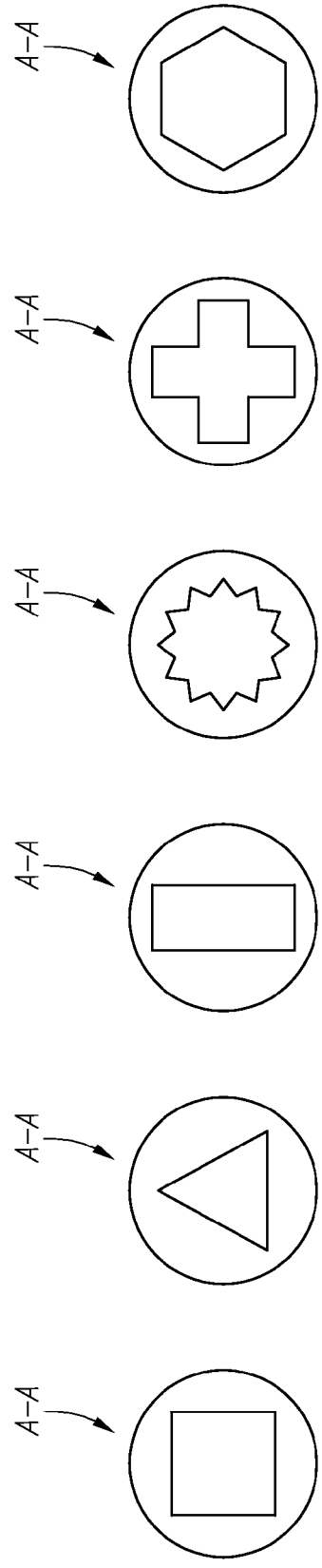
FIG. 11B
FIG. 11C  FIG. 11D  FIG. 11E  FIG. 11F  FIG. 11G  FIG. 11H

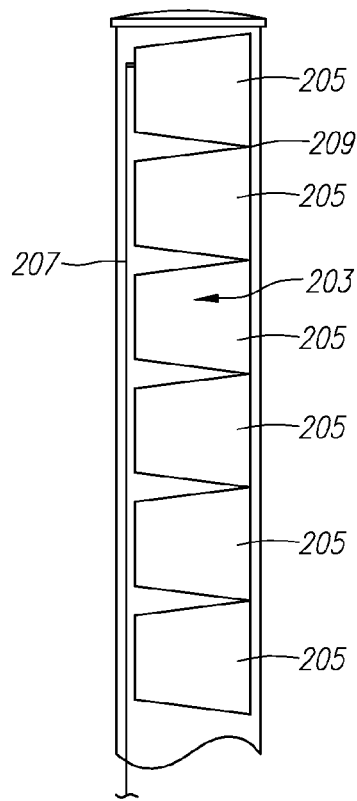
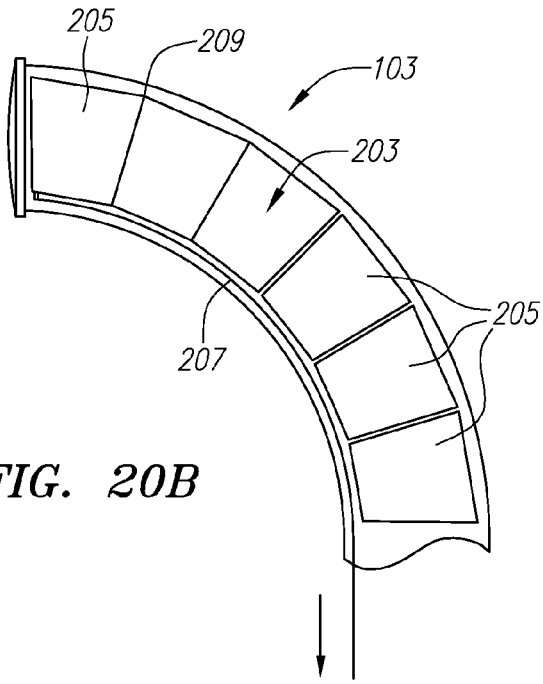
FIG. 20A
FIG. 20B
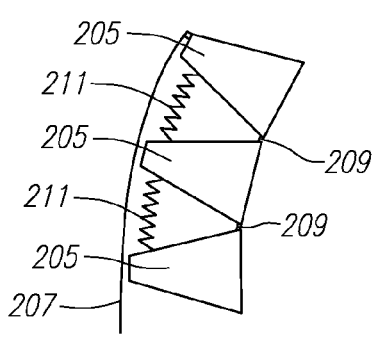
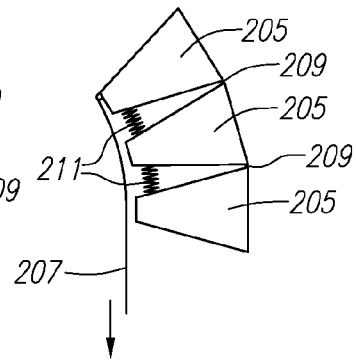
FIG. 20C
FIG. 20D
FIG. 20E

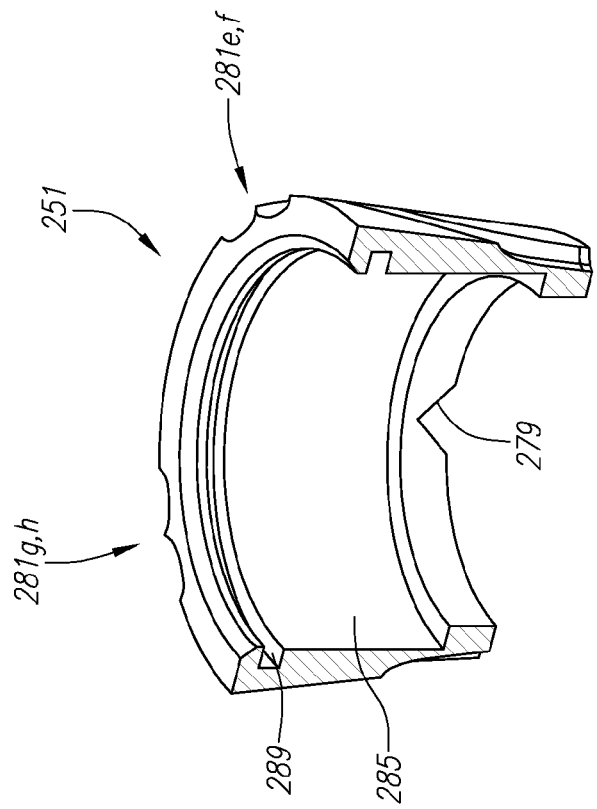
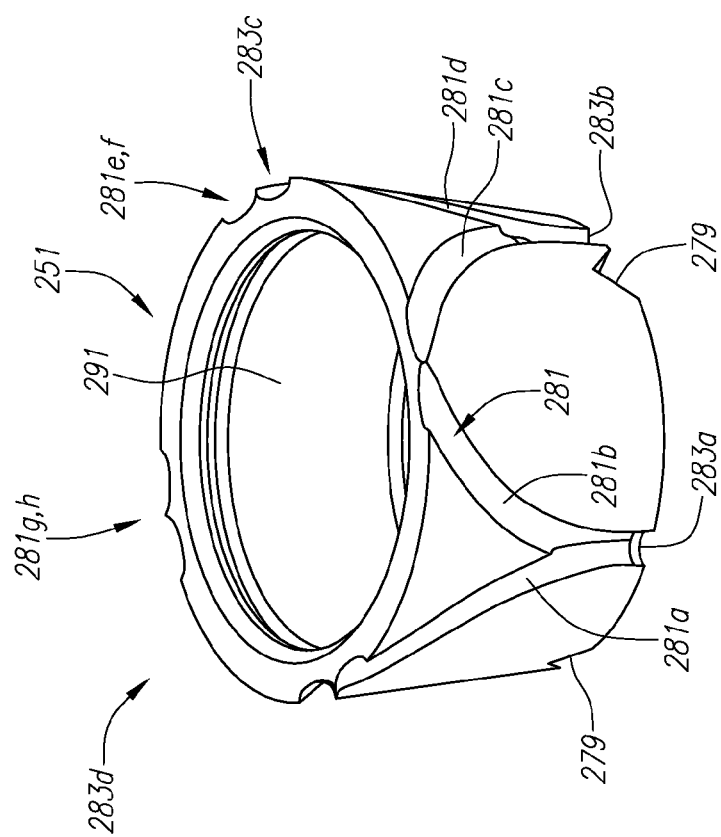
FIG. 22B
FIG. 22A

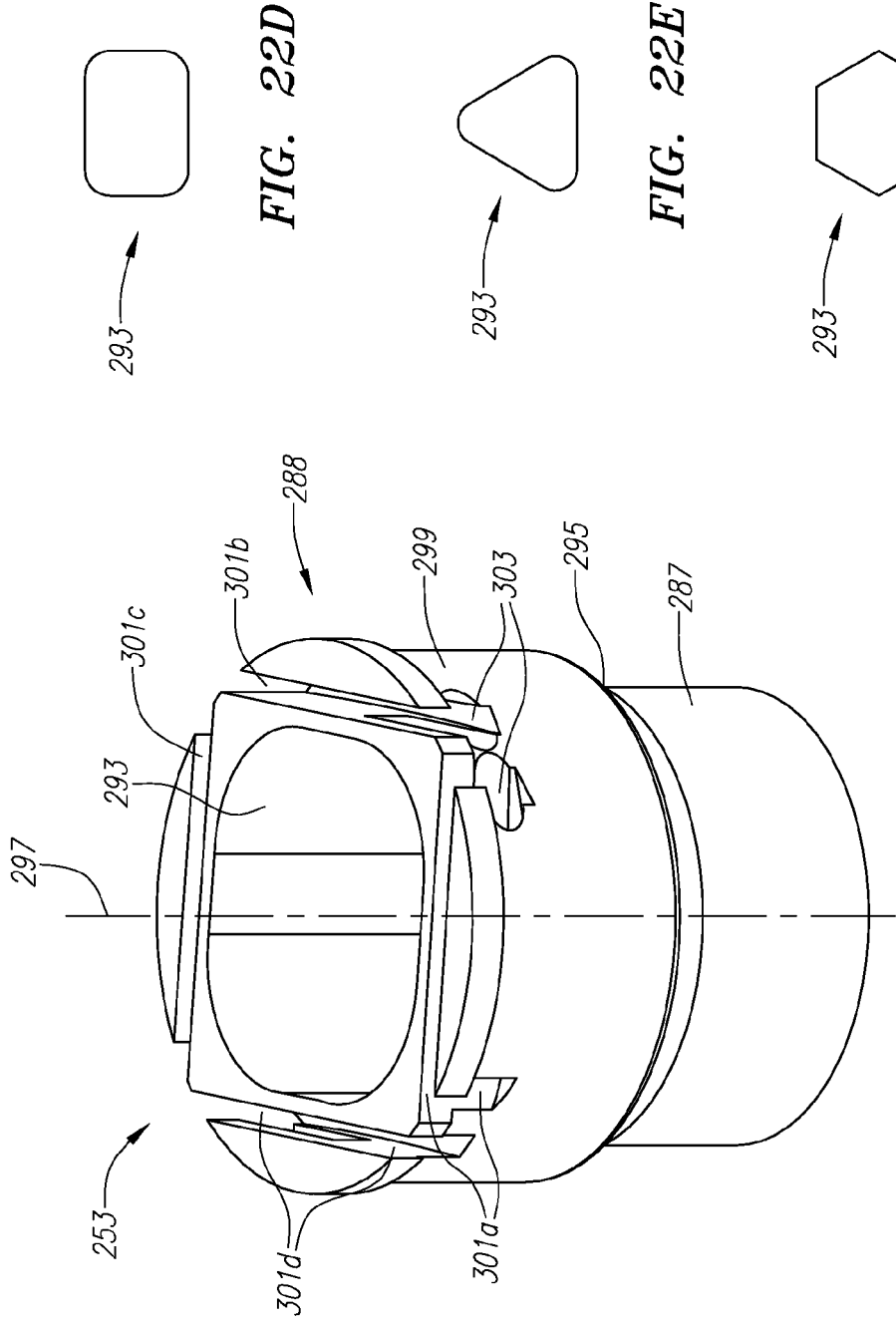

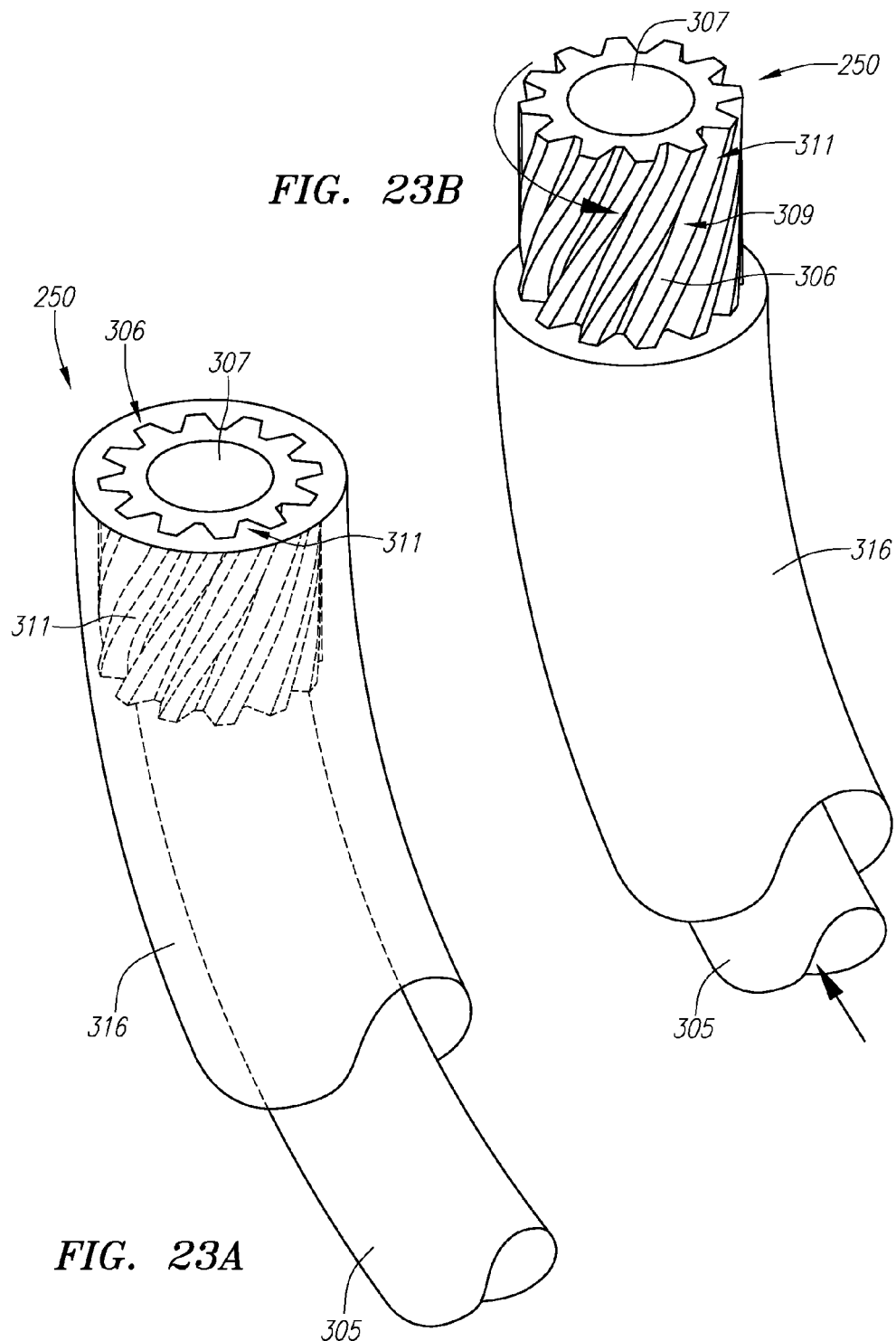

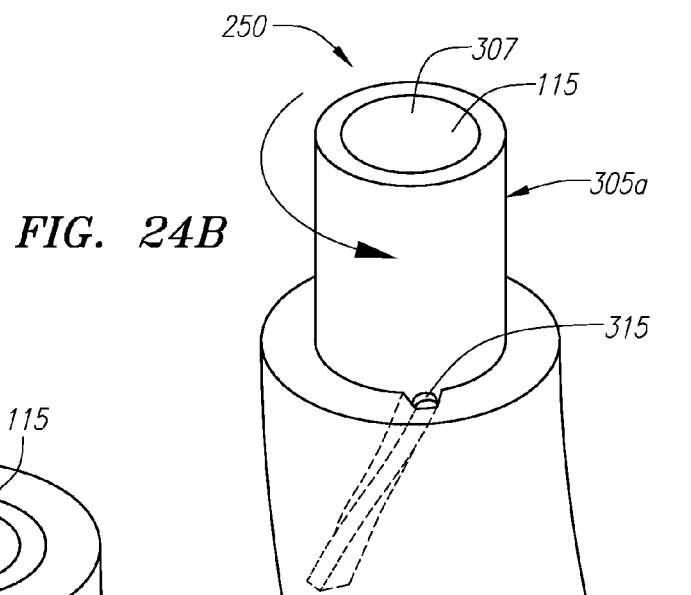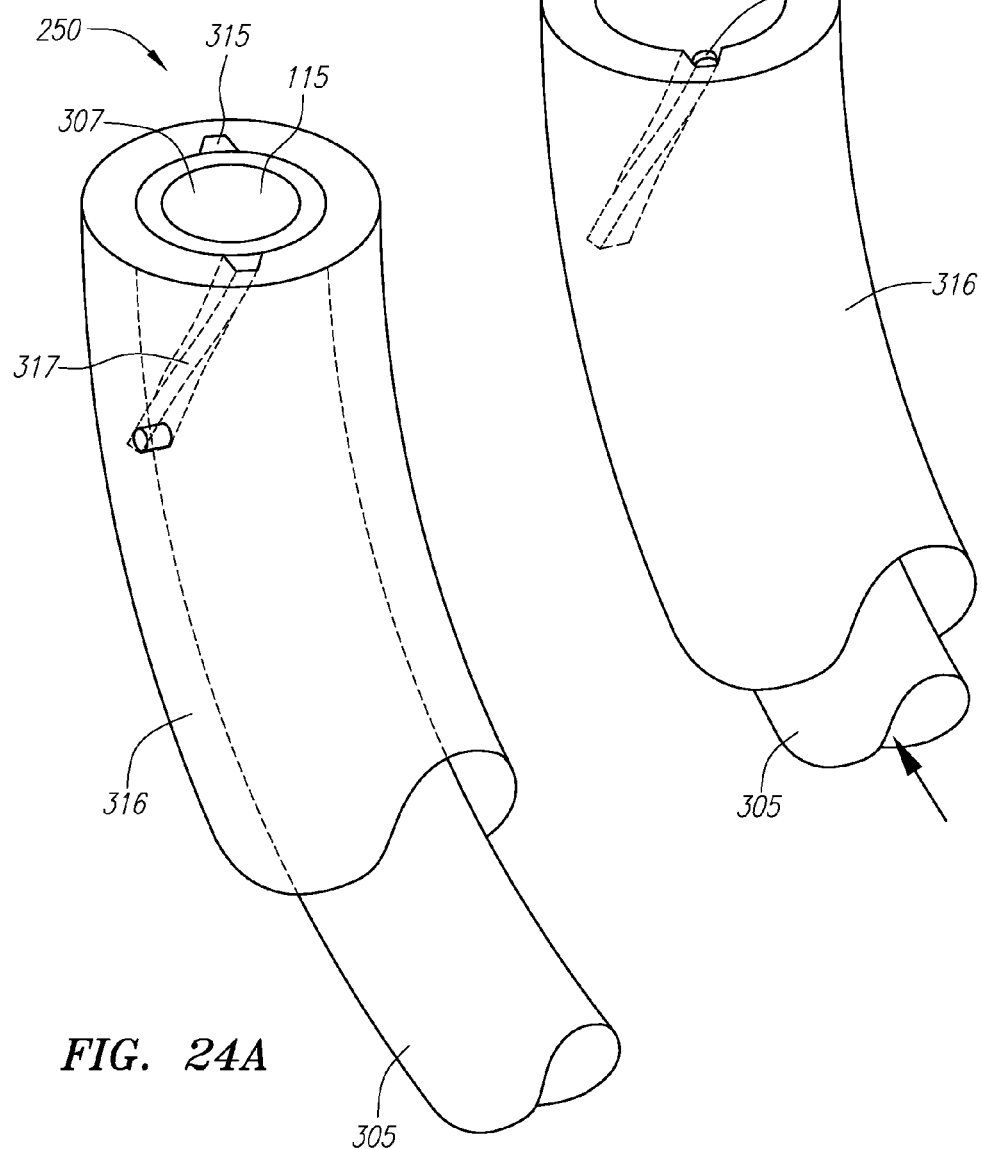
FIG. 24B
FIG. 24A

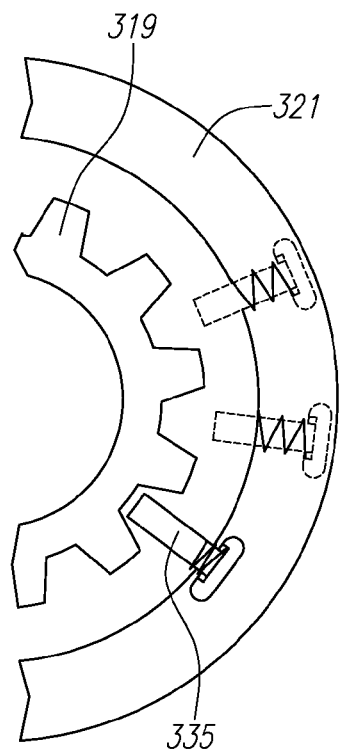
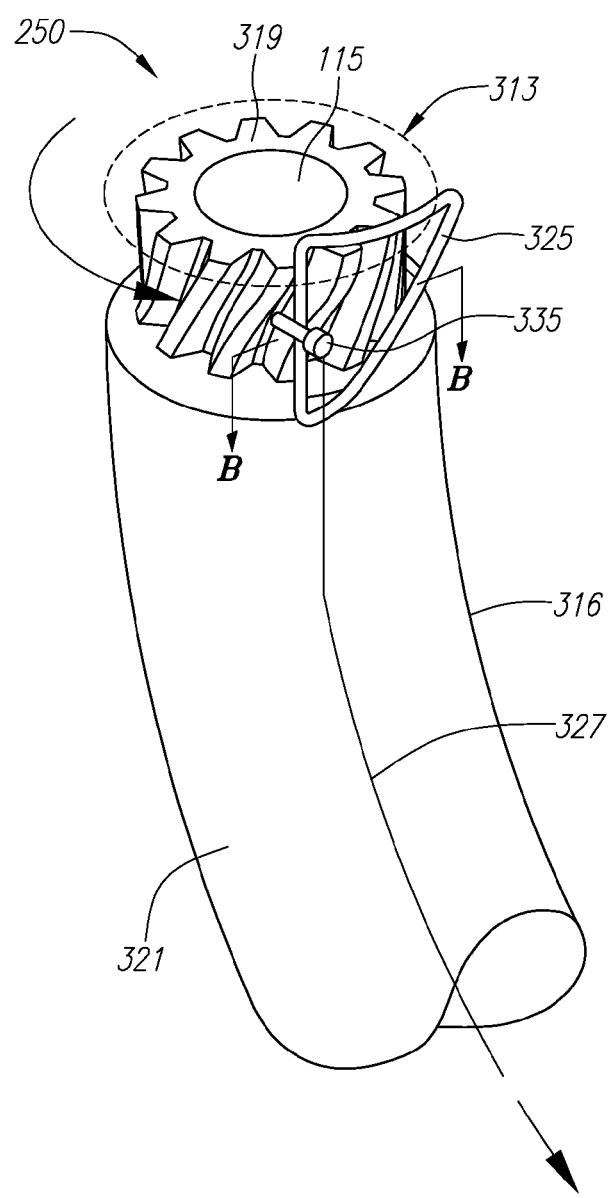
FIG. 25B
FIG. 25A

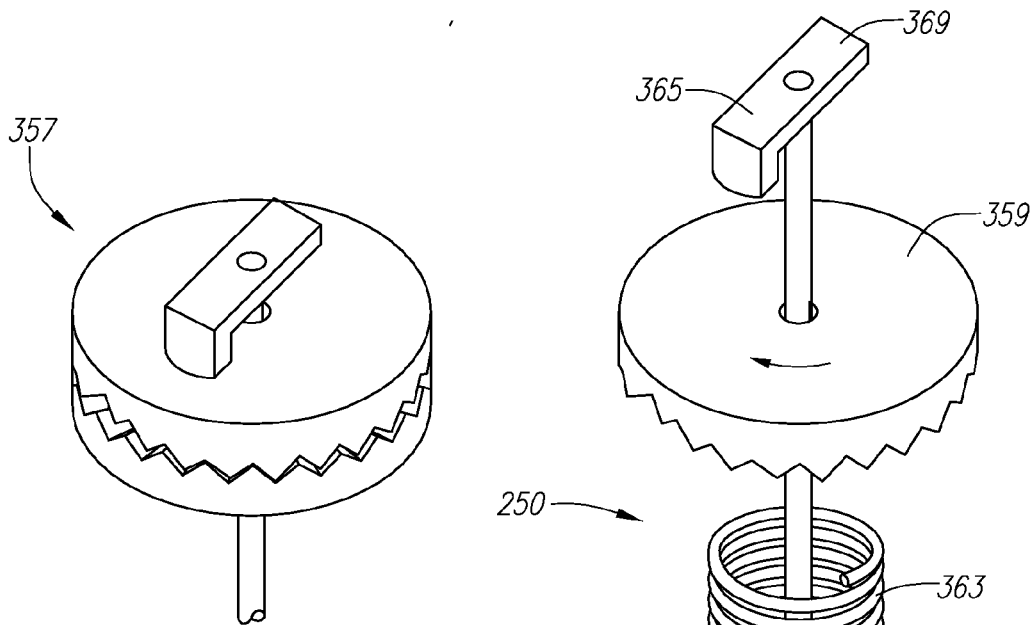
FIG. 28A
FIG. 28B
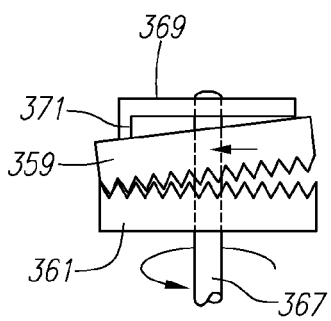
FIG. 28C
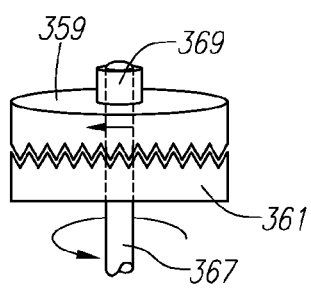
FIG. 28D
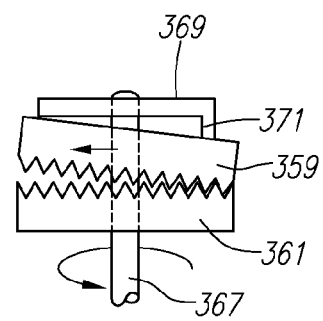
FIG. 28E

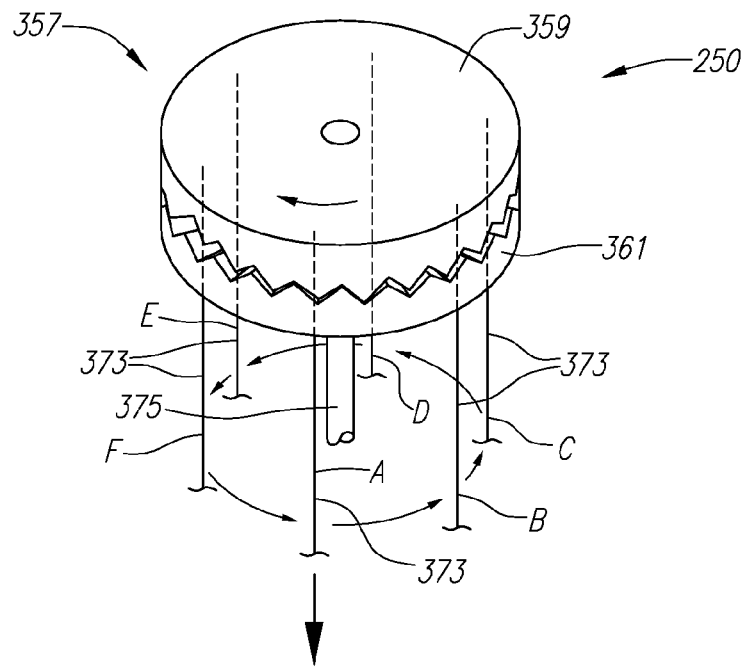
FIG. 29A
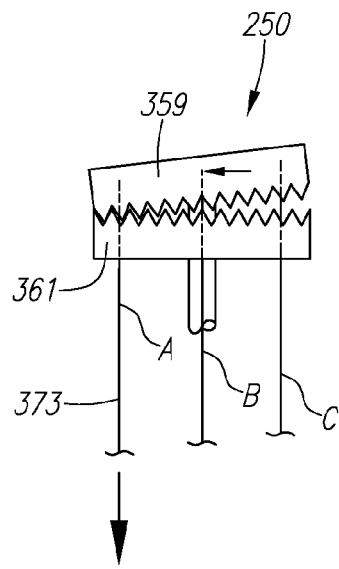 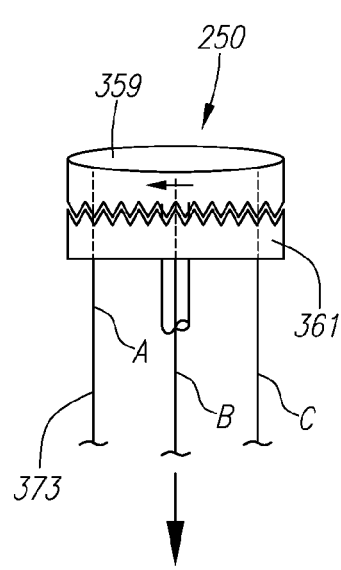 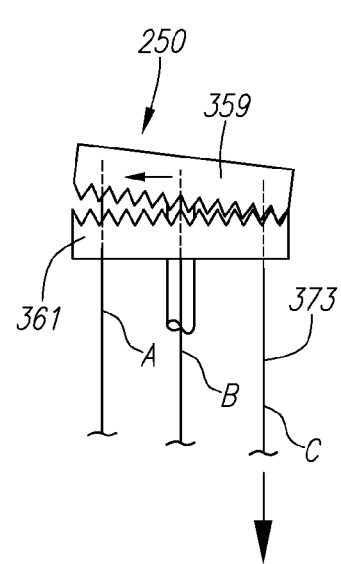
FIG. 29B   FIG. 29C   FIG. 29D

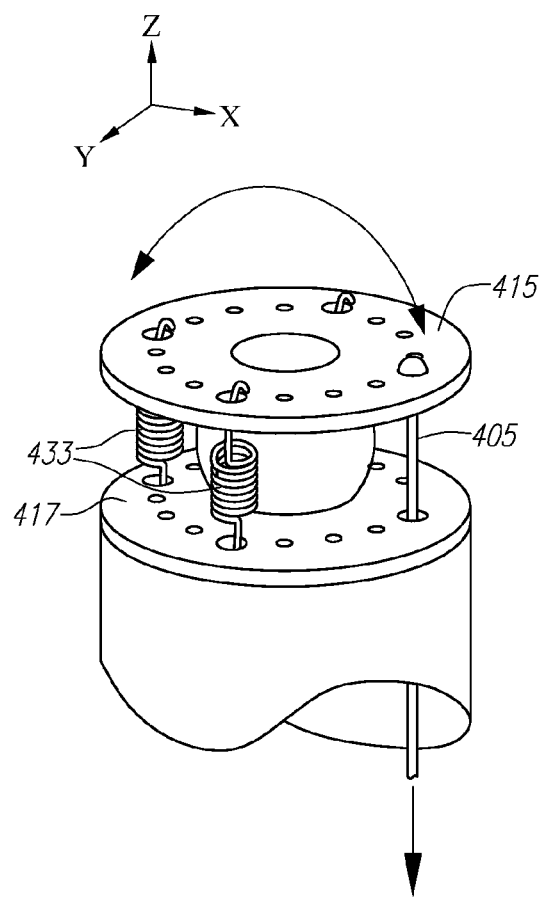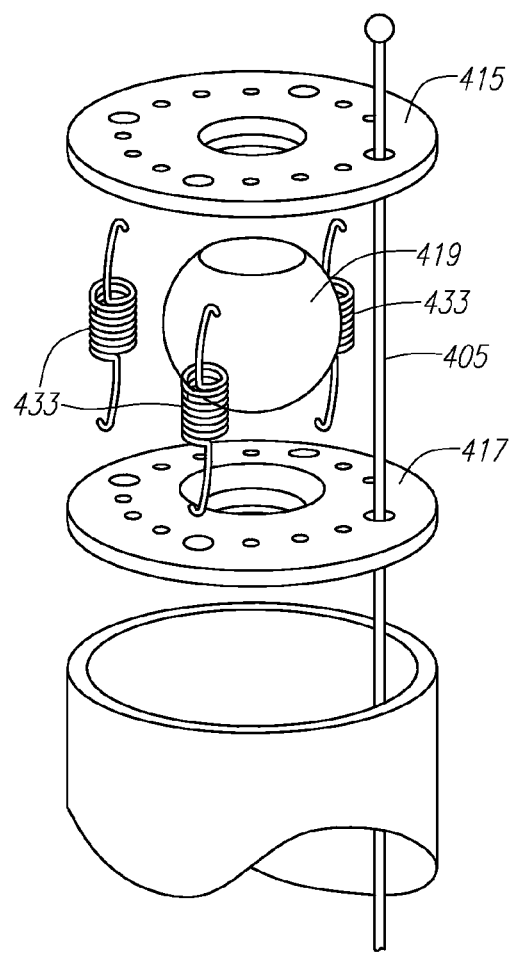
FIG. 34B
FIG. 34C

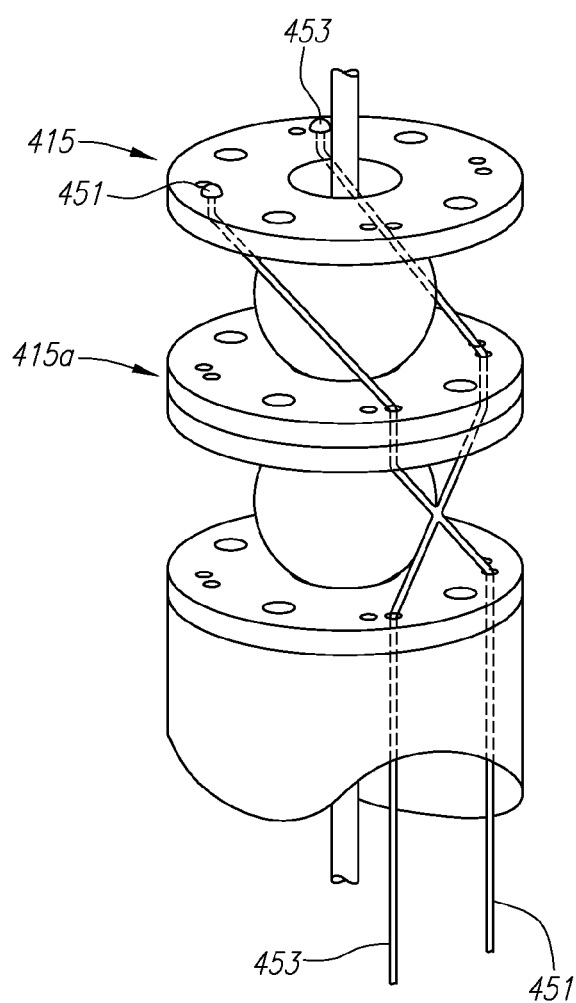
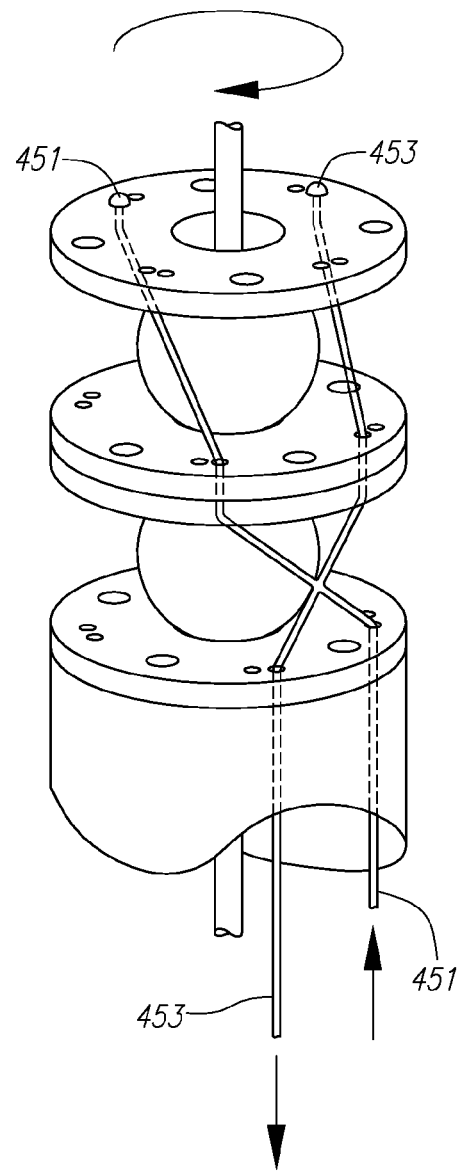
FIG. 56A
FIG. 56B

ROTATIONAL APPARATUS SYSTEM AND METHOD FOR A ROBOTIC INSTRUMENT SYSTEM

CROSS-REFERENCE TO RELATED APPLICATIONS

The present application claims the benefit under 35 U.S.C. §119 to U.S. Provisional Application No. 60/931,827, filed on May 25, 2007, and to U.S. Provisional Application No. 60/934,639, filed on Jun. 15, 2007, the contents of both of which are incorporated herein by reference as though set forth in full.

The present application may also be related to subject matter disclosed in the following applications and patents, the contents of which are also incorporated herein by reference as though set forth in full: U.S. application Ser. No. 12/114,720, entitled Apparatus, Systems and Methods for Forming a Working Platform of a Robotic Instrument System by Manipulation of Components Having Controllable Rigidity," filed on May 2, 2008; U.S. patent application Ser. No. 10/923,660, entitled "System and Method for 3-D Imaging", filed Aug. 20, 2004; U.S. patent application Ser. No. 10/949,032, entitled "Balloon Visualization for Transversing a Tissue Wall", filed Sep. 24, 2005; U.S. patent application Ser. No. 11/073,363, entitled "Robotic Catheter System", filed Mar. 4, 2005; U.S. patent application Ser. No. 11/173,812, entitled "Support Assembly for Robotic Catheter Assembly", filed Jul. 1, 2005; U.S. patent application Ser. No. 11/176,954, entitled "Instrument Driver for Robotic Catheter System", filed Jul. 6, 2005; U.S. patent application Ser. No. 11/179,007, entitled "Methods Using A Robotic Cather System", filed Jul. 6, 2005; U.S. patent application Ser. No. 11/185,432, entitled "System and method for denaturing and fixing collagenous tissue", filed Jul. 19, 2005; U.S. patent application Ser. No. 11/202,925, entitled "Robotically Controlled Intravascular Tissue Injection System", filed Aug. 12, 2005; and U.S. patent application Ser. No. 12/032,626, entitled Instrument Assembly for Robotic Instrument System, filed Feb. 15, 2008; U.S. patent application Ser. No. 12/032,634, entitled Support Structure for Robotic Medical Instrument filed Feb. 15, 2008; U.S. patent application Ser. No. 12/032,622, entitled Instrument Driver Having Independently Rotatable Carriages, filed Feb. 15, 2008; U.S. patent application Ser. No. 12/032,639, entitled Flexible Catheter Instruments and Methods, filed Feb. 15, 2008.

The present application may also be related to subject matter disclosed in the following applications, the contents of which are also incorporated herein by reference as though set forth in full: U.S. Provisional Patent Application No. 60/902,144, entitled, Flexible Catheter Instruments and Methods, filed on Feb. 15, 2007; U.S. Provisional Patent Application No. 60/750,590, entitled "Robotic Catheter System and Methods", filed Dec. 14, 2005; U.S. Provisional Patent Application No. 60/756,136, entitled "Robotic Catheter System and Methods", filed Jan. 3, 2006; U.S. patent application Ser. No. 11/331,576, entitled "Robotic Catheter System", filed Jan. 13, 2006; U.S. Provisional Patent Application No. 60/776,065, entitled "Force Sensing for Medical Instruments", filed Feb. 22, 2006; U.S. Provisional Patent Application No. 60/785,001, entitled "Fiberoptic Bragg Grating Medical Instrument", filed Mar. 22, 2006; U.S. Provisional Patent Application No. 60/788,176, entitled "Fiberoptic Bragg Grating Medical Instrument", filed Mar. 31, 2006; U.S. patent application Ser. No. 11/418,398, entitled "Robotic Catheter System", filed May 3, 2006; U.S. Provisional Patent Application No. 60/801,355, entitled "Sheath and Guide Catheter Apparatuses For A Robotic Catheter System With Force Sensing", filed May 17, 2006; U.S. Provisional Patent Application No. 60/801,546, entitled "Robotic Catheter System and Methods", filed May 17, 2006; U.S. Provisional Patent Application No. 60/801,945, entitled "Robotic Catheter System and Methods", filed May 18, 2006; U.S. patent application Ser. No. 11/481,433, entitled "Robotic Catheter System and Methods", filed Jul. 3, 2006; U.S. Provisional Patent Application No. 60/833,624, entitled "Robotic Catheter System and Methods", filed Jul. 26, 2006; U.S. Provisional Patent Application No. 60/835,592, entitled "Robotic Catheter System and Methods", filed Aug. 3, 2006; U.S. Provisional Patent Application No. 60/838,075, entitled "Robotic Catheter System and Methods", filed Aug. 15, 2006; U.S. Provisional Patent Application No. 60/840,331, entitled "Robotic Catheter System and Methods", filed Aug. 24, 2006; U.S. Provisional Patent Application No. 60/843,274, entitled "Robotic Catheter System and Methods", filed Sep. 8, 2006; U.S. Provisional Patent Application No. 60/873,901, entitled "Robotic Catheter System and Methods", filed Dec. 8, 2006; U.S. patent application Ser. No. 11/637,951, entitled "Robotic Catheter System and Methods", filed Dec. 11, 2006; U.S. patent application Ser. No. 11/640,099, entitled "Robotic Catheter System and Methods", filed Dec. 14, 2006; U.S. Provisional Patent Application No. 60/879,911, entitled "Robotic Catheter System and Methods", filed Jan. 10, 2007; and U.S. Provisional Patent Application No. 60/900,584, entitled "Robotic Catheter System and Methods", filed Feb. 8, 2007.

FIELD OF INVENTION

The invention relates generally to surgical tools, and more particularly, to flexible catheter instruments for performing minimally invasive diagnostic and therapeutic procedures with a robotic catheter system.

BACKGROUND

Robotic interventional systems and devices are well suited for use in performing minimally invasive medical procedures as opposed to conventional procedures that involve opening the patient's body to permit the surgeon's hands to access internal organs. Traditionally, surgery utilizing conventional procedures meant significant pain, long recovery times, lengthy work absences, and visible scarring. However, advances in technology have lead to significant changes in the field of medical surgery such that less invasive surgical procedures are increasingly popular, in particular, minimally invasive surgery (MIS). A "minimally invasive medical procedure" is generally considered a procedure that is performed by entering the body through the skin, a body cavity, or an anatomical opening utilizing small incisions rather than larger, more invasive open incisions in the body.

Various medical procedures are considered to be minimally invasive including, for example, mitral and tricuspid valve procedures, patent formen ovale, atrial septal defect surgery, colon and rectal surgery, laparoscopic appendectomy, laparoscopic esophagectomy, laparoscopic hysterectomies, carotid angioplasty, vertebroplasty, endoscopic sinus surgery, thoracic surgery, donor nephrectomy, hypodermic injection, air-pressure injection, subdermal implants, endoscopy, percutaneous surgery, laparoscopic surgery, arthroscopic surgery, cryosurgery, microsurgery, biopsies, videoscope procedures, keyhole surgery, endovascular surgery, coronary catheterization, permanent spinal and brain electrodes, stereotactic surgery, and radioactivity-based medical imaging methods. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. Images of the body interior are transmitted to an external video monitor to allow a surgeon to analyze the images, make a diagnosis, visually identify internal features, and perform surgical procedures based on the images presented on the monitor.

MIS procedures may involve minor surgery as well as more complex operations. Such operations may involve robotic and computer technologies, which have led to improved visual magnification, electromechanical stabilization and reduced number of incisions. The integration of robotic technologies with surgeon skill into surgical robotics enables surgeons to perform surgical procedures in new and more effective ways.

Although MIS techniques have advanced, physical limitations of certain types of medical equipment still have shortcomings and can be improved. For example, during a MIS procedure, catheters (e.g., a sheath catheter, a guide catheter, an ablation catheter, etc.), endoscopes or laparoscopes may be inserted into a body cavity duct or vessel. A catheter is an elongated tube that may, for example, allow for drainage or injection of fluids or provide a path for delivery of working or surgical instruments to a surgical or treatment site. In known robotic instrument systems, however, the ability to control and manipulate system components such as catheters and associated working instruments may be limited. These limitations are due, in part, to a surgeon not having direct access to the target site and not being able to directly handle or control the working instrument that is utilized at the target site.

More particularly, MIS diagnostic and interventional operations require the surgeon to remotely approach and address the operation or target site by using instruments that are guided, manipulated and advanced through a natural body orifice such as a blood vessel, esophagus, trachea, small intestine, large intestine or urethra, or through a small incision in the body of the patient to a target site. In some situations, the surgeon may approach the target site through both a natural body orifice as well as a small incision in the body of the patient.

For example, one or more catheters and other surgical instruments used to treat cardiac arrhythmias such as atrial fibrillation (AF), are inserted through an incision at the femoral vein near the thigh or pelvic region of the patient, which is at some distance away from the operation or target site. In this example, the operation or target site for performing cardiac ablation is in the left atrium of the heart. Catheters are guided (e.g., by a guide wire, etc.) manipulated, and advanced toward the target site by way of the femoral vein to the inferior vena cava into the right atrium through the interatrial septum to the left atrium of the heart. The catheters may be used to apply cardiac ablation therapy to the left atrium of the heart to restore normal heart function.

Controlling one or more catheters, however, can be a difficult task, and remotely controlling distal portions of one or more catheters to precisely position system components and perform cardiac ablation at certain locations or spots in the left atrium of the heart can be particularly difficult. These difficulties are due in part to limited control of movement and articulation of system components, which can complicate or limit the effectiveness of surgical procedures performed using robotic instrument systems.

SUMMARY

One embodiment of the invention is directed to a medical instrument system comprising an instrument defining a longitudinal axis, a tool and a control element. The tool is rotatably coupled to a distal end portion of the instrument. The control element extends from the instrument and is coupled to the tool, which is controllably rotatable about the instrument axis by axial movement of the control element relative to the instrument.

In accordance with another embodiment, a medical instrument system comprises an instrument defining a longitudinal axis, a tool and first and second control elements. The tool is rotatably coupled to a distal end portion of the instrument, and the first and second control elements extend from the instrument and are coupled to the tool. The tool is controllably rotatable about the instrument axis in a first direction by axial movement of the first control element relative to the instrument, and controllably rotatable about the instrument axis in a second direction opposite to the first direction by axial movement of the second control element relative to the instrument.

According to a further embodiment, a medical instrument system comprises an elongate instrument, a rotatable apparatus, a guide catheter, a working instrument and a control element. The rotatable apparatus is coupled to the elongate instrument and defines a lumen therethrough and a longitudinal axis. The guide catheter is disposed within the lumen of the rotatable apparatus, and the working instrument is operatively coupled to the guide catheter. The control element is operatively coupled to the rotatable apparatus. Respective rotation of the rotatable apparatus and the working instrument are controllable by manipulation of the control element.

In accordance with a further embodiment, a medical instrument system comprises an instrument defining a longitudinal axis, an adapter and a control element. The adapter is rotatably coupled to a distal end portion of the instrument, and the control element extends from the instrument and is coupled to the adapter. The adapter is controllably rotatable about the longitudinal axis by axial movement of the control element relative to the instrument.

In one or more embodiments, the instrument has a fixed tool interface, e.g., which may be integral with the distal end portion of the instrument, and the tool has a base that is rotatably coupled to the interface. A control element passes through respective guide channels in the interface and tool base. The instrument distal end portion may be bendable, but the control element may be coupled to the tool in such a manner that axial movement of the control element relative to the instrument does not cause appreciable bending of the instrument distal end portion. In one or more embodiments, the instrument include a plurality of interlocking segments that are drawn together by at least one of the first and second control elements being placed in tension.

In one or more embodiments, the interface of a tool, adapter or rotatable apparatus is integral with a working instrument such as a catheter. In another embodiment, the interface is rotatably coupled to a rotatable tool base or collar, which together form a single unit or component. In a further embodiment, the tool base is integral with another medical system component, such as a working instrument. For example, the tool base may form a base or proximal/bottom portion of a working instrument, and is configured to be rotatably coupled to a separate interface component, or an interface integral with a medical instrument such as a catheter.

In one or more embodiments, a system may also include multiple control elements. For example, a first control element may pass through first respective guide channels in the interface and the tool base, and a second control element may pass through second respective guide channels in the interface and the tool base, and respective ends of the first and second control elements are secured to the tool base within the respective first and second guide channels in the tool base. Further, in one or more embodiments, the first and second control elements extend from the instrument at circumferentially offset locations, and the first and second guide channels in the interface, which may have arcuate shapes, direct respective first and second control elements to cross one another, e.g., one or multiple times. Further, control elements may wrap around portions of a rotatable base or collar between respective guide channels of the interface and the tool base or collar.

In one or more embodiments, the guide channels in the interface and the guide channels in the tool base may have different shapes or configurations and lie within different planes. For example guide channels defined by interface of the instrument or of a rotatatable apparatus may have arcuate shapes, which may form a V-shaped or a Y-shaped channel and share a common channel portion, whereas the guide channels in the tool base have substantially linear shapes.

In one or more embodiments, a working instrument is operably coupled to an adapter or tool base and is configured for a minimally invasive procedure. The working instrument may be rotatable with the rotatable adapter or tool base and may be, for example, a clasper, a clamp, a scissors, an electrode, or an endoscope.

BRIEF DESCRIPTION OF THE DRAWINGS

The foregoing and other aspects of various embodiments of the present invention will best be appreciated with reference to the detailed description of embodiments in conjunction with the accompanying drawings, wherein:

FIG. 3A illustrates a long lever arm (LA) resulting from use of known robotic instrument systems, and FIG. 3B illustrates a reduced or short lever arm (SLA) resulting from use of a substantially rigid platform at or near a target site;

FIG. 4A illustrates a curved Maryland dissector, FIG. 4Z illustrates a Maryland bipolar cautery instrument;

FIG. 5A illustrates a robotic medical instrument system including a flexible instrument such as a flexible catheter, FIG. 5B illustrates an operator workstation, FIG. 5C illustrates an operator workstation that includes a master input device and data gloves, FIG. 5D illustrates another operator workstation with which a flexible instrument control can be input using a master input device and a wireless data glove, and FIG. 5E is a block diagram of a system architecture of a robotic medical instrument system in which embodiments may be implemented or with which embodiments may be utilized;

FIG. 7A is a rear perspective view of a support assembly having an instrument driver mounted thereto, FIG. 7B illustrates a support assembly separately from the instrument driver, FIG. 7C is another perspective view of a support assembly, FIG. 7D is a rearward perspective view of a support assembly including a mounting plate and locking lever, and FIG. 7E is a forward perspective view of a support assembly and shows front and top portions of the instrument driver, and FIG. 7E is another view of a support assembly;

FIGS. 8A-C illustrate an arrangement for controlling a flexible catheter assembly with an instrument driver, where FIG. 8A is a forward perspective view of an instrument driver having a flexible instrument assembly mounted thereon, FIG. 8B is a front perspective view of an instrument driver without a flexible instrument assembly mounted thereon, and FIG. 8C is a rear perspective view of an instrument driver without a flexible instrument assembly mounted thereon;

FIGS. 9A-D illustrate a flexible catheter assembly of a robotic instrument system with which embodiments may be utilized, where FIG. 9A is a forward perspective view of a catheter assembly, FIG. 9B is a rear perspective view of FIG. 9A, FIG. 9C illustrates a flexible sheath instrument, and FIG. 9D illustrates a flexible catheter instrument;

FIGS. 10A-D illustrate various examples of flexible catheters having varying degrees of flexibility or different flexible sections where FIG. 10A illustrates a catheter having a flexible distal end, FIG. 10B illustrates a catheter having a flexible distal end and flexible segment disposed between rigid segments, FIG. 10C illustrates a catheter having a rigid proximal segment, a flexible medial segment, and a flexible distal segment, and FIG. 10D illustrates a catheter having a flexible proximal segment and a flexible distal segment;

FIGS. 11A-H illustrate how a distal portion of a flexible catheter instrument can be manipulated and various keyed arrangements that may be used to facilitate component rotation, where FIGS. 11C-H are cross sectional views along line A-A in FIG. 11B;

FIG. 14A illustrates a sheath catheter forming a platform and a system instrument in the form of an endoscope that can be advanced through the master sheath, FIG. 14B illustrates two sheath catheters forming one or more platforms, FIG. 14C illustrates three sheath catheters forming one or more platforms, FIG. 14D illustrates the system shown in FIG. 14D with an endoscope, and FIG. 14E illustrates a substantially rigid structure including substantially rigid and straight or linear sheath catheters to form one or more platforms;

Figure 1:
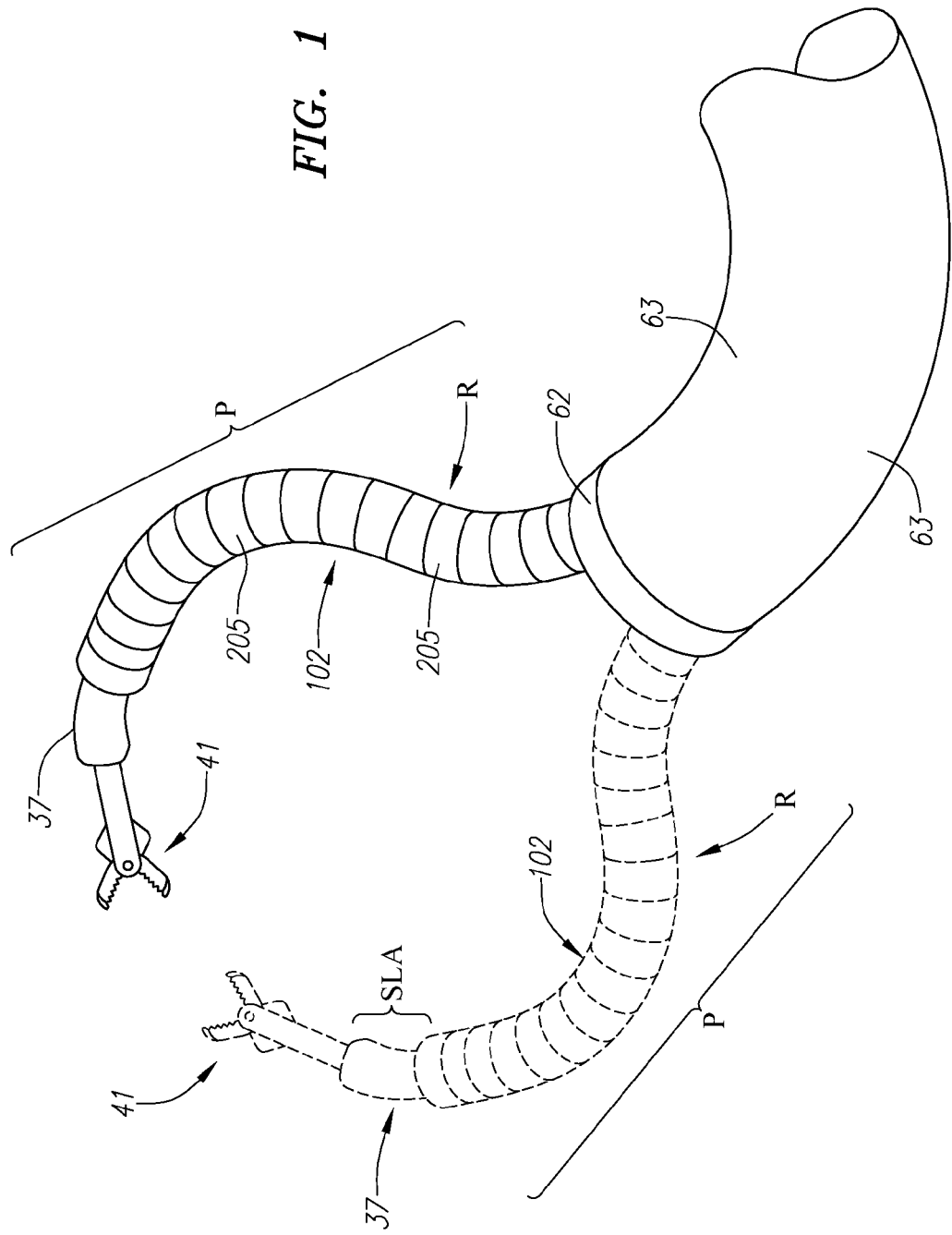
FIG. 1 illustrates a robotic instrument system in which embodiments may be implemented and that includes a substantially rigid platform that extends from or beyond a distal end of a master sheath and includes a plurality of segments that interlock or matingly engage each other.
Figure 19:
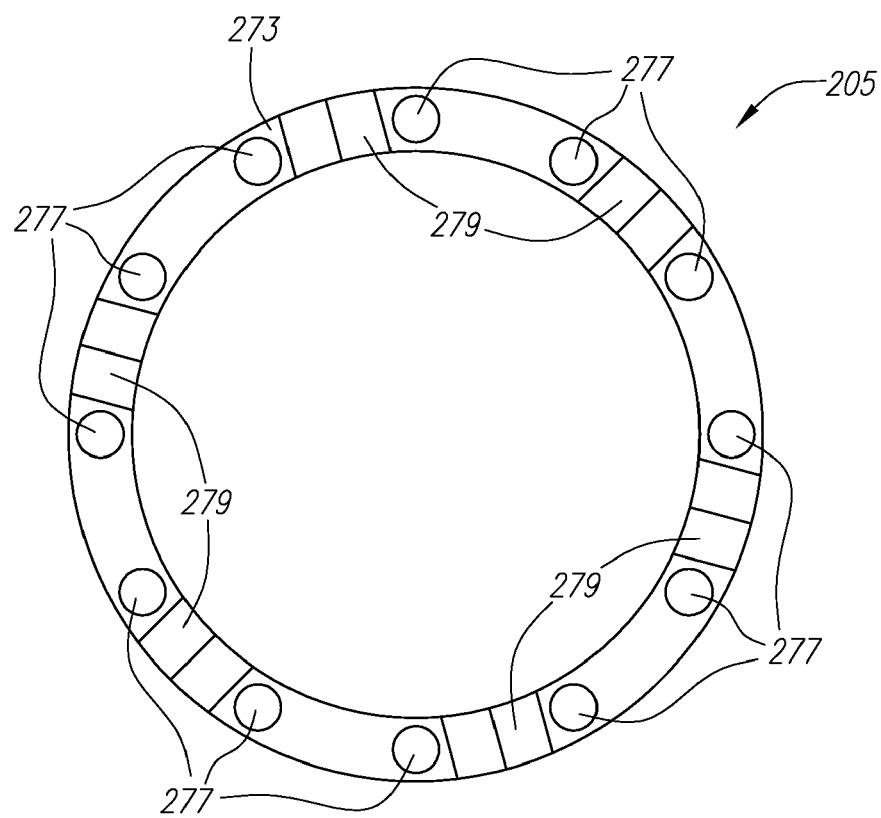
Figure 18C:
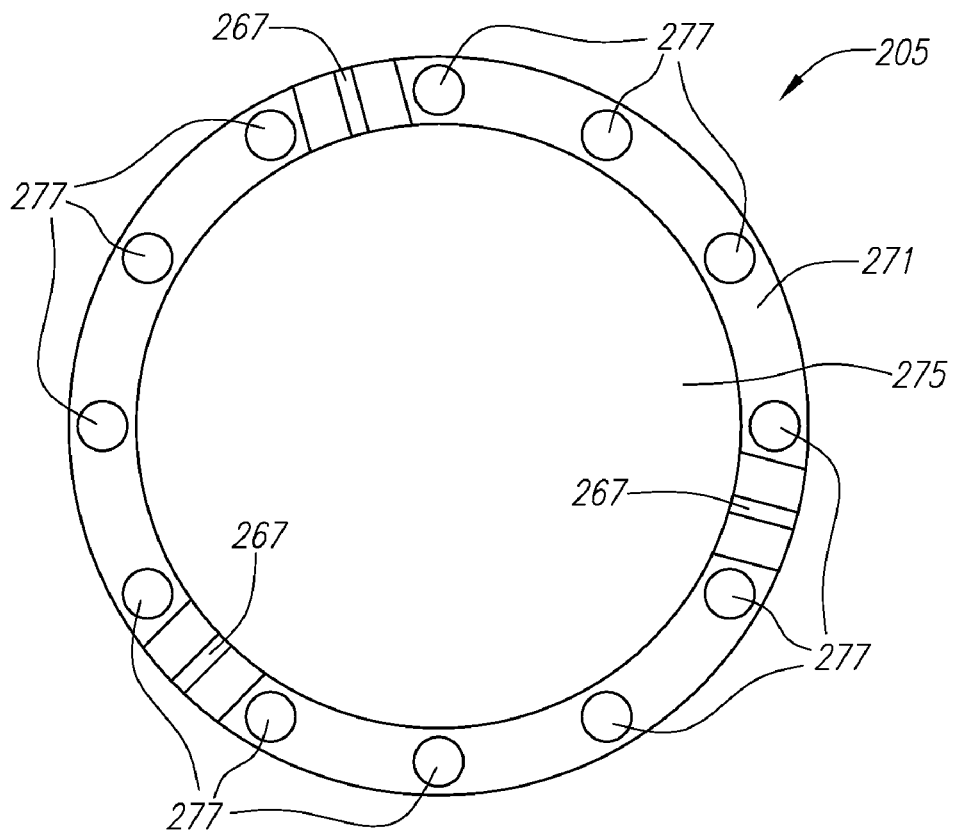
Figure 18D:
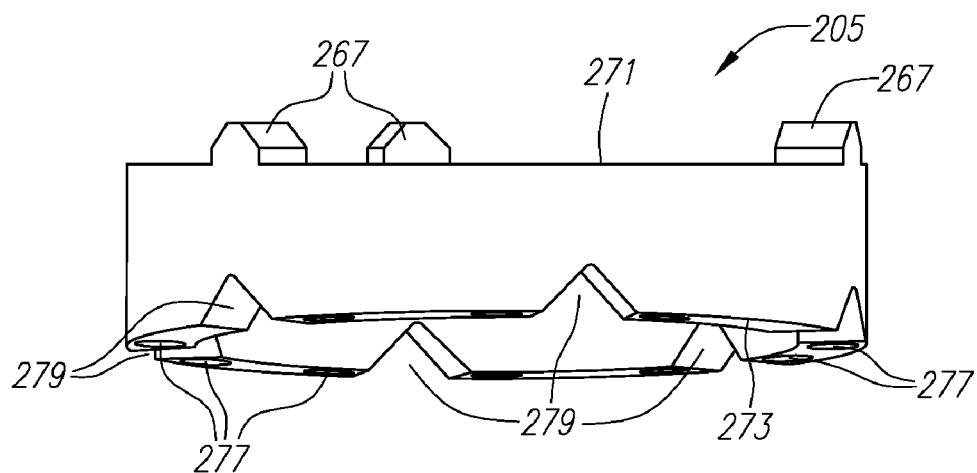
Figure 22G:
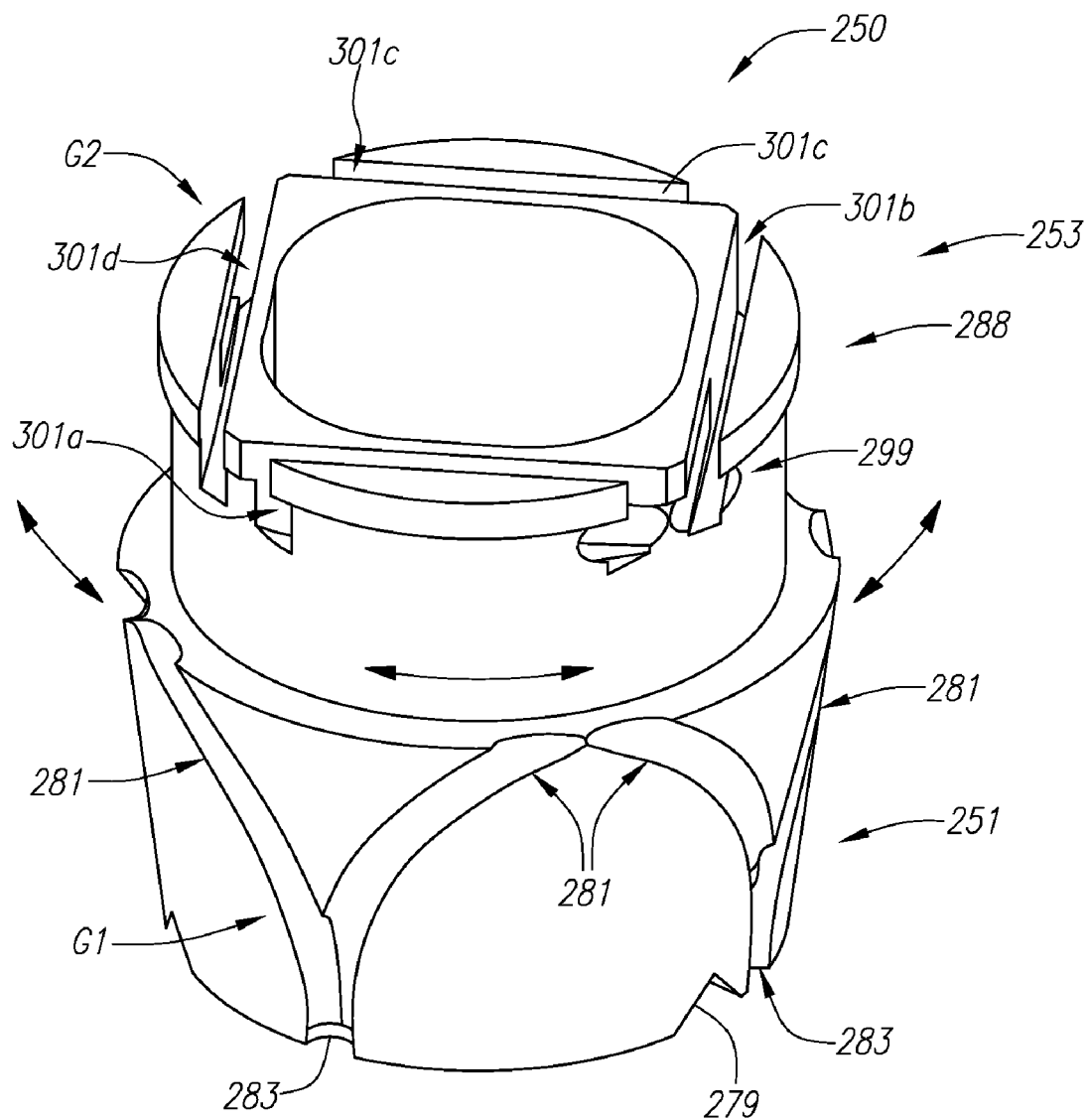
Figure 22H:
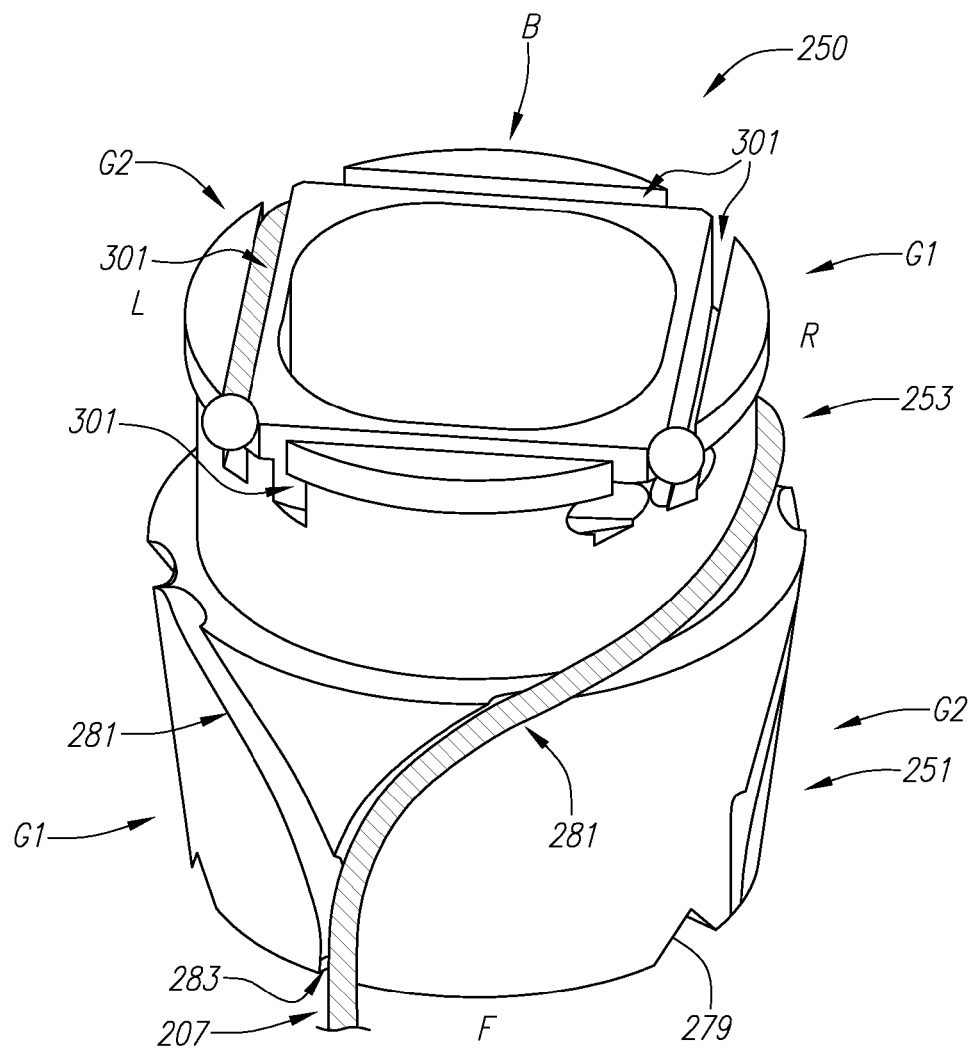
Figure 22I:
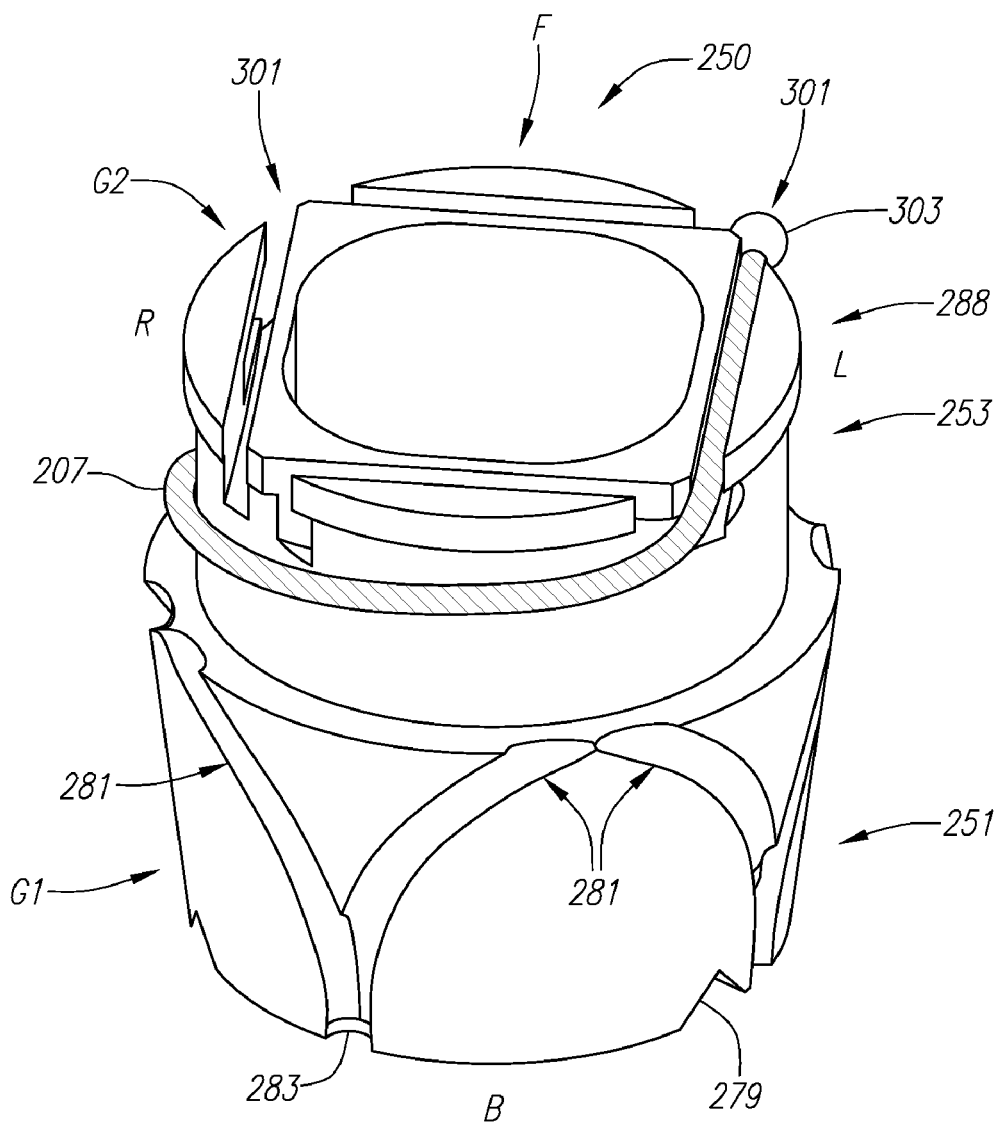
Figure 22J:
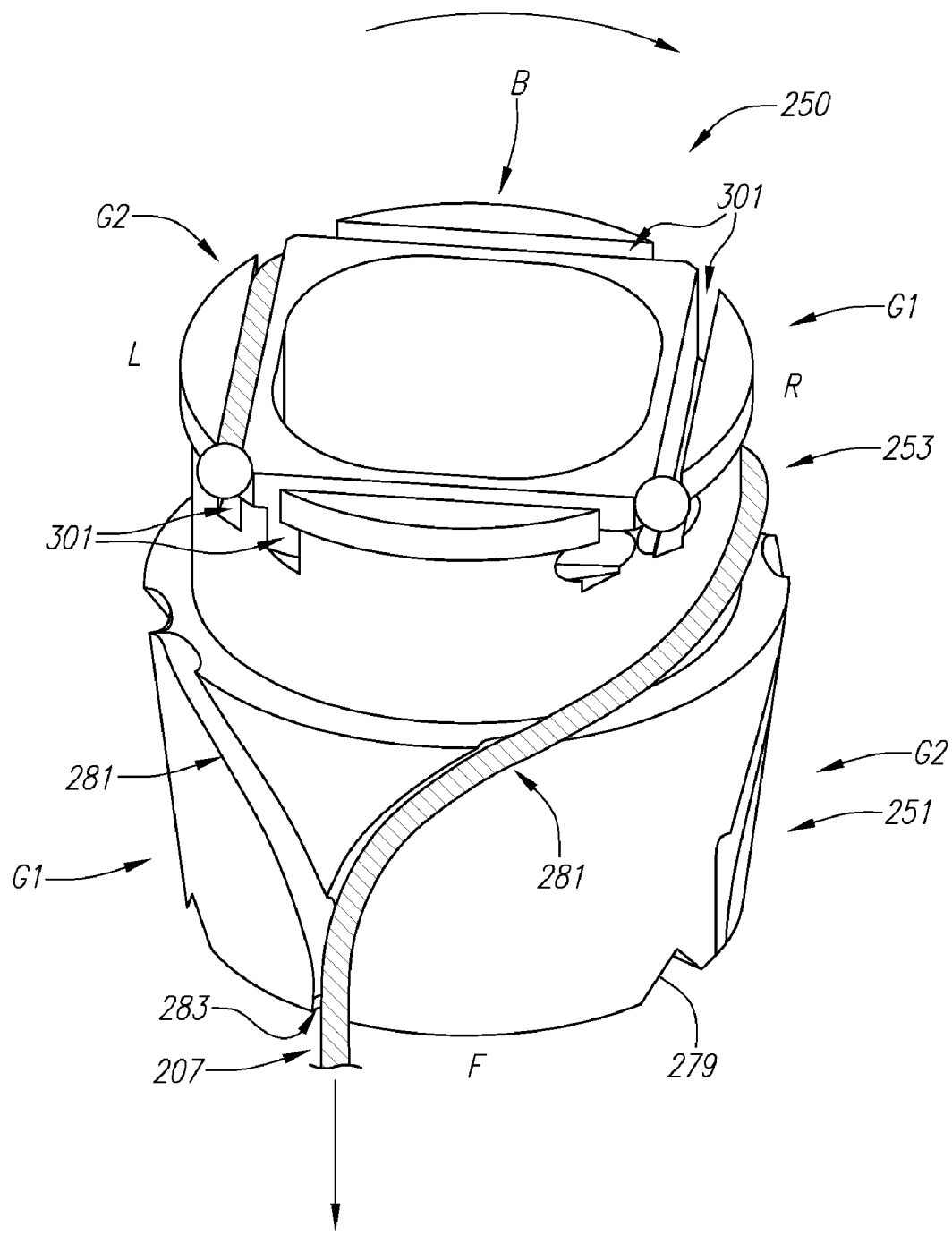
Figure 22K:
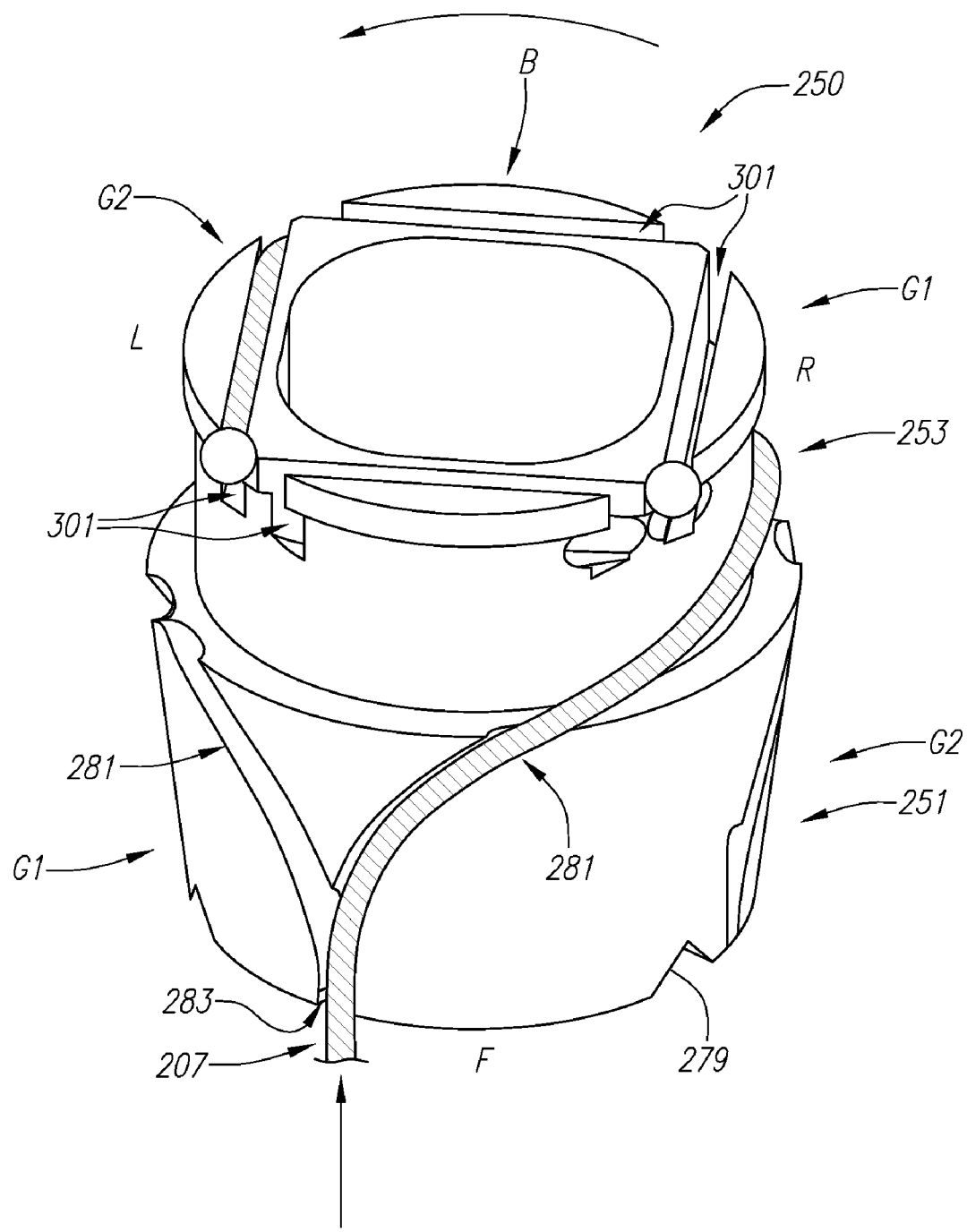
Figure 22L:
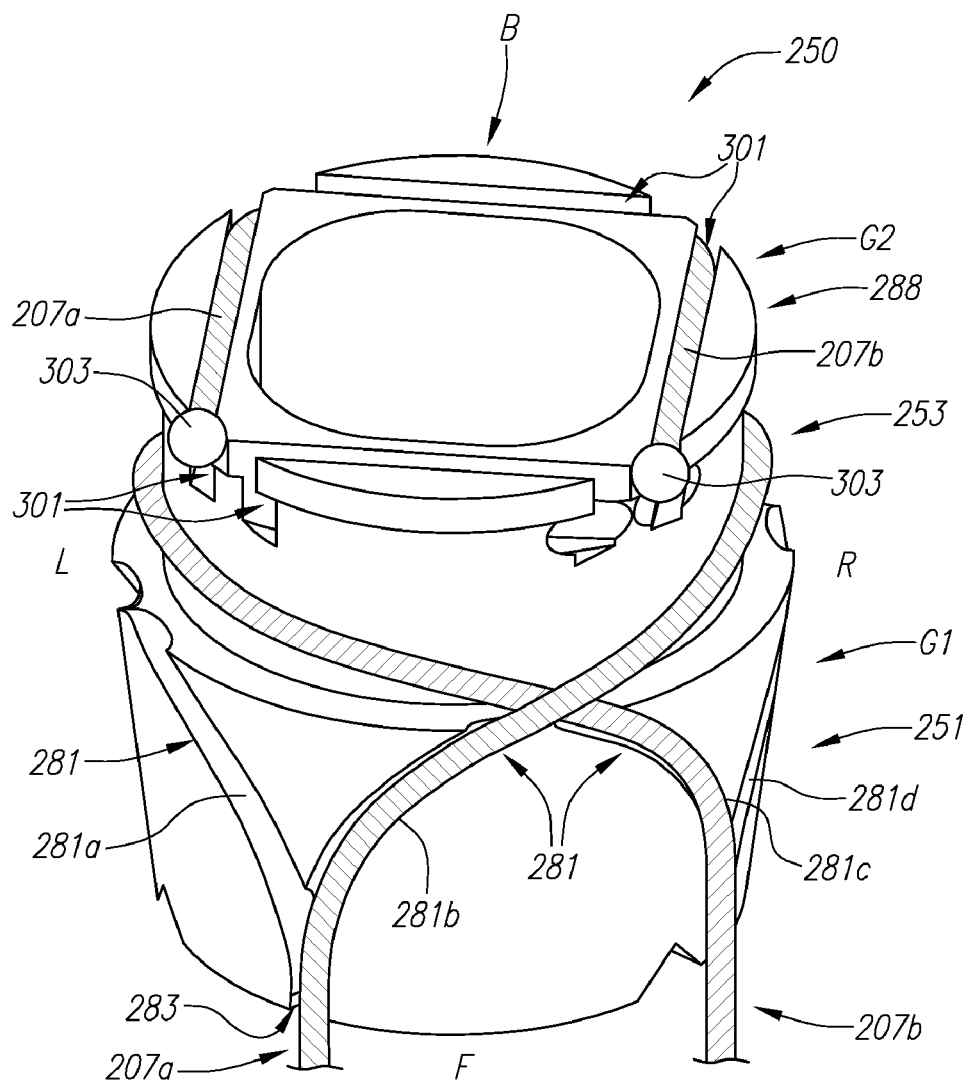
Figure 22M:
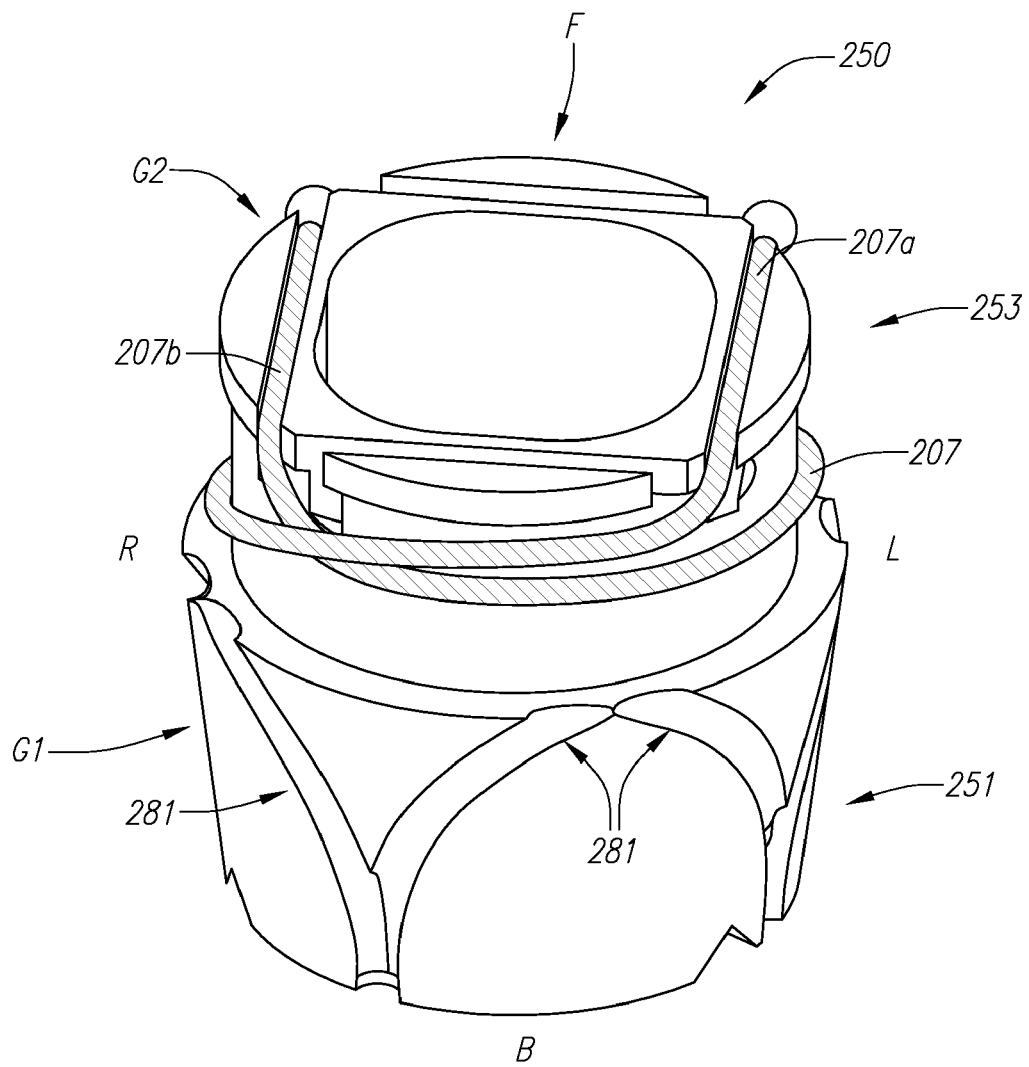
Figure 22N:
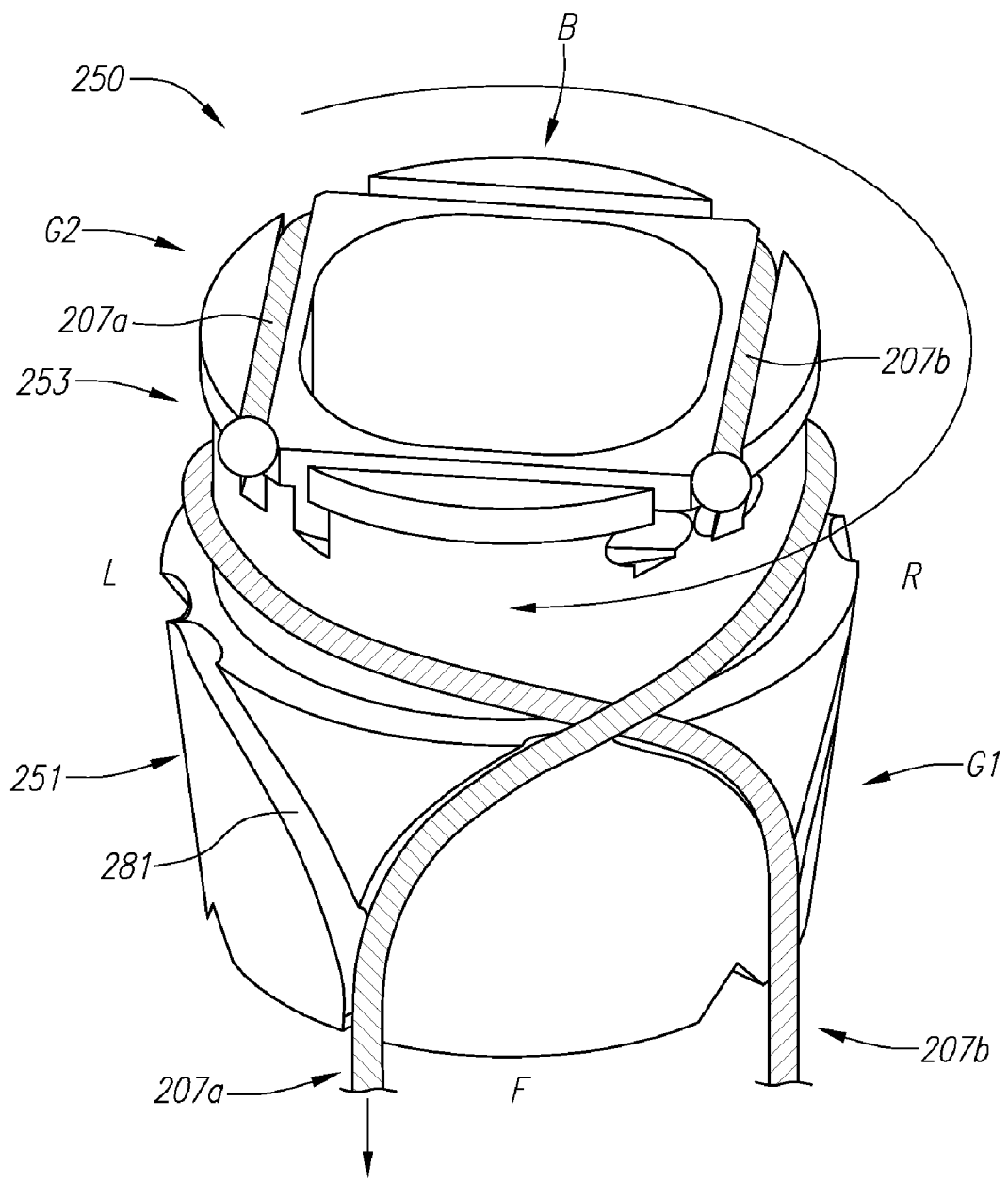
Figure 220:
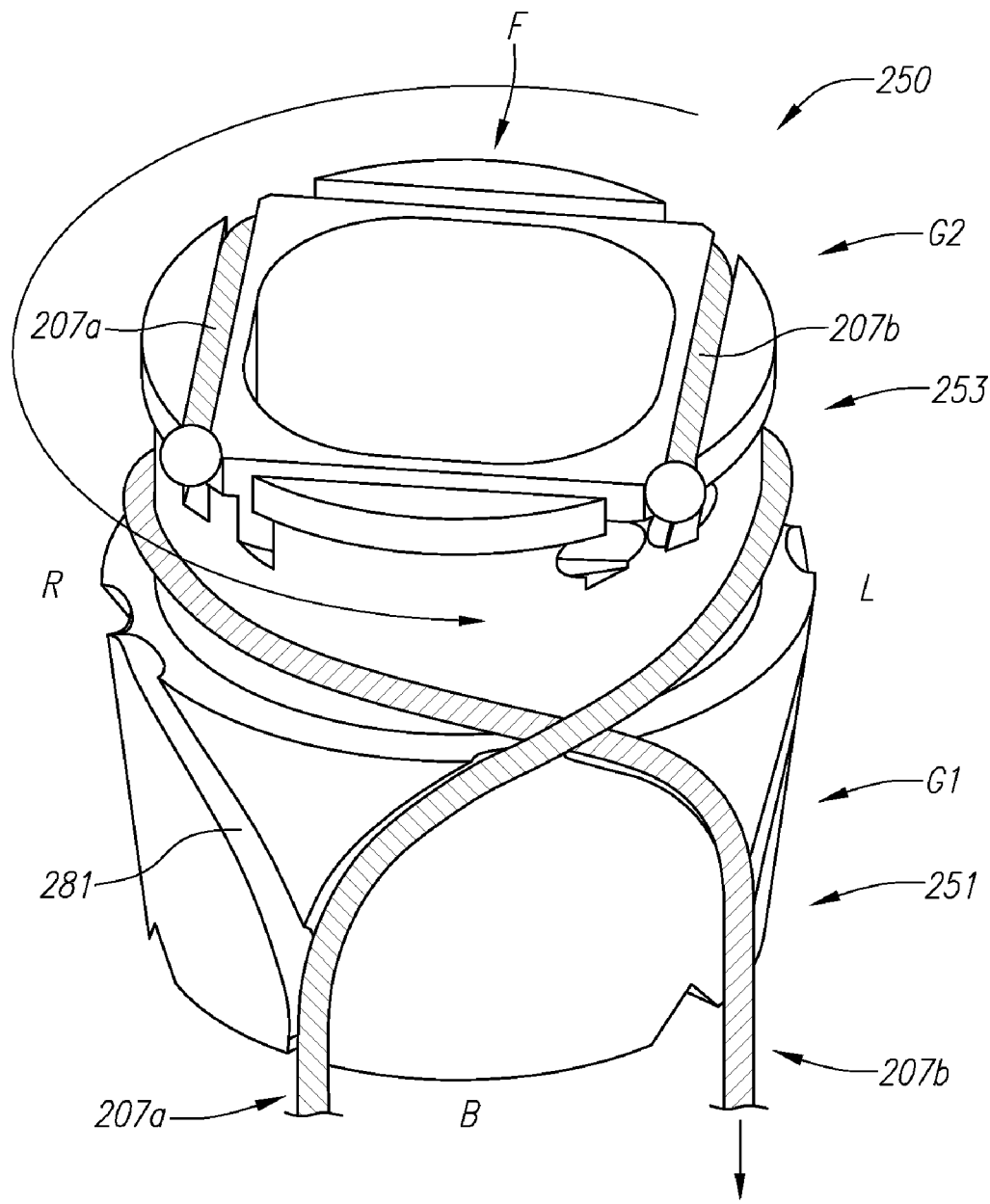
Figure 23C:
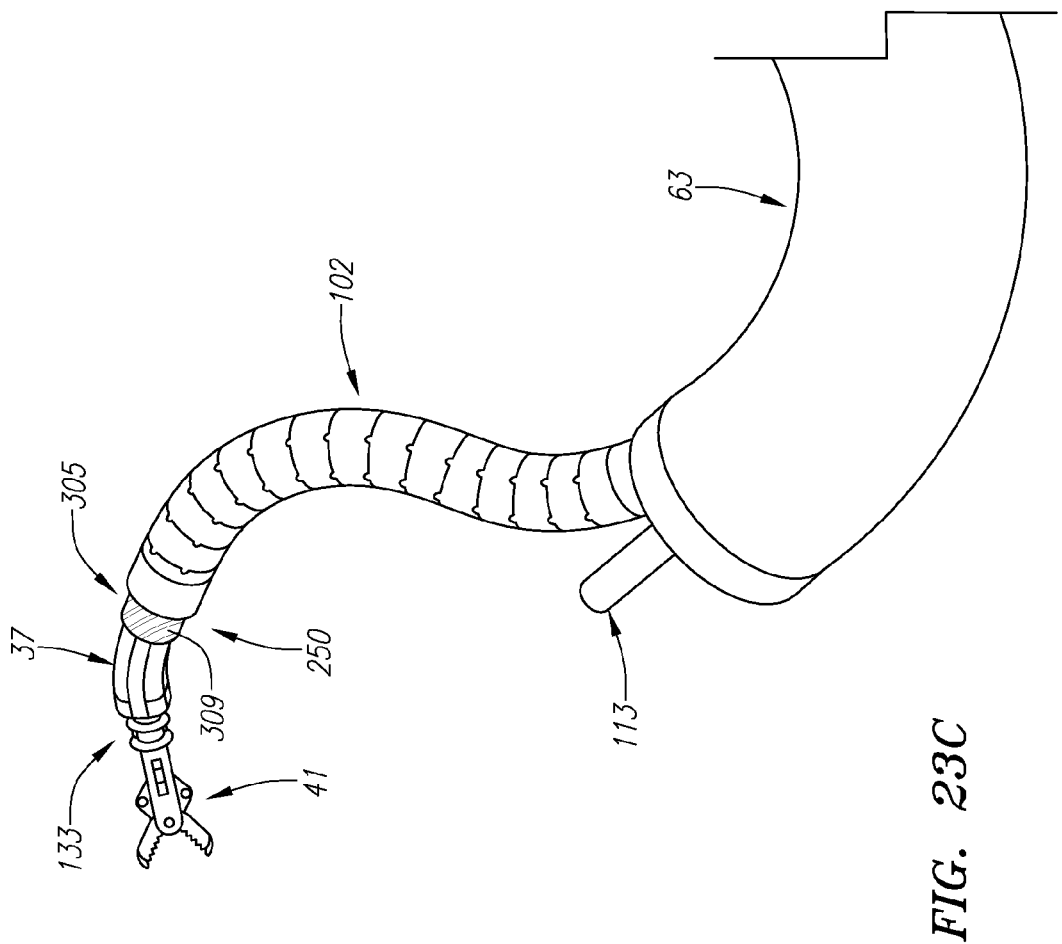
Figure 23D:
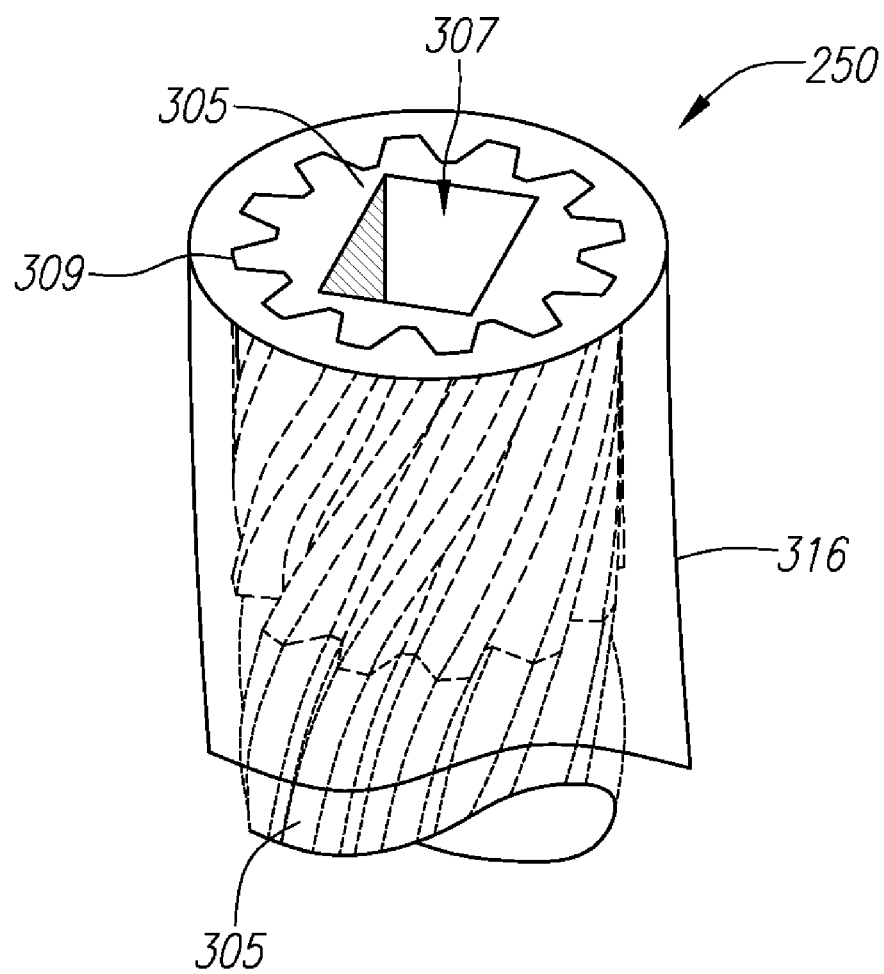
Figure 23E:
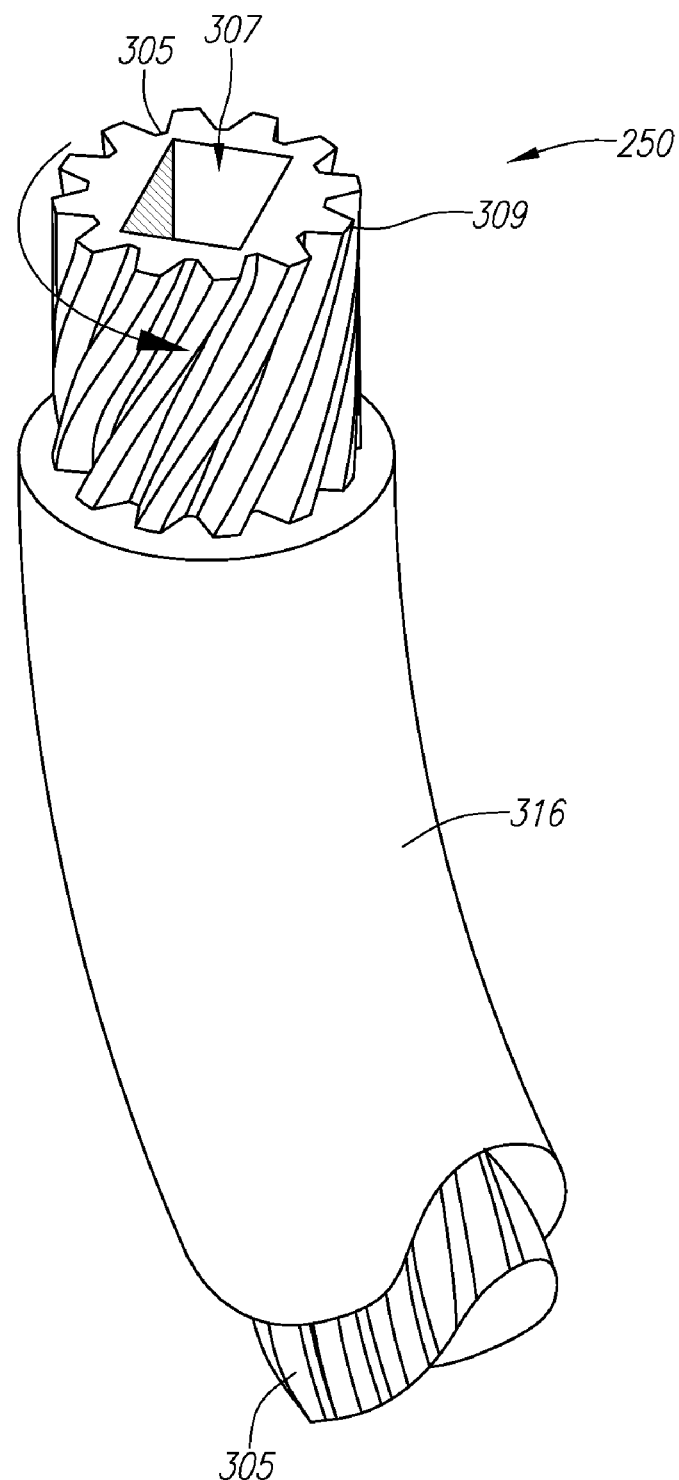
Figure 24C:
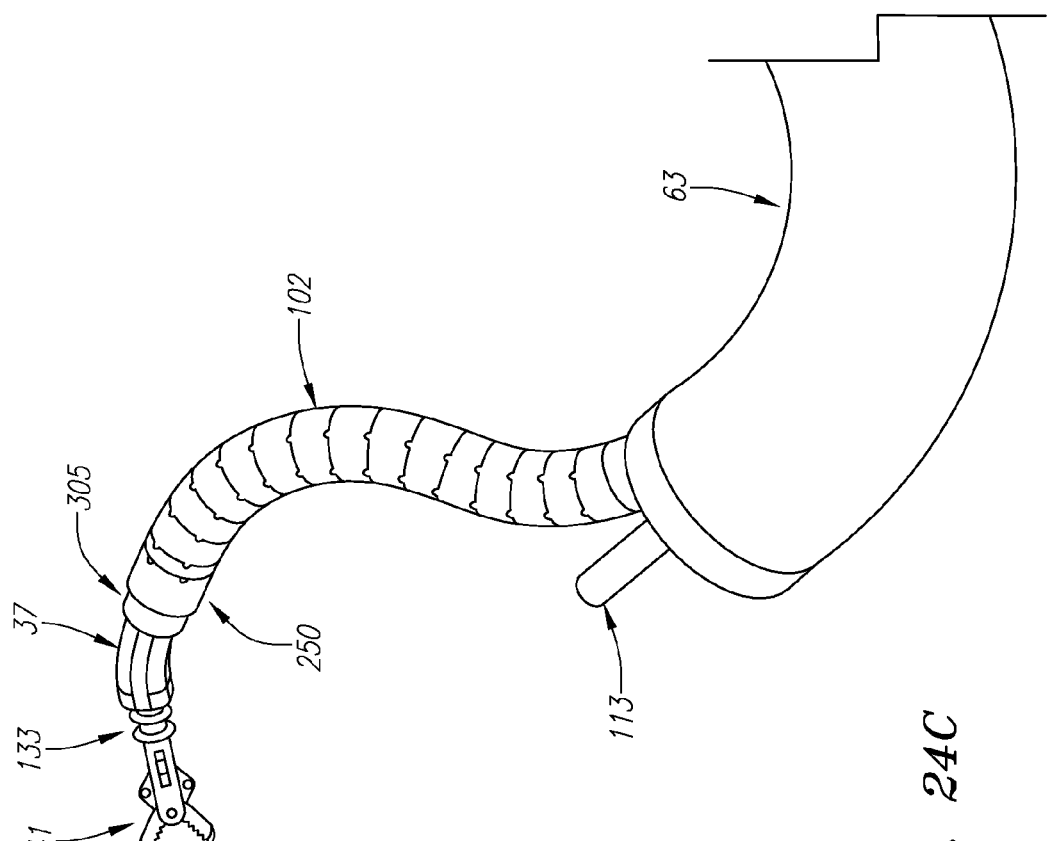
Figure 24D:
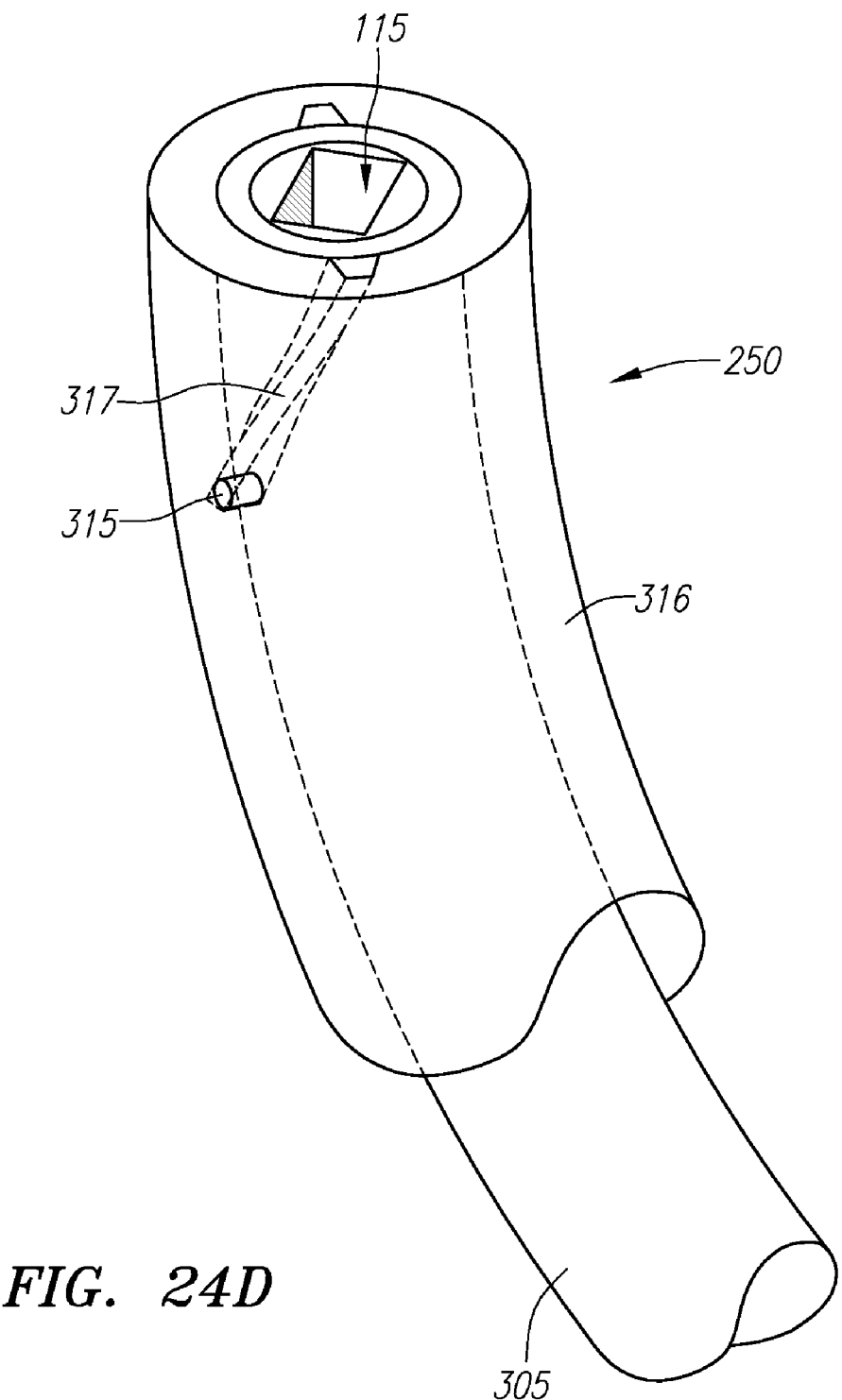
Figure 24E:
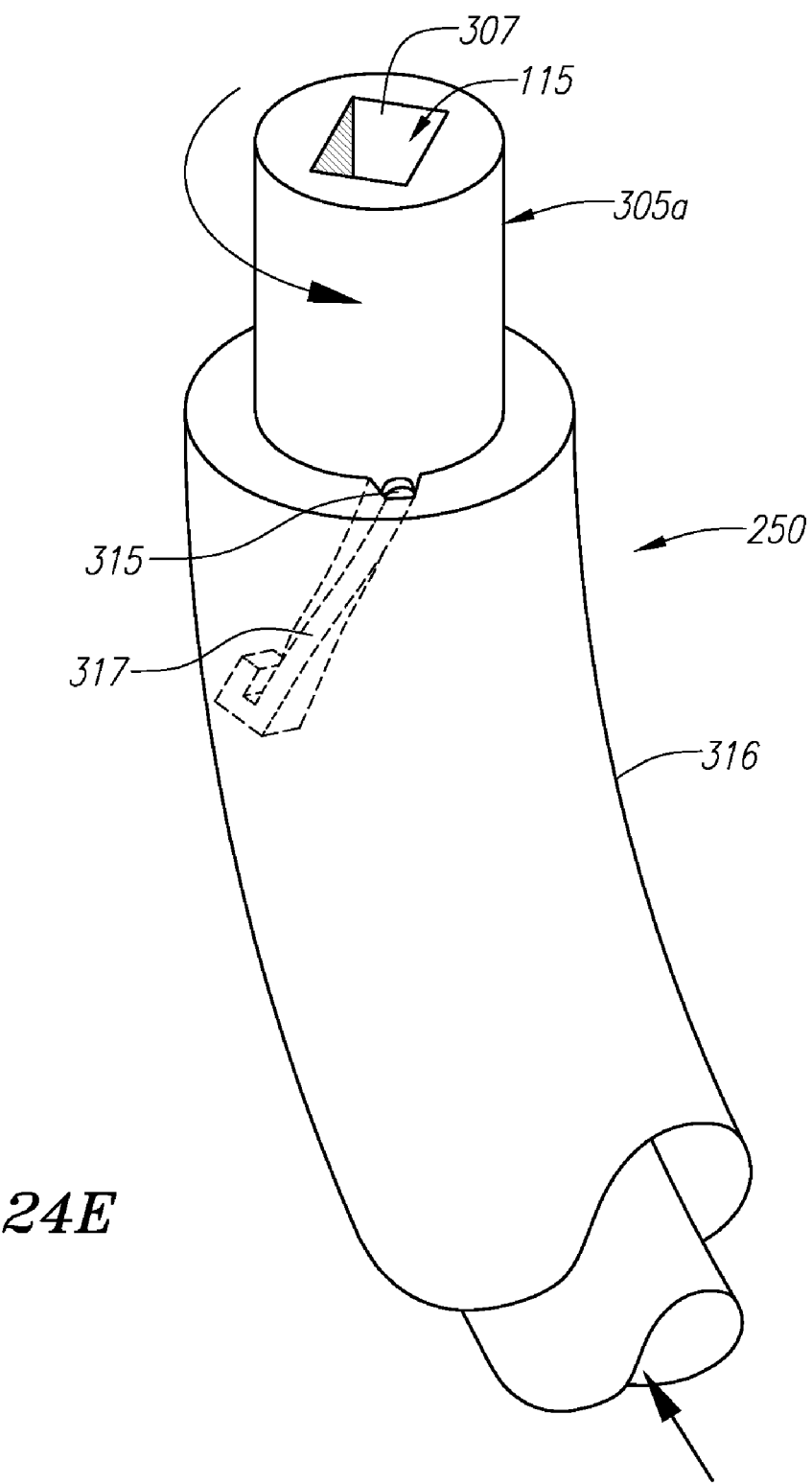
Figure 25C:
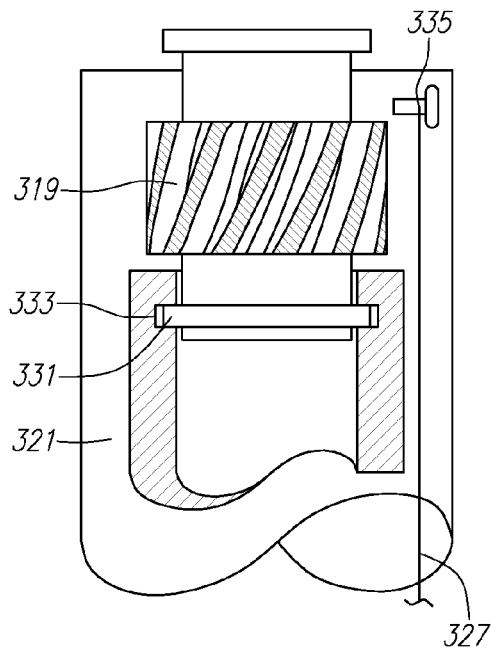
Figure 25D:
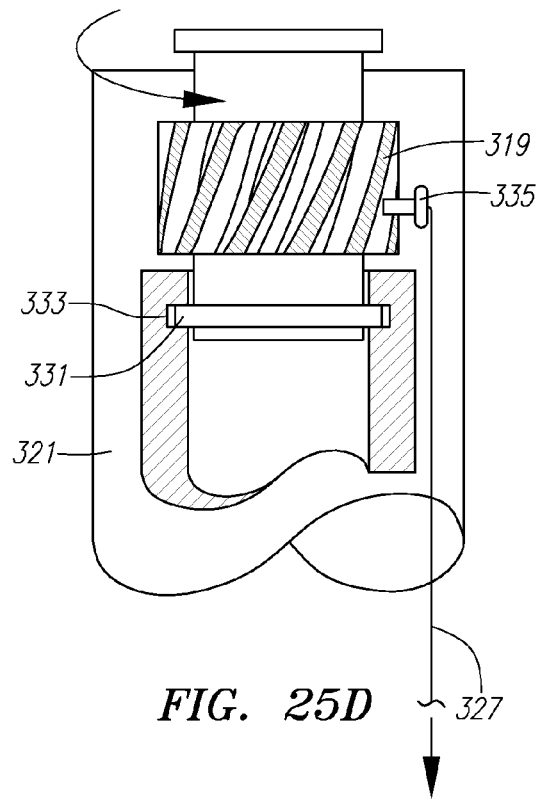
Figure 25E:
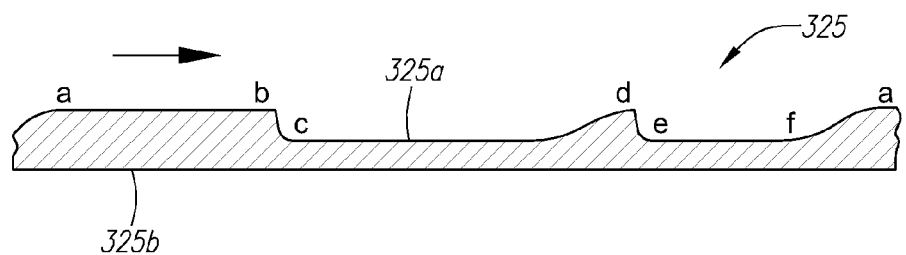
Figure 25F:
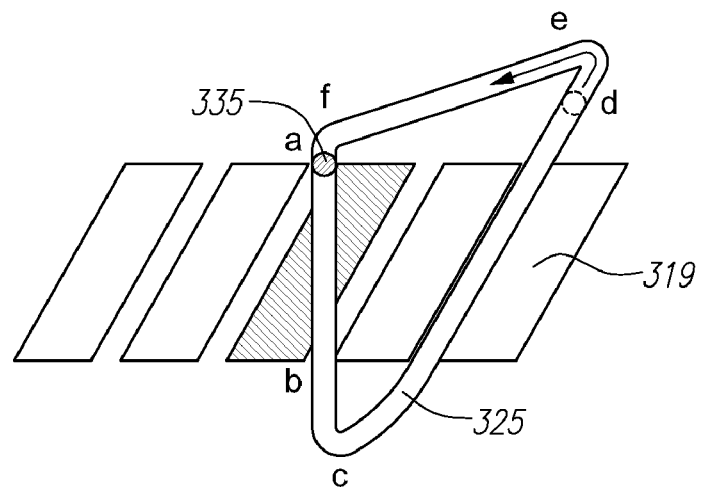
Figure 25G:
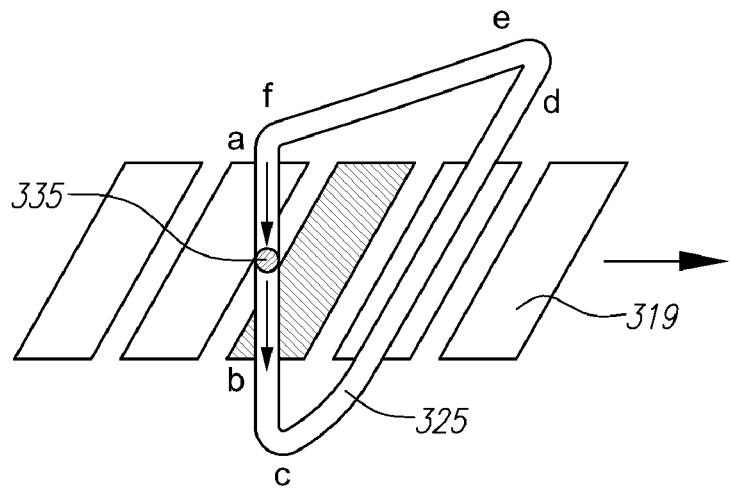
Figure 25H:
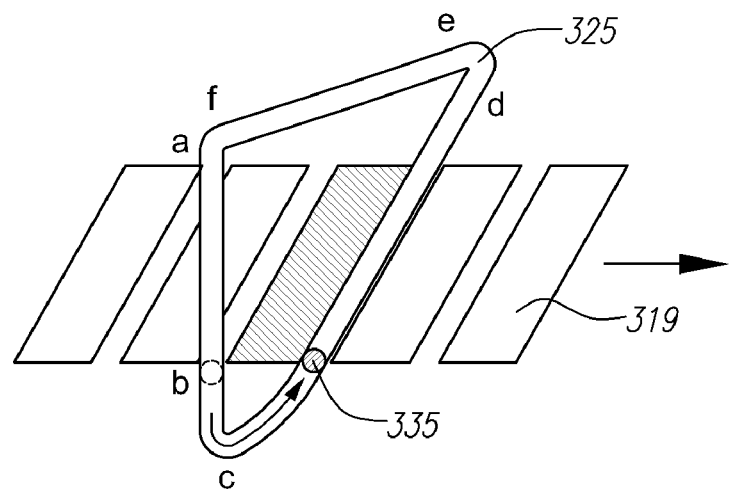
Figure 26A:
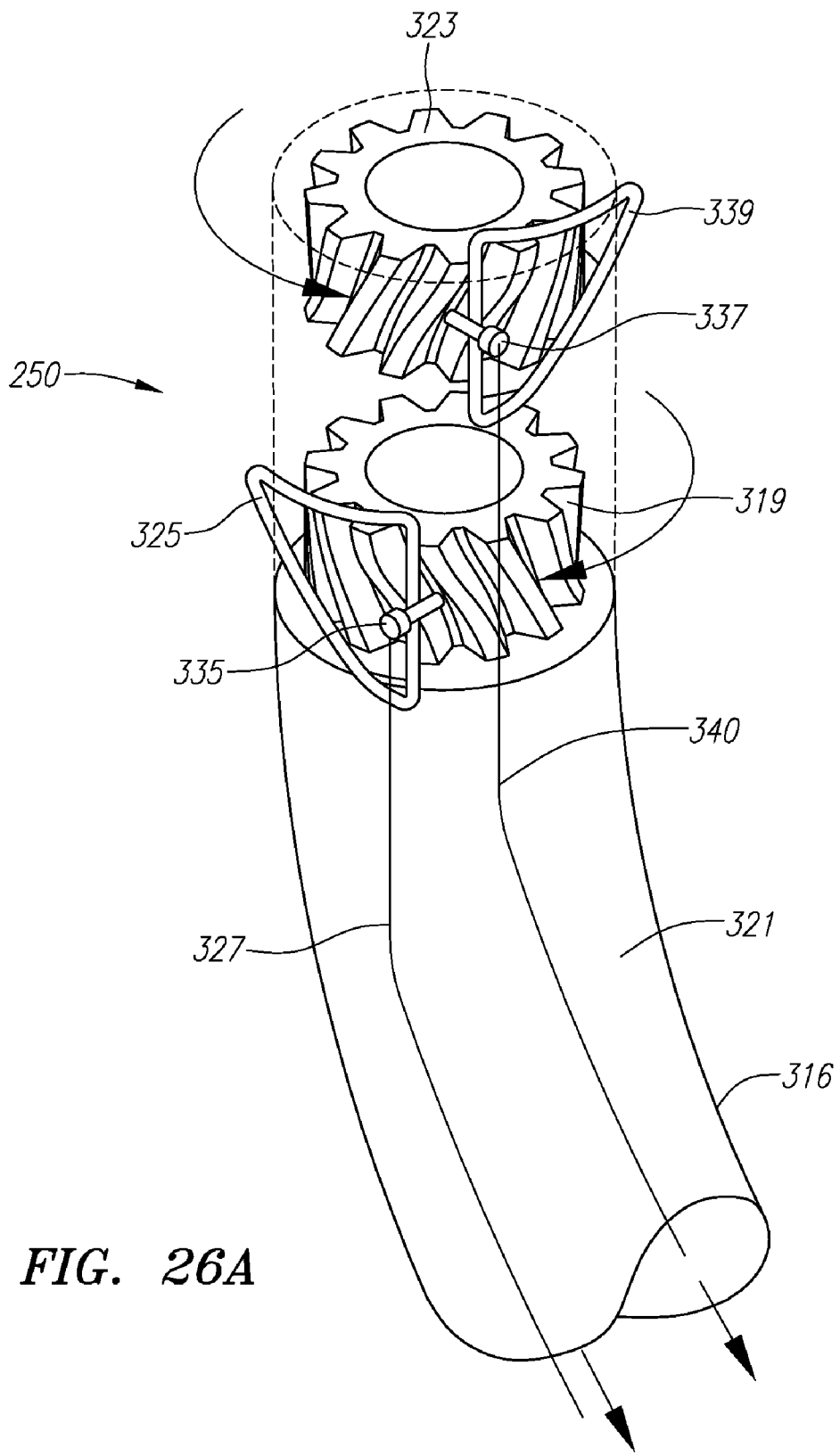
Figure 26B:
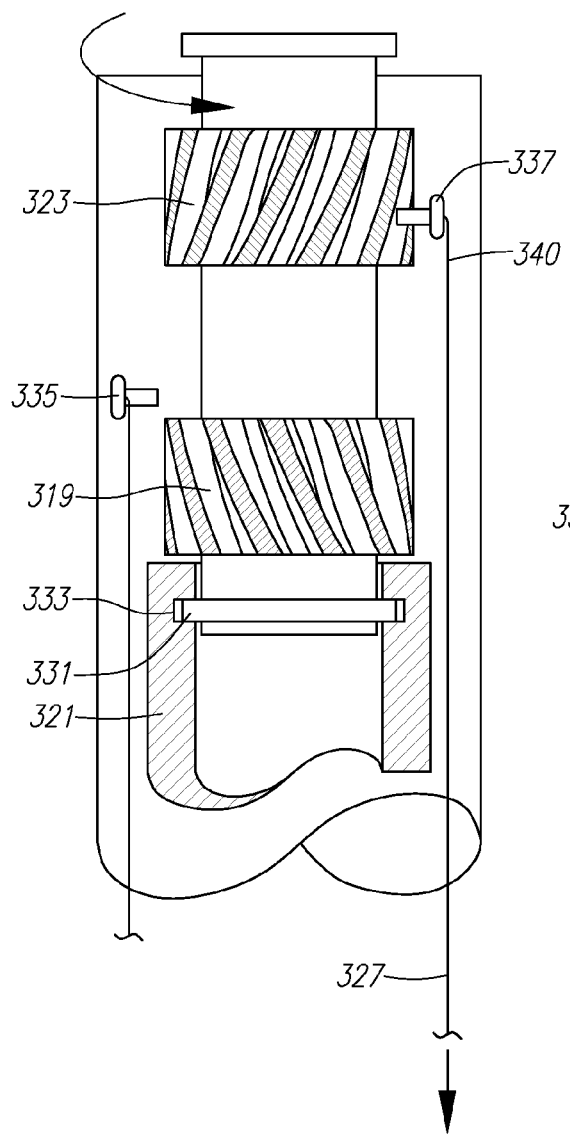
Figure 26C:
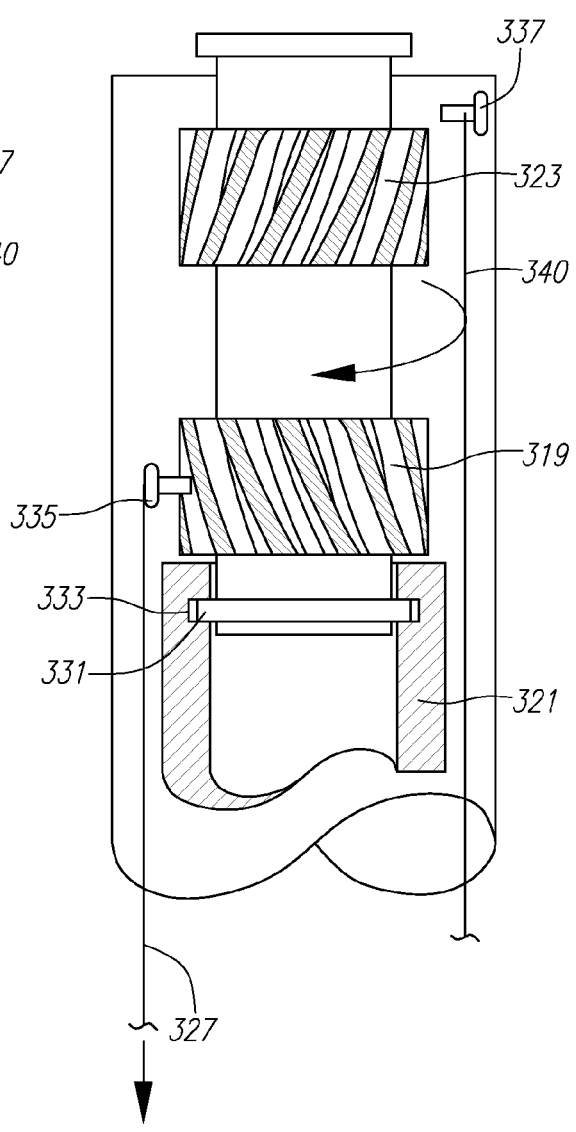
Figure 26D:
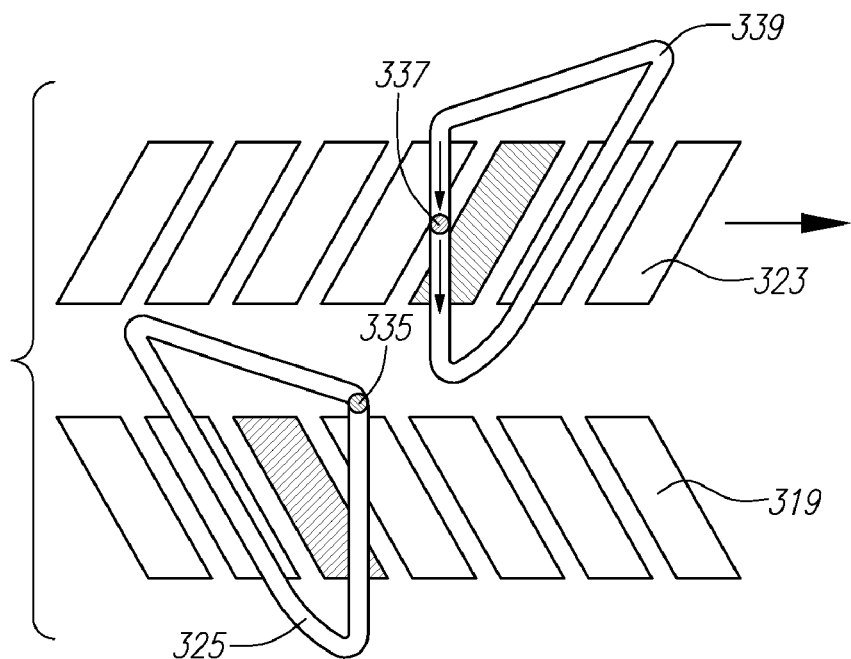
Figure 26E:
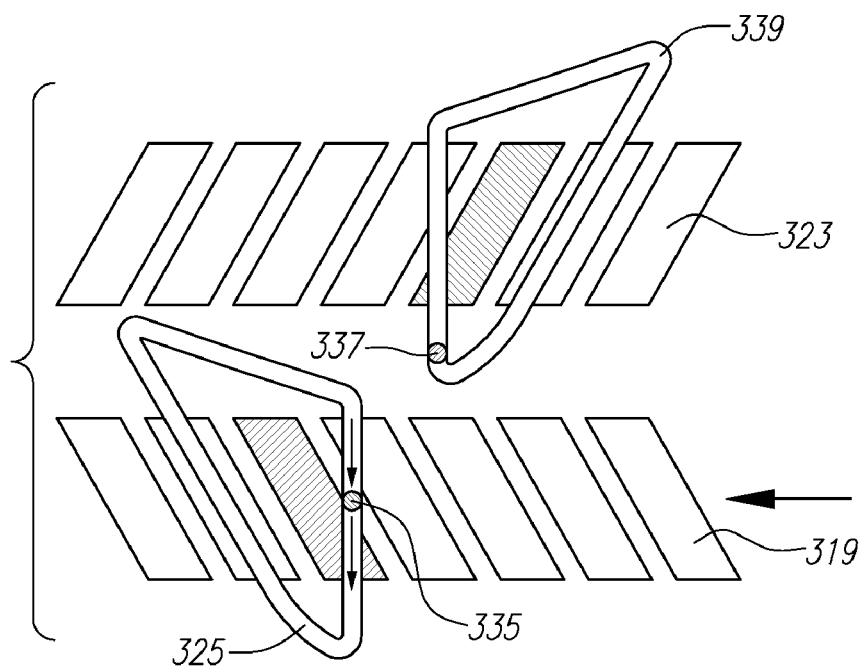
Figure 27A:
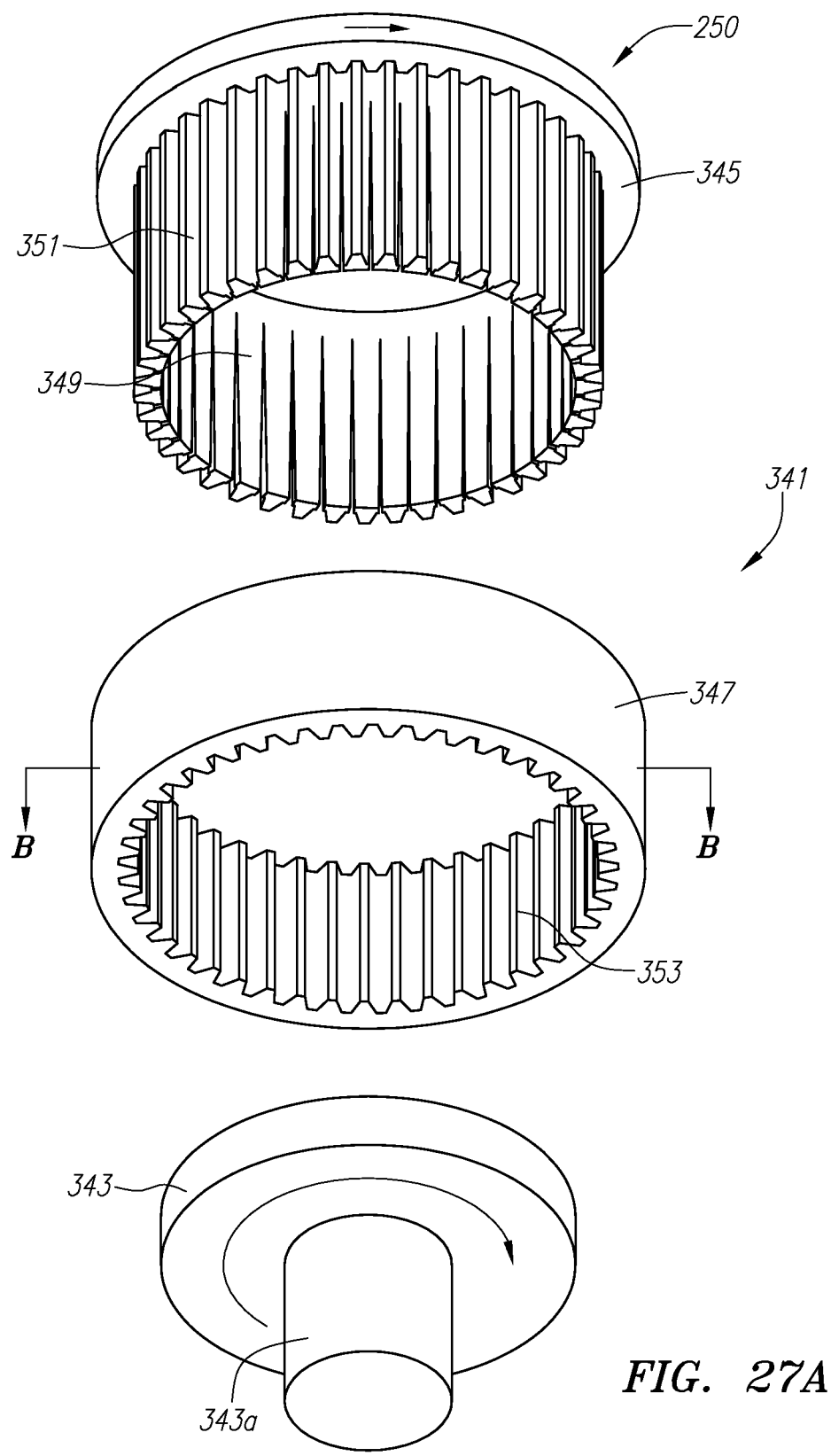
Figure 27B:
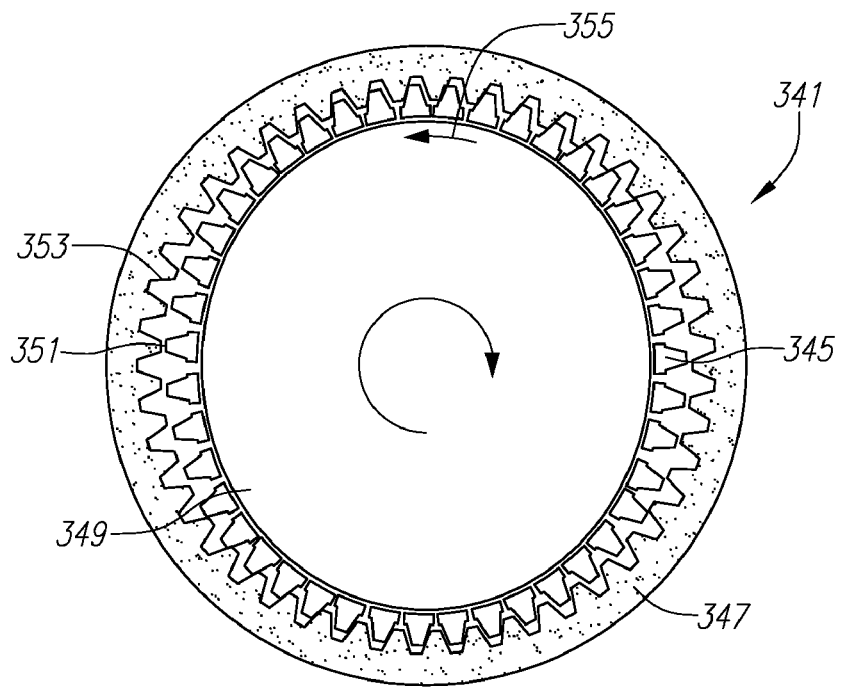
Figure 27C:
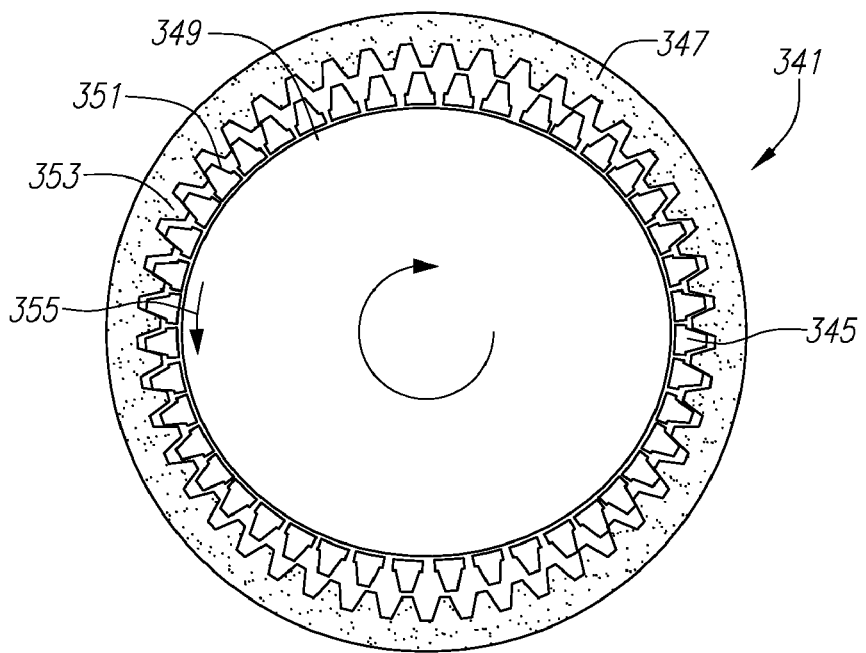
Figure 27D:
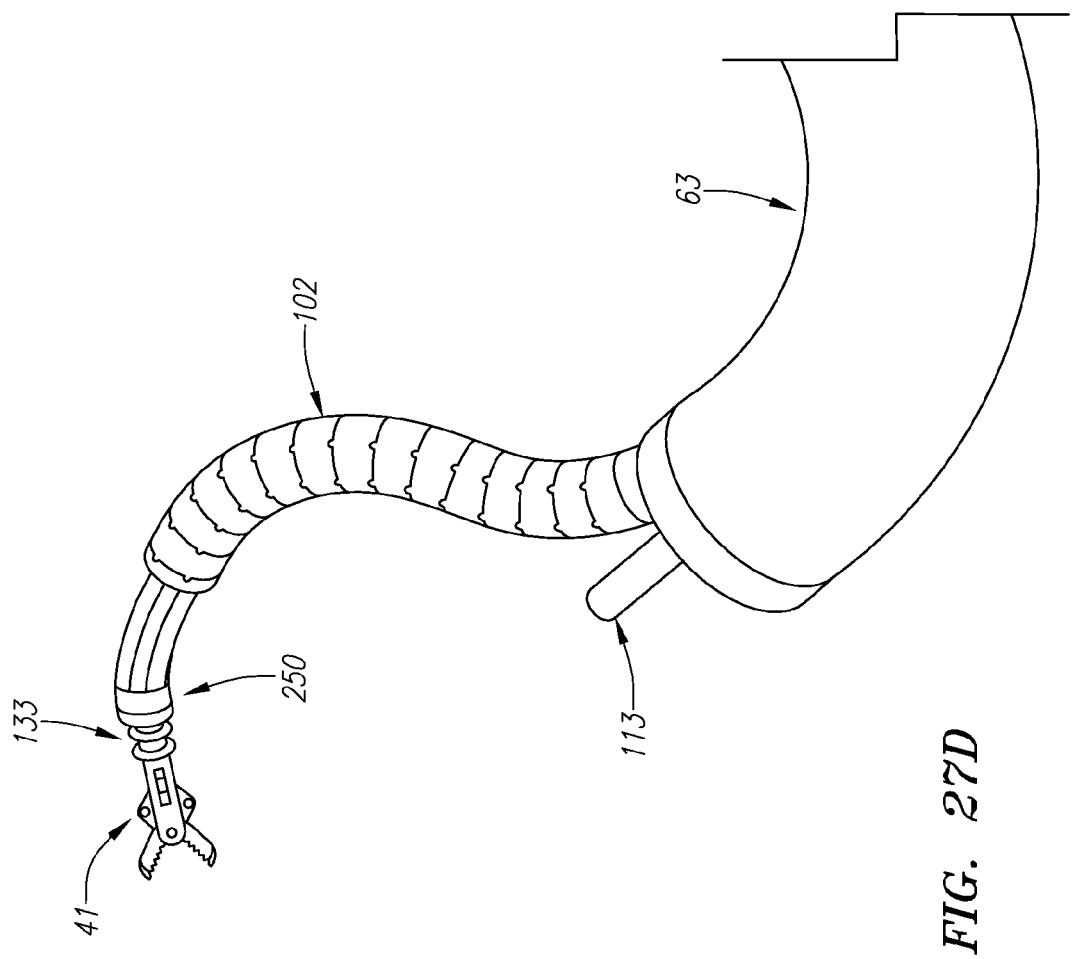
Figure 30:
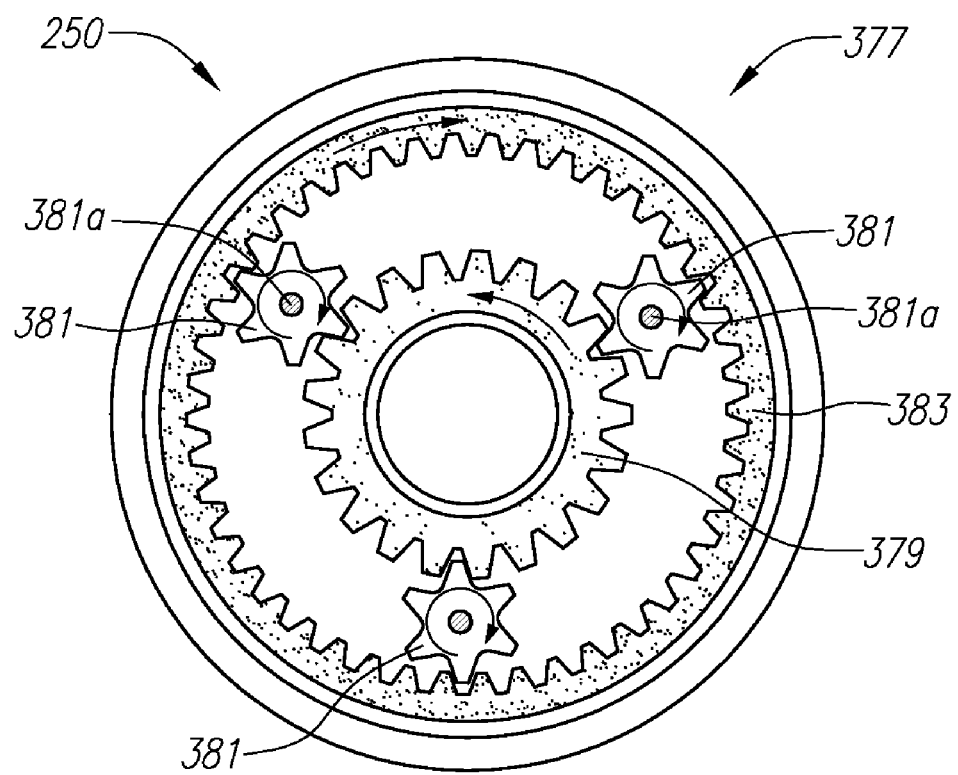
Figure 30A:
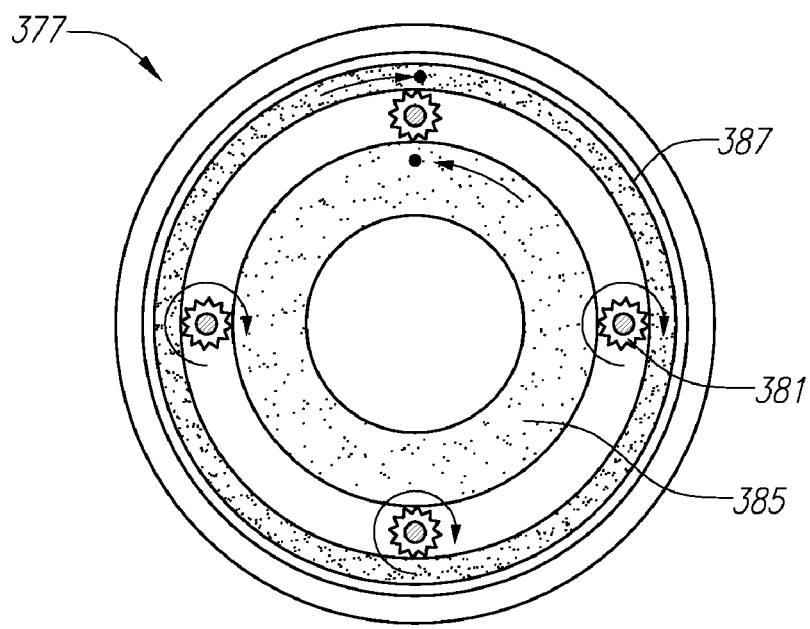
Figure 30B:
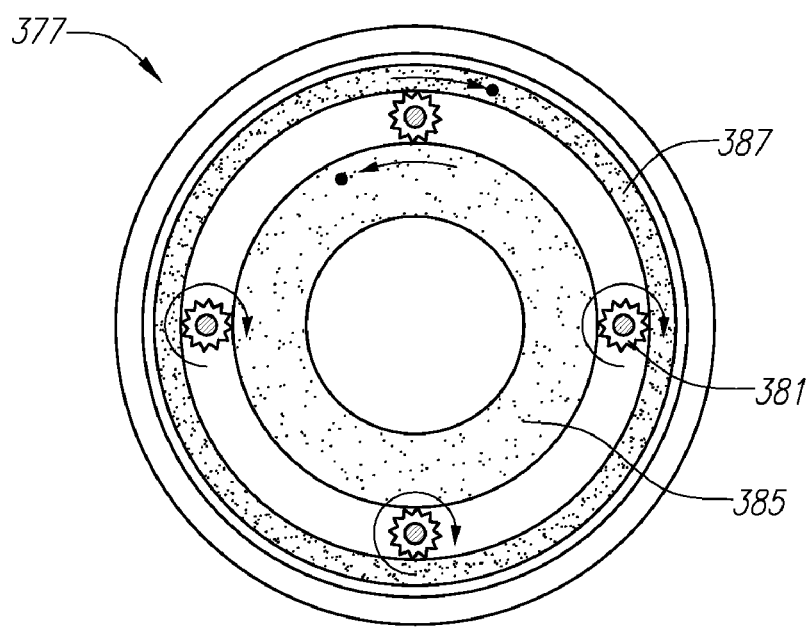
Figure 30C:
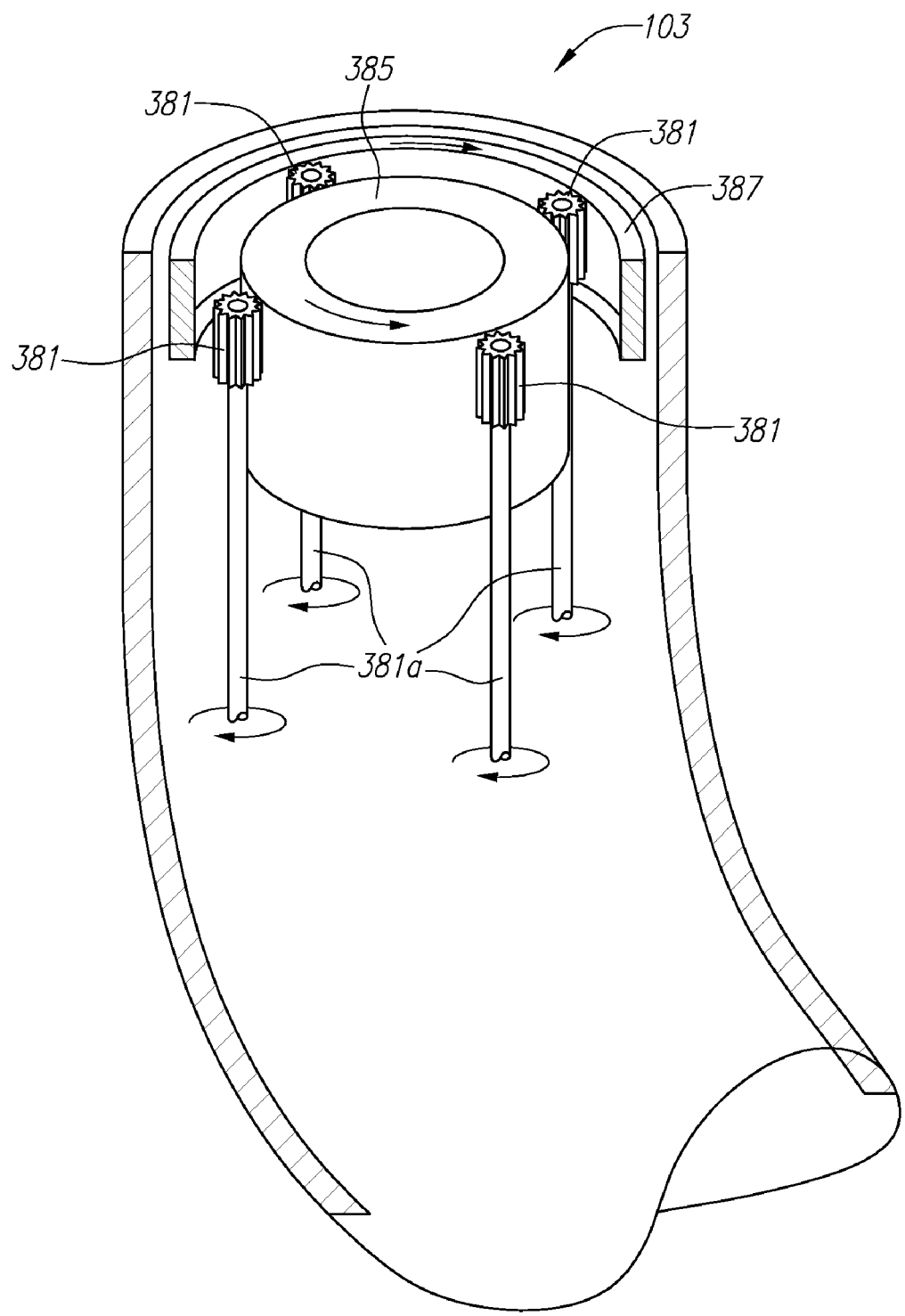
Figure 30D:
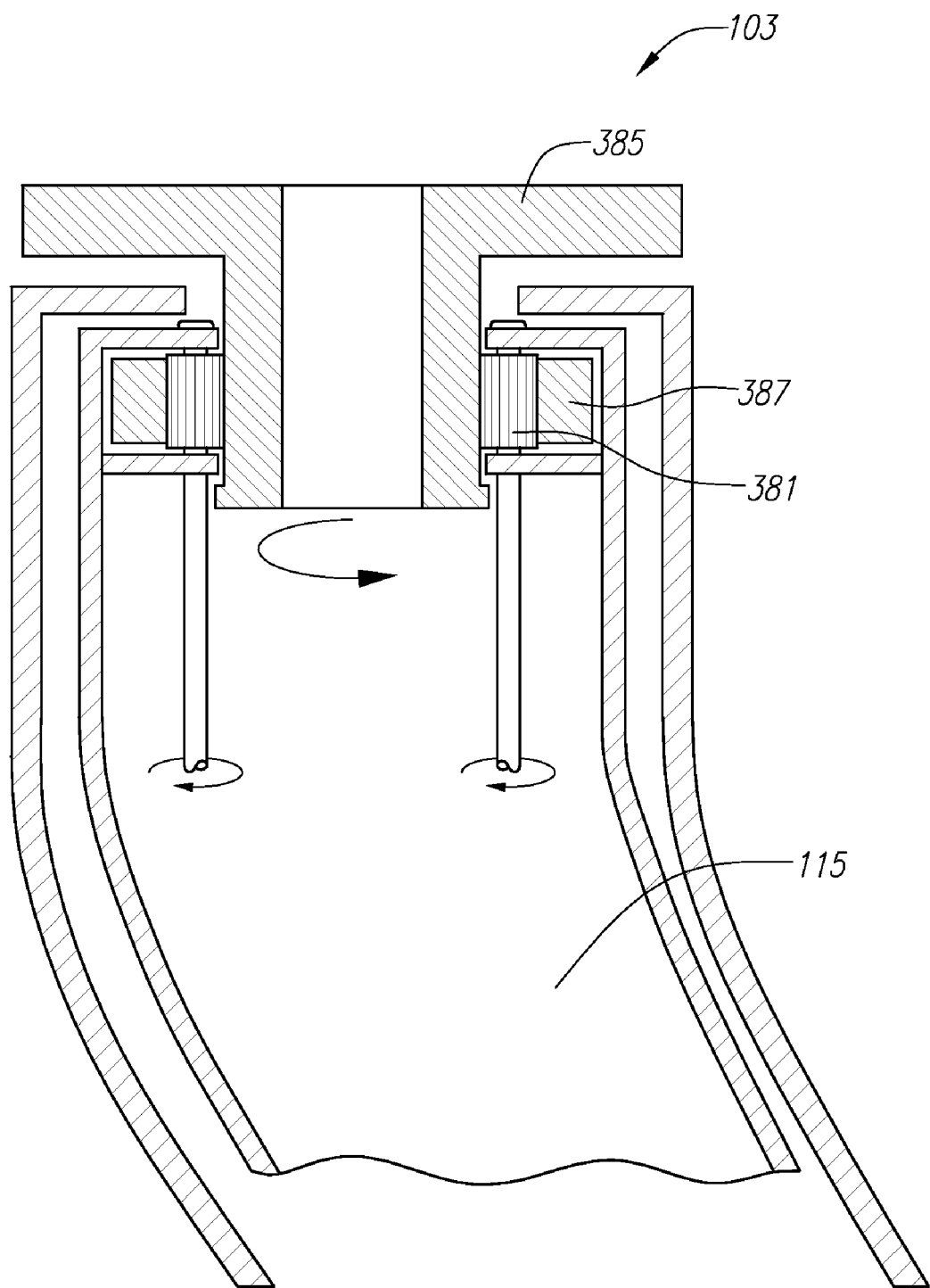
Figure 30F:
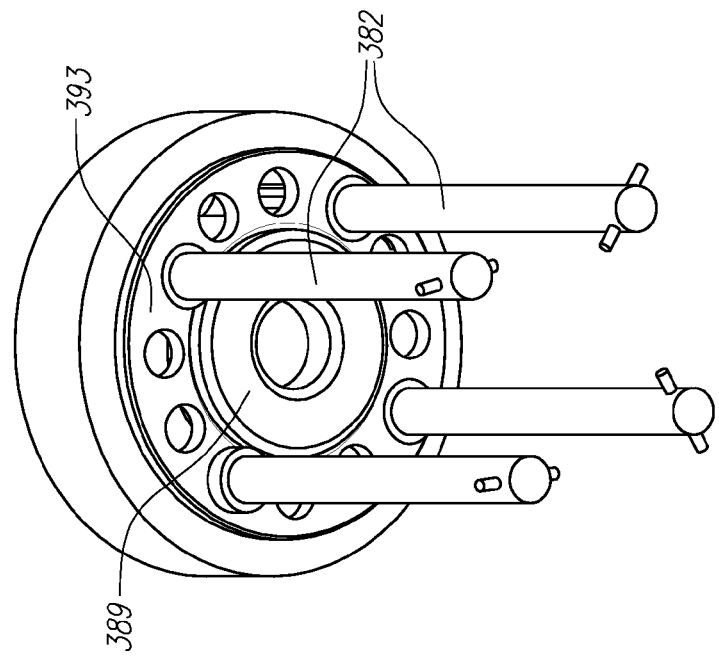
Figure 30E:
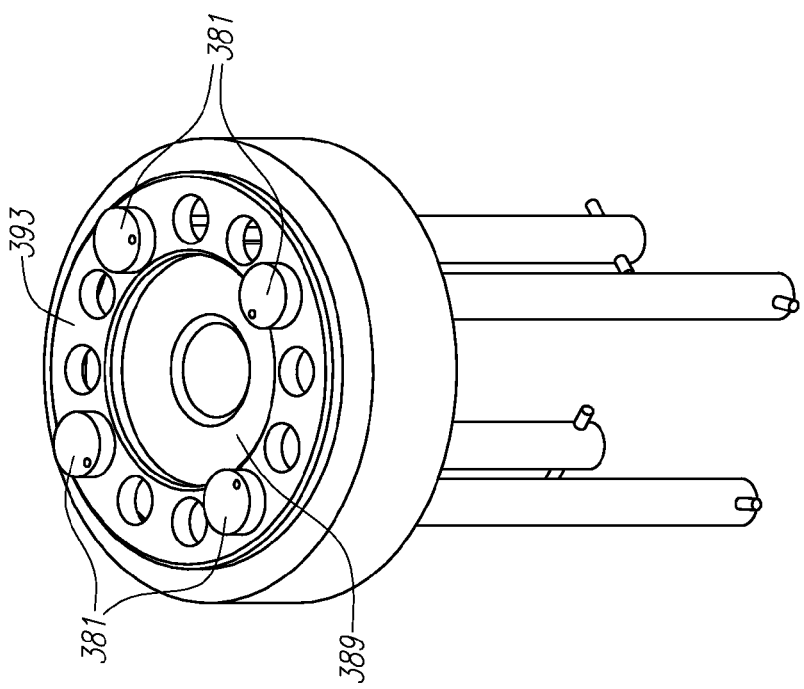
Figures 30G, 30L:
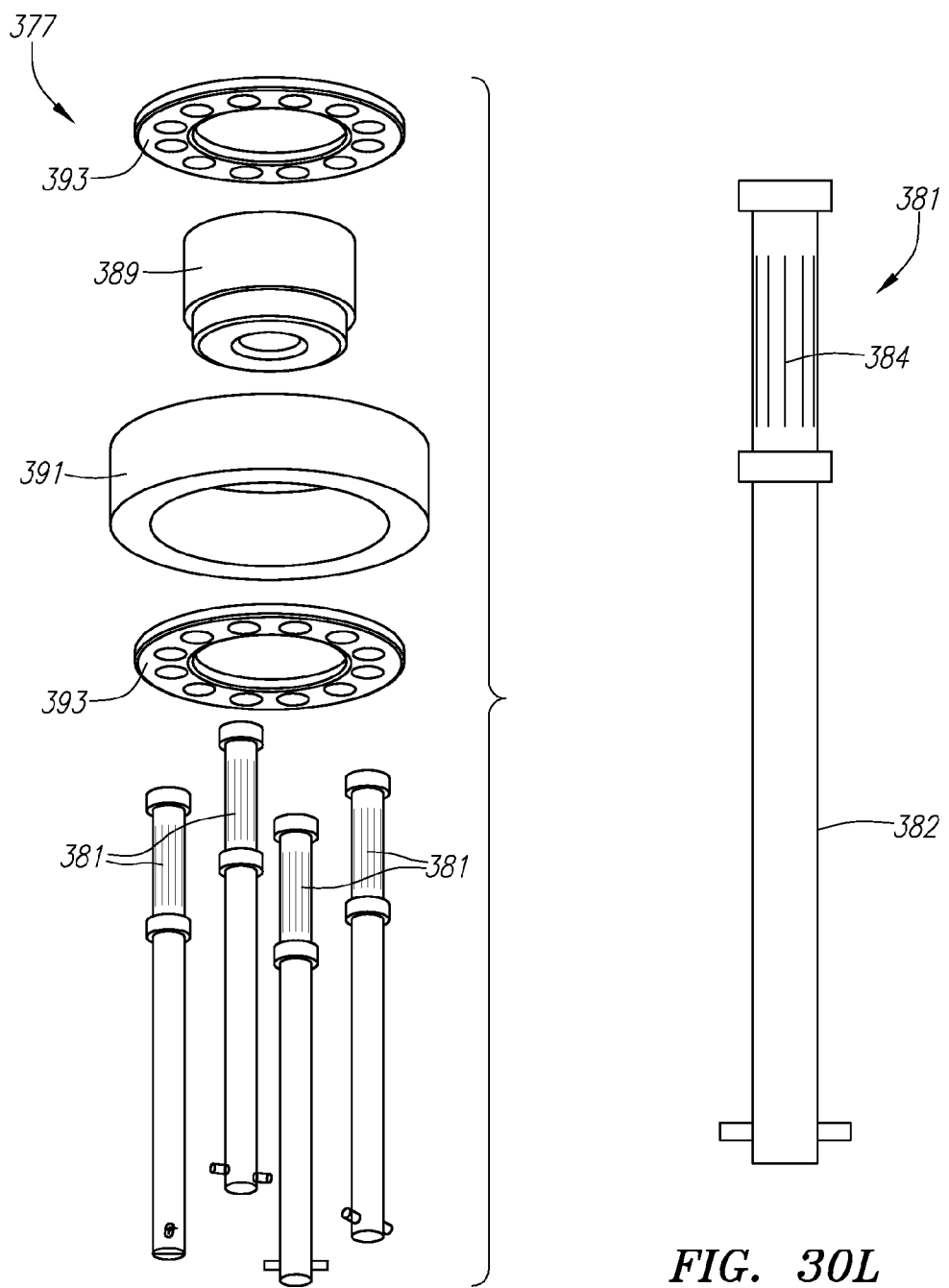
Figure 30H:
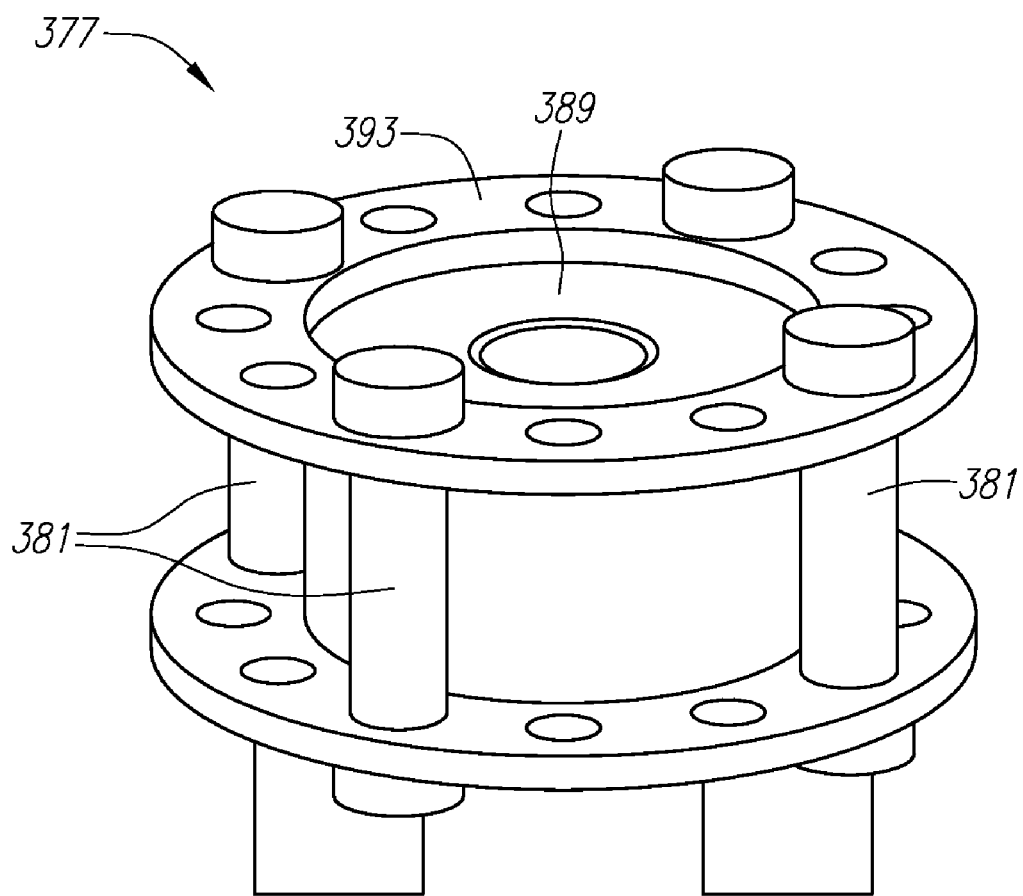
Figure 30I:
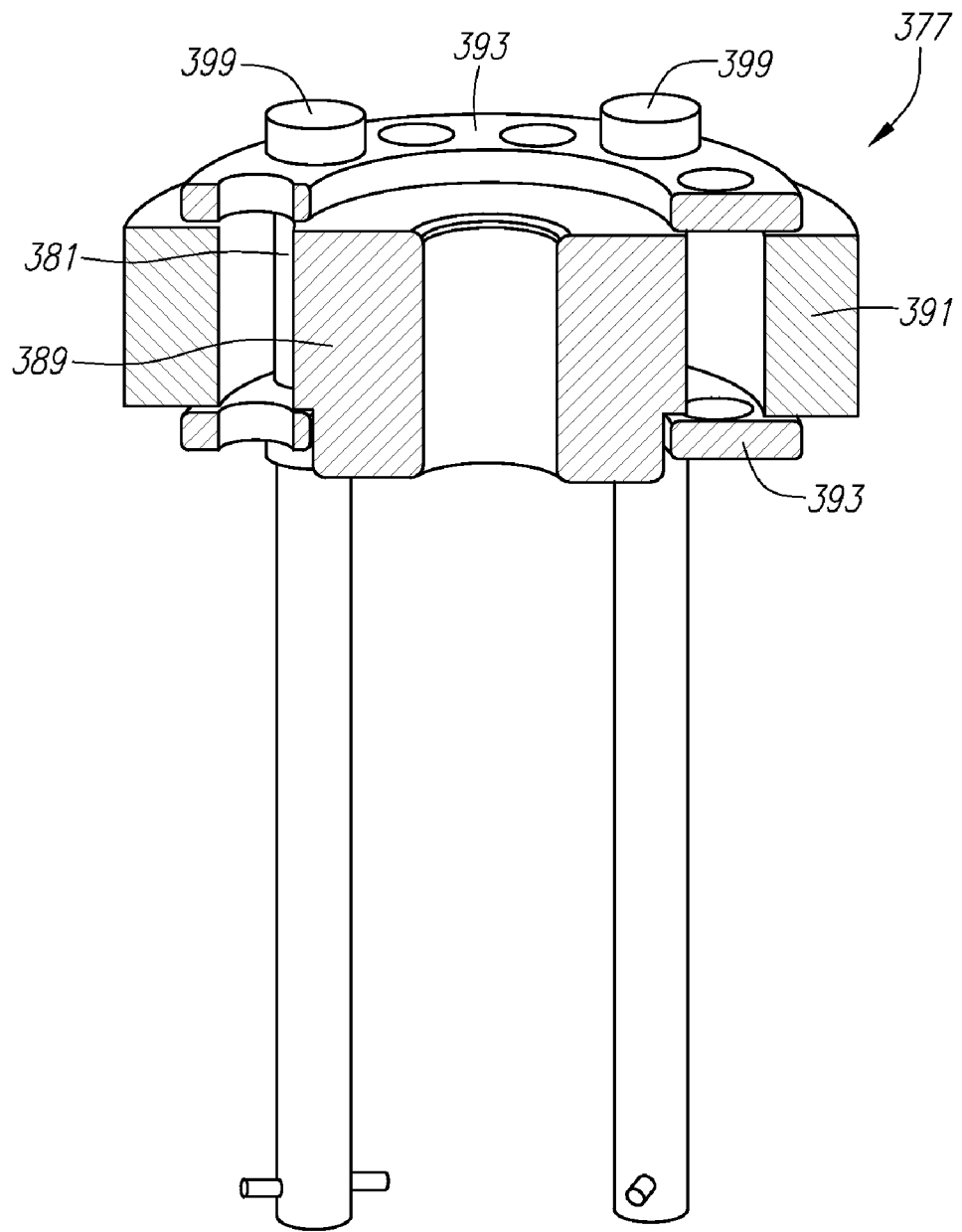
Figure 30J:
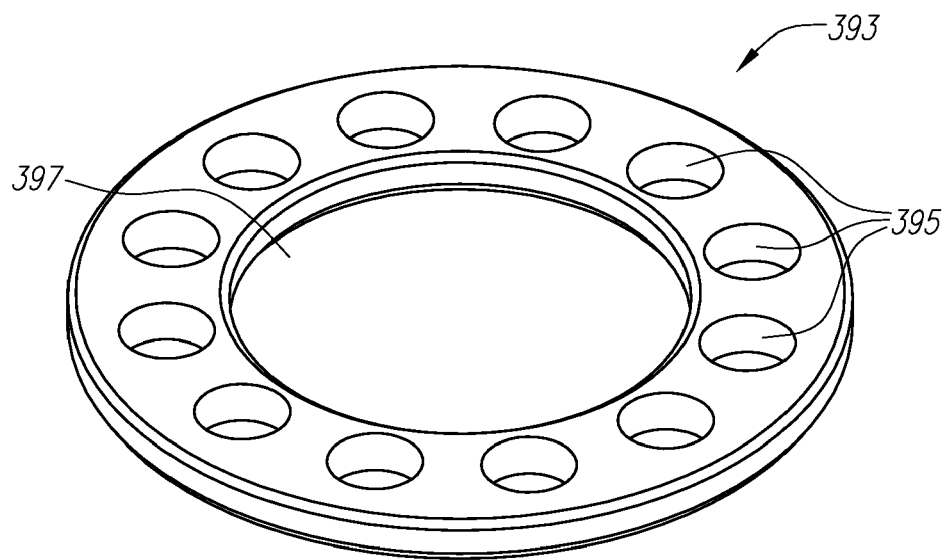
Figure 30K:
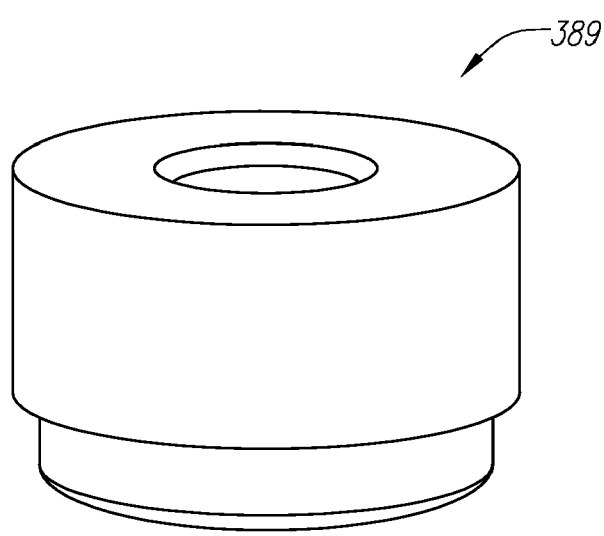
Figure 31A:
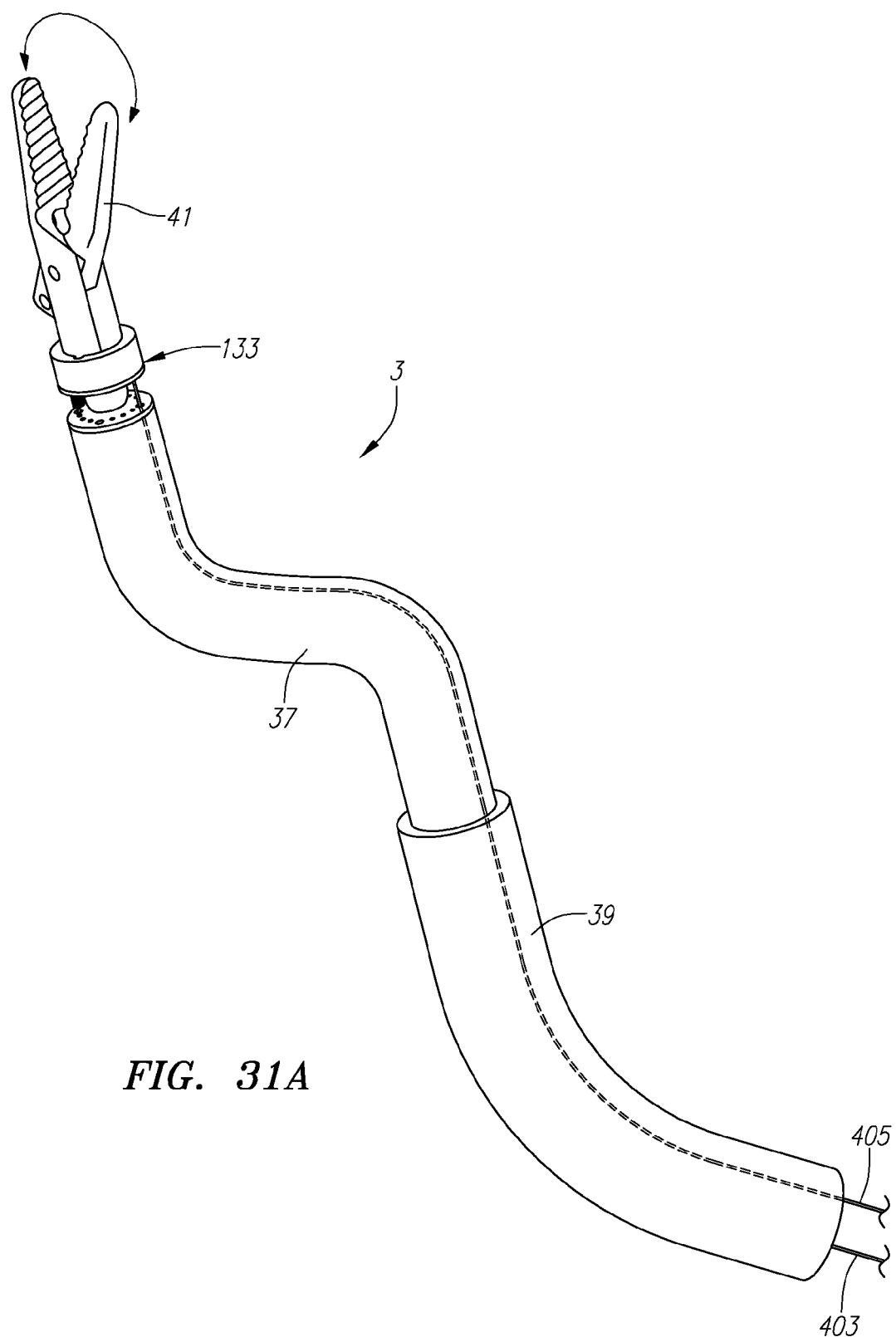
Figures 31B, 31C:
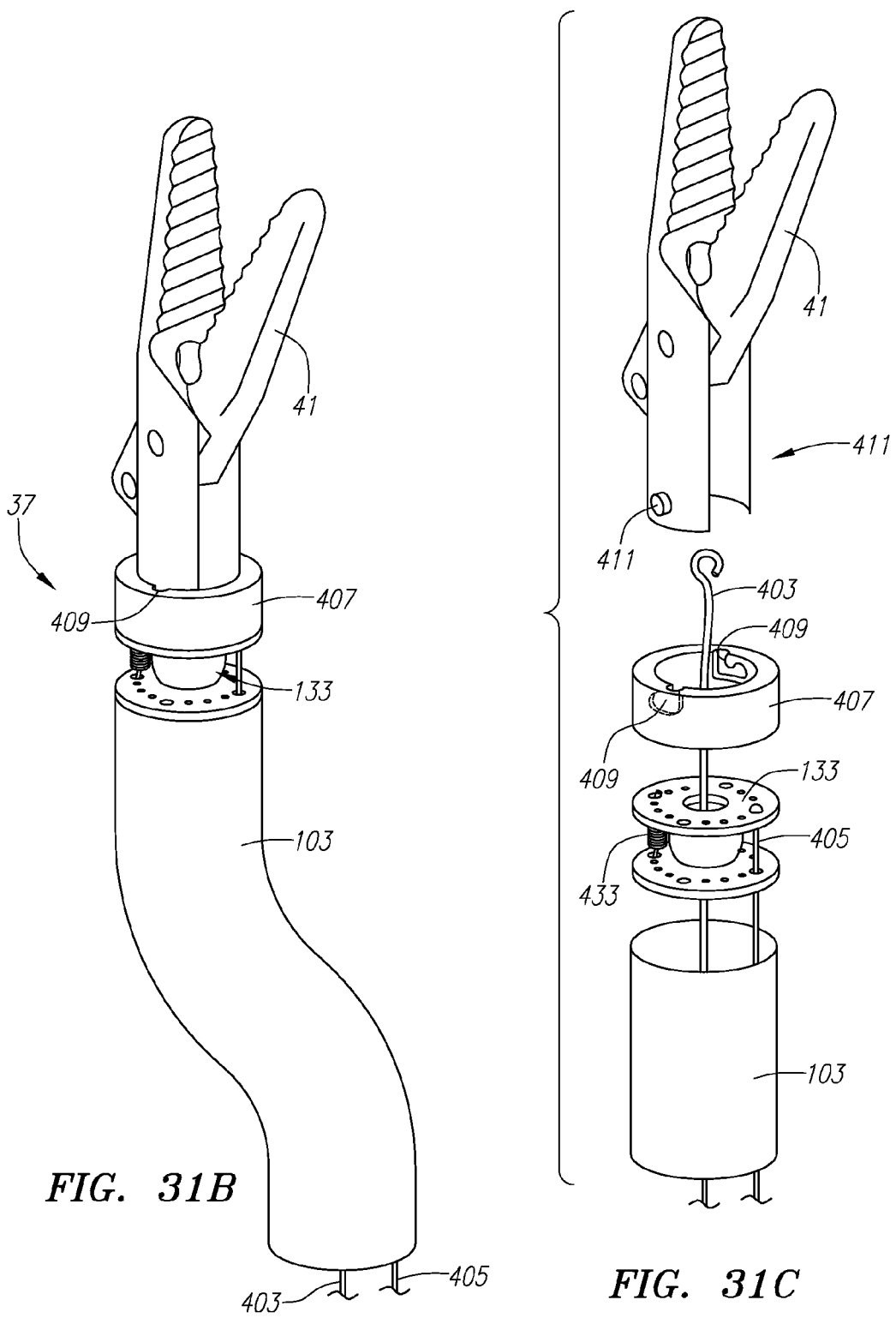
Figures 31D, 31E:
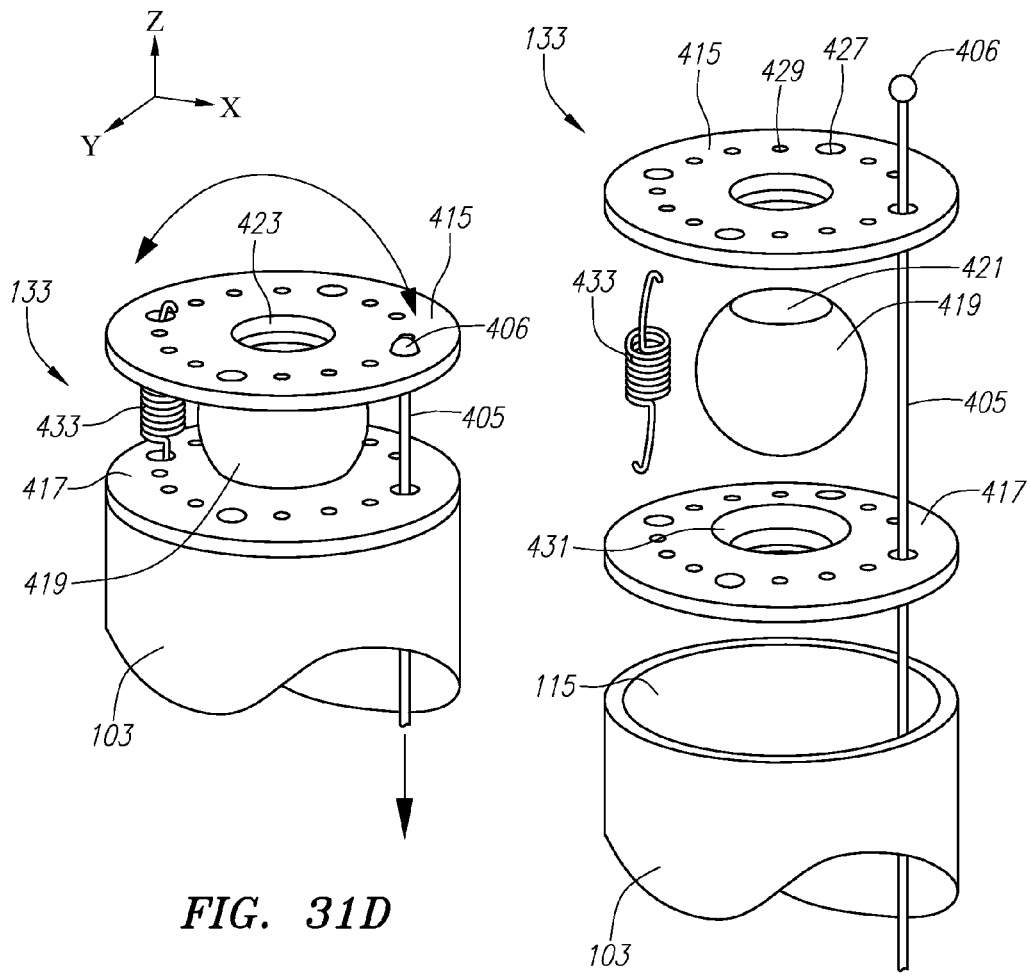
Figure 31F:
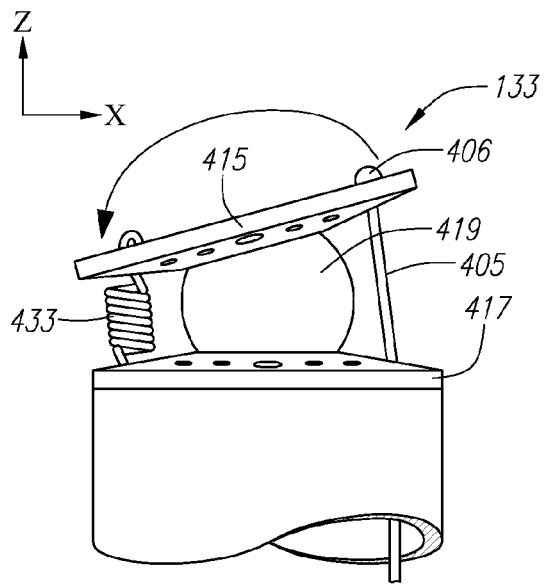
Figure 31G:
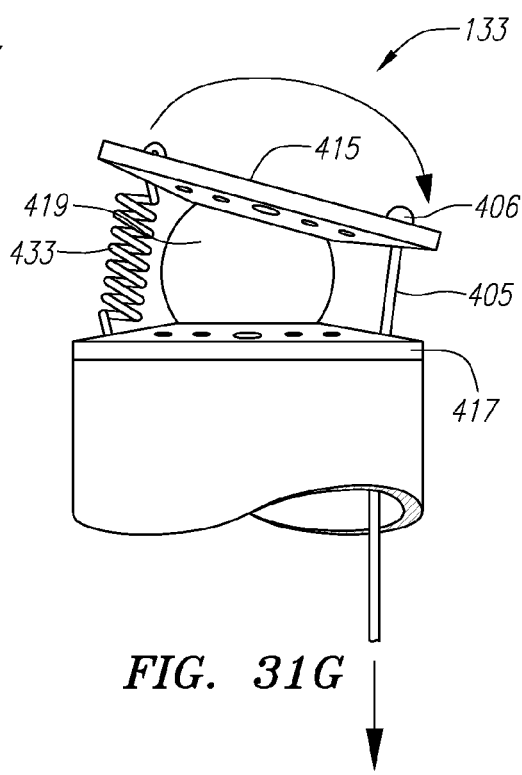
Figure 31H:
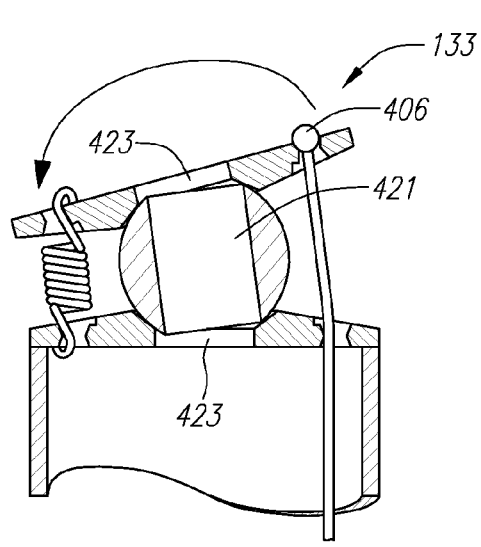
Figure 31I:
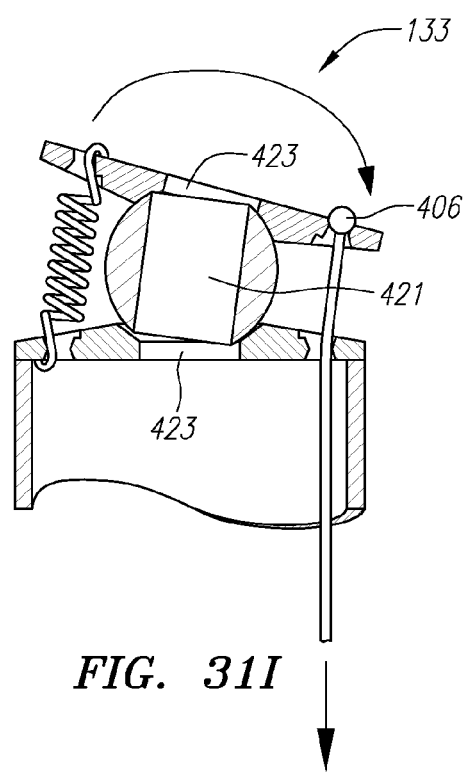
Figure 31J:
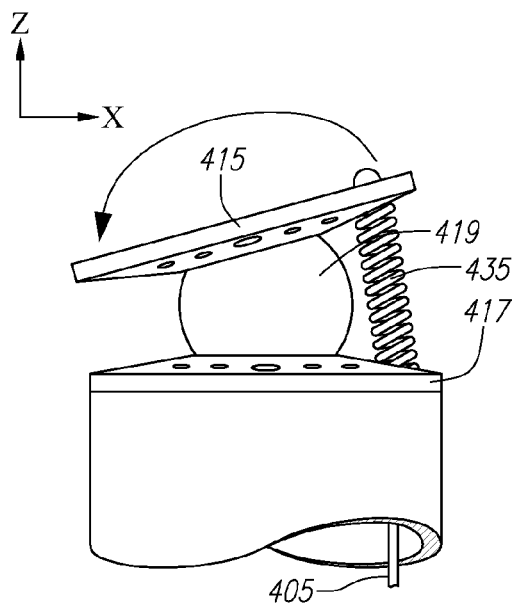
Figure 31K:
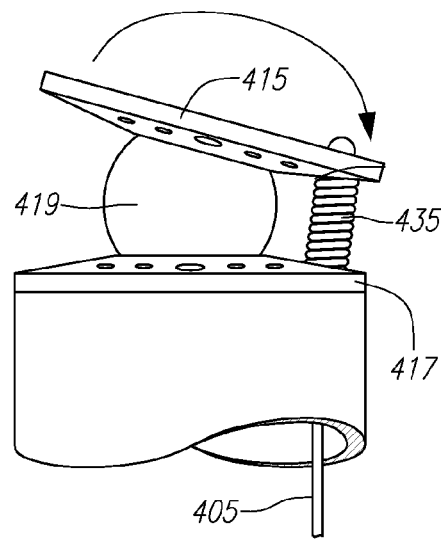
Figure 31L:
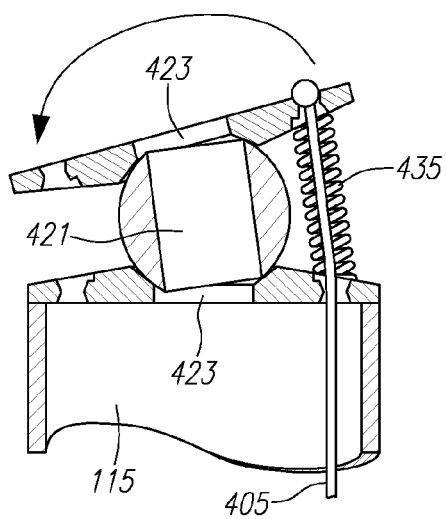
Figure 31M:
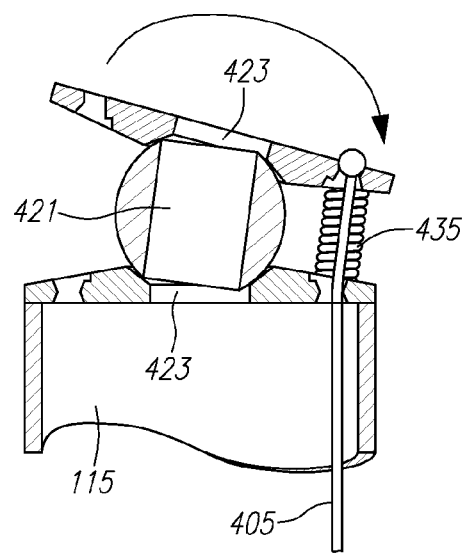
Figure 31N:
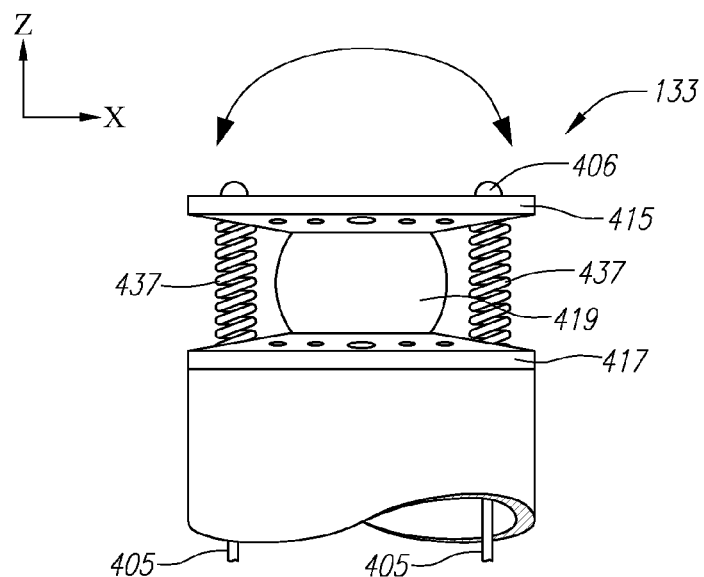
Figure 31O:
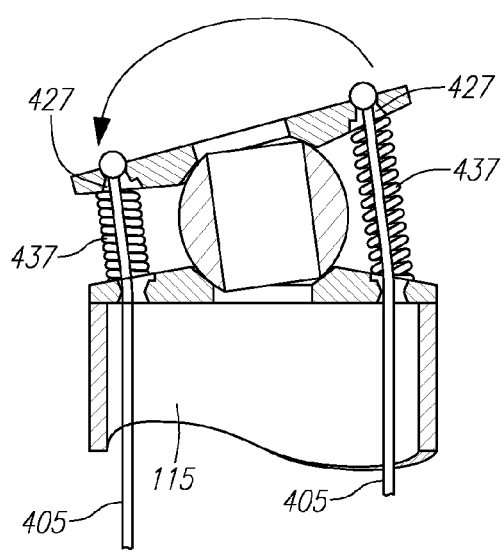
Figure 31P:
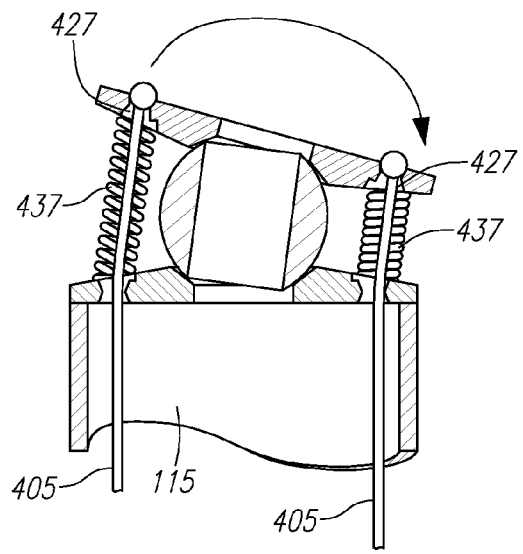
Figure 32A:
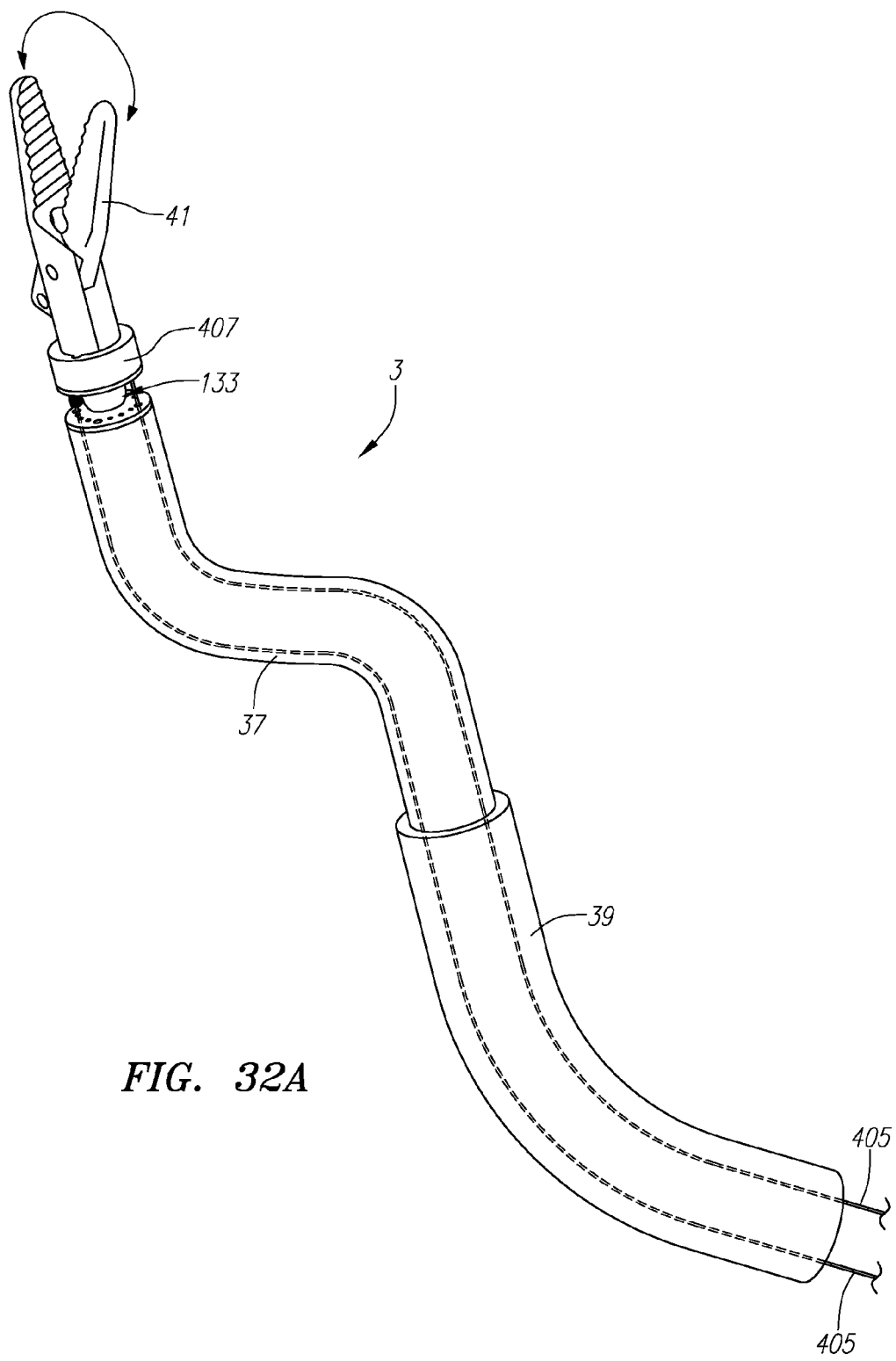
Figure 32B:
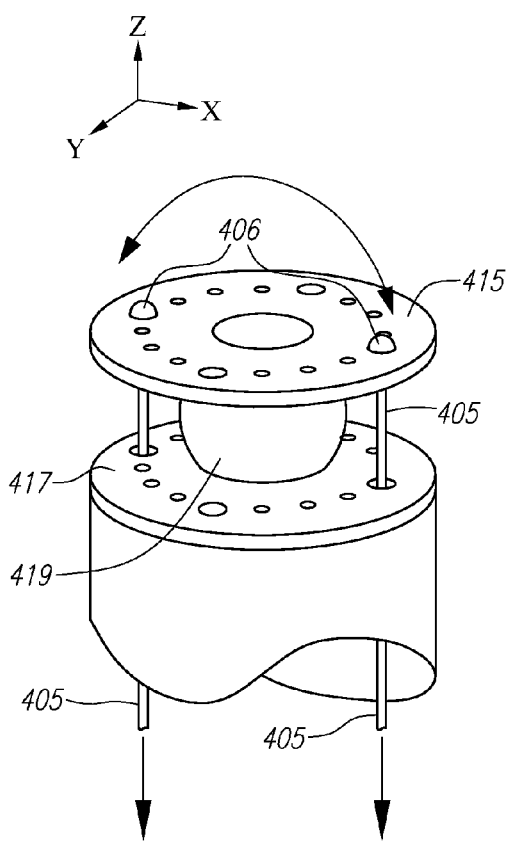
Figure 32C:
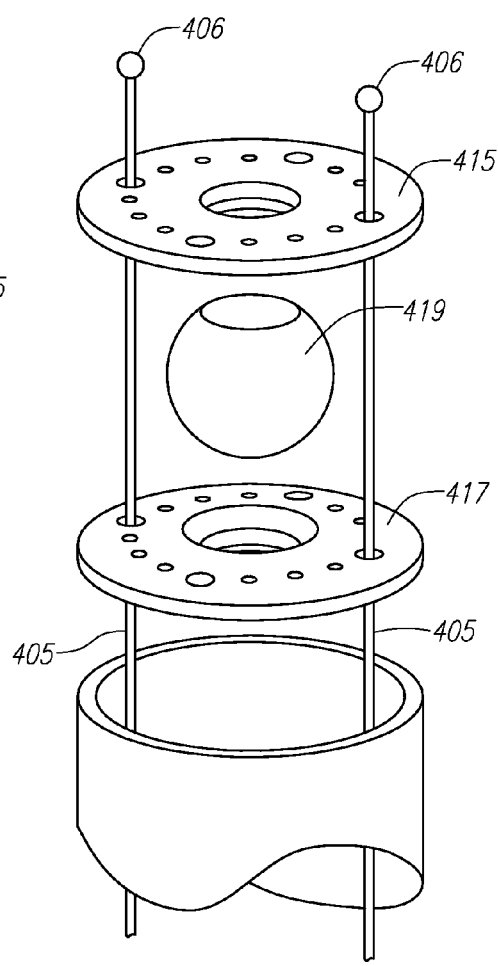
Figure 33A:
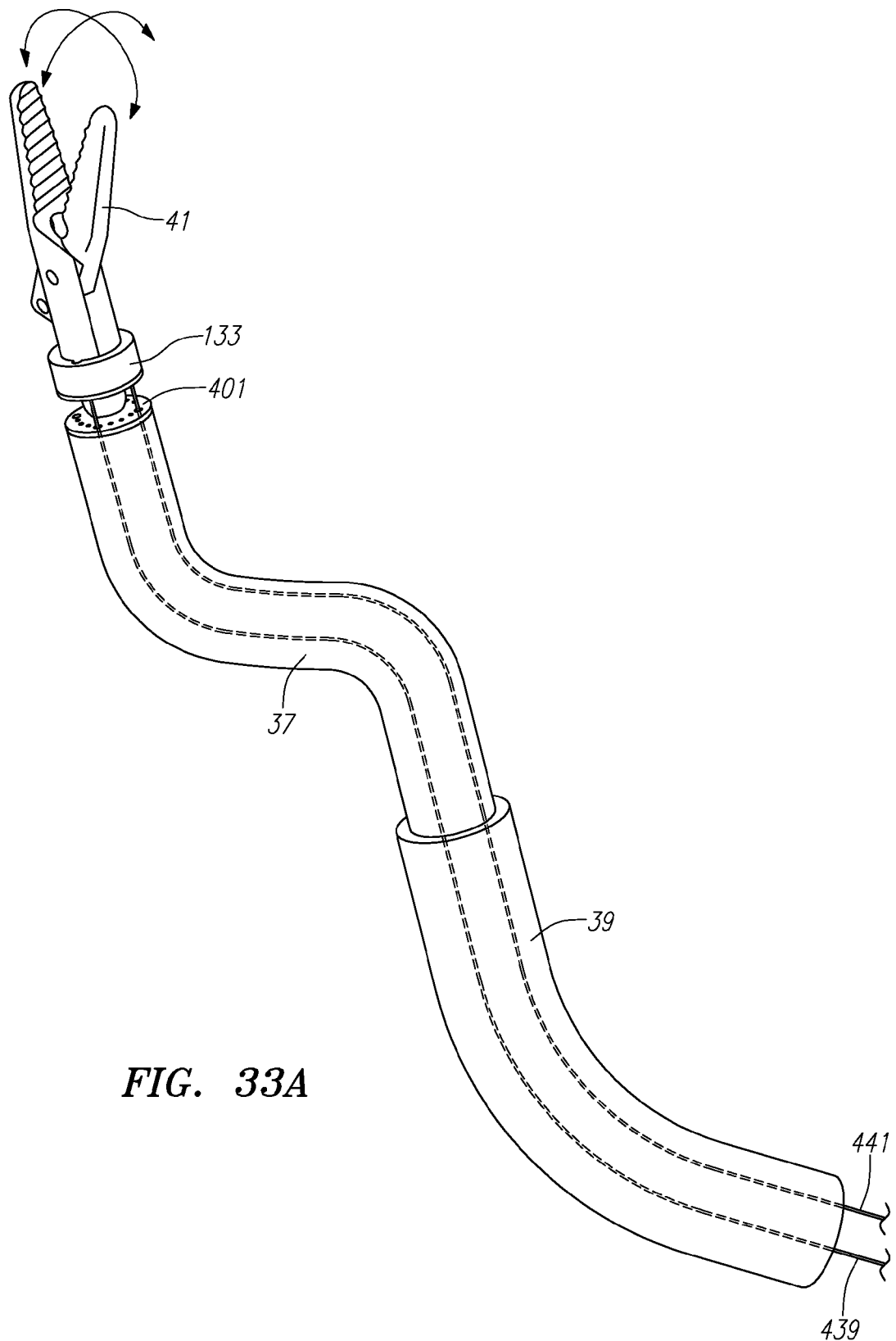
Figure 33B:
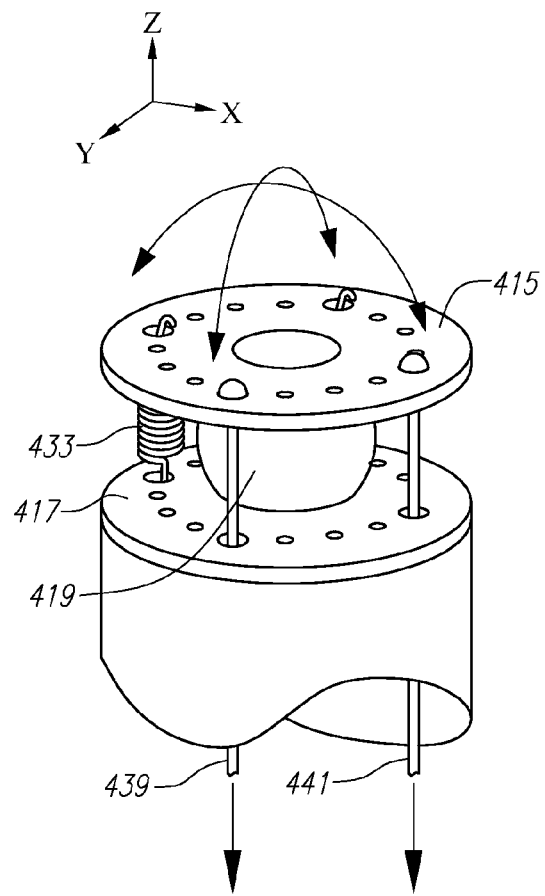
Figure 33C:
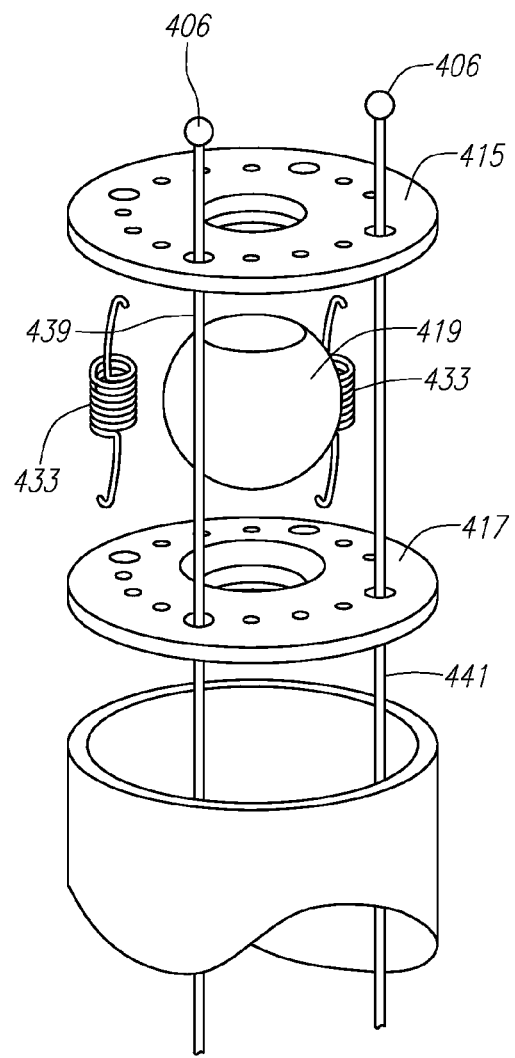
Figure 34A:
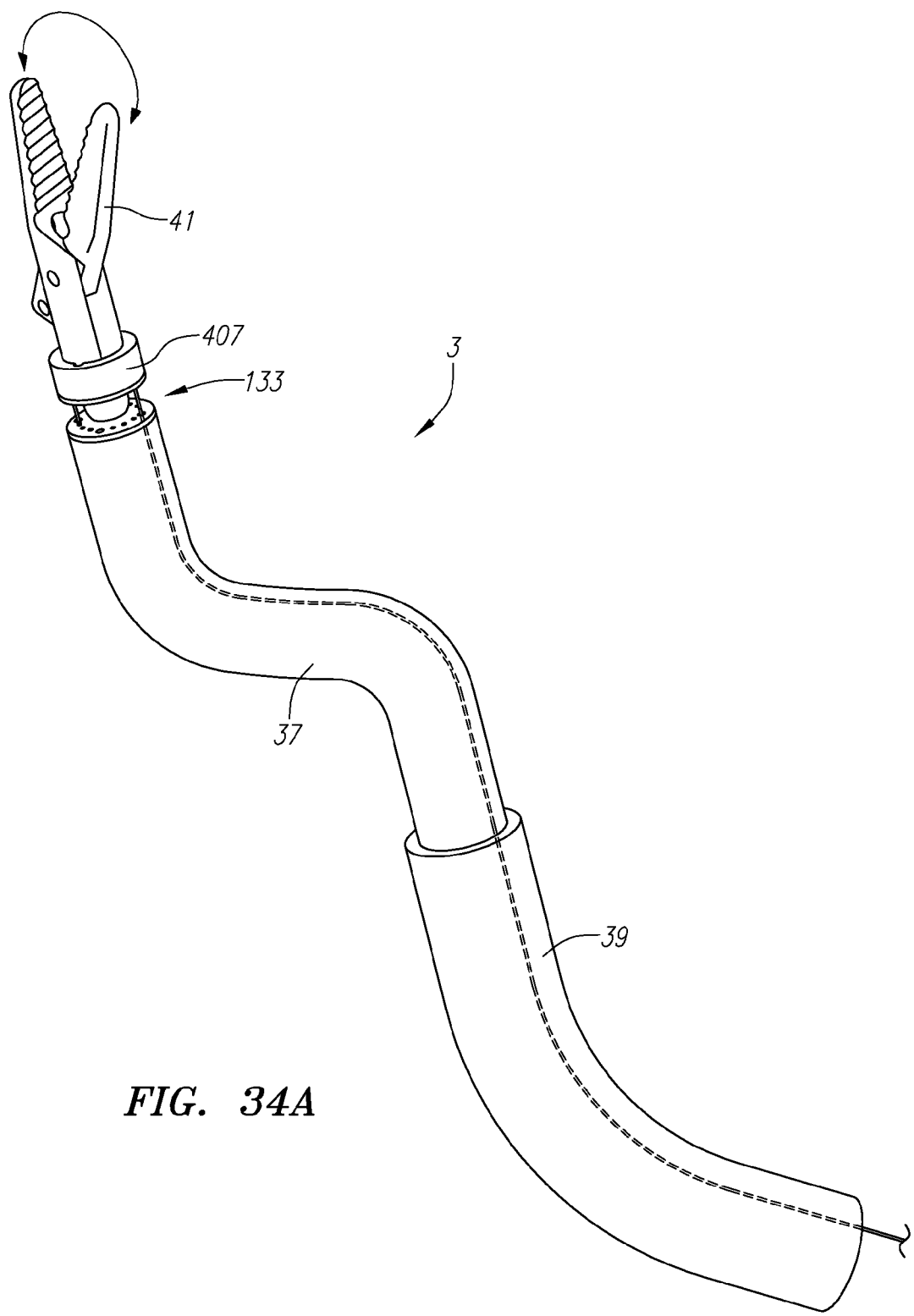
Figure 35A:
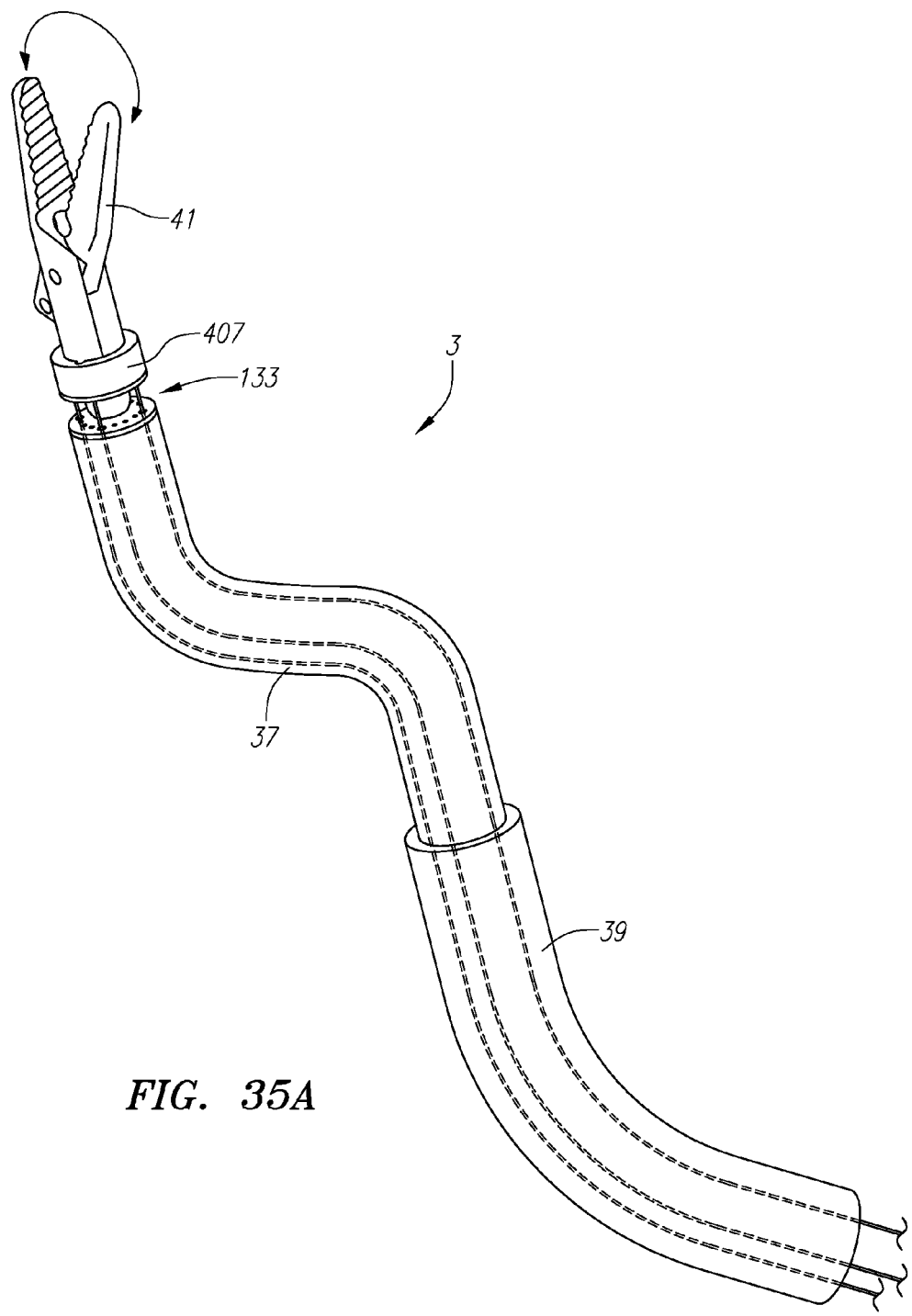
Figure 35B:
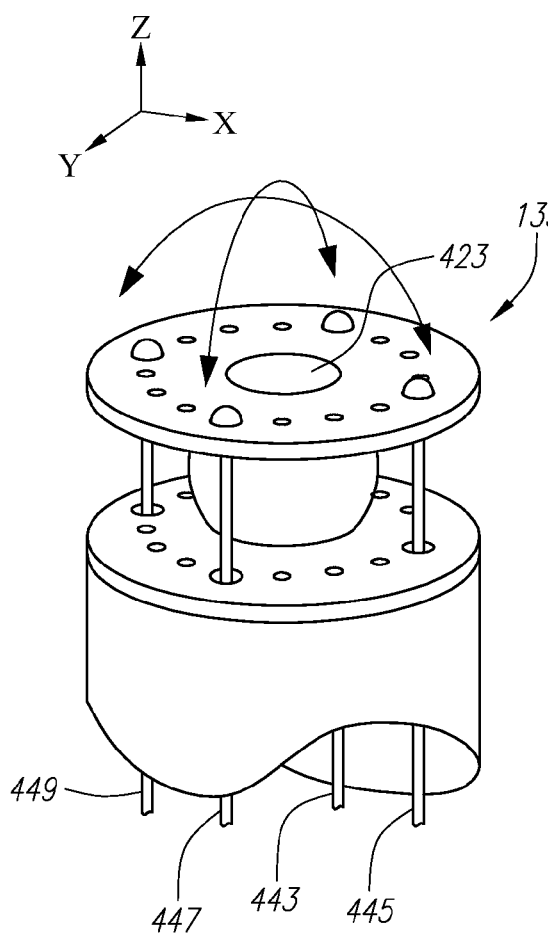
Figure 35C:
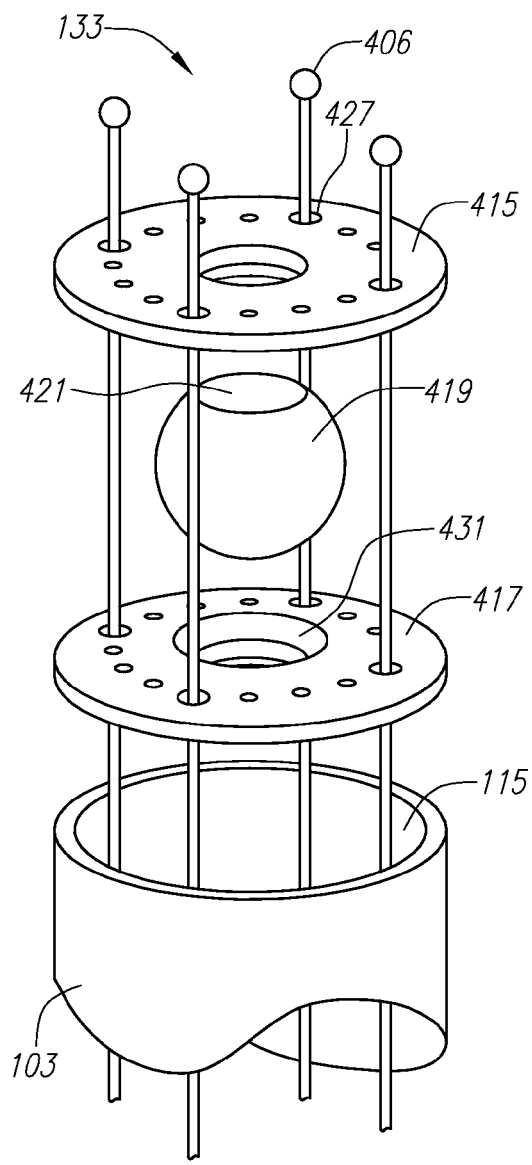
Figure 36A:
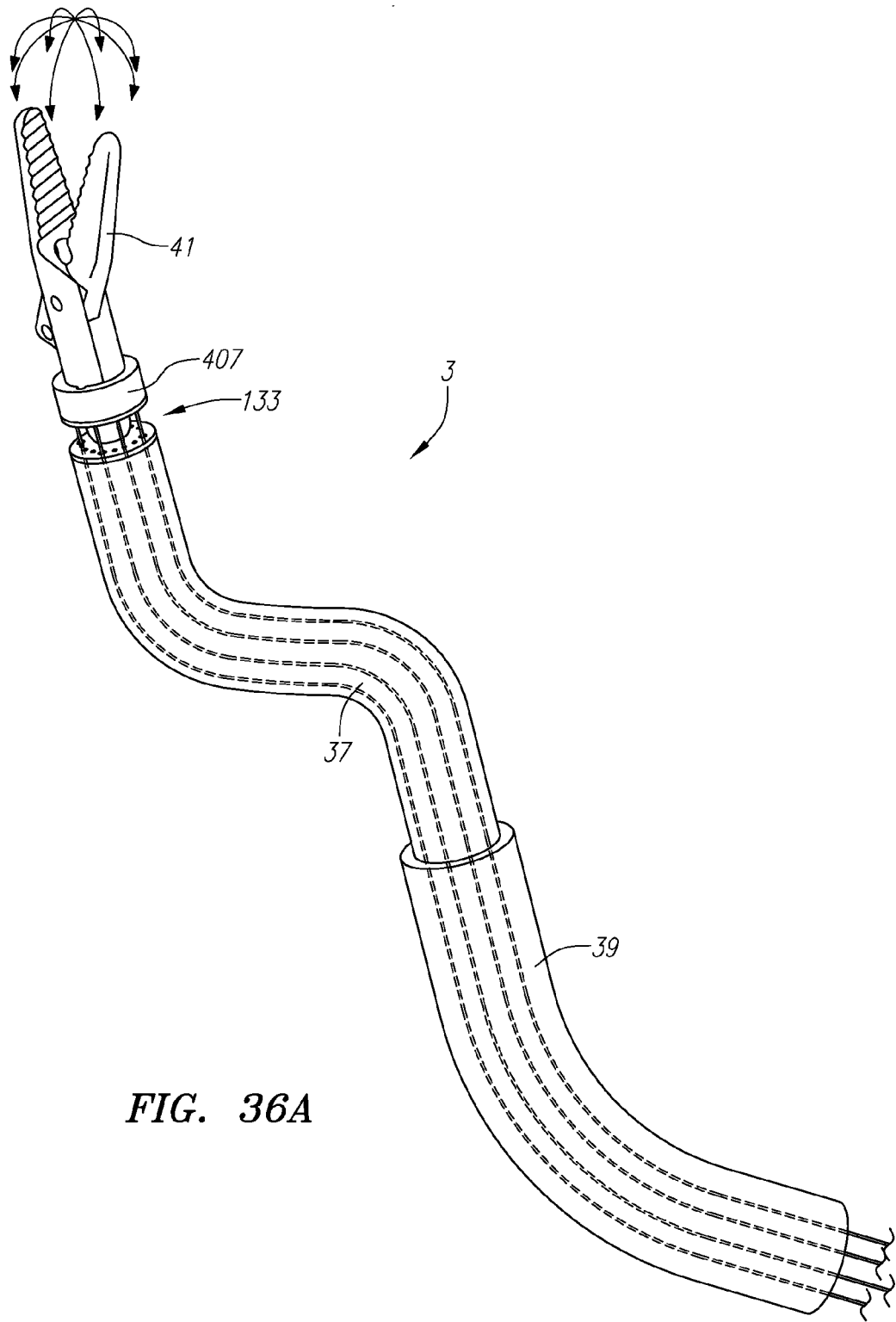
Figure 36B:
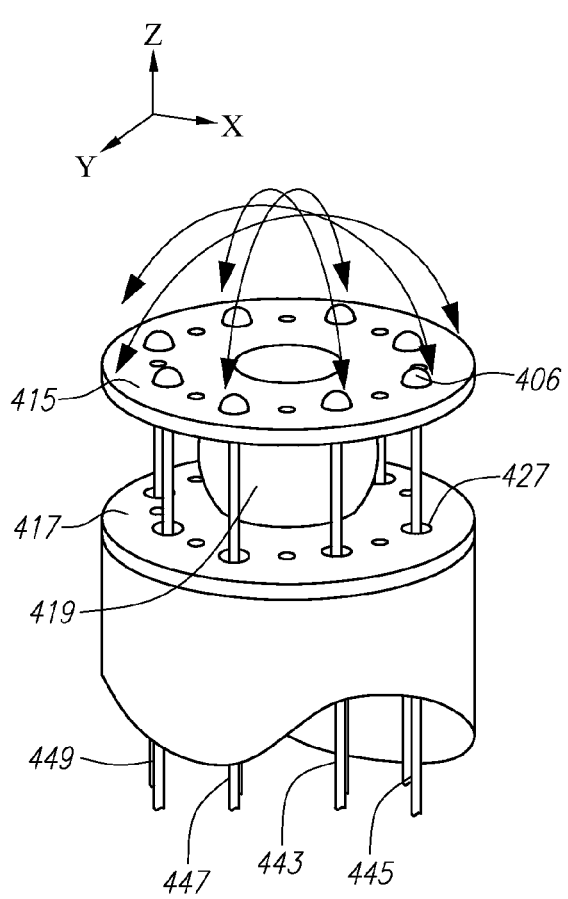
Figure 36C:
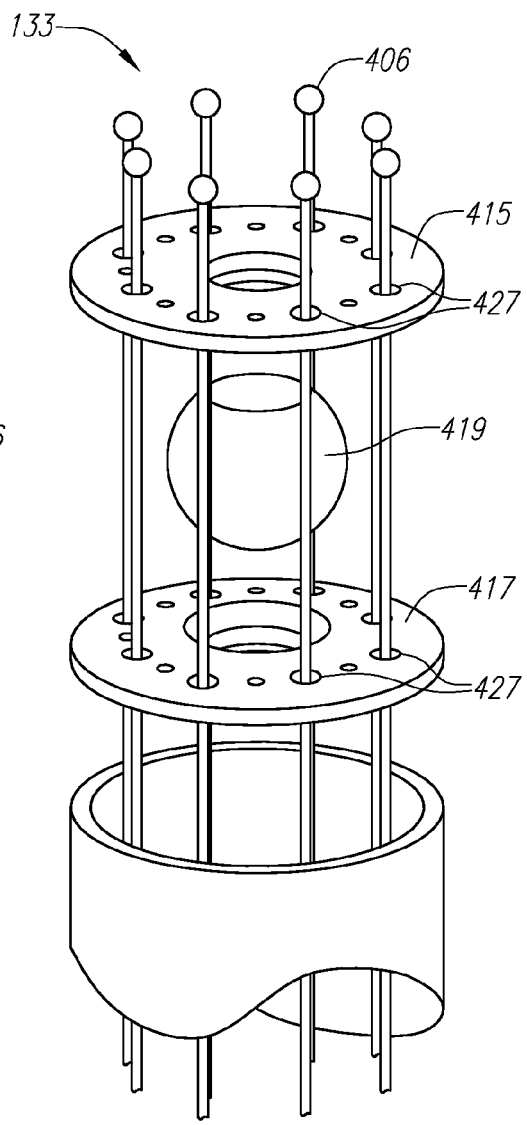
Figures 37A, 37B:
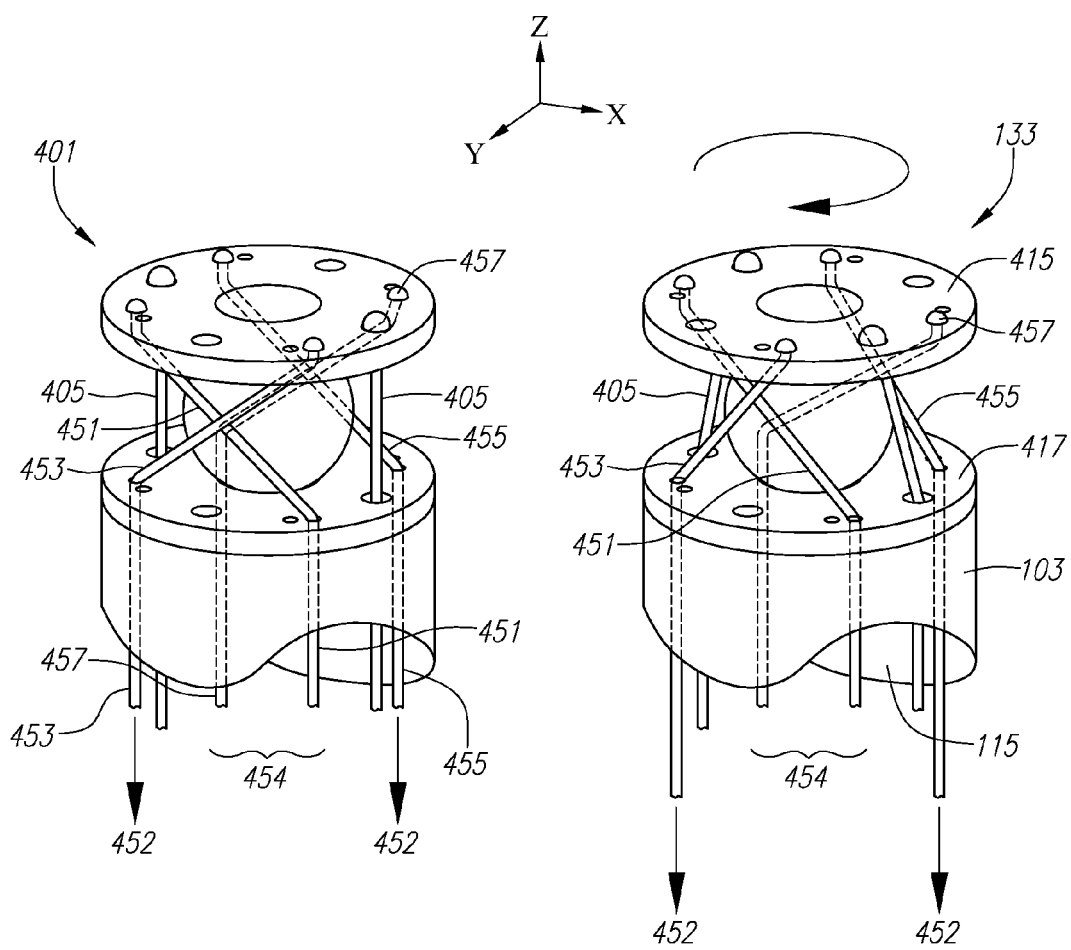
Figures 37C, 37D:
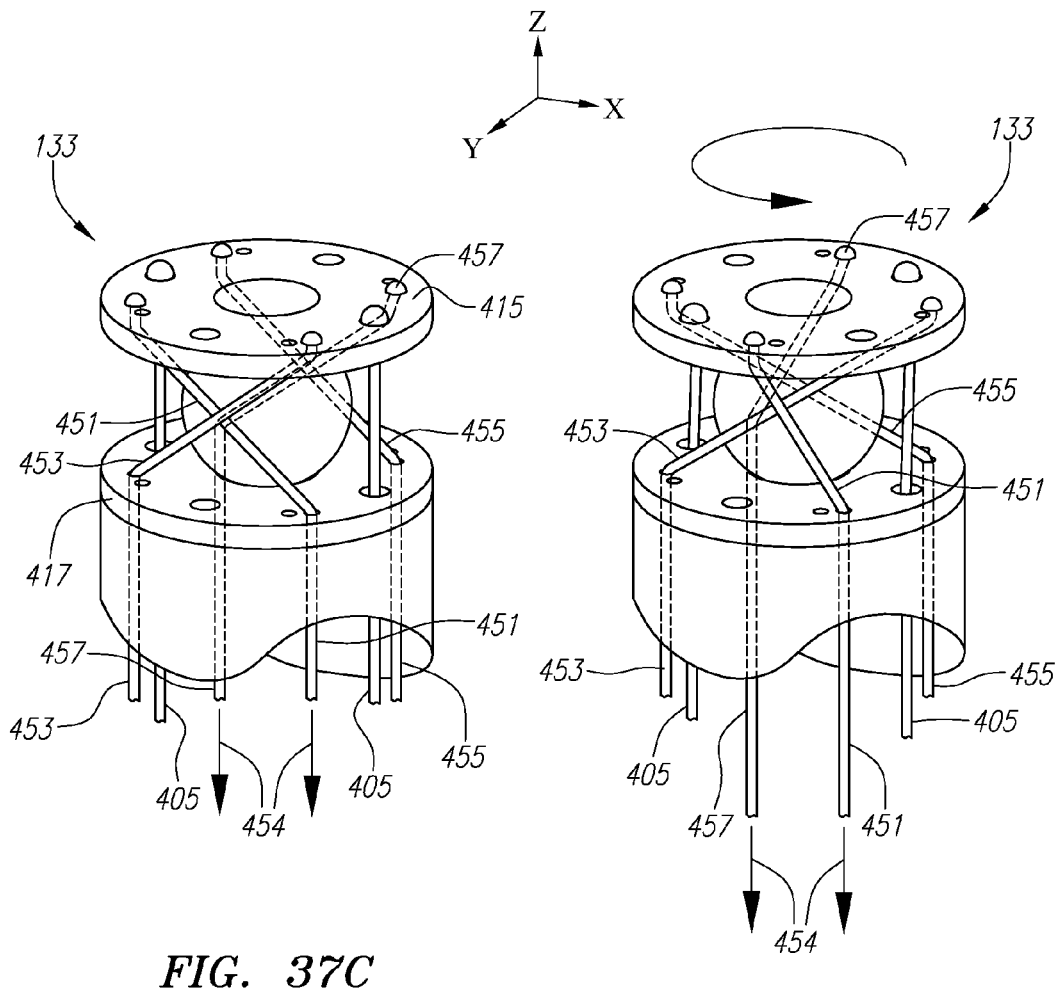
Figure 37E:
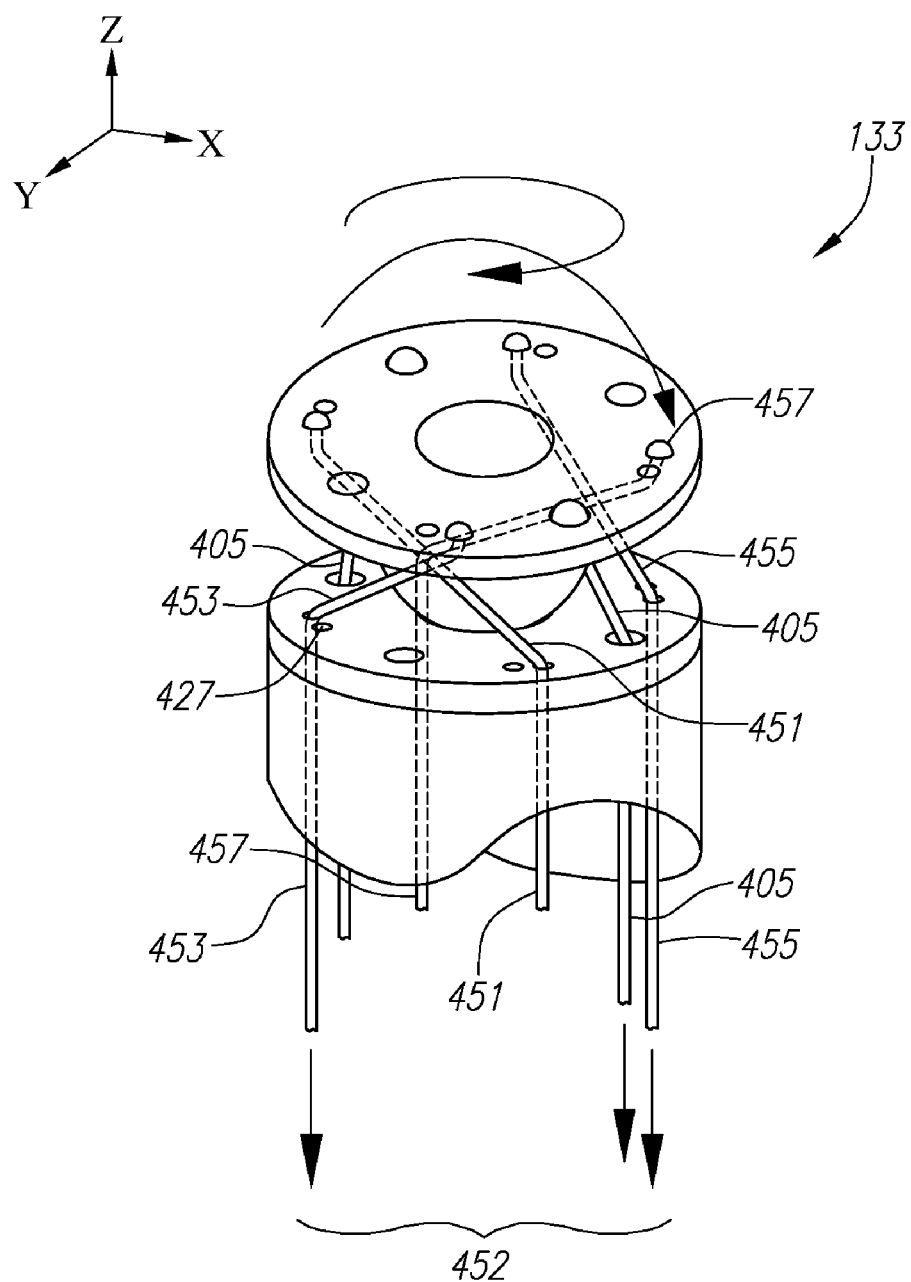
Figures 38A, 38B:
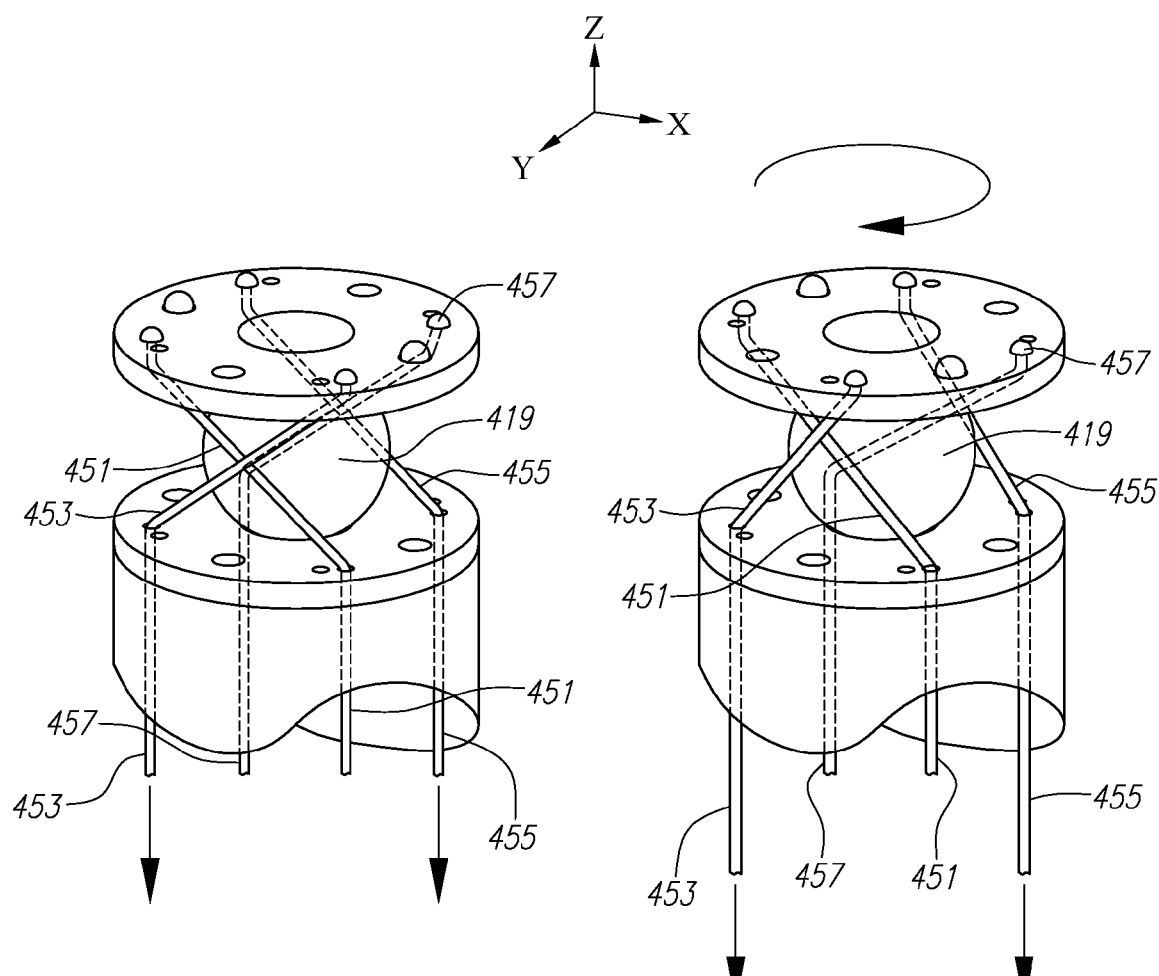
Figure 38C:
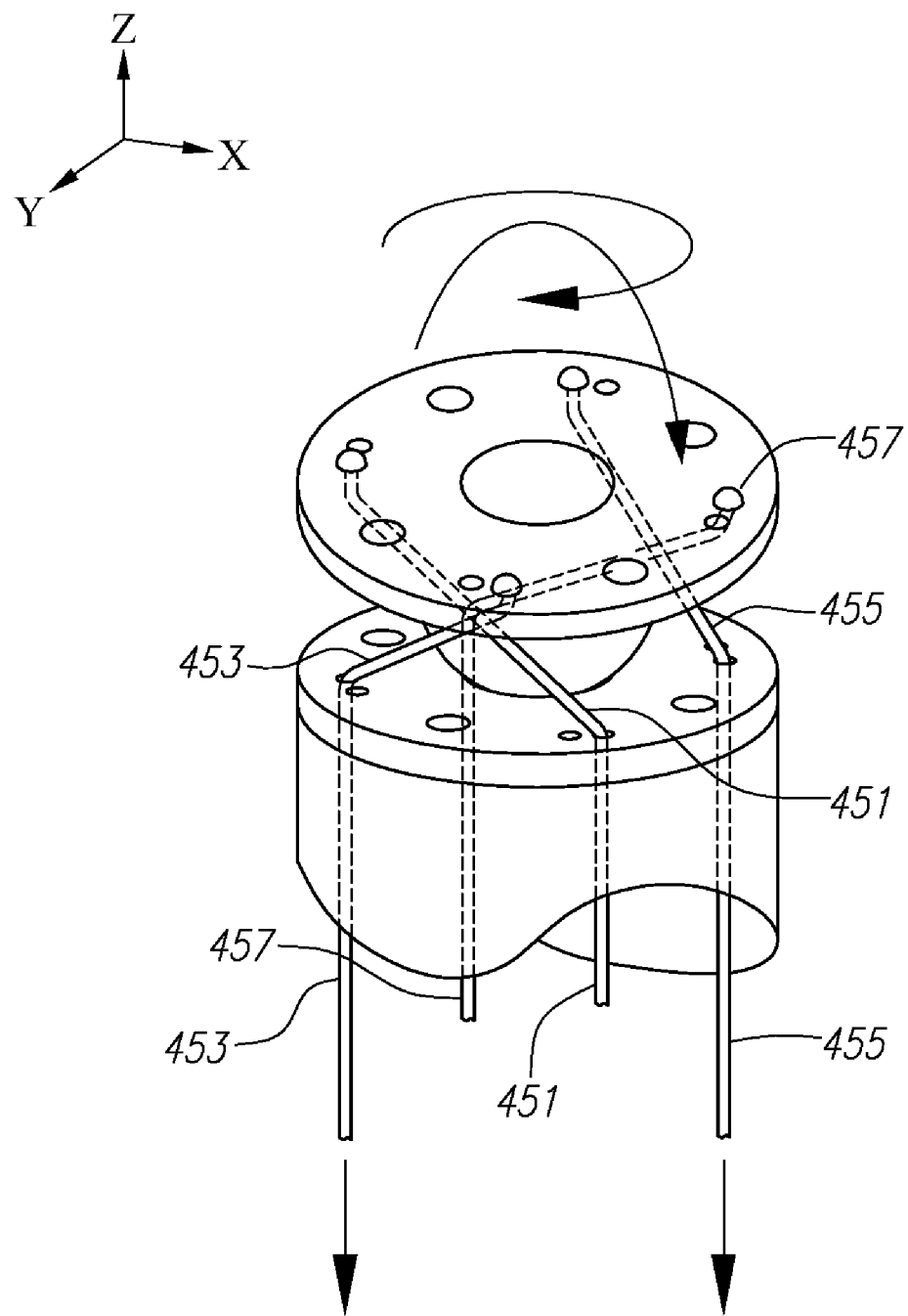
Figure 39A:
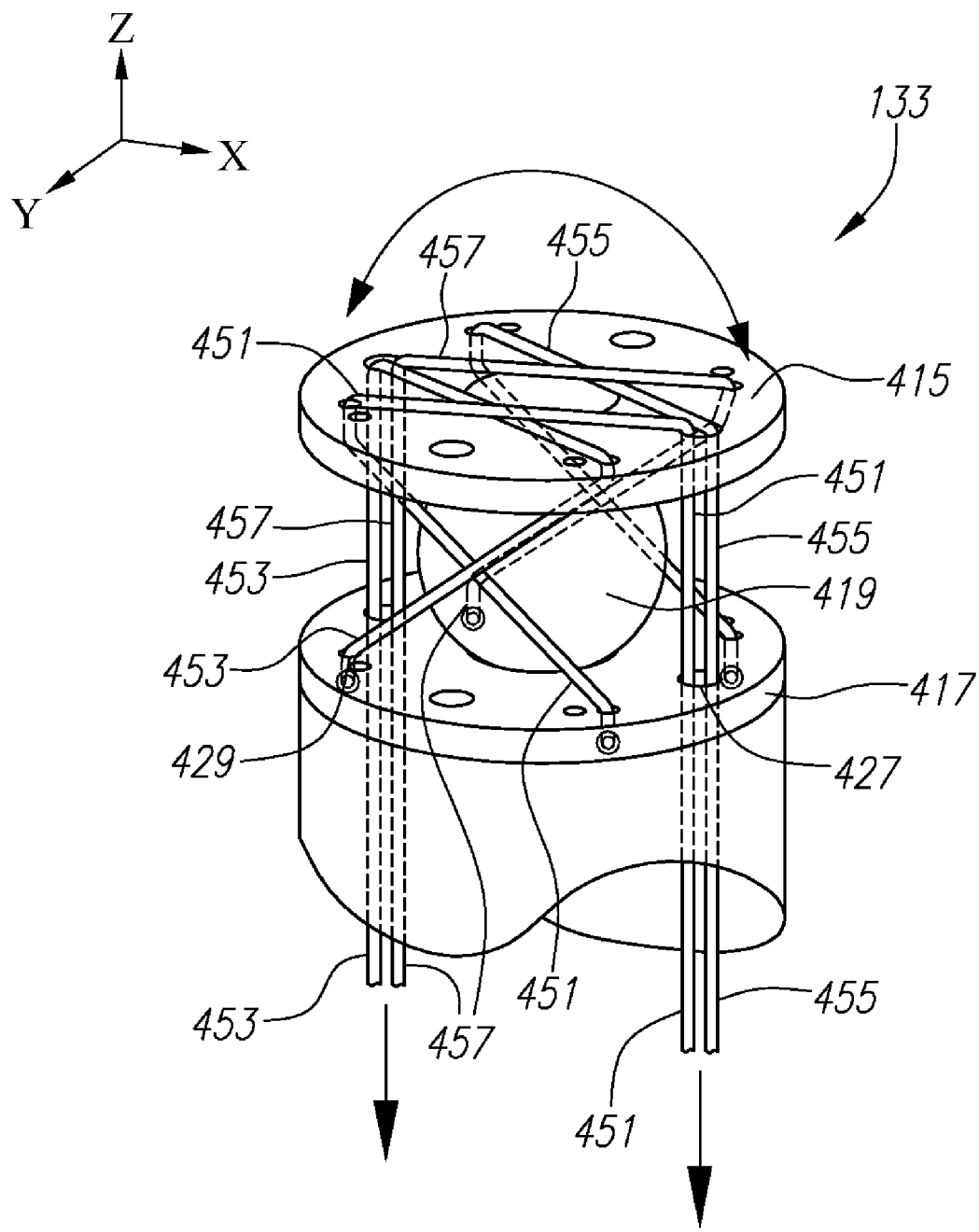
Figure 39B:
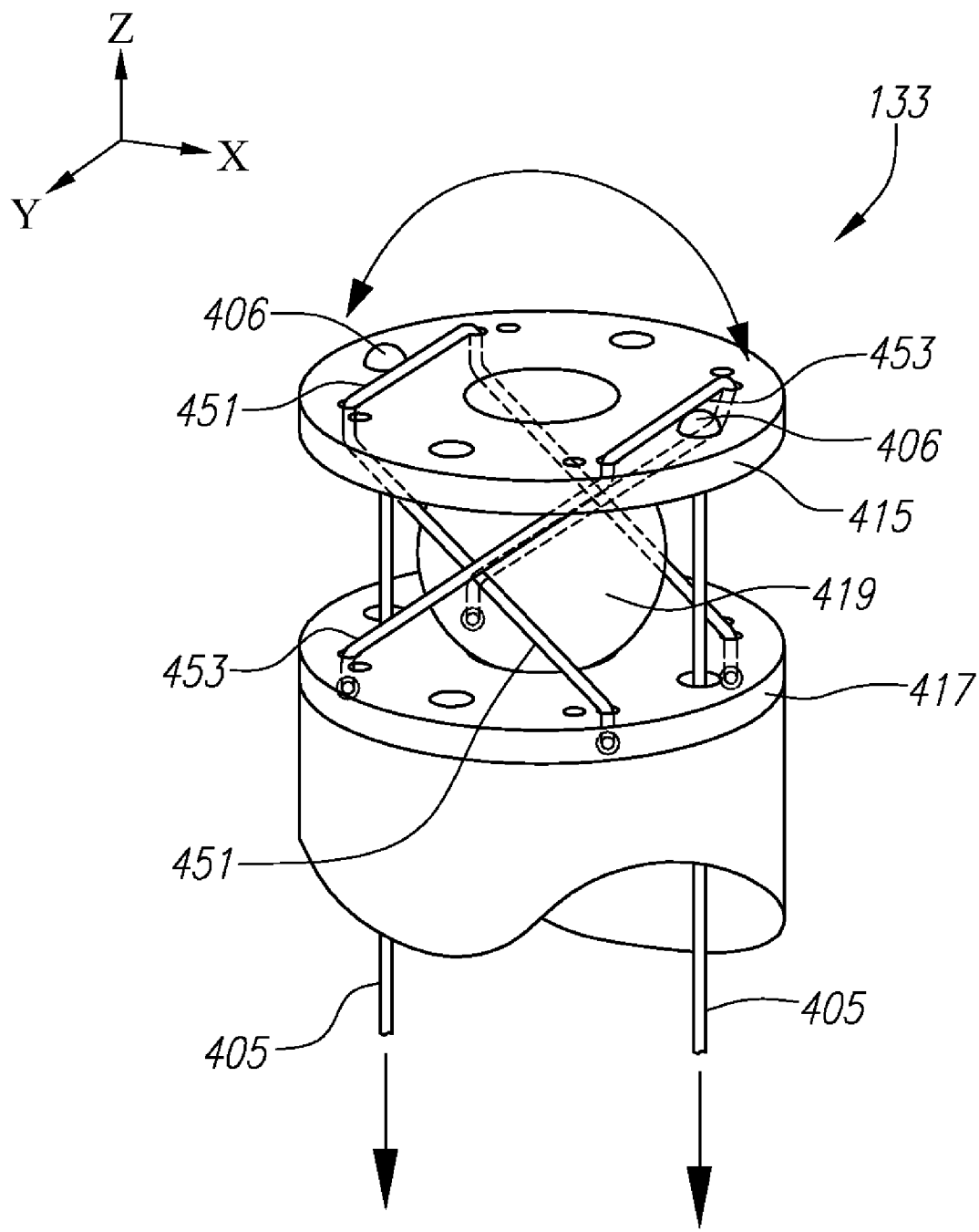
Figures 40A, 40B:
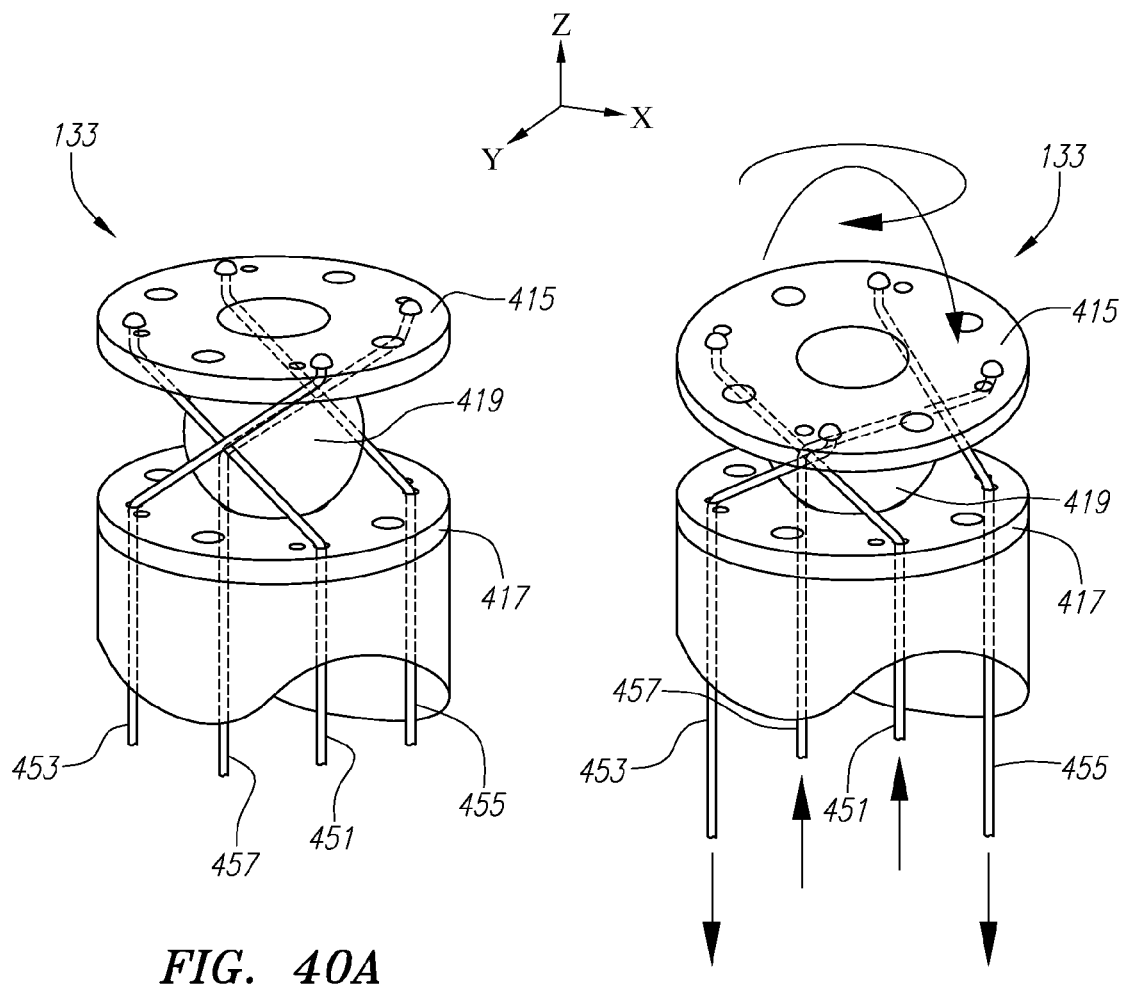
Figures 41A, 41B:
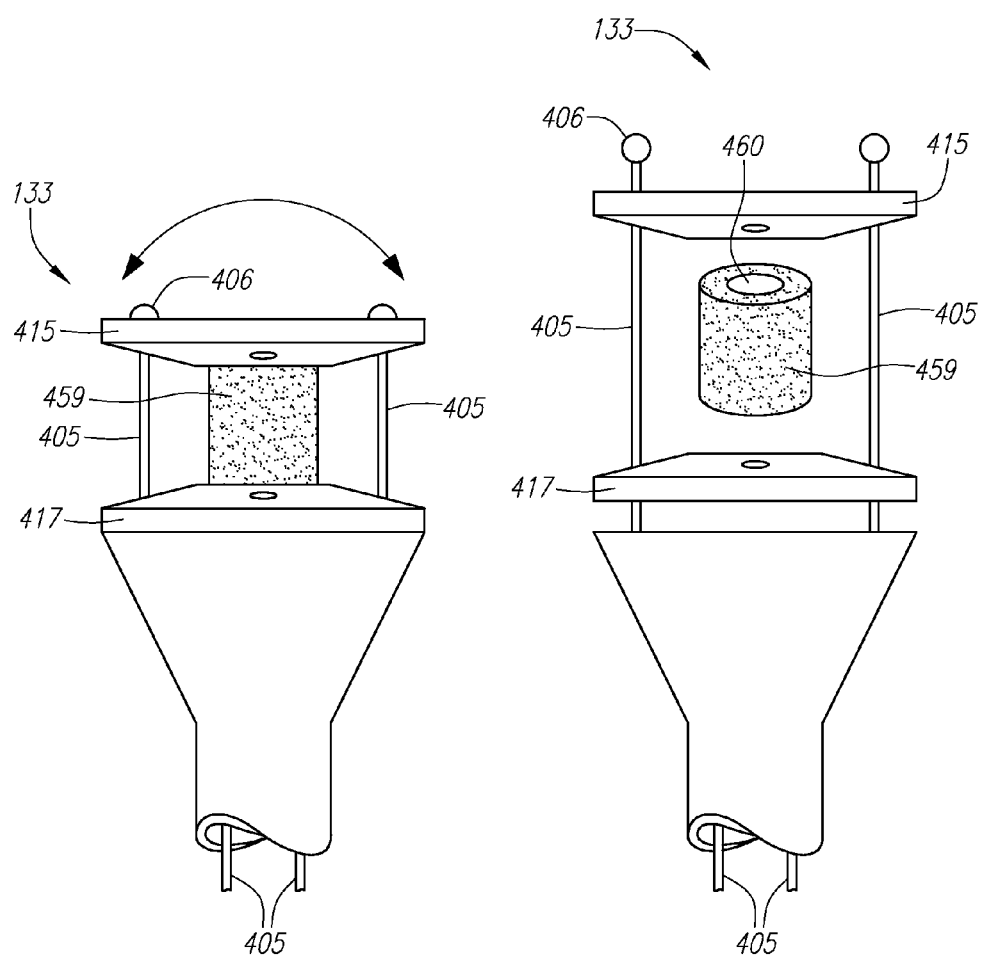
Figures 42A, 42B:
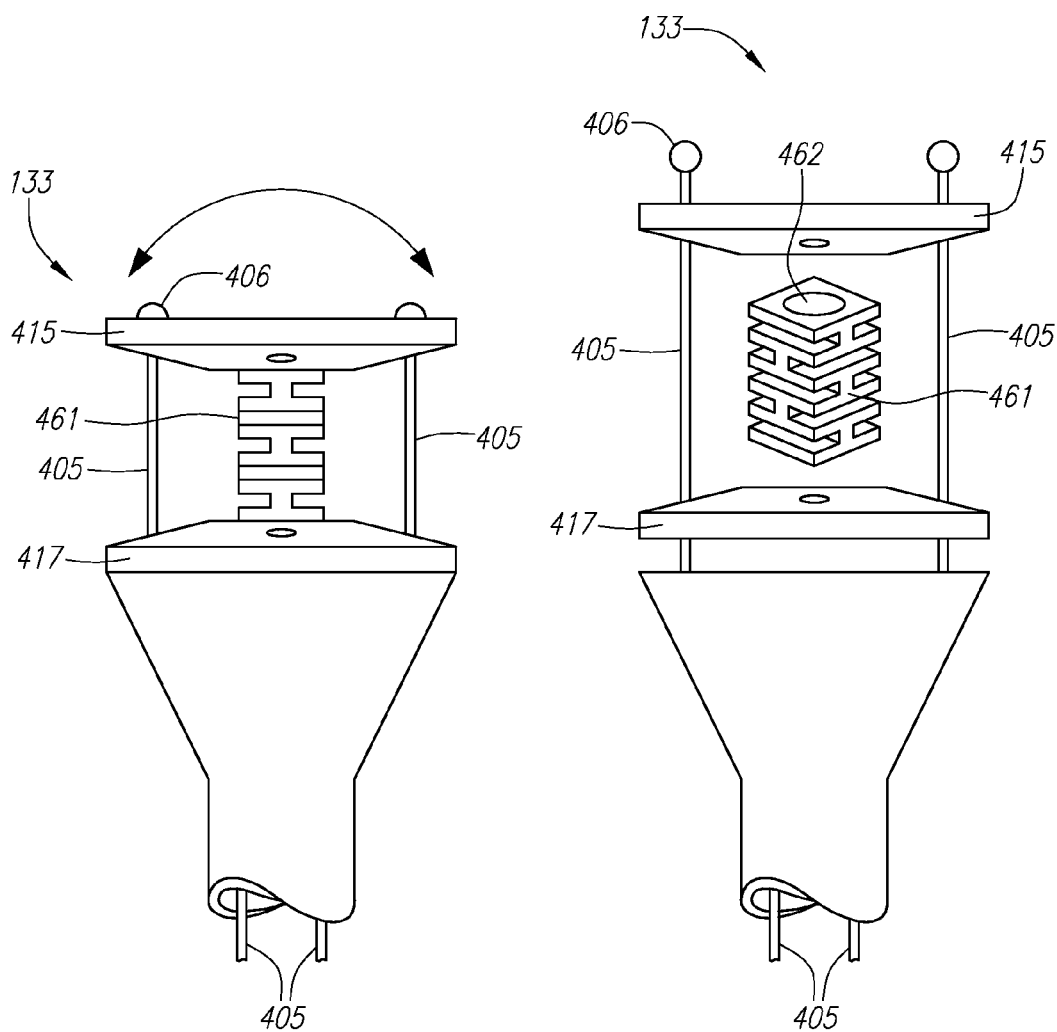
Figure 43A:
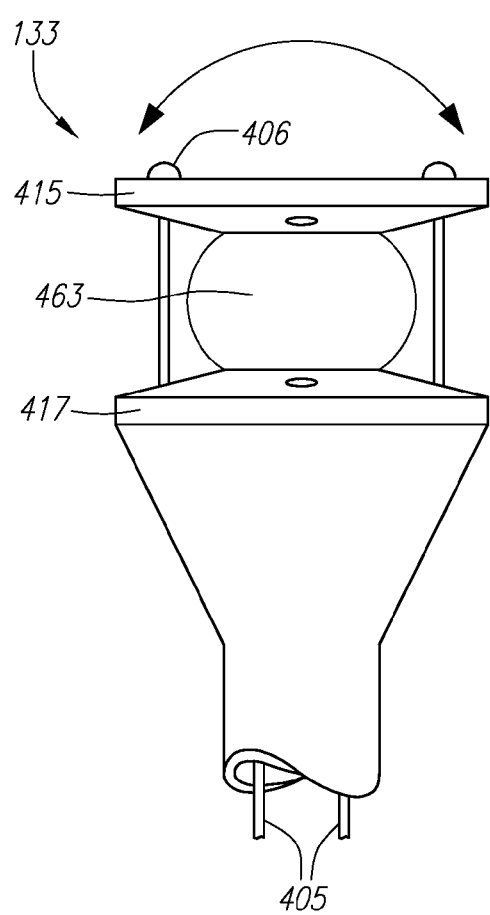
Figure 43B:
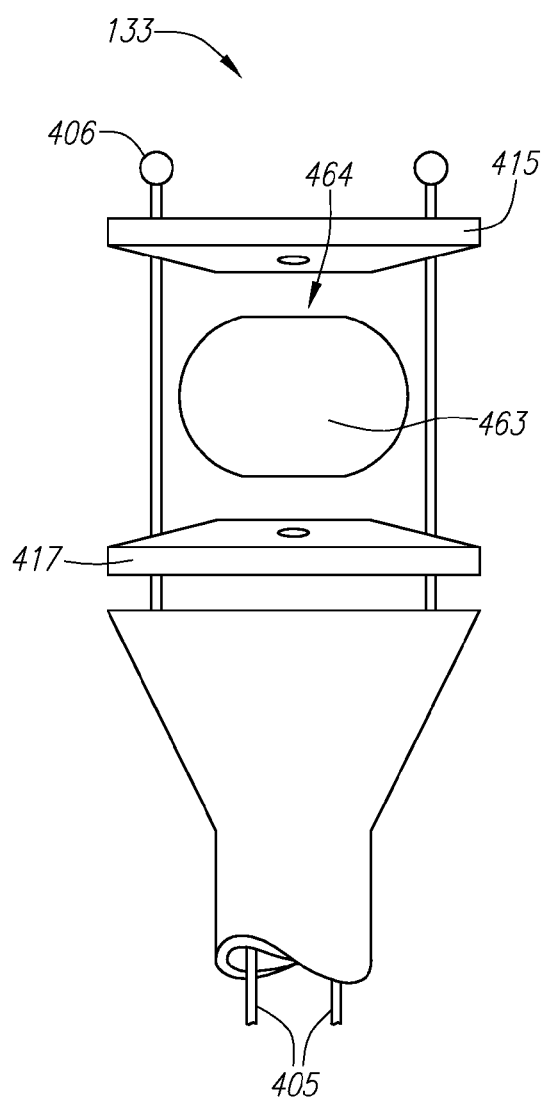
Figure 44:
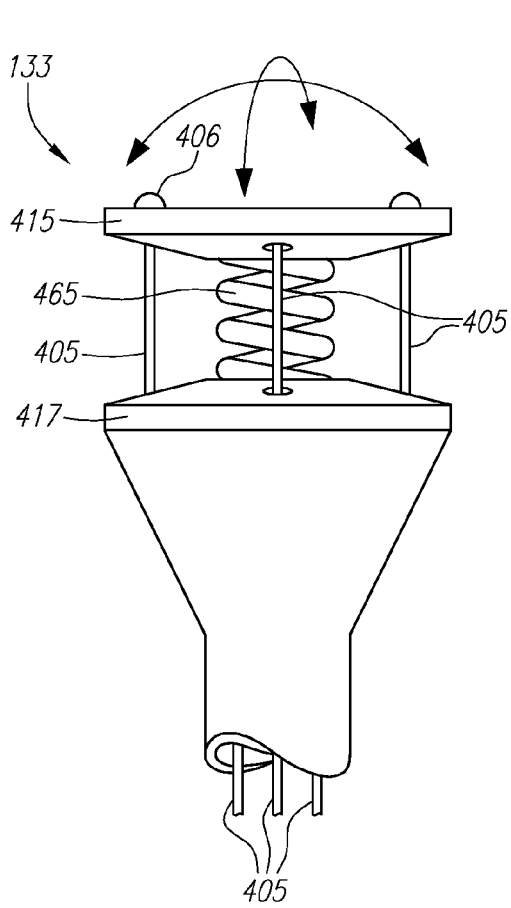
Figure 45:
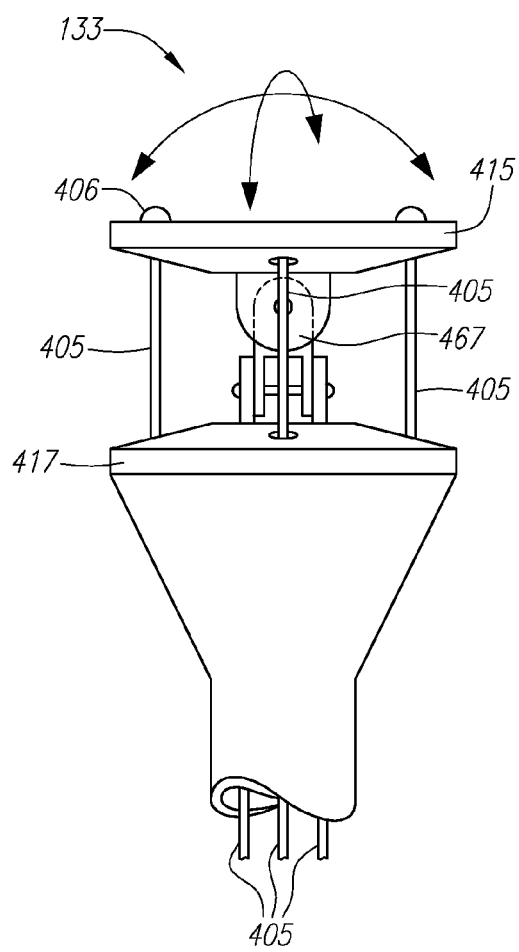
Figure 46A:
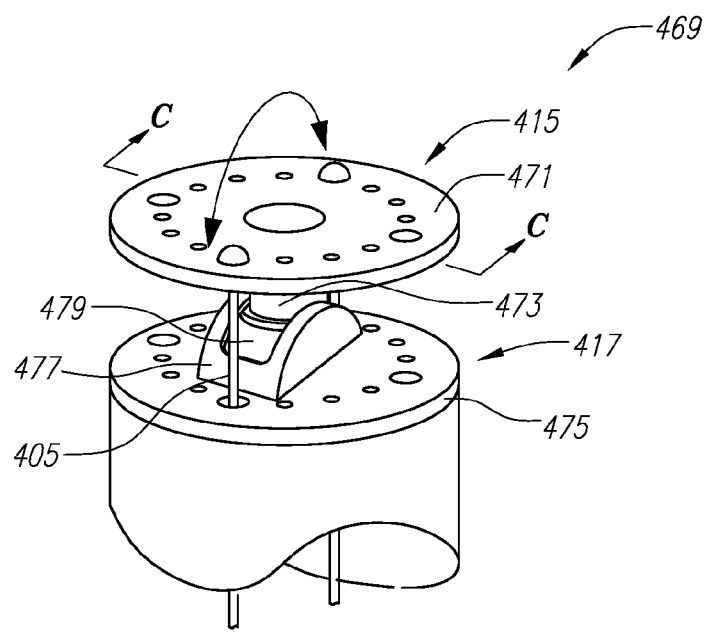
Figures 46B, 46C:
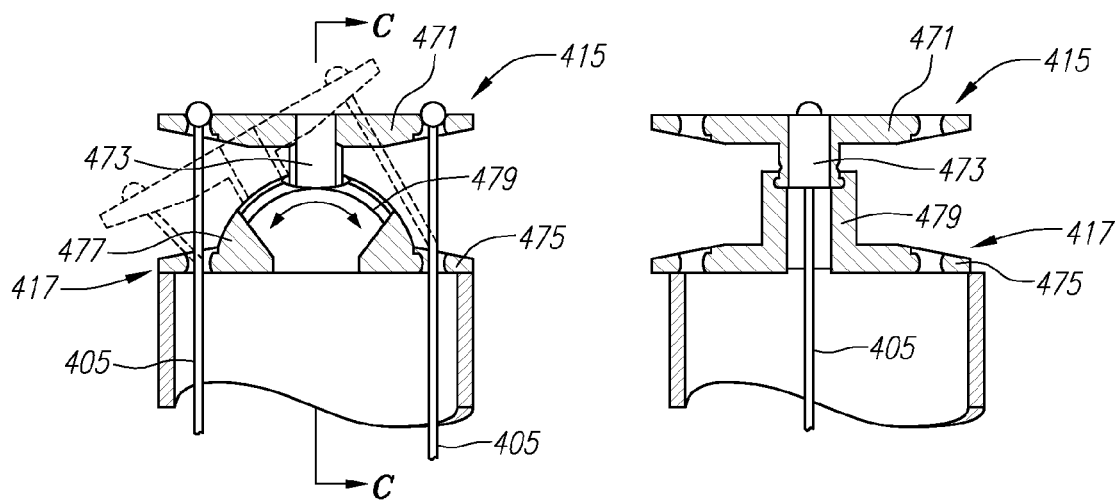
Figure 47A:
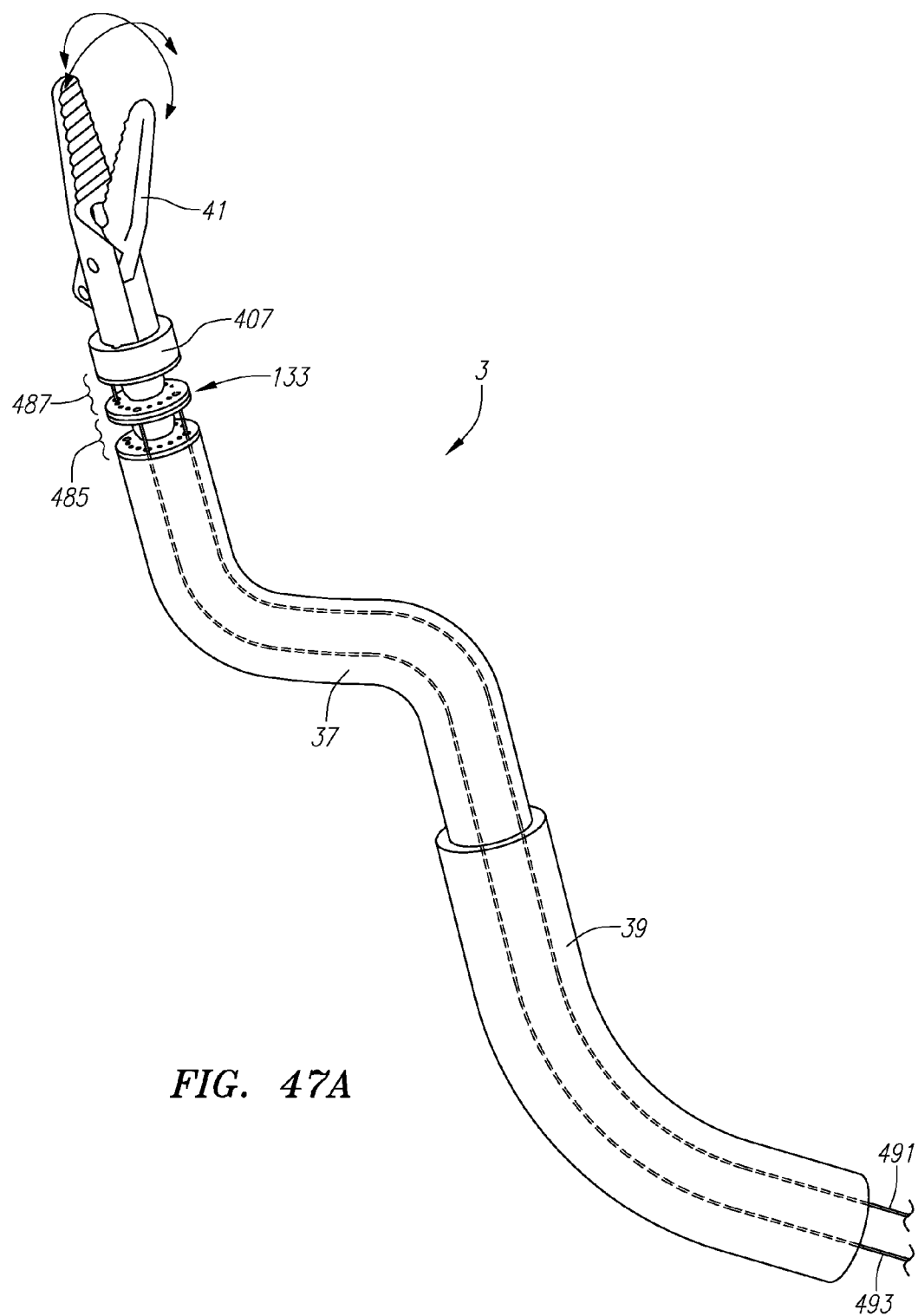
Figures 47B, 47C:
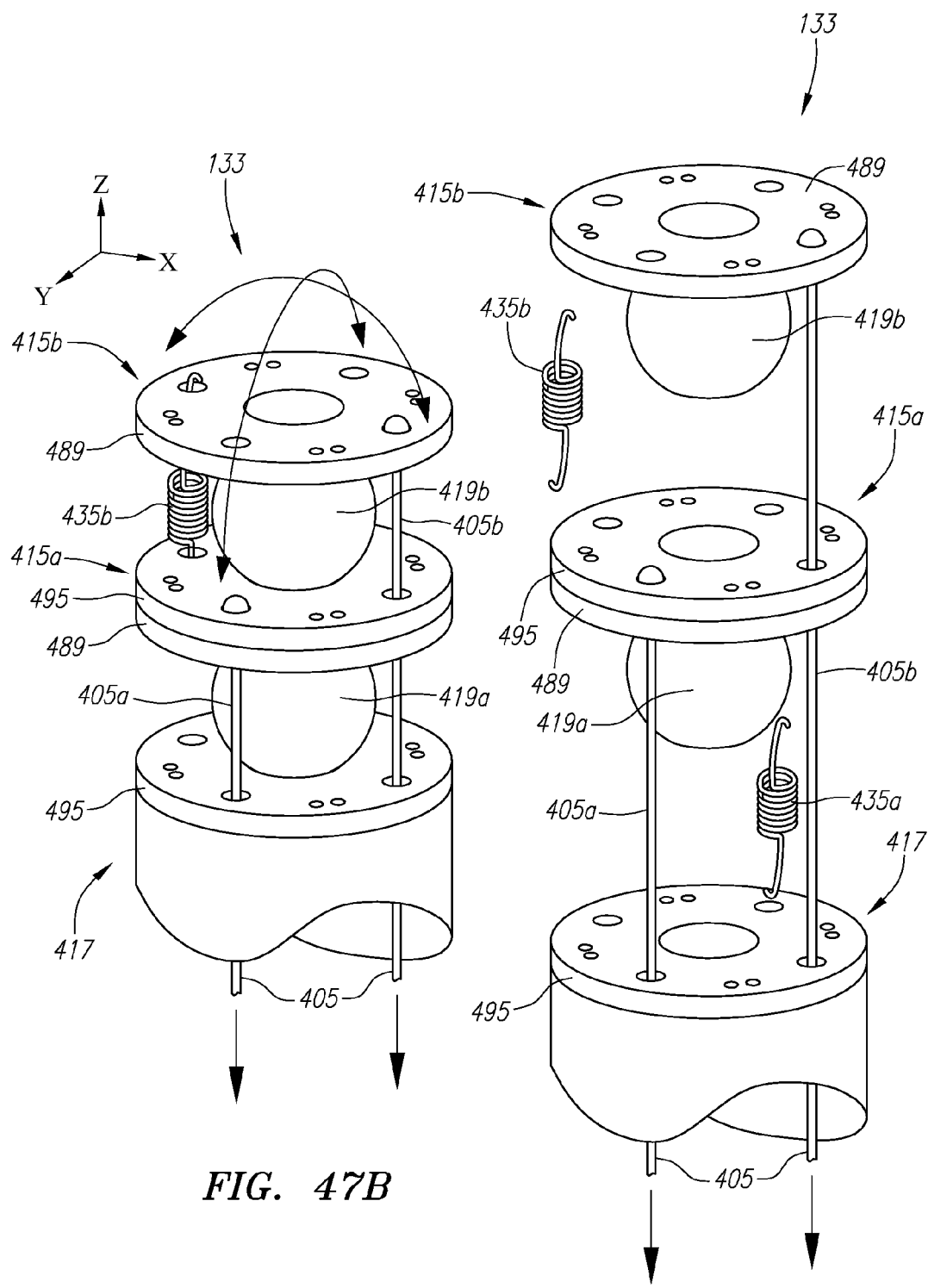
Figures 47D, 47E:
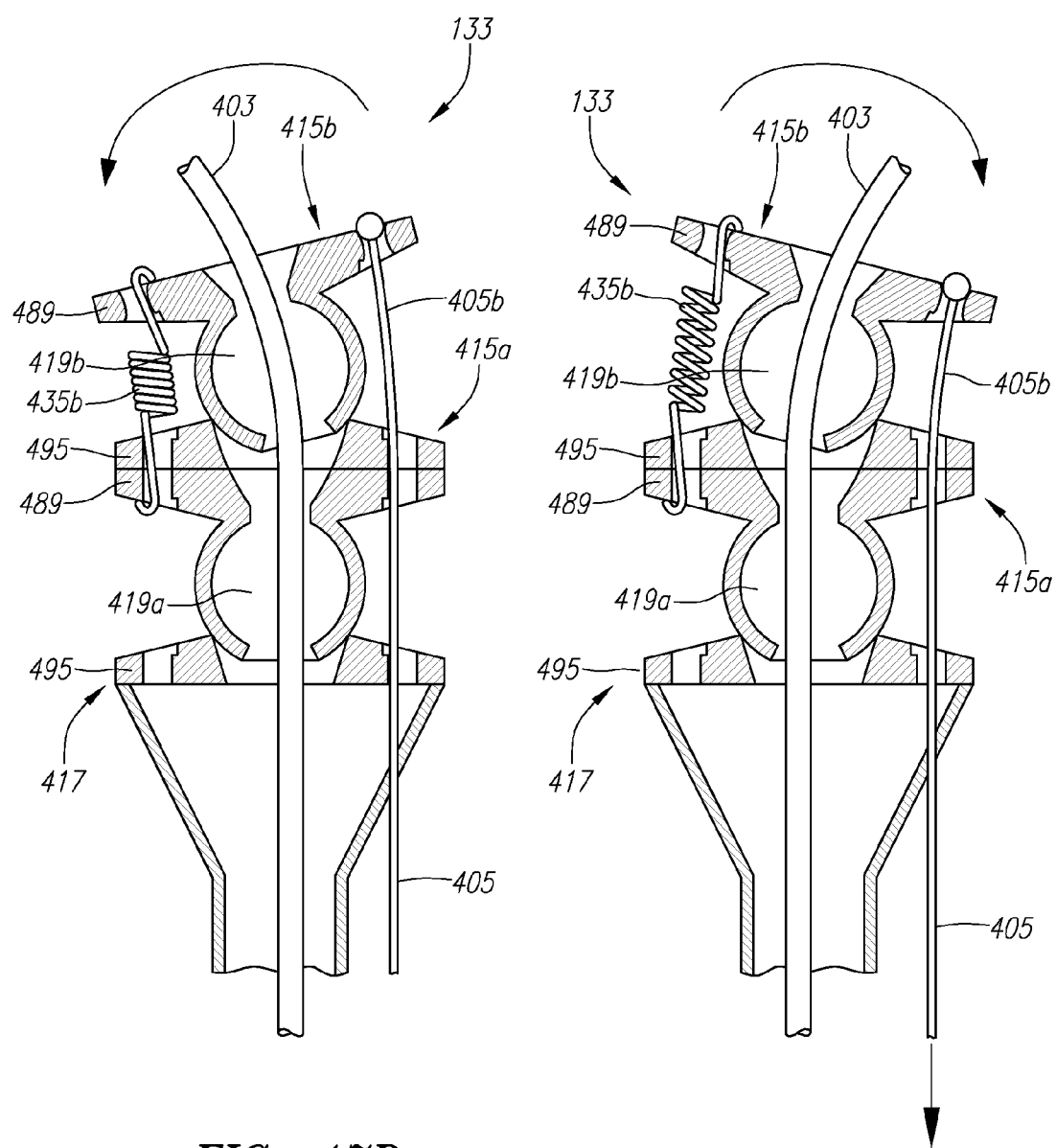
Figures 47F, 47G:
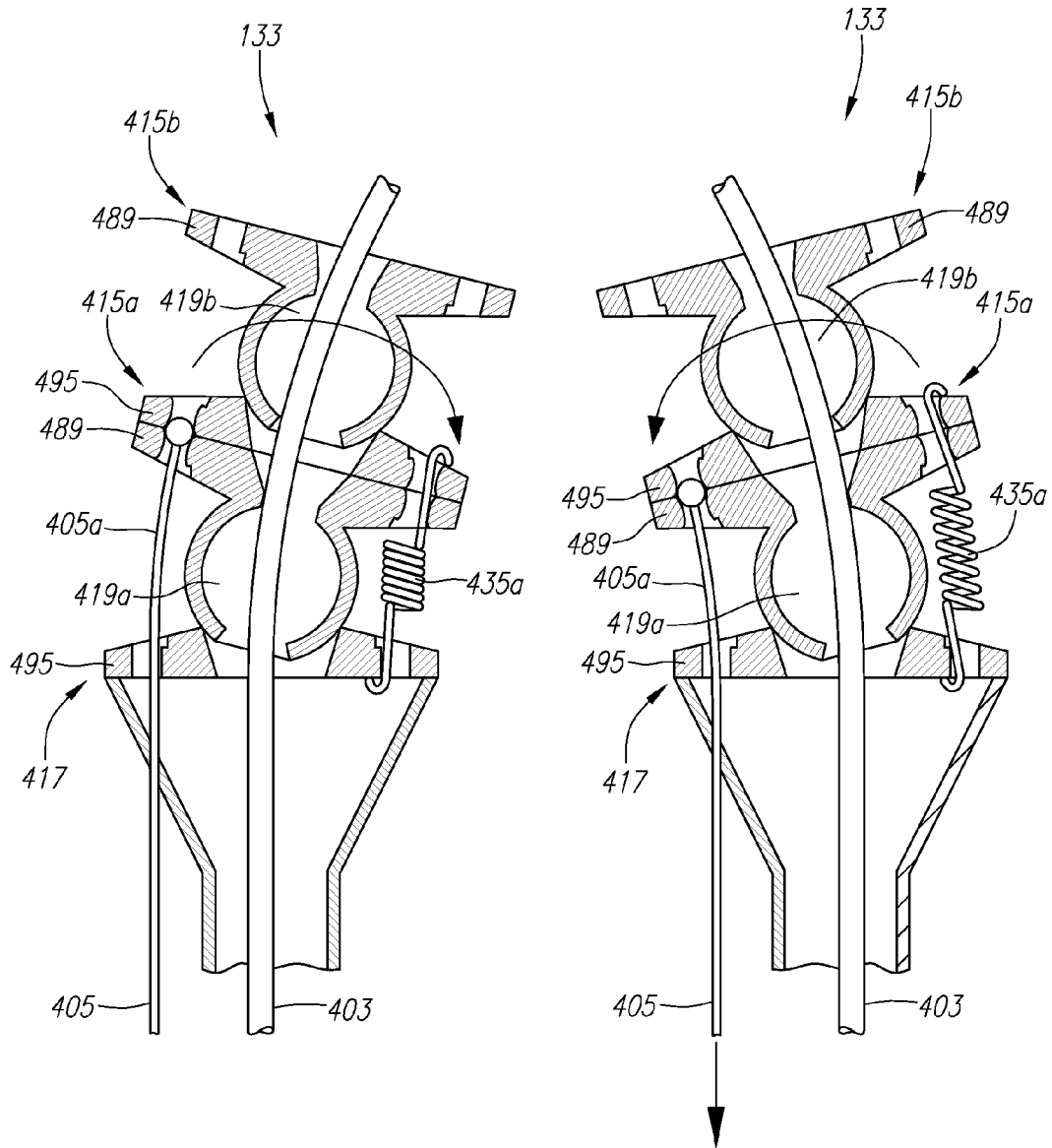
Figure 47H:
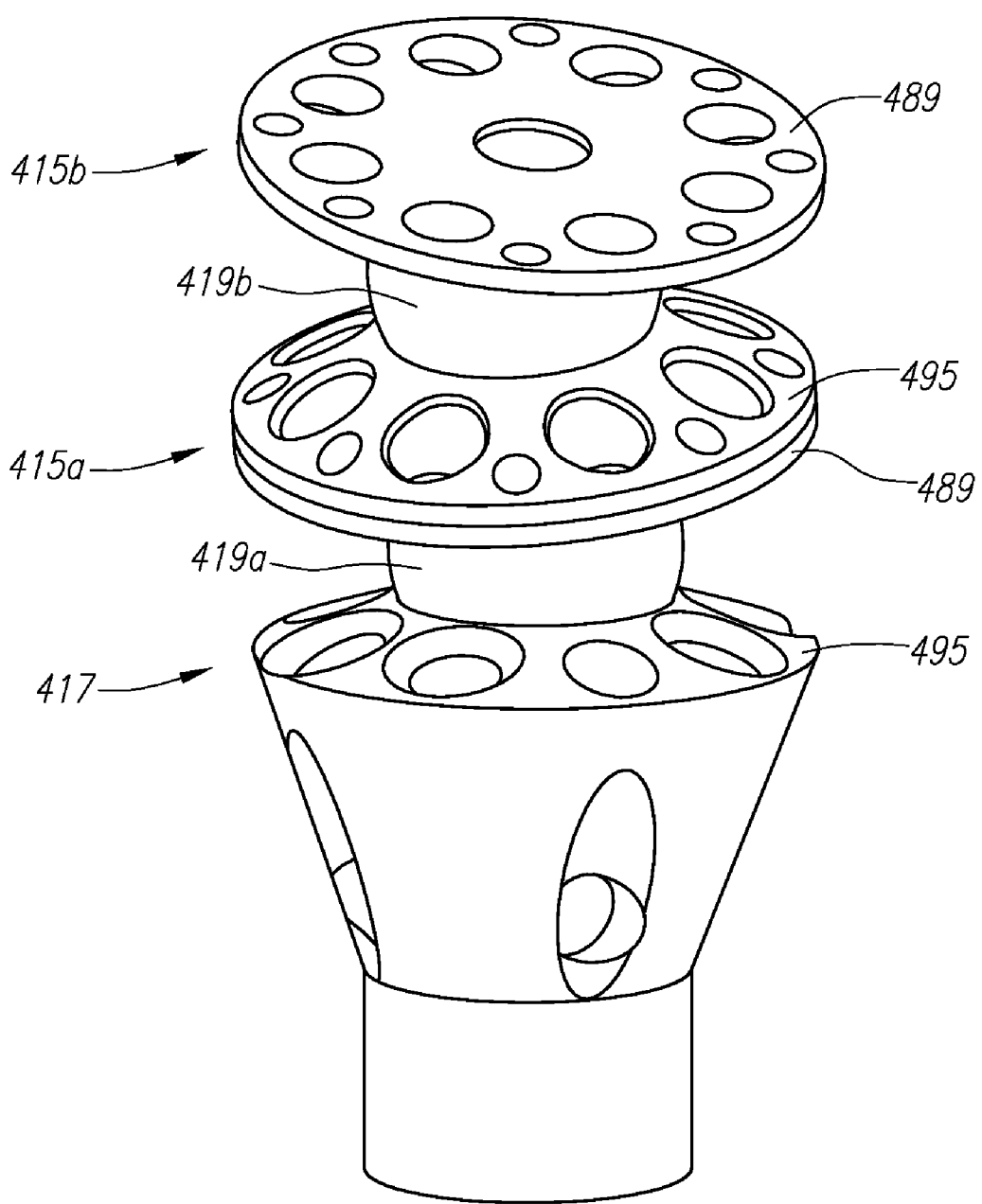
Figure 47I:
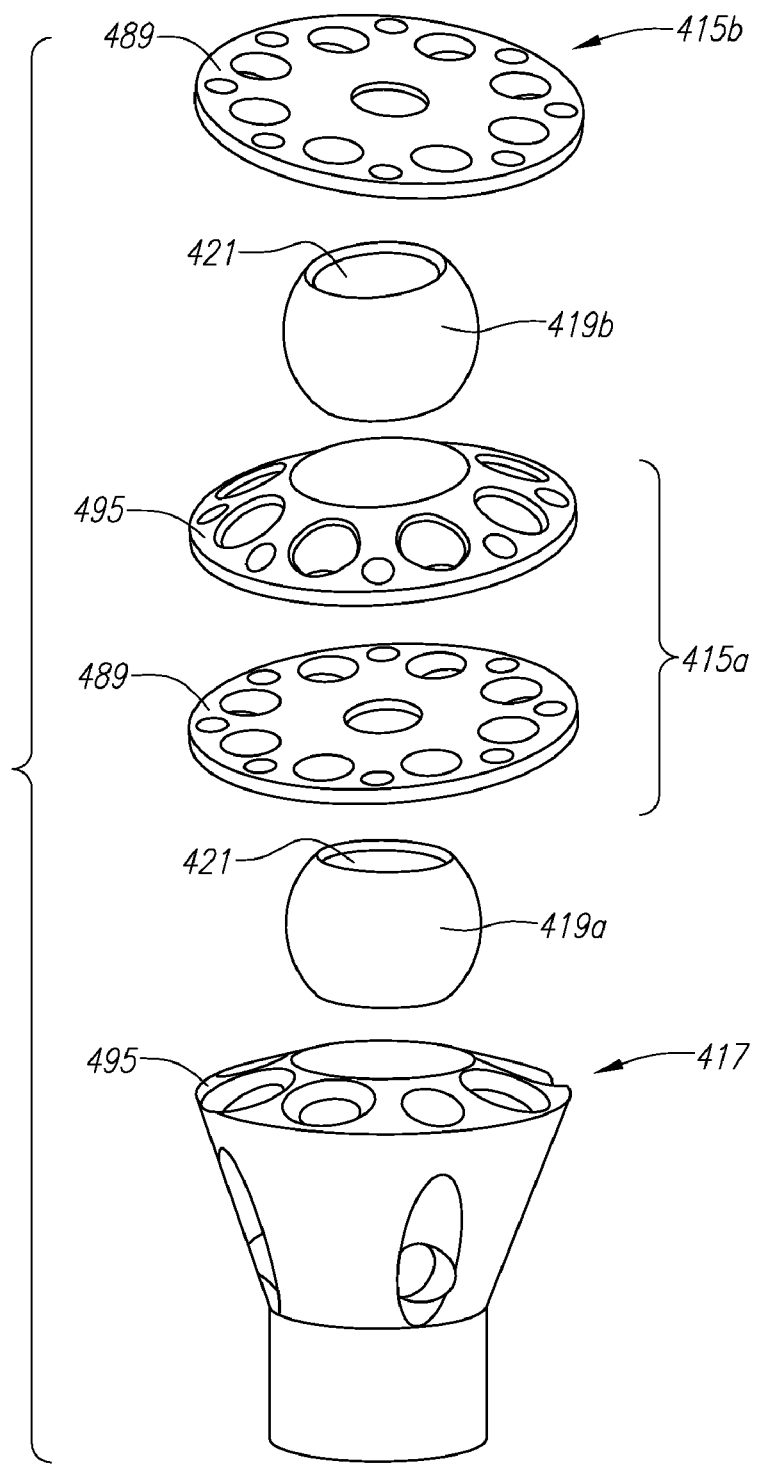
Figure 47J:
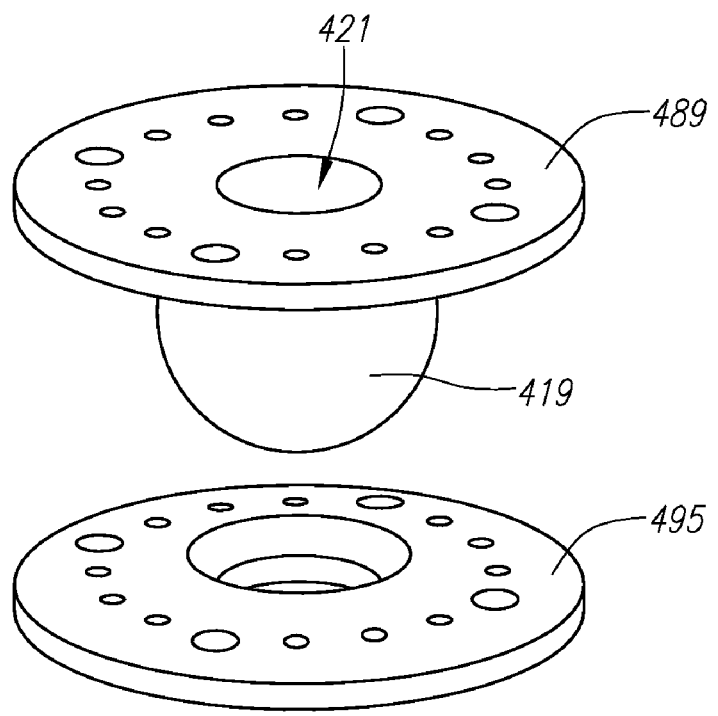
Figure 47K:
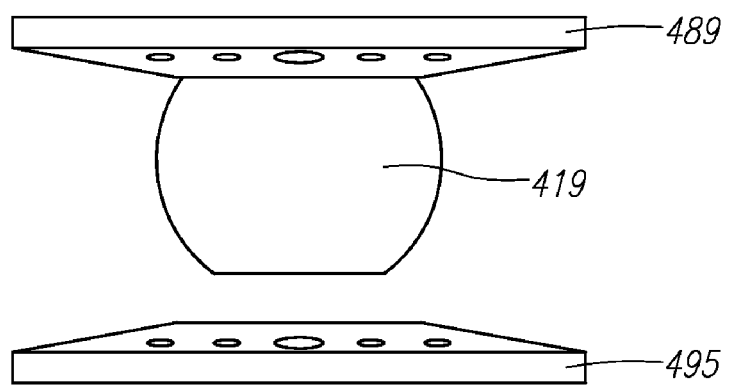
Figure 47L:
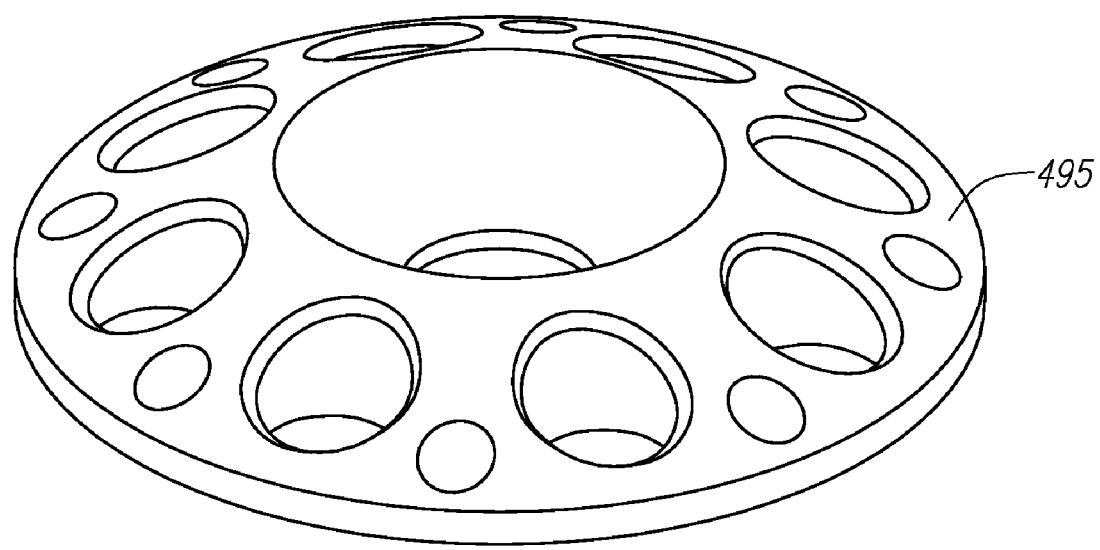
Figure 47M:
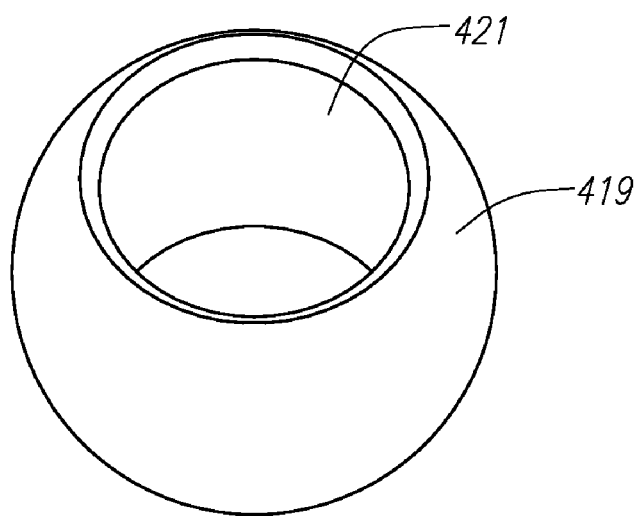
Figure 47N:
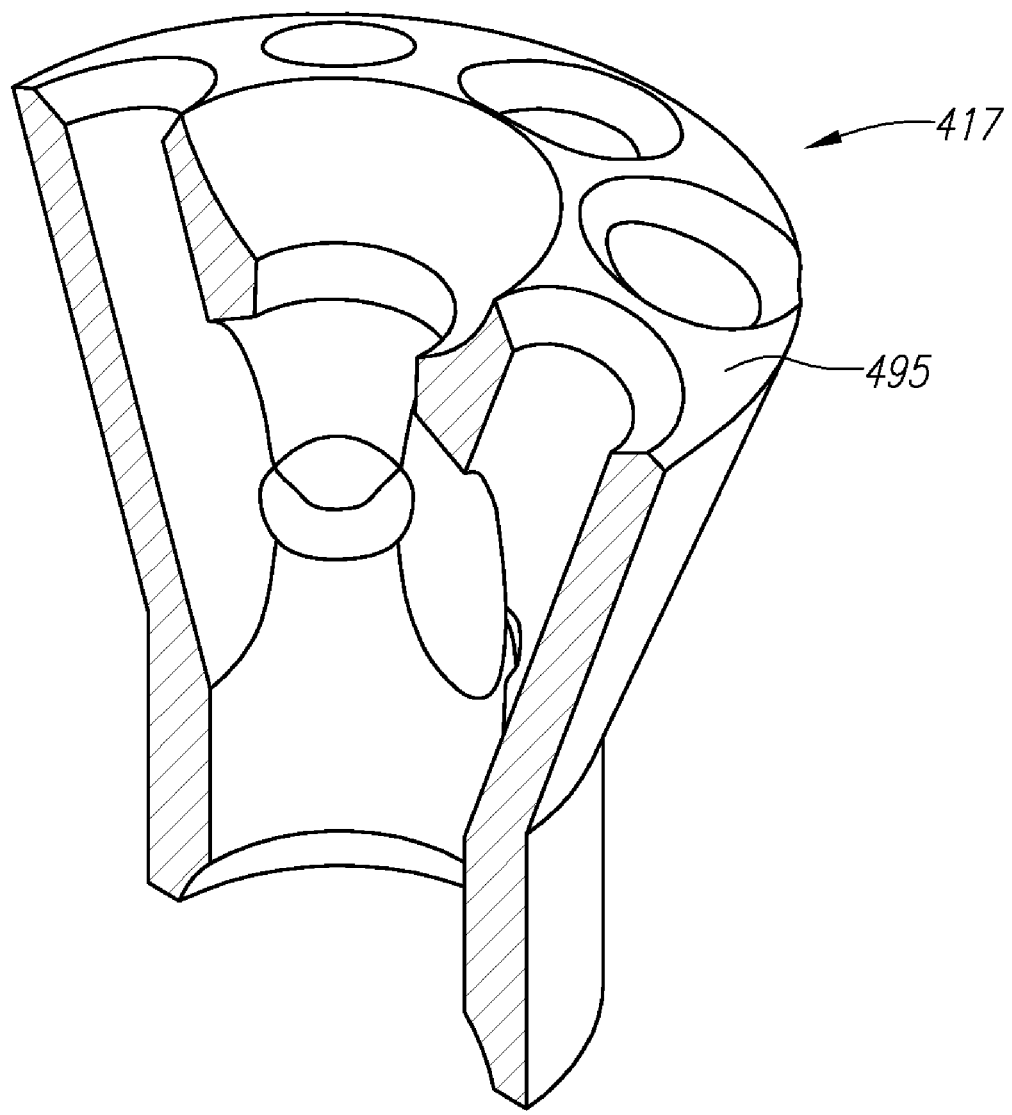
Figure 470:
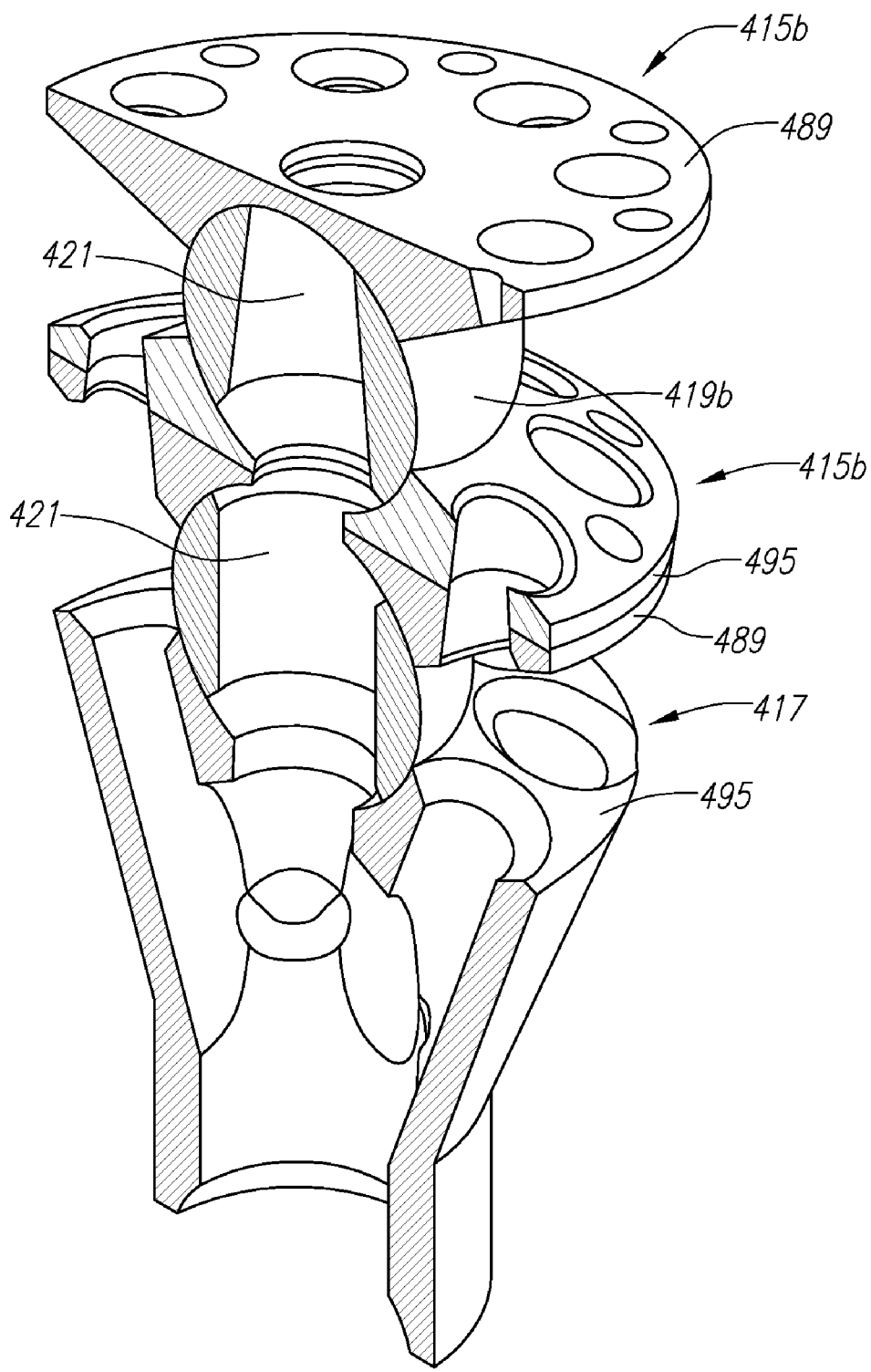
Figure 48A:
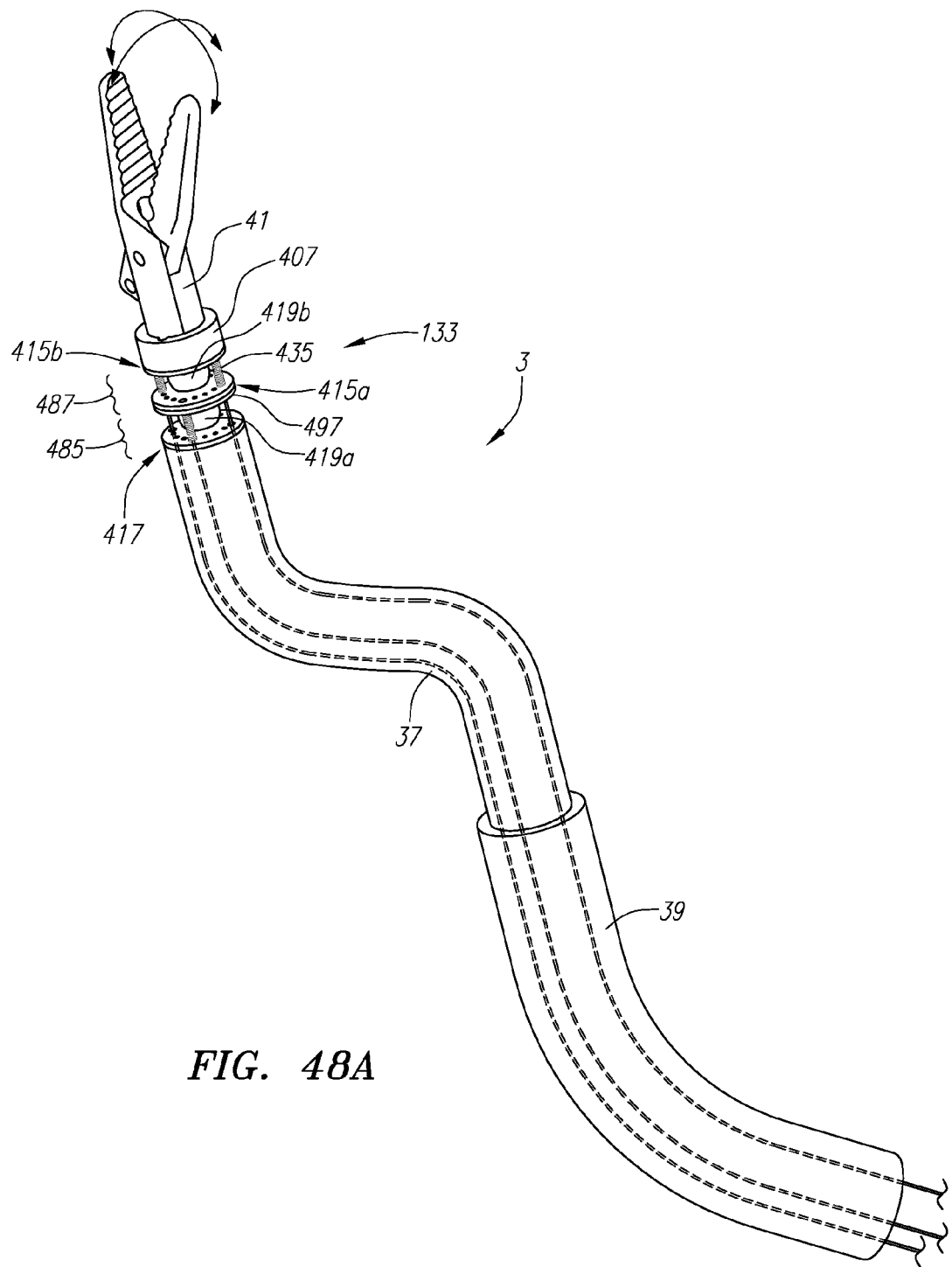
Figures 48B, 48C:
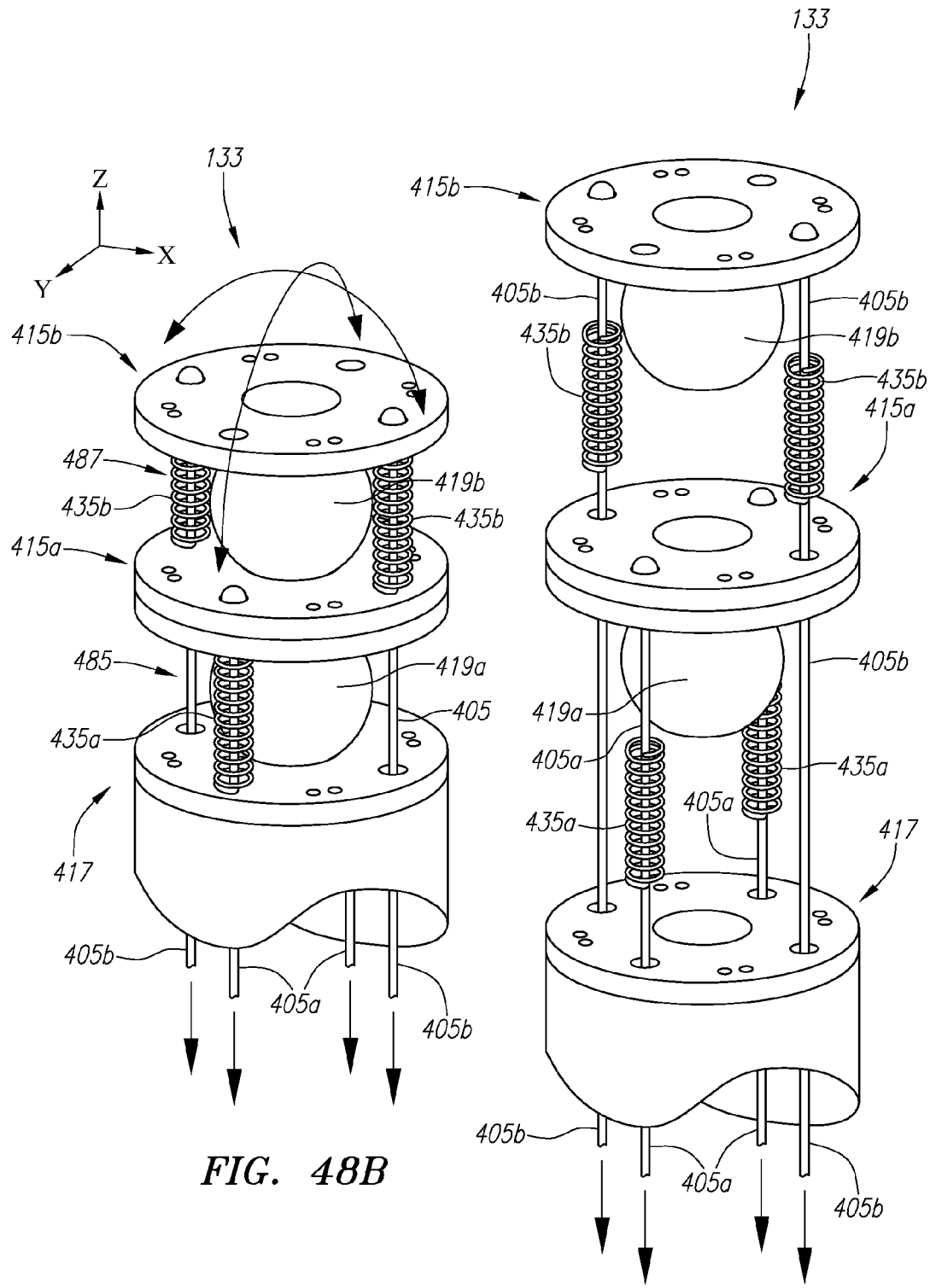
Figures 48D, 48E:
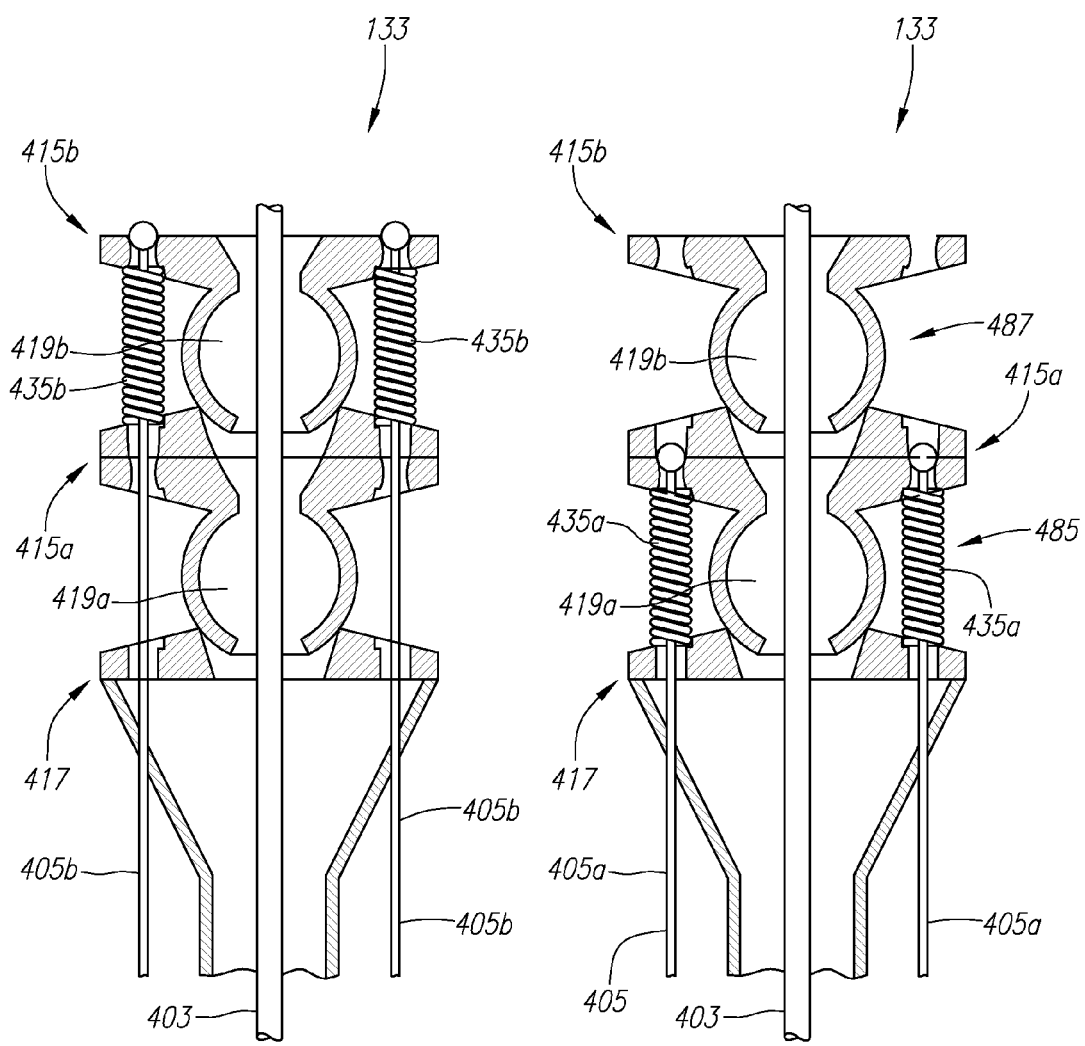
Figures 48F, 48G:
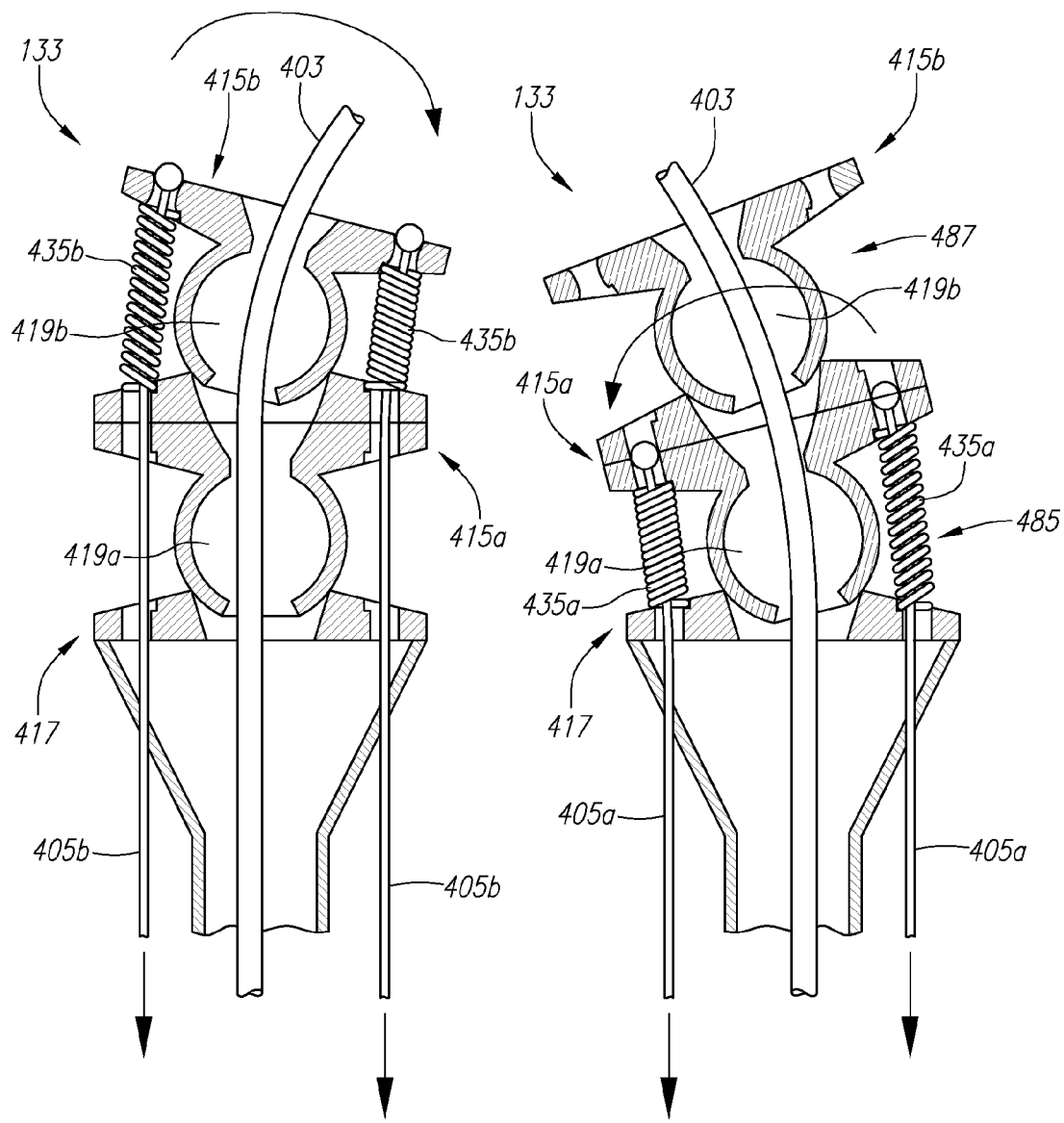
Figure 49A:
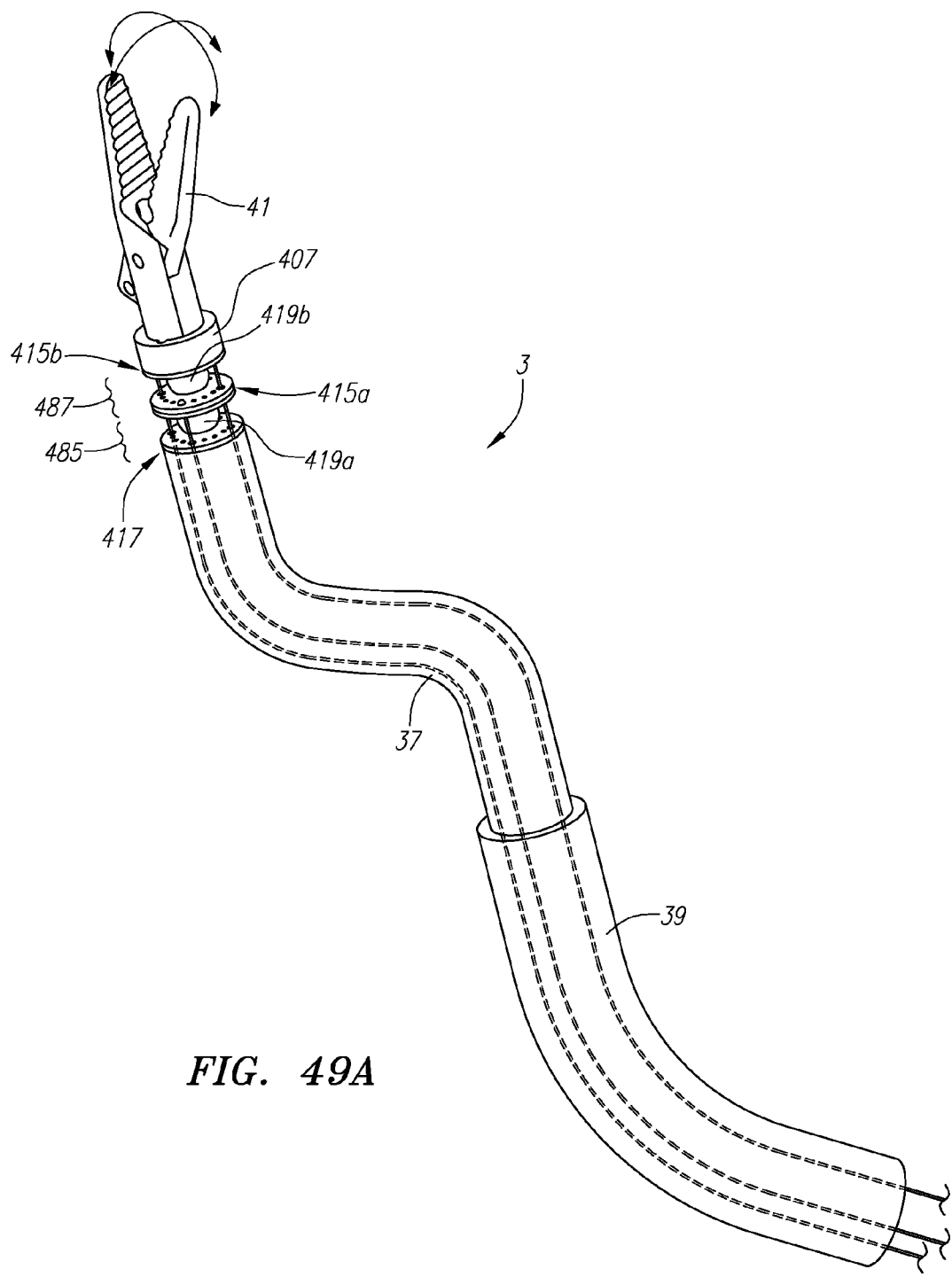
Figure 49B:
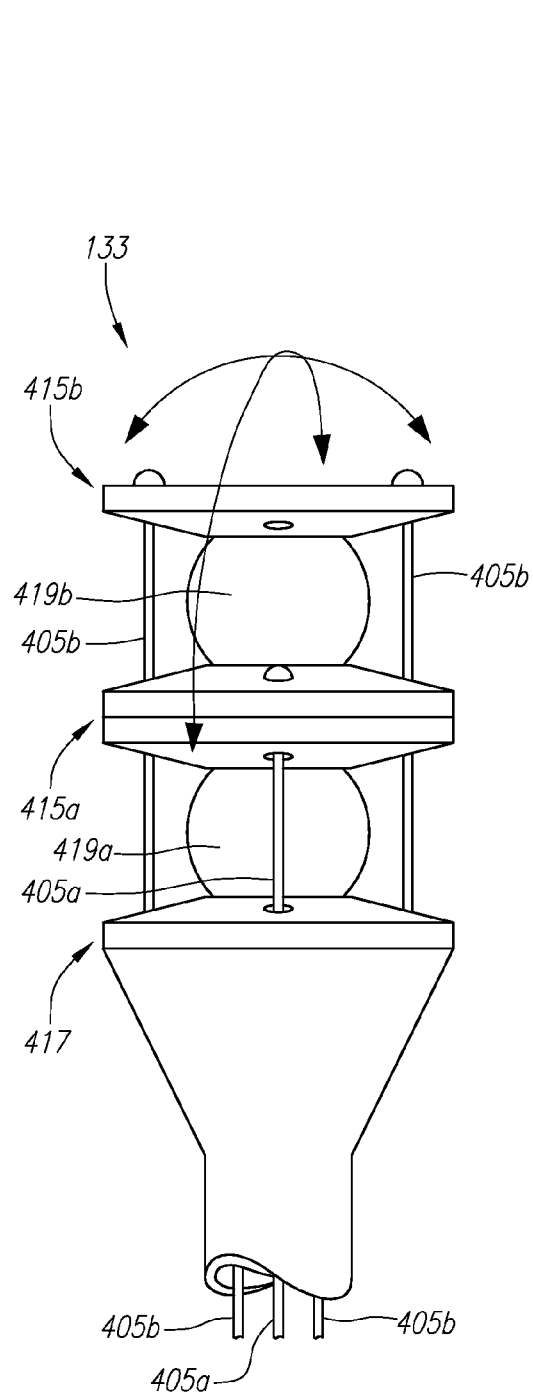
Figure 49C:
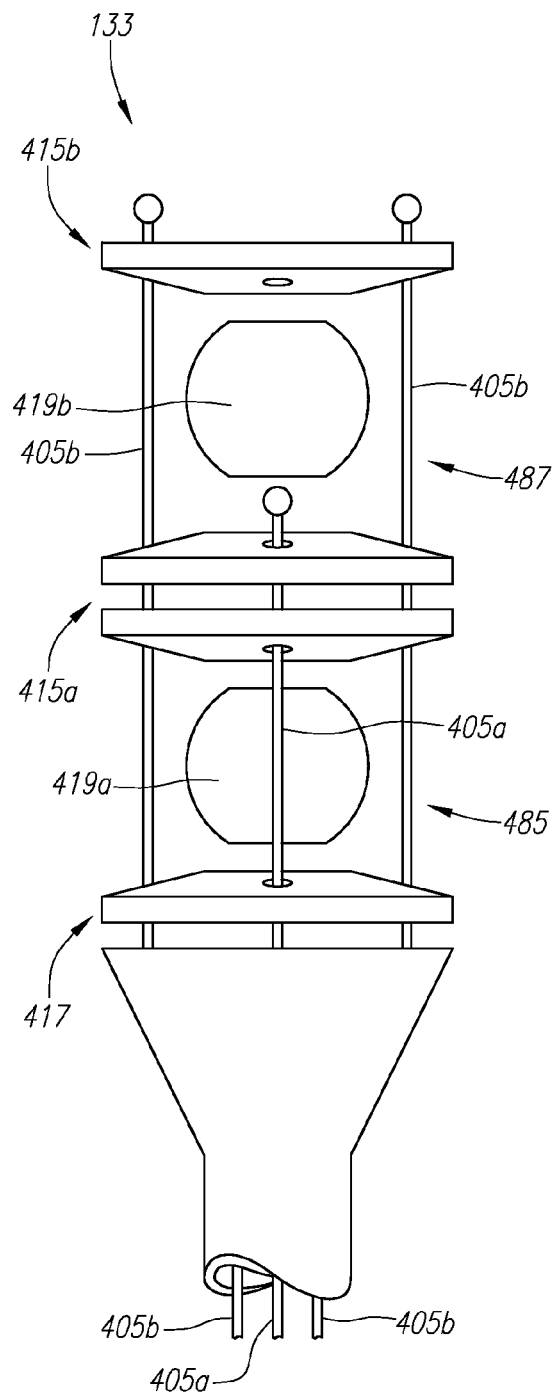
Figures 50A, 50B:
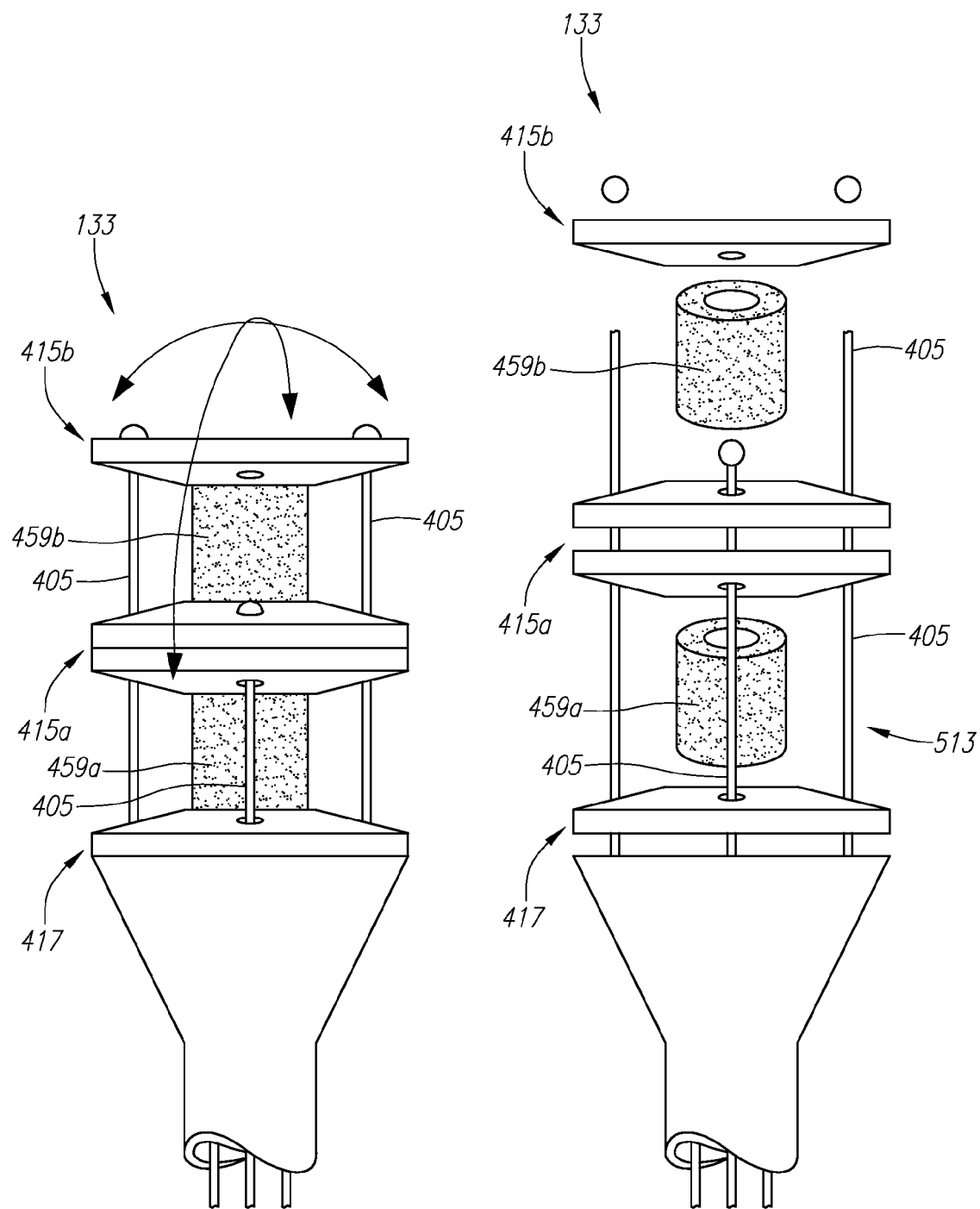
Figure 51A:
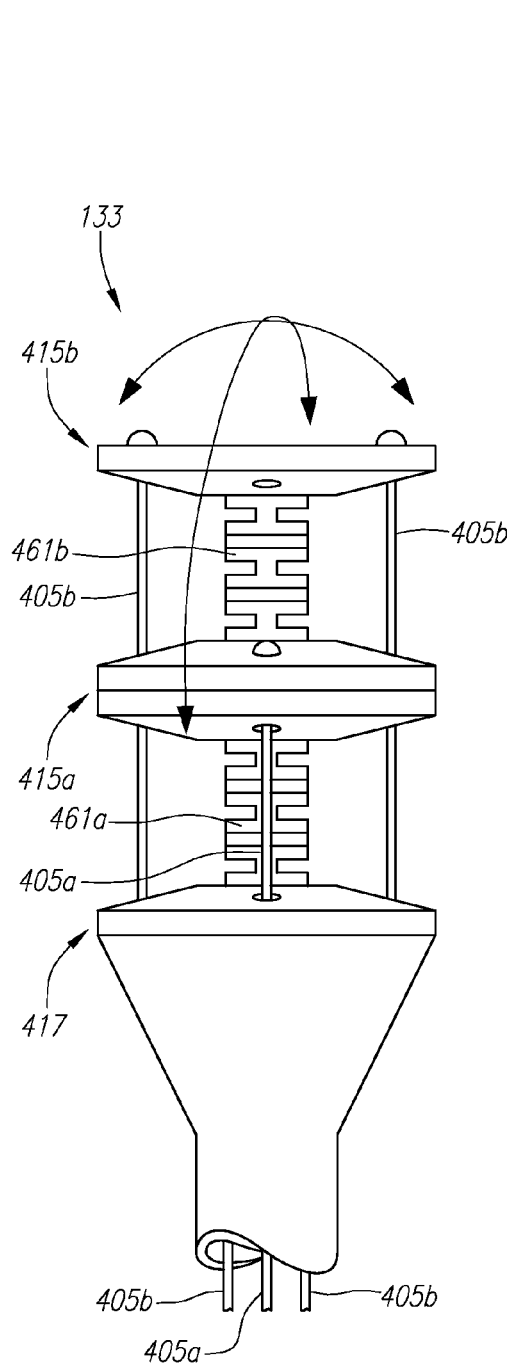
Figure 51B:
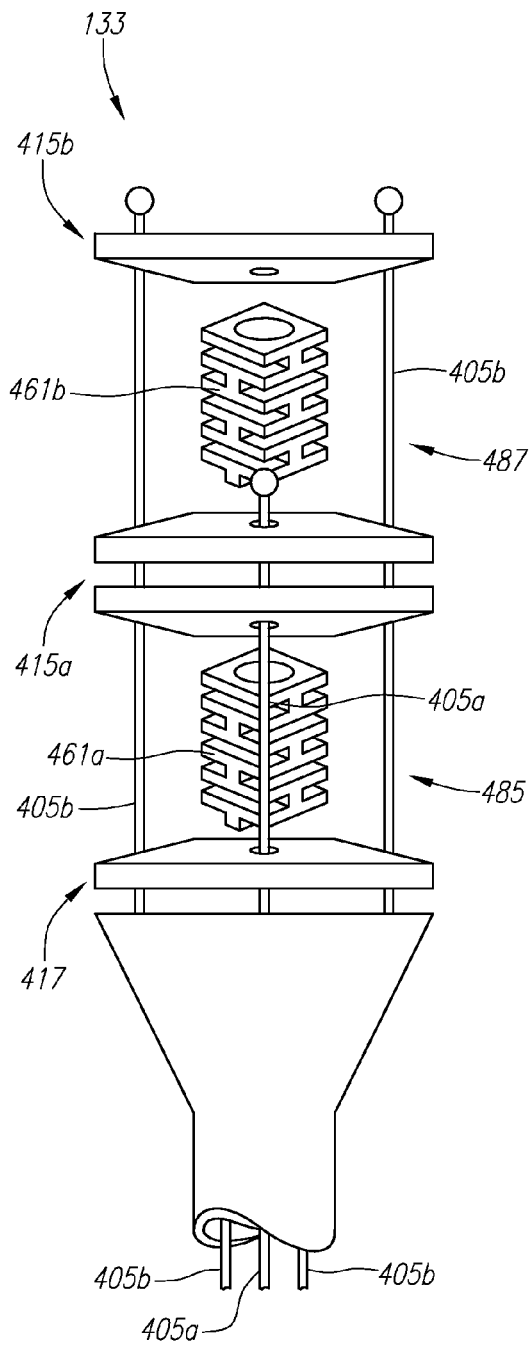
Figures 52A, 52B:
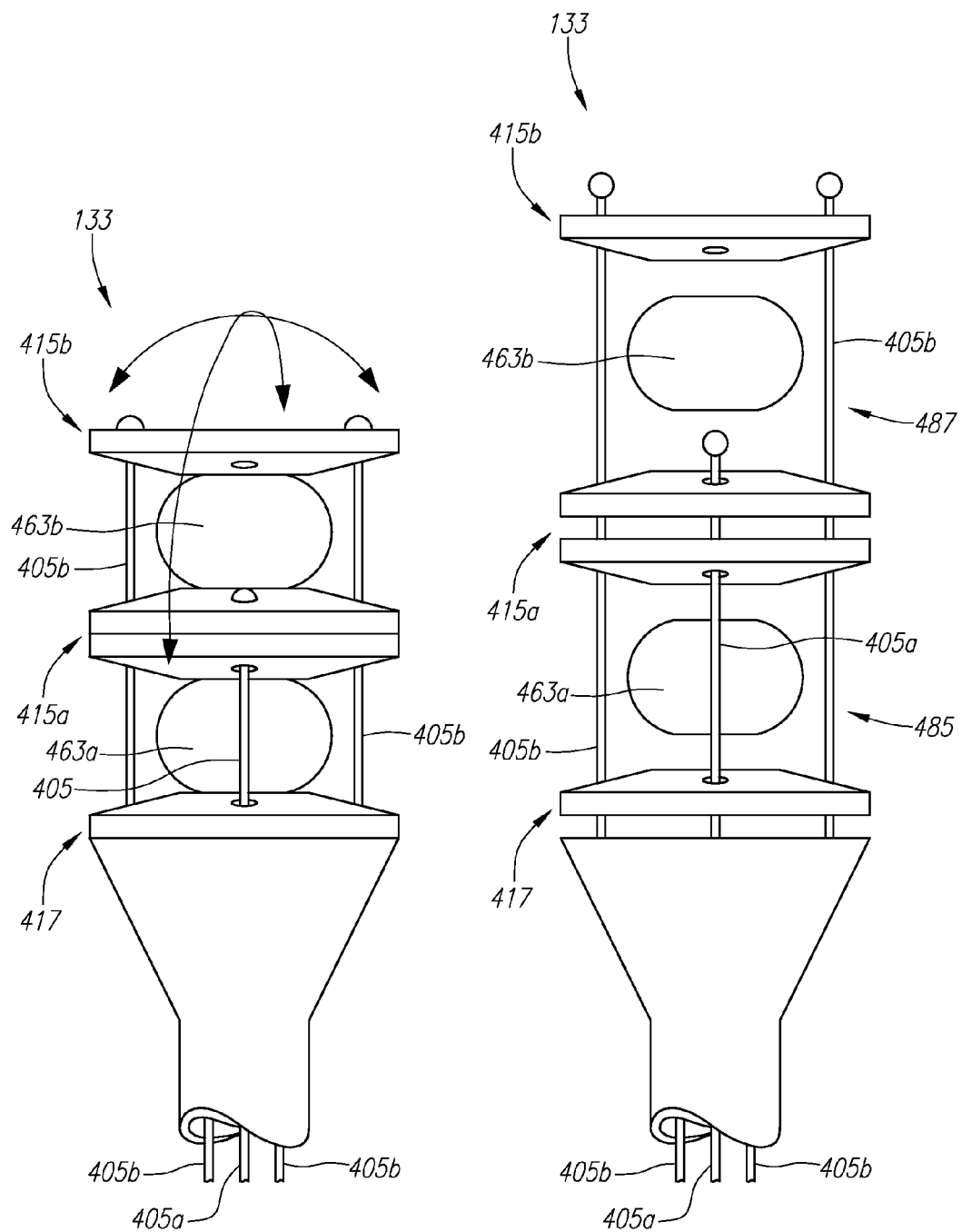
Figures 53, 54:
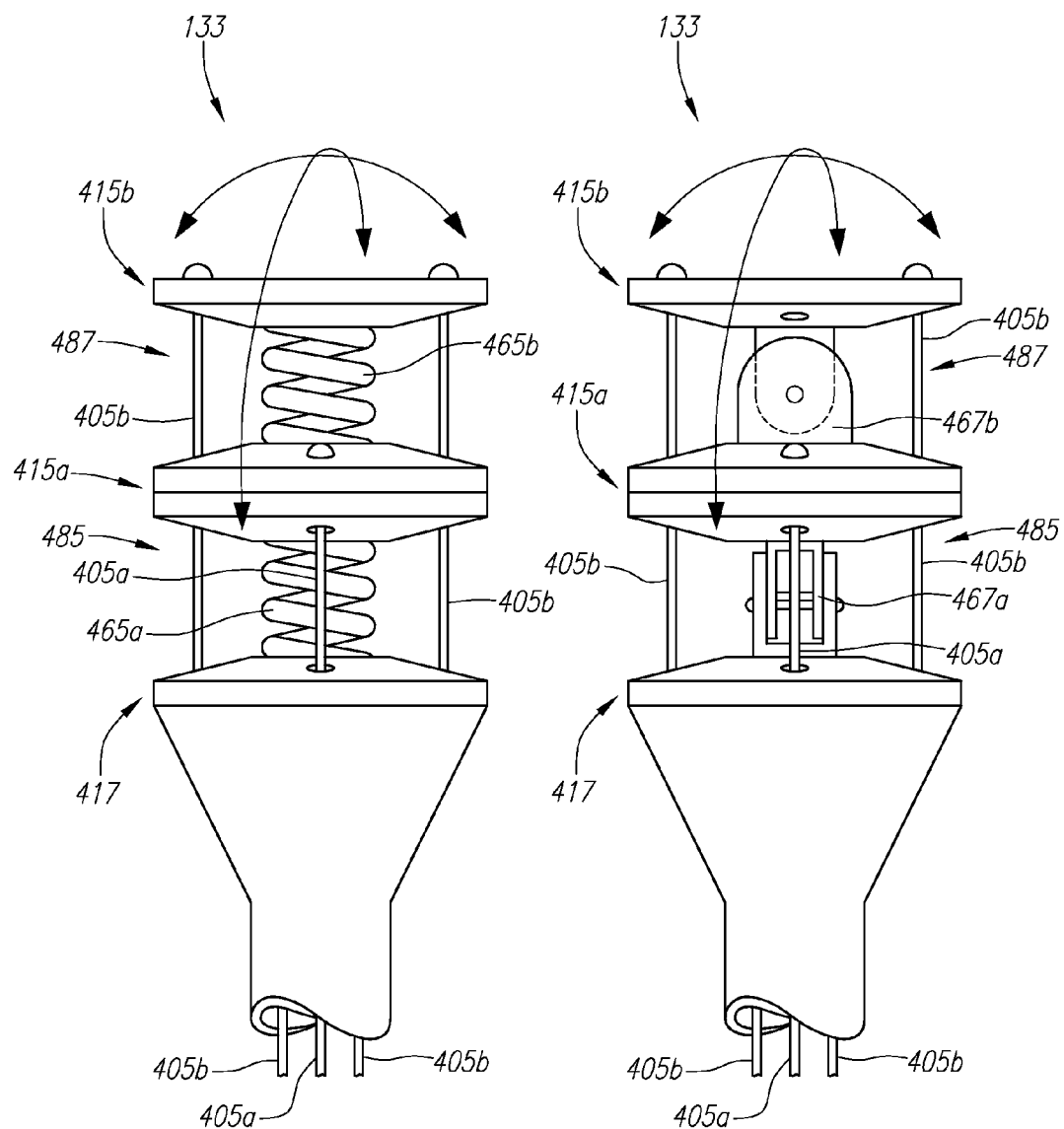
Figure 55A:
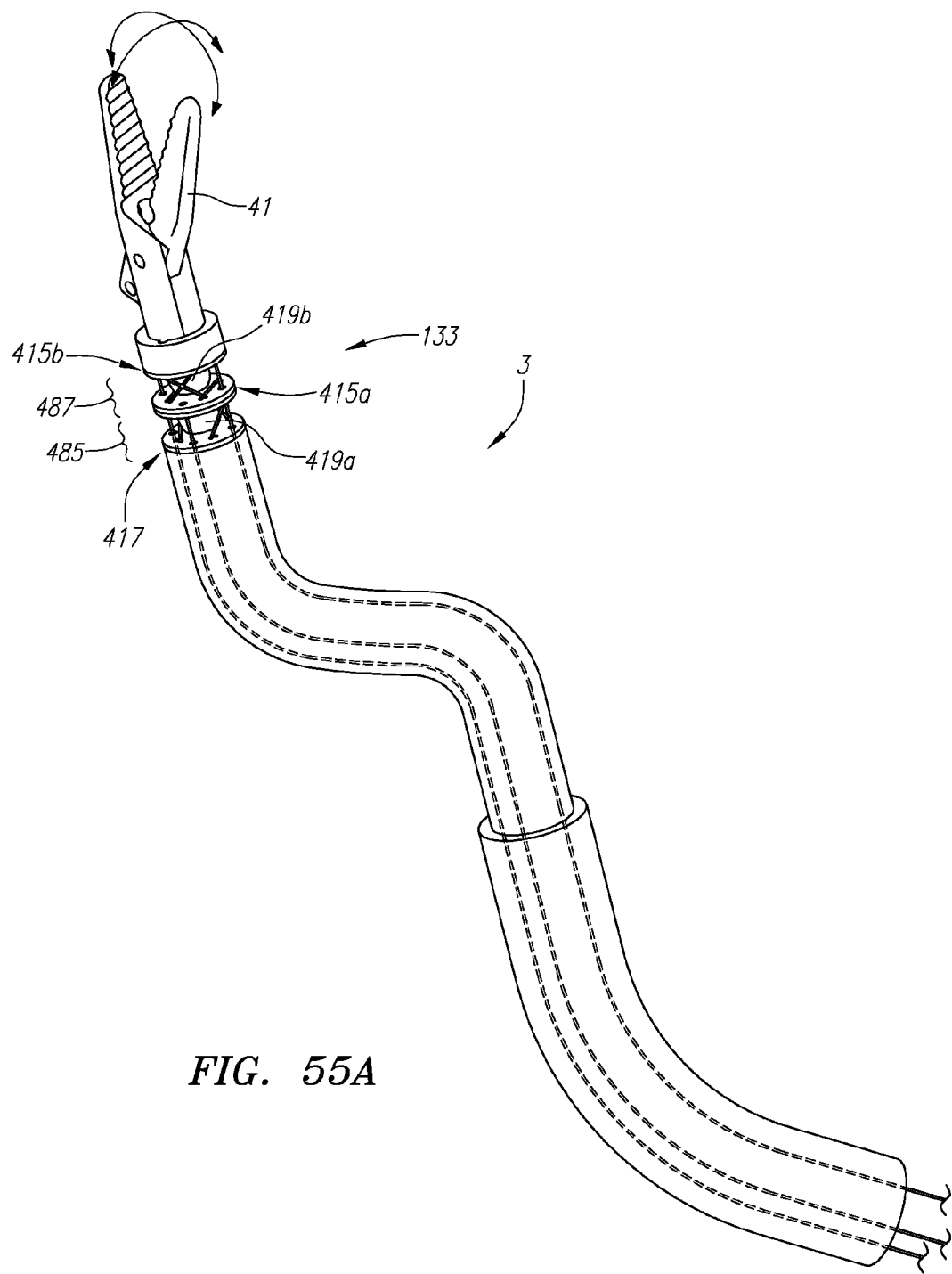
Figure 55B:
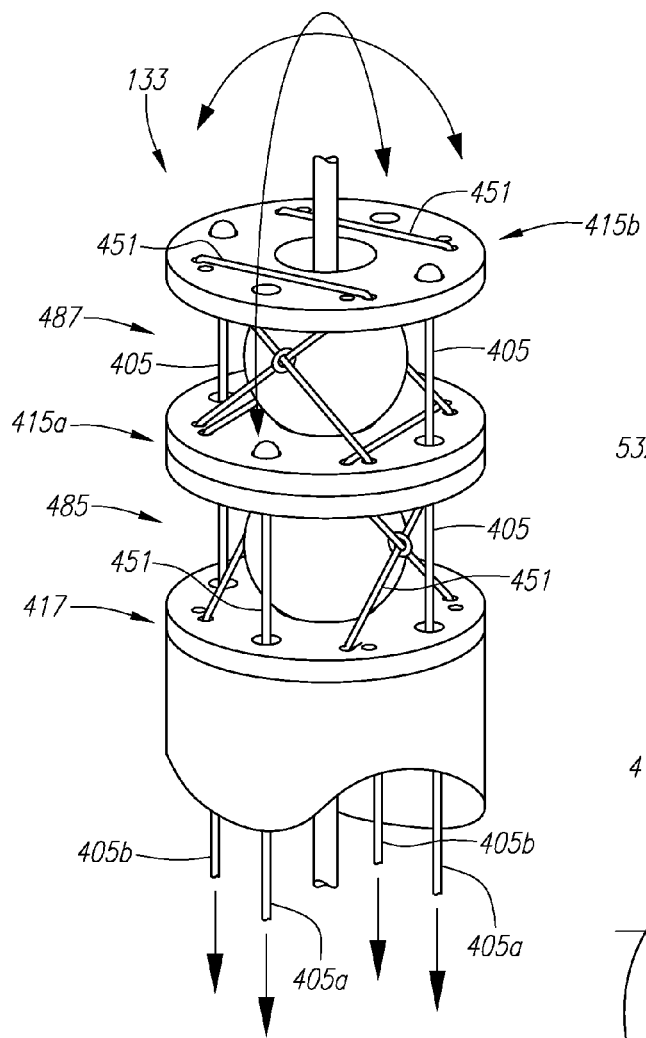
Figures 1, 55B:
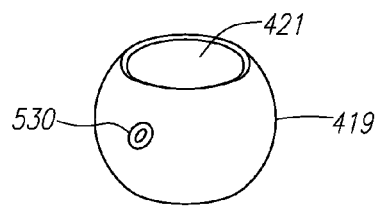
Figures 2, 55B:
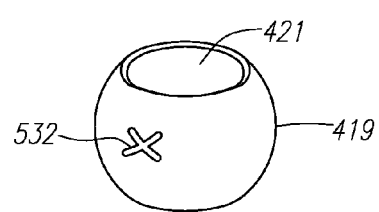
FIG. 2A illustrates a sheath catheter placed in a flexible state (F) during advancement through a sheath.
FIG. 2B illustrates a distal portion of a sheath catheter controllably manipulated to transition from a flexible state to a substantially rigid state (R) to form a substantially rigid platform.
Figure 55C:
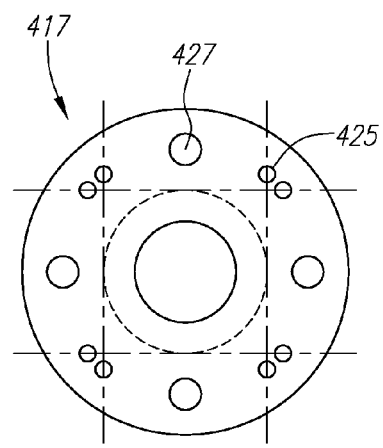
Figure 55D:
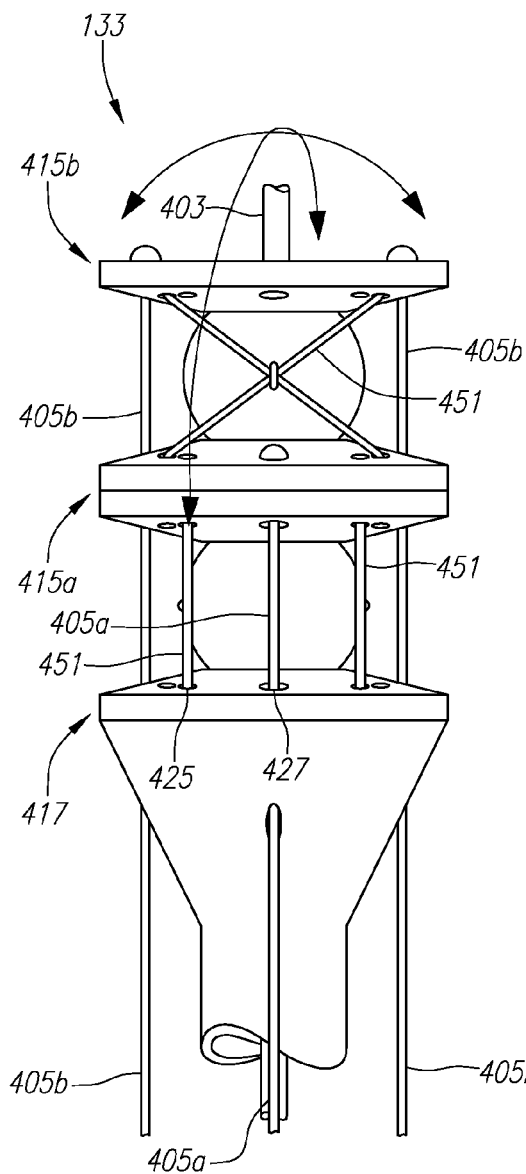
Figure 55E:
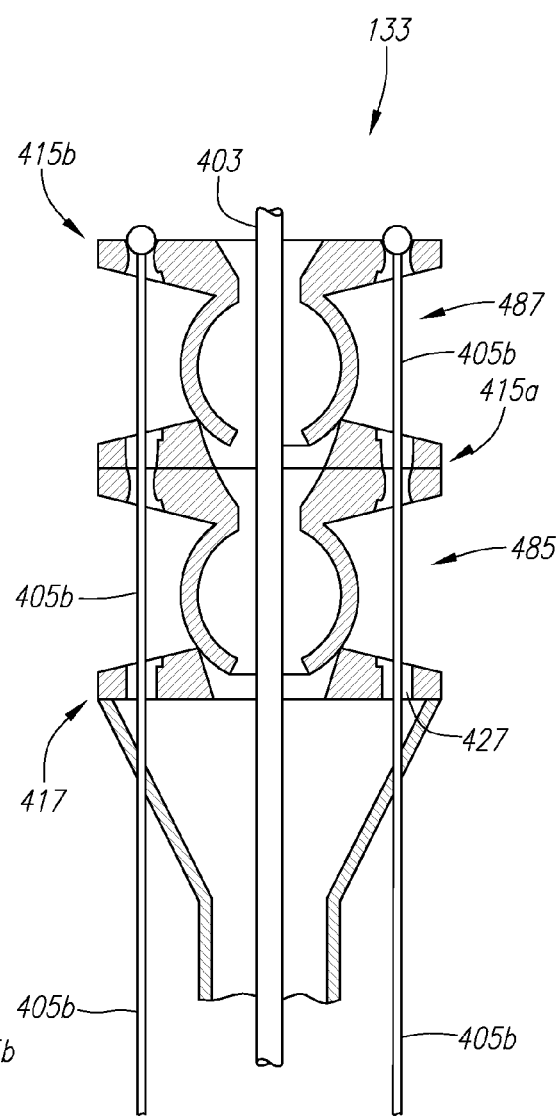
Figures 55F, 55G:
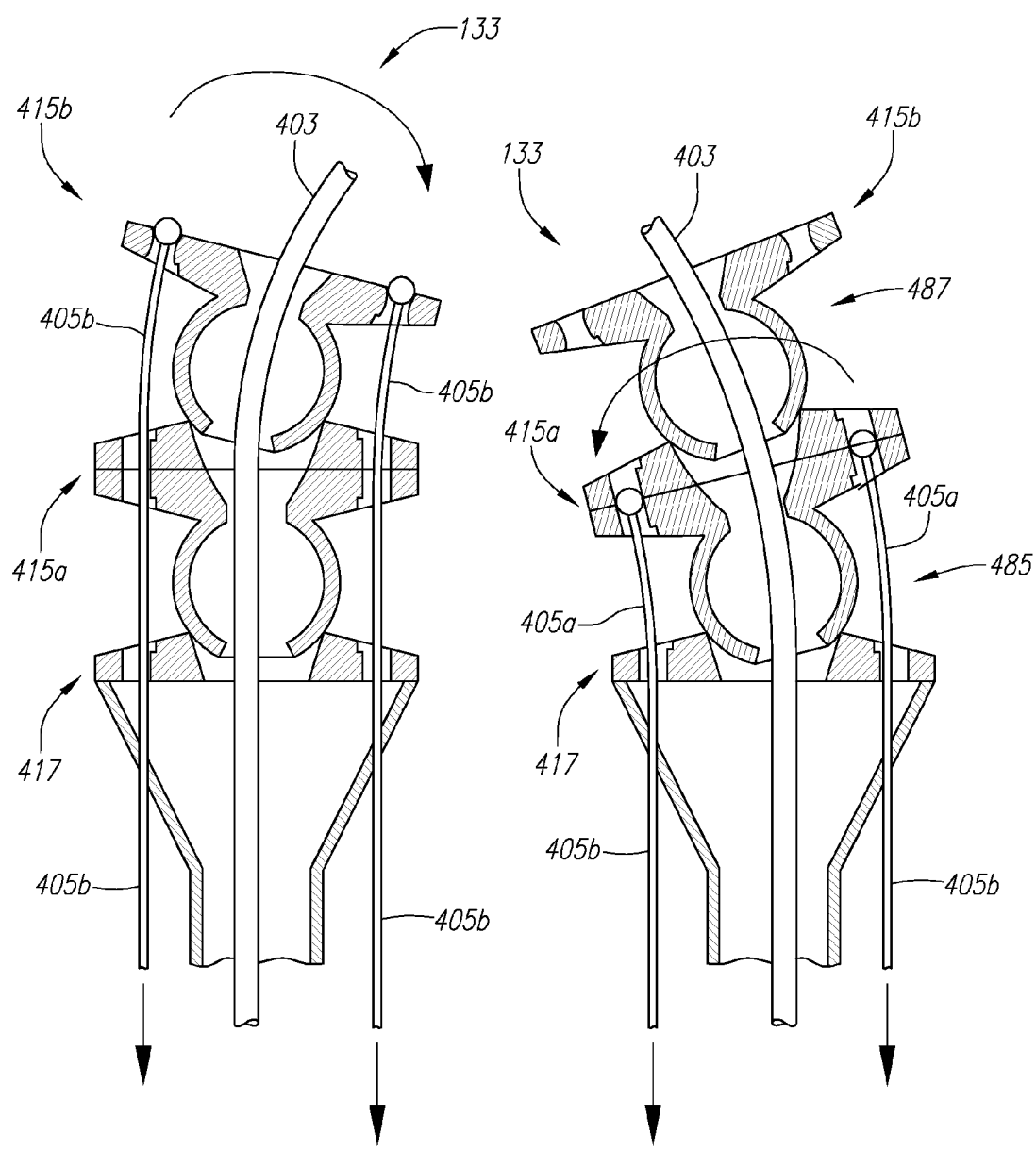
Figure 56C:
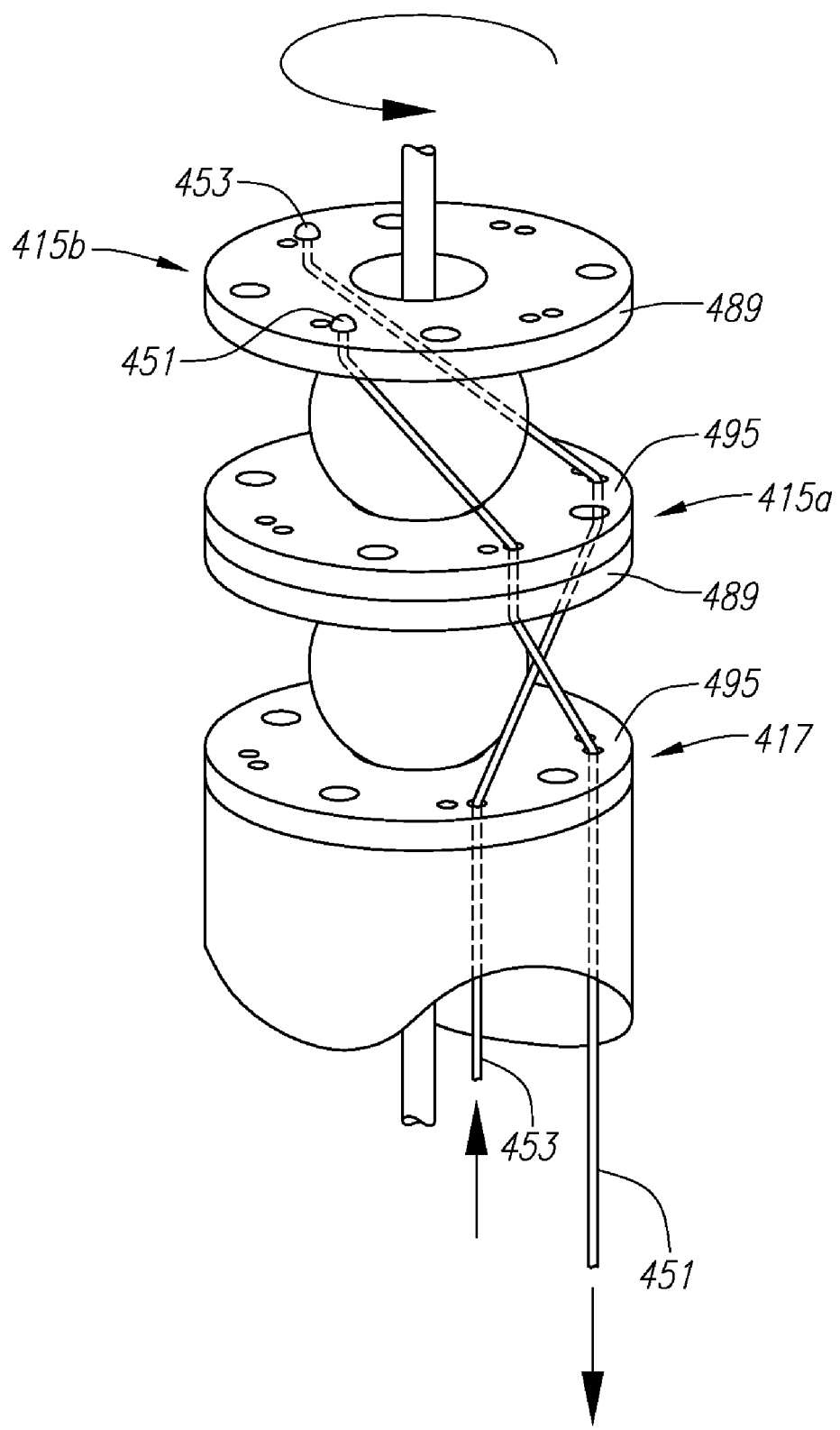
Figure 57:
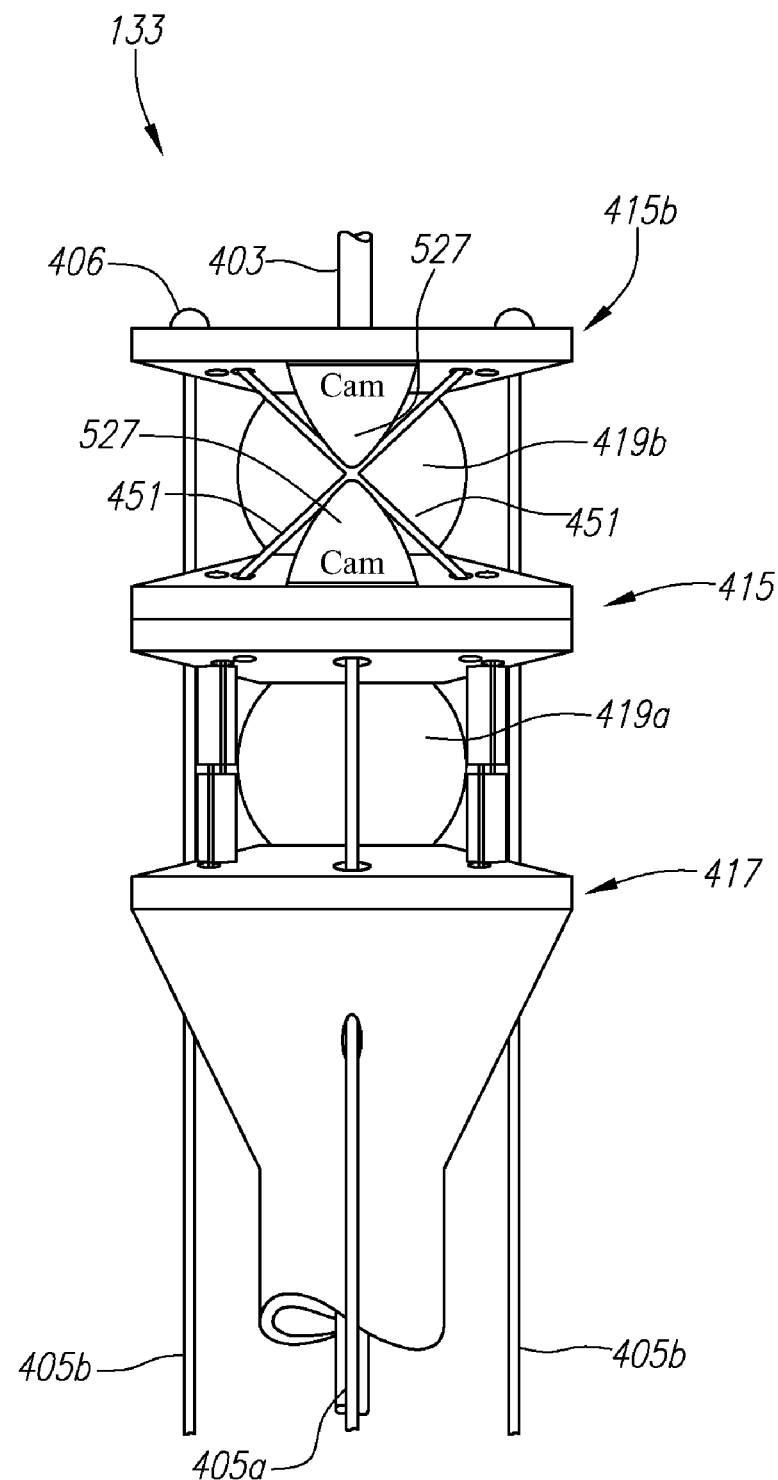

18A-D illustrate different views of another segment of a sheath catheter with which embodiments may be utilized and that includes shaped bottom and top surfaces for matingly engaging or interlocking with one or more adjacent segments;

FIG. 19 illustrates a further segment of a sheath catheter with which embodiments may be utilized;

FIGS. 20A-E illustrate a sheath catheter with which embodiments may be utilized and that includes wedge-like structures;

FIGS. 21A-F illustrate various views of unassembled and assembled components of a sheath catheter with which embodiments may be utilized and how the components are arranged and interlock with each other;

FIGS. 22A-M illustrate an adapter an rotatable apparatus constructed according to various embodiments and that includes an interface or wire guide apparatus, which may be a part of or integral with an instrument such as a catheter, or which may be a part of a separate component or rotational apparatus as illustrated, and a wire receiving apparatus, rotatable apparatus or rotatable or collar or tool (or portion thereof) configured to translate axial movement of a control element into rotational motion of a tool, which may be the collar or base, or a platform or working instrument operably coupled thereto, wherein FIGS. 22A-B are respective perspective and partial cross-sectional perspective views of an interface component constructed according to one embodiment, FIG. 22C is a perspective view of a tool base or rotatable collar of a rotatable apparatus constructed according to one embodiment, FIGS. 22D-F illustrate different inner lumen configurations of a rotatable apparatus, FIG. 22G is a perspective view of an interface and rotatable collar or tool base assembled together in an embodiment in which the interface is part of a separate rotatable apparatus; FIG. 22H is a front perspective view of a rotatable apparatus constructed according to one embodiment and one manner in which a control element is routed through channels or guides of the interface and rotatable collar or tool base; FIG. 22I is a rear perspective view of FIG. 22H, FIGS. 22J-K illustrate how the rotatable apparatus configured as shown in FIGS. 22H-I can be rotated by moving or adjusting the tension on a control element or relaxing a control element in tension, FIG. 22L is a front perspective view of a rotatable apparatus constructed according to another embodiment and one manner in which multiple control elements are routed through respective channels or guides of interface and rotatable collar or tool base components, FIG. 22M is a rear perspective view of the rotatable apparatus shown in FIG. 22L, FIGS. 22N-O illustrate how the rotatable apparatus configured as shown in FIGS. 22M-L can be rotated by moving or adjusting the tension of a control element;

FIGS. 23A-E illustrate embodiments of a rotatable apparatus constructed according to another embodiment that includes a catheter drive shaft, inner body or tool base that includes a helical drive element and is configured such that axial displacement of a catheter drive shaft also generates rotational motion, where FIG. 23A illustrates a helically threaded shaft in a retracted position, FIG. 23B illustrates the shaft shown in FIG. 23A in an extended position, FIG. 23C illustrates how the rotational apparatus embodiment shown in FIGS. 23A-B can be integrated within a system including a sheath catheter, FIG. 23D shows the shaft configured and retracted as shown in FIG. 23A and having a rectangular or square shaped lumen, and FIG. 23E shows the shaft configured and extended as shown in FIG. 23B and having a rectangular or square shaped lumen;

FIGS. 24A-E illustrate embodiments of a rotatable apparatus constructed according to another embodiment that includes a catheter drive shaft, inner body or tool base that includes a BNC drive or peg-groove element that is operable such that axial displacement of a catheter drive shaft also generates rotational motion, where FIG. 24A illustrates a shaft having a peg or protrusion in a retracted position, FIG. 23B illustrates the shaft shown in FIG. 24B in an extended position, FIG. 23C illustrates how the rotational apparatus embodiment shown in FIGS. 24A-B can be integrated within a system including a sheath catheter, FIG. 23D shows the shaft configured and retracted as shown in FIG. 24A and having a rectangular or square shaped lumen, and FIG. 24E shows the shaft configured and extended as shown in FIG. 24B and having a rectangular or square shaped lumen;

FIGS. 25A-H illustrate an embodiment of a rotatable apparatus that includes a ratchet drive element to rotate a segment, wherein FIG. 25A is a perspective view of a distal portion of an inner body including a helically threaded surface and a guide apparatus, FIG. 25B is partial top view of a portion of a helical gear and an associated pin, FIG. 25C is a cross-sectional view of a helical gear and its associated pin in a first position, FIG. 25D is a cross-sectional view of a helical gear and its associated pin in another position, FIG. 25E is cross-sectional view of a surface of a slotted track or guide upon which a pin traverses, FIG. 25F illustrates a pin carried by a guide and positioned at a top of a track or groove of a gear, FIG. 25G illustrates the pin shown in FIG. 25F moving along the guide and through a track or groove of the gear, and FIG. 25H illustrates the pin traversing a different portion of the guide and the gear;

FIGS. 26A-E illustrate an embodiment of a rotatable apparatus that includes a dual ratchet drive element to allow bidirectional rotation, wherein FIG. 26A is a perspective view of internal components of a distal portion of a rotational apparatus, FIG. 26B is a cross-sectional view helical gears and associated pins in a first position, FIG. 26C is a cross-sectional view of helical gears and pins at different positions, FIG. 26D illustrates pins carried by respective guides and at respective initial positions, and FIG. 26E illustrates pins carried by respective guides being moved along the guides and through tracks of associated gears;

FIGS. 27A-D illustrate an embodiment of a rotatable apparatus that includes a harmonic drive element to rotate, wherein FIG. 27A illustrates various components of a harmonic drive element, FIG. 27B is a cross-sectional view of FIG. 27A along line B-B with engagement at the tops and bottoms of gears, and FIG. 27C is a cross-sectional view of FIG. 27A along line B-B with engagement at the sides of gears, and FIG. 27D illustrates how the rotational apparatus embodiment shown in FIGS. 27A-C can be integrated within a system including a sheath catheter;

FIGS. 28A-E illustrate an embodiment of a rotatable apparatus that includes a wobble plate drive plate that utilizes an arm or finger element that engages a top surface of a gear element of a wobble plate drive, wherein FIG. 28A is a perspective view of one embodiment of a wobble plate drive element, FIG. 28B is an expanded view further illustrating components of the wobble drive element shown in FIG. 28A, and FIGS. 28C-E illustrate operation of the wobble plate drive element as force is applied to different portions of a top surface of a gear element;

FIGS. 29A-D illustrate an embodiment of a rotatable apparatus that includes a wobble plate drive plate that is rotatable utilizing control elements, wherein FIG. 29A is a perspective view of a wobble plate drive element driven by control elements, and FIGS. 29C-E illustrate operation of the wobble plate drive element as force is sequentially applied to different portions of a top surface of a gear element by sequentially pulling control elements;

FIG. 30 illustrates one embodiment of a rotatable apparatus in the form of a planetary gear drive, FIGS. 30A-K illustrate other embodiments of planetary gear drives, wherein FIG. 30A is a top view of a planetary gear drive element and showing driving of planetary gears, FIG. 30B is a top view of a planetary gear drive element and showing rotation of a sun gear after a revolution of a planetary gear, FIG. 30C is a cross-sectional view of the drive assembly within a flexible instrument member, FIG. 30D is an exploded cross-sectional view of a drive assembly, FIG. 30E is a top perspective view of a planetary gear drive, FIG. 30F is a bottom perspective view of a planetary gear drive, FIG. 30G further illustrates components of a planetary gear drive assembly, FIG. 30H is a further perspective view of a planet gear drive element, FIG. 30I is a cross-sectional view of a planet gear drive element, FIG. 30J is a perspective view of a retention disc, FIG. 30K is a perspective view of a sun band piece, FIG. 30L further illustrates a planet gear component;

FIGS. 31A-P illustrate orientation platform or interface for a working instrument with which rotational apparatus embodiments can be utilized and that is coupled to a distal end of a catheter and includes a ball and socket apparatus, wherein FIG. 31A is a perspective view of an assembly including an orientation platform, FIG. 31B further illustrates a distal portion of the assembly shown in FIG. 31A, FIG. 31C is an exploded view of assembly components shown in FIGS. 31A-B, FIG. 31D is a perspective view of a platform constructed according to one embodiment, FIG. 31E is an exploded view of the platform shown in FIG. 31D, FIGS. 31F-I illustrate how the platform shown in FIGS. 31D-D can be controlled, and FIGS. 31J-M illustrate how a platform constructed according to another embodiment in which a control element extends through a spring may be controlled, and FIGS. 31N-P illustrate how a platform constructed according to another embodiment in which a control elements extends through respective springs may be controlled;

FIGS. 32A-G illustrate an orientation platform or interface with which rotational apparatus embodiments can be utilized and that is constructed with a ball and socket assembly, wherein FIG. 32A is a perspective view of an assembly including an orientation platform, FIG. 32B further illustrates a distal portion of the assembly shown in FIG. 32A, FIG. 32C is an exploded view of assembly components shown in FIGS. 32A-B, FIGS. 32D-G illustrate how the platform shown in FIGS. 32B-C can be controlled;

FIGS. 33A-C illustrate yet another orientation platform or interface that includes a ball and socket apparatus, wherein FIG. 33A is a perspective view of an assembly that includes an orientation platform, FIG. 33B further illustrates a distal portion of the assembly shown in FIG. 33A and including two springs, and FIG. 33C is an exploded view of assembly components shown in FIGS. 33A-B;

FIGS. 34A-C illustrate still another orientation platform or interface constructed with a ball and socket apparatus, wherein FIG. 34A is a perspective view of an assembly that includes an orientation platform, FIG. 34B further illustrates a distal portion of the assembly shown in FIG. 34A and including three springs and a control element, and FIG. 34C is an exploded view of assembly components shown in FIGS. 34A-B;

FIGS. 35A-C illustrate a further orientation platform or interface constructed with a ball and socket apparatus, wherein FIG. 35A is a perspective view of an assembly that includes an orientation platform, FIG. 35B further illustrates a distal portion of the assembly shown in FIG. 35A and including four equidistantly spaced control elements, and FIG. 35C is an exploded view of assembly components shown in FIGS. 35A-B;

FIGS. 36A-C illustrate yet another orientation platform or interface constructed with a ball and socket apparatus, wherein FIG. 36A is a perspective view of a flexible catheter assembly that includes an orientation platform, FIG. 36B further illustrates a distal portion of the assembly including eight equidistantly spaced control elements, and FIG. 36C is an exploded view of assembly components shown in FIGS. 36A-B;

FIGS. 37A-E illustrate an orientation platform or interface with which embodiments may be utilized and that is constructed with a ball and socket apparatus that includes non-crossing control elements and control elements in the form of crossing cables, wherein FIGS. 37A-B illustrate a platform including crossing cables and clockwise platform rotation, FIGS. 37C-D illustrate counter-clockwise platform rotation, and FIG. 37E illustrates a platform rotating clockwise with positive pitch;

FIGS. 38A-C illustrate an orientation platform or interface constructed with a ball and socket apparatus that includes control elements in the form of crossing cables, wherein FIGS. 38A-B illustrate counter-clockwise platform rotation, and FIG. 38C illustrates clock-wise platform rotation with positive pitch;

FIGS. 39A-B illustrate yet another orientation platform or interface constructed with a ball and socket apparatus that includes crossing control elements and control elements extending across a distal platform surface, wherein FIG. 39A is a perspective view of a platform including only control cables, and FIG. 39B is a perspective view of a platform including both non-overlapping control elements and overlapping cables;

FIGS. 40A-B illustrate a further orientation platform or interface having a ball and socket configuration and crossing control elements and counter-clockwise rotation of the platform with positive pitch and positive yaw;

FIGS. 41A-B illustrate another orientation platform or interface that includes a spacer element in the form of an elastomeric cylinder, wherein FIG. 41A is a side view of a platform according to another embodiment, and FIG. 41B is an exploded view of the platform shown in FIG. 41A;

FIGS. 42A-B illustrate a further orientation platform or assembly that includes a flexure spacer element, wherein FIG. 42A is a side view of a platform according to another embodiment, and FIG. 42B is an exploded view of the platform shown in FIG. 42A;

FIGS. 43A-B illustrate another orientation platform or interface with which embodiments may be utilized and that includes a non-spherical spacer element, wherein FIG. 43A is a side view of a platform according to another embodiment, and FIG. 43B is an exploded view of the platform shown in FIG. 43A;

FIG. 44 is a side view of another orientation platform or interface that includes a flexible coil spacer element;

FIG. 45 is a side view of a further orientation platform or interface employing a universal joint spacer element;

FIGS. 46A-C illustrate a further orientation platform or interface with which rotational apparatus embodiments may be utilized and that includes a spacer element in the form of a pin and groove arrangement, wherein FIG. 46A is a perspective view of a platform including a pin and groove arrangement, FIG. 46B is a cross-sectional side view of the platform shown in FIG. 46A along line C-C, and FIG. 46C a cross-sectional front view of the platform shown in FIG. 46B parallel to line C-C;

FIGS. 47A-O illustrate a multi-level platform or interface including multiple ball and socket apparatus and components thereof, wherein FIG. 47A is a perspective view an assembly including a multi-stage or multi-level platform constructed according to another embodiment, FIG. 47B further illustrates a distal portion of the multi-level platform shown in FIG. 47A, FIG. 47C is an exploded view of the multi-level platform shown in FIGS. 47A-B FIGS. 47D-E are cross-sectional views of the multi-level platform shown in FIGS. 47A-C and pitch motion of the platform, FIGS. 47F-G are cross-sectional views showing yaw motion of the platform, FIG. 47H illustrates platform components and different types of possible motion of first and second platform members; FIG. 47I is an exploded view of a platform constructed according to one embodiment; FIGS. 47J-K further illustrate spacer element of a platform movably retained between plates; FIG. 47L illustrates a base member constructed according to one embodiment, FIG. 47M illustrates a spacer element constructed according to one embodiment, FIG. 47N is a cross-sectional view of a base member, FIG. 47O is a cross-sectional view of assembled platform components including a base member, platform members, and spacer elements;

FIGS. 48A-G illustrate another multi-level platform or interface including multiple ball and socket assemblies, wherein 48A is a perspective view of an assembly including a multi-stage or multi-level platform constructed according to another embodiment, FIG. 48B is a perspective view showing the platform in further detail, FIG. 48C is an exploded view of the platform shown in FIG. 48B, FIG. 48D is a front cross-sectional view of the platform shown in FIG. 48B, FIG. 48E is a side cross-sectional view of the platform shown in FIG. 48B, FIG. 48F is a cross-sectional view of the platform shown in FIG. 48D with pitch motion, and FIG. 48G is a cross-sectional view of the platform shown in FIG. 48E with yaw motion;

FIGS. 49A-C illustrate a further multi-level platform or interface including spacer elements in the form of semi-spherical balls, wherein FIG. 49A is a perspective view of an assembly including a multi-stage or multi-level platform constructed according to another embodiment, FIG. 49B is a side view of the platform, FIG. 49C is an exploded view showing the platform components in further detail;

FIGS. 50A-B illustrate another multi-level platform or interface with which embodiments may be utilized and that includes spacer elements in the form of elastomeric cylinders, wherein FIG. 50A is a side view of the platform, and FIG. 50B is an exploded view of the platform;

FIGS. 51A-B illustrate a multi-level platform or interface having multiple orientation platforms with spacer elements in the form of flexures, wherein FIG. 51A is a side view of the platform, and FIG. 51B is an exploded view of the platform;

FIGS. 52A-B illustrate another multi-level platform or interface having spacer elements in the form of non-spherical balls, wherein FIG. 52A is a side view of the platform, and FIG. 52B is an exploded view of the platform;

FIG. 53 is a side view of another multi-level platform or interface having spacer elements in the form of flexible coils;

FIG. 54 is a side view of another multi-level platform or interface having spacer elements in the form of universal joints;

FIGS. 55A-G illustrate a multi-level platform or interface with which embodiments may be utilized and that includes crossing control elements and multiple ball and socket assemblies, wherein FIG. 55A is a perspective view of an assembly including a multi-stage or multi-level platform constructed according to another embodiment, FIG. 55B is a perspective view of the platform showing crossing cable elements, FIG. 55B-1 illustrates a spacer element having an eyelet for use in facilitating crossing or overlapping of control cables, FIG. 55B-2 illustrates a spacer element having a the down element for use in facilitating crossing or overlapping of control cables, FIG. 55C is a top view of a platform base member, FIG. 55D is front view of the platform shown in FIG. 55B, FIG. 55E is a cross-sectional view of the platform shown in FIG. 55D, FIG. 55F is a cross-sectional view of the platform shown in FIG. 55E with pitch motion, FIG. 55G is a cross-sectional view of the platform shown in FIG. 55D with yaw motion;

FIGS. 56A-C illustrate another multi-level platform or interface having crossing control elements and components thereof, wherein FIG. 56A is a perspective view of a multi-level platform constructed according to another embodiment, FIG. 56B illustrates how the platform shown in FIG. 56A can be rotated clockwise, and FIG. 56C illustrates how the platform shown in FIG. 56A can be rotated counter-clockwise; and FIG. 57 is a side view of multi-level platform or interface having crossing control elements and cams to facilitate crossing arrangements.

DETAILED DESCRIPTION OF ILLUSTRATED EMBODIMENTS

Embodiments of the present invention are directed to apparatus, systems and methods for controllably rotating a tool, such as a tool base, guide catheter, and/or working instrument, coupled to a distal end portion of a medical instrument such as a catheter of a robotic instrument system. Embodiments provide a rotatable wrist-like device to controllably rotate system components and can be utilized with various robotic instrument systems including an extension system that provides control of the rigidity of one or more flexible catheter instruments such as a multi-segment sheath catheter in order to controllably form one or more platforms from which other instruments can be manipulated. In such systems, segments of the sheath catheter can be manipulated or controlled such that the sheath catheter assumes a flexible, no tension, low tension or substantially non-rigid state (hereafter referred to as flexible (F) or a flexible state (F)) or a rigid or substantially rigid (R) state (hereafter referred to as a substantially rigid state (R)).

While in the flexible state (F), the sheath catheter can be advanced through an elongate main, master, or outer sheath (generally referred to as a master or elongate sheath) with sufficient flexibility and maneuverability to traverse curves and turns within the patient and be positioned at a target site or area of interest. After the main sheath is advanced into the patient and positioned adjacent to or near target tissue or another desired area, the sheath catheter may extend or be deployed from the main sheath and be controllably transformed from the flexible state (F) to the substantially rigid state (R). A rotatable apparatus, adapter or tool may controllably rotated such that a system component such as a guide catheter and/or working instrument are controllably rotated, e.g., when the sheath catheter is placed in a substantially rigid state (R). In this manner, embodiments of the invention advantageously provide controllable articulation or bending and controllable rotation of robotic system components in order to more effectively manipulate and precise position system components at a target site, thereby enabling more effective and precise surgical procedures.

Examples of robotic surgical systems and components thereof in which, or with which, system, apparatus and method embodiments directed to controllable rotation may be implemented or utilized are described with reference to 1-11H. Multi-segment, interlocking components with which embodiments may be utilized and having rigidity that is controllable by manipulating a control element for controllably forming flexible and substantially rigid structures are described with reference to FIGS. 12-21F. Rotatable apparatus or tool embodiments and their operation are described in further detail with reference to FIGS. 22A-30L. FIGS. 31A-57 illustrate orientation platforms that may be included within systems in which embodiments may be implemented.

FIG. 1 illustrates an extension system that includes a sheath catheter 102 having controllable rigidity and that can be placed in the substantially rigid state (R) to form a substantially rigid platform (P). As shown in FIG. 1, the sheath catheter 102 extends from a distal end 62 of a master sheath 63, and from which another system instrument, such as a guide catheter 37 and/or working instrument 41, may be controlled or manipulated. In the illustrated system, one rigid sheath catheter 102 may form a platform (P). Another sheath catheter 102 is shown in phantom to illustrate that one or more additional sheath catheters 102 may be advanced through the master sheath 63 and controlled to cooperatively form a substantially rigid platform or to form multiple substantially rigid platforms that extend beyond the distal end 62 of the master sheath 63. Thus, a platform (P) may be formed by one or more substantially rigid sheath catheters 102, and for ease of explanation, reference is made to a platform (P) being formed by one or more substantially rigid sheath catheters 102.

In this manner, the rigidity of components of robotic instrument systems can be controlled and manipulated while advantageously reducing the lever arm (LA) of the working instrument 41, thereby assisting the surgeon with the manipulation and control of the catheter sheath 102 and other instruments at the operation or target site. In other words, the platform (P) serves as an extension platform, or a new, more distal point of reference or orientation for manipulating and controlling a system component. With this configuration, the point of reference or orientation is moved from the proximal location of the catheter (as in known systems) to a location that is closer to the distal portion of the catheter and the target site such that a previously long lever (LA) arm is substantially reduced to a shorter lever arm (SLA).

For example, as shown in FIGS. 2A and 3A, in known systems, the longer lever arm (LA) of a working instrument such as an ablation catheter may extend between a proximal point of a catheter or point of entry into the patient and wind all the way to a distal portion of the catheter, target area, or point of treatment. This longer lever arm (LA) may extend a substantial length, and may even extend outside of the patient's body if the proximal end of the catheter is located outside of the patient (OP).

However, referring to FIGS. 2B and 3B, with extension systems that include or that may be utilized with rotational apparatus embodiments, a shorter lever arm (SLA) is advantageously substantially reduced or minimized by controllably forming an intermediate platform (P) inside of the patient (IP). The platform (P) extends from or beyond a distal end 62 of the master sheath 63, thereby providing a point of reference that is near or adjacent to the target site and enhancing control over bending and manipulation of guide catheters 37 and associated working instruments 41 that may not otherwise be possible utilizing known systems and longer lever arms (LA) that must traverse significant vasculature and long distances.

Figure 4P:
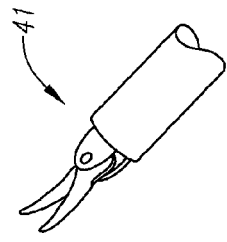
FIG. 4P illustrates a pair of curved scissors.
Figure 4U:
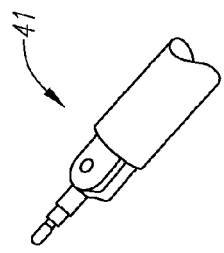
FIG. 4U illustrates a cautery spatula.
Figure 4Z:
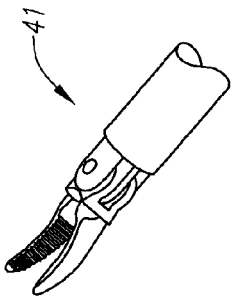
FIGS. 4A-Z illustrates various working instruments that can be utilized with embodiments, where
Figure 4O:
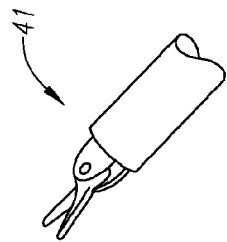
FIG. 4O illustrates a pair of round tip scissors.
Figure 4T:
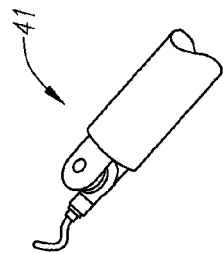
FIG. 4T illustrates a cautery hook.
Figure 4Y:
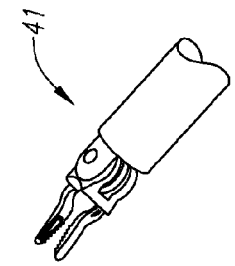
FIG. 4B illustrates a serrated Manhes grasping forceps.
FIG. 4C illustrates surgical and serrated Manhes grasping forceps.
FIG. 4D illustrates cobra type forceps with claw and twin rows of teeth for myomis.
FIG. 4E illustrates Davis & Geak forceps.
FIG. 4F illustrates Johann atraumatic grasping forceps.
FIG. 4G illustrates a Metzenbaum type of serrated curved scissors.
FIG. 4H illustrates a pair of straight micro dissection scissors.
FIG. 4I illustrates a pair of hook scissors.
FIG. 4J illustrates needle holder forceps with short jaws.
FIG. 4K illustrates biopsy forceps with up and down thorns.
FIG. 4L illustrates long tip forceps.
FIG. 4M illustrates Cadiere forceps.
FIG. 4N illustrates a pair of Potts scissors.
FIG. 4Q illustrates a bowel grasper.
FIG. 4R illustrates Resano forceps.
FIG. 4S illustrates hot shears.
FIG. 4V illustrates a double fenestrated grasper.
FIG. 4W illustrates a cobra grasper.
FIG. 4X illustrates a bipolar cautery instrument, FIG. 4Y illustrate a micro bipolar cautery instrument.
Figure 4N:
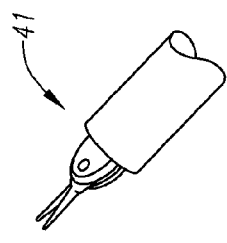
Figure 4S:
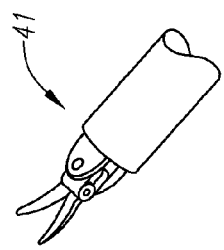
Figure 4X:
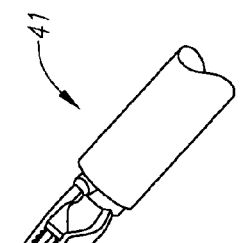
Figure 4M:
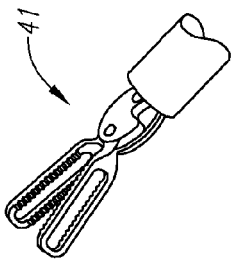
Figure 4R:
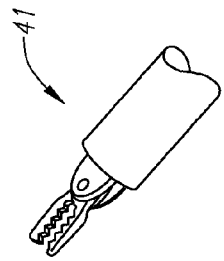
Figure 4W:
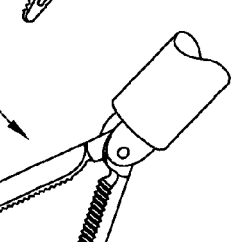
Figure 4L:
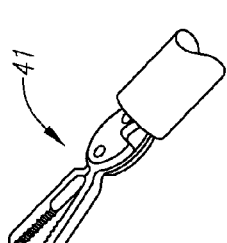
Figure 4Q:
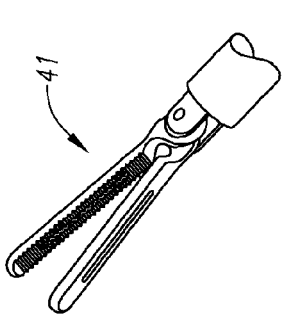
Figure 4V:
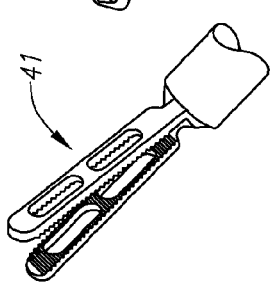

Apparatus and systems for providing controllable rigidity may be utilized with various robotic system components and working instruments 41, including an end effector. An end effector includes a working distal part that is located at the distal tip or working end of a catheter member for effecting an action. Examples of suitable end effectors are shown in FIGS. 1 and 4A-Z. The working instrument 41 may be, e.g., an electrode, blade, clasper, clamp, scissors, endoscope, and may include a single element or multiple elements. The working instrument 41 may also be a steerable catheter, an endoscope and other end-effectors. Further, embodiments may be configured to include one or more lumens through which working instruments, such as tools, other catheters, optical fibers, illumination fibers, etc. may be deployed to a working or surgical site. Embodiments may be part of a robotic instrument system that is used for treating cardiac arrhythmias such as atrial fibrillation. It should be understood, however, that embodiments can be used with various working instruments 41 including, for example, endoscopes and laparoscopes, and for performing various other surgical operations or procedures. For ease of illustration, this specification generally refers to a working instrument 41, but it should be understood that various working instruments 41 may be utilized for different purposes.

Figure 5A:
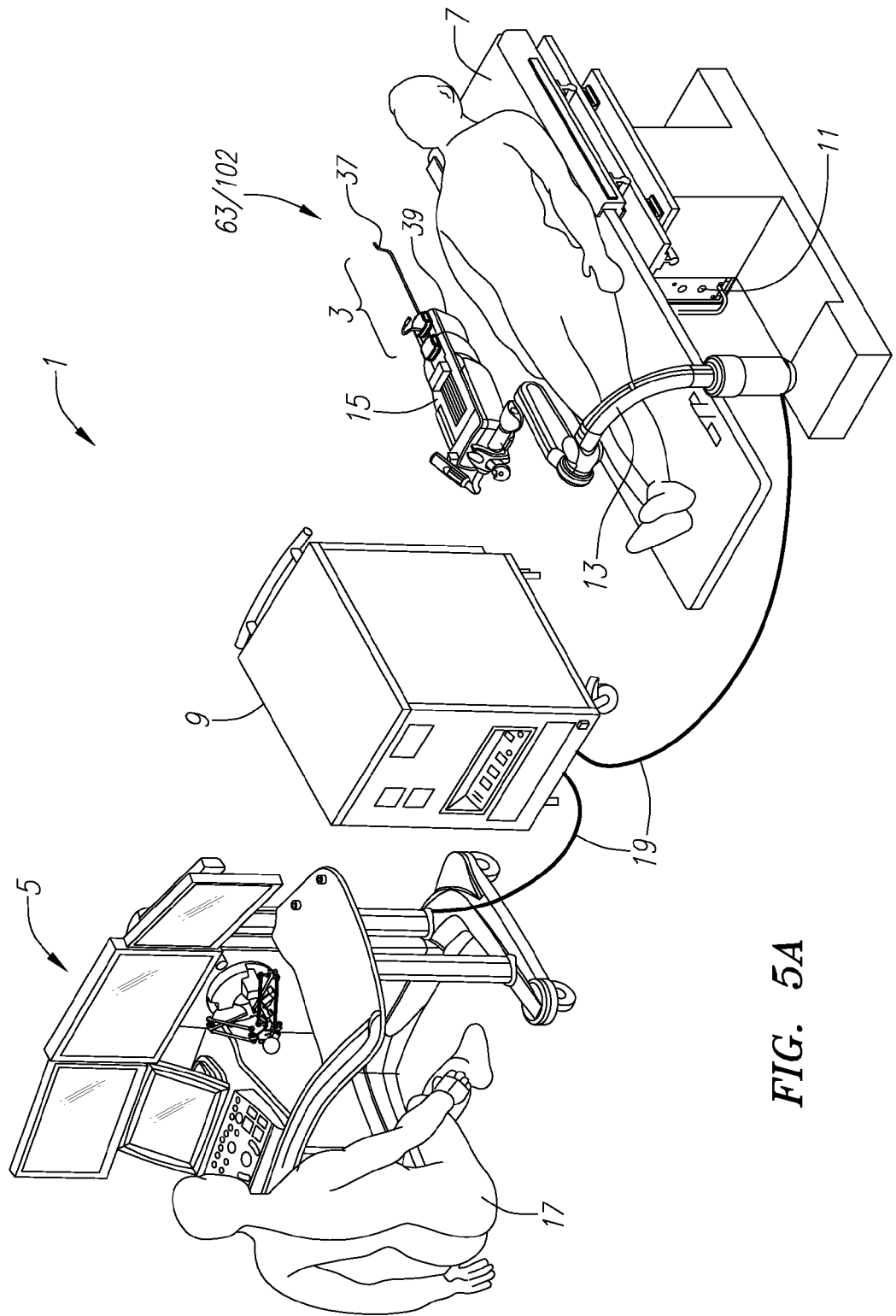
FIGS. 5A-E illustrate a robotic instrument system in which embodiments may be implemented or with which embodiments may be utilized, where

Referring to FIG. 5A, one example of a robotic catheter system 1 in which embodiments and a sheath 102 having controllable rigidity may be implemented includes a flexible assembly 3, an operator workstation 5 located remotely from an operating table 7, an electronics rack 9, a bedside electronics box 11, a setup joint mounting brace 13, and an instrument driver 15. A surgeon 17 seated at the operator workstation 5 monitors a surgical procedure, patient vitals, and controls one or more flexible catheter assemblies 3. Although the various components of the system 1 are illustrated in close proximity to each other, in other embodiments, components may be separated from each other, e.g., in separate rooms. For example, the instrument driver 15, the operating table 7, and the bedside electronics box 11 may be located in the surgical area, whereas the operator workstation 5 and the electronics rack 9 may be located outside of the surgical area behind a shielded partition.

In one embodiment, system 1 components may communicate with other components via a network, thus allowing for remote surgery such that the surgeon 17 may be in the same or different building or hospital site. For this purpose, a communication link may be provided to transfer signals between the operator control station 5 and the instrument driver 15. Components may be coupled together via cables 19 as necessary for data communication. Wireless communications may also be utilized.

Figure 5B:
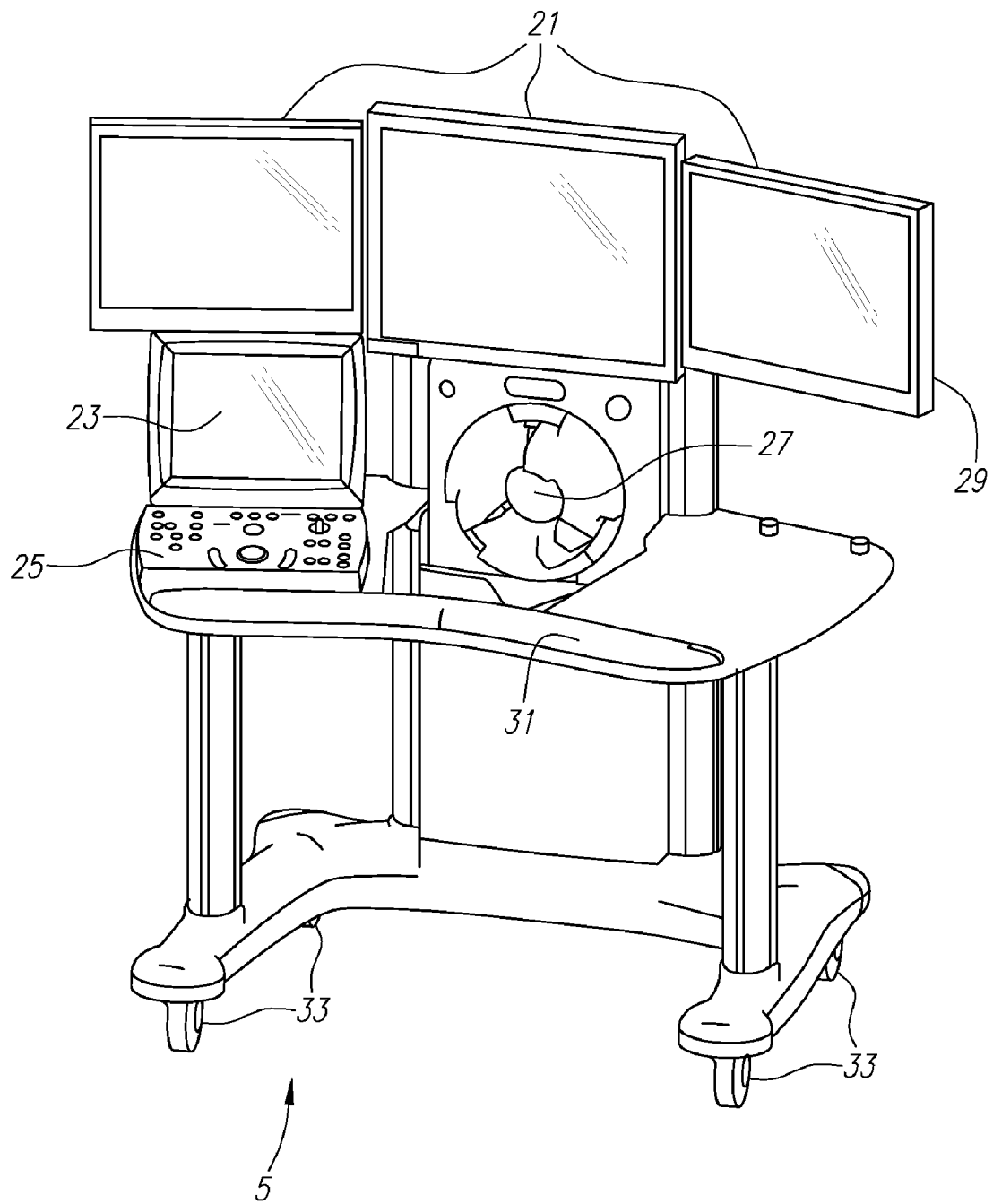
Figure 5C:
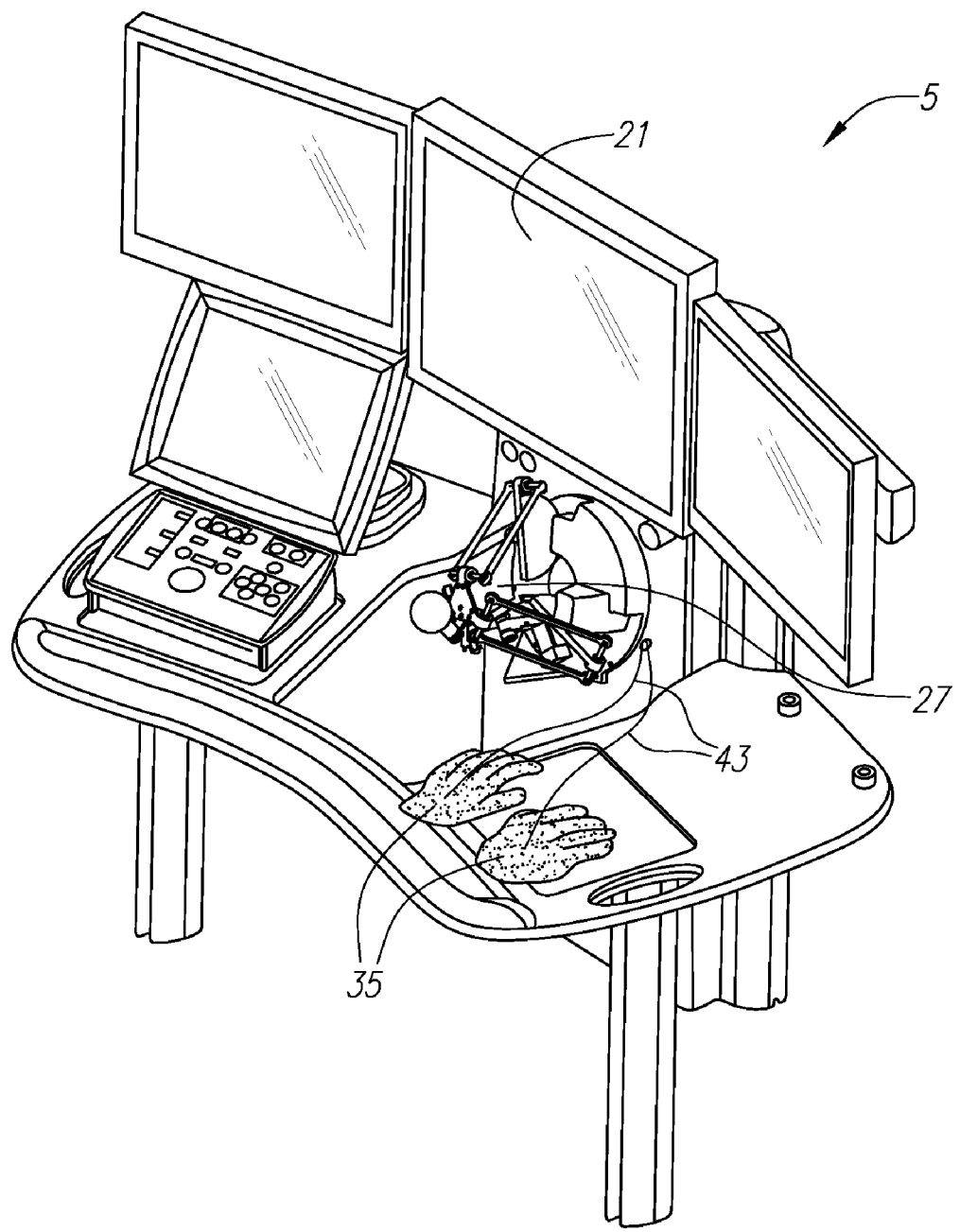
Figure 5D:
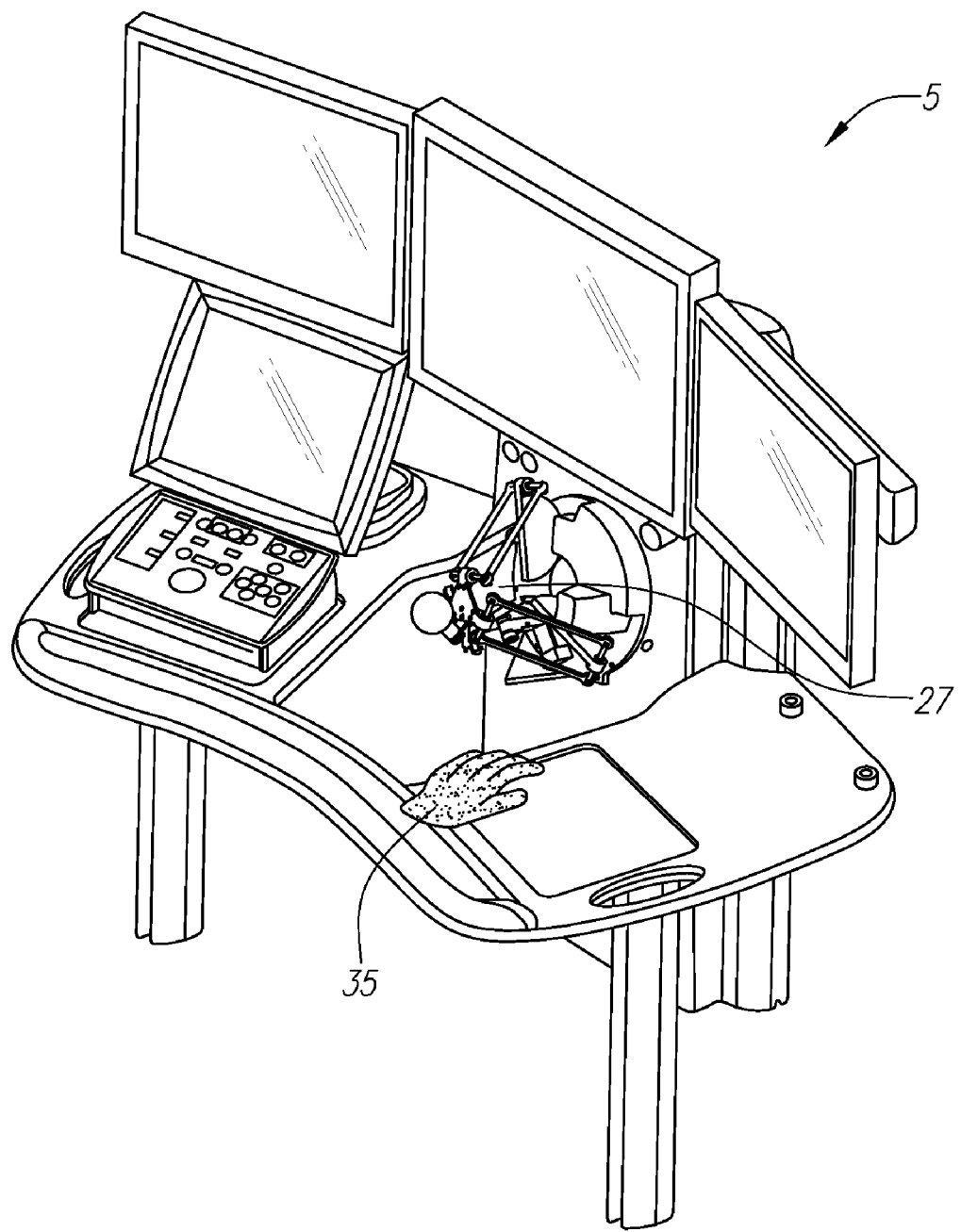

Referring to FIGS. 5B-D, one example of a suitable operator workstation 5 includes a console 31 having display screens 21, a touchscreen user interface 23, a control button console or pendant 25, and a master input device (MID) 27. The MID 27 may be a multi-degree-of-freedom device that includes multiple joints and associated encoders. The MID 27 software may be a proprietary module packaged with an off-the-shelf master input device system, such as the Phantom® from SensAble Technologies, Inc., which is configured to communicate with the Phantom® Haptic Device hardware at a relatively high frequency as prescribed by the manufacturer. Other suitable MIDs 27 are available from suppliers such as Force Dimension of Lausanne, Switzerland. The MID 27 may also have haptics capability to facilitate feedback to the operator, and software modules pertinent to such functionality may be operated on the master computer 49. An example of data glove 35 software is a device driver or software model such as a driver for the 5DT Data Glove. In other embodiments, software support for the data glove master input device is provided through application drivers such as Kaydara MOCAP, Discreet 3D Studio Max, Alias Maya, and SoftImage|XSI.

The instrument driver 15 and associated flexible catheter assembly 3 and working instruments 41 may be controlled by an operator 17 via the manipulation of the MID 27, data gloves 35, or a combination of thereof. During use, the operator 17 manipulates the pendant 25 and MID 27 to cause the instrument driver 15 to remotely control flexible catheters 3 that are mounted thereon. Inputs to the operator workstation 5 to control the flexible catheter assembly 3 can entered using the MID 27 and one or more data gloves 35. The MID 27 and data gloves 35, which may be wireless, serve as user interfaces through which the operator 17 may control the operation of the instrument driver 15 and any instruments attached thereto. A disable switch 29 may be used to temporarily disable the system or instrument. It should be understood that while an operator 17 may robotically control one or more flexible catheter devices via an inputs device, a computer or other controller of the robotic catheter system 1 may be activated to automatically position a catheter instrument and/or its distal extremity inside of a patient or to automatically navigate the patient anatomy to a designated surgical site or region of interest.

Figure 5E:
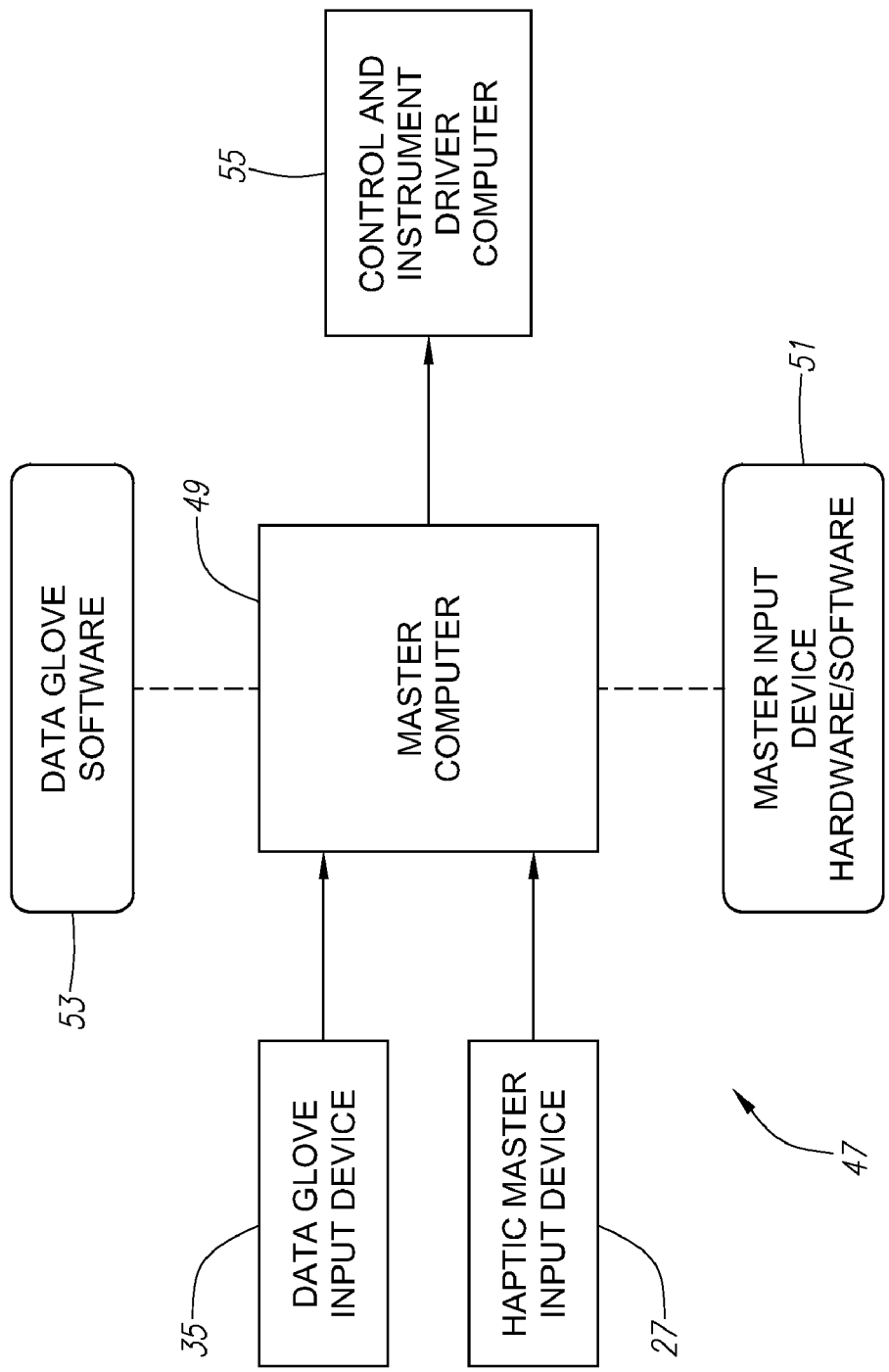
Figure 6:
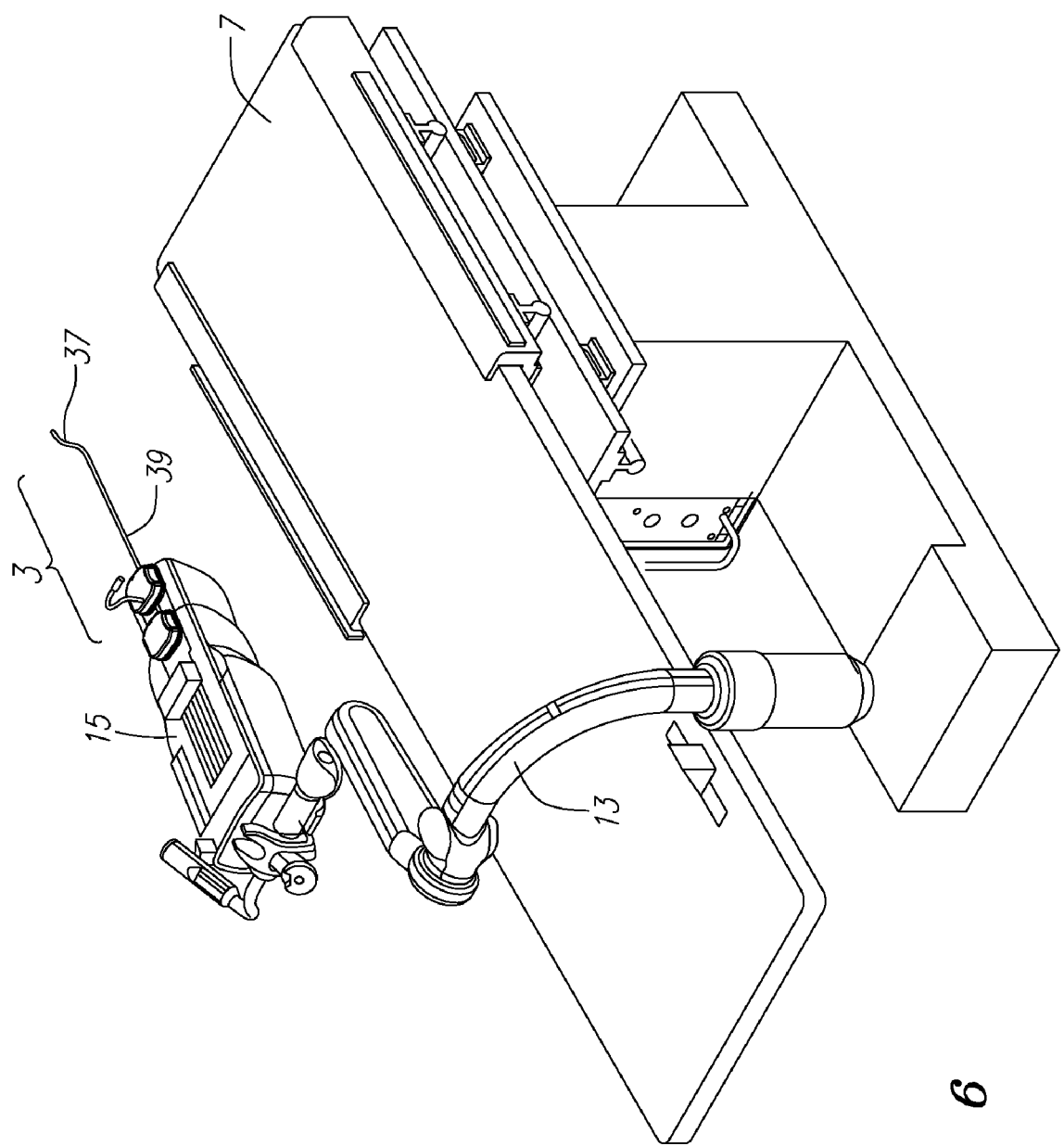
FIG. 6 illustrates a setup joint or support assembly of a robotic instrument system with which embodiments may be utilized.
Figure 7A:
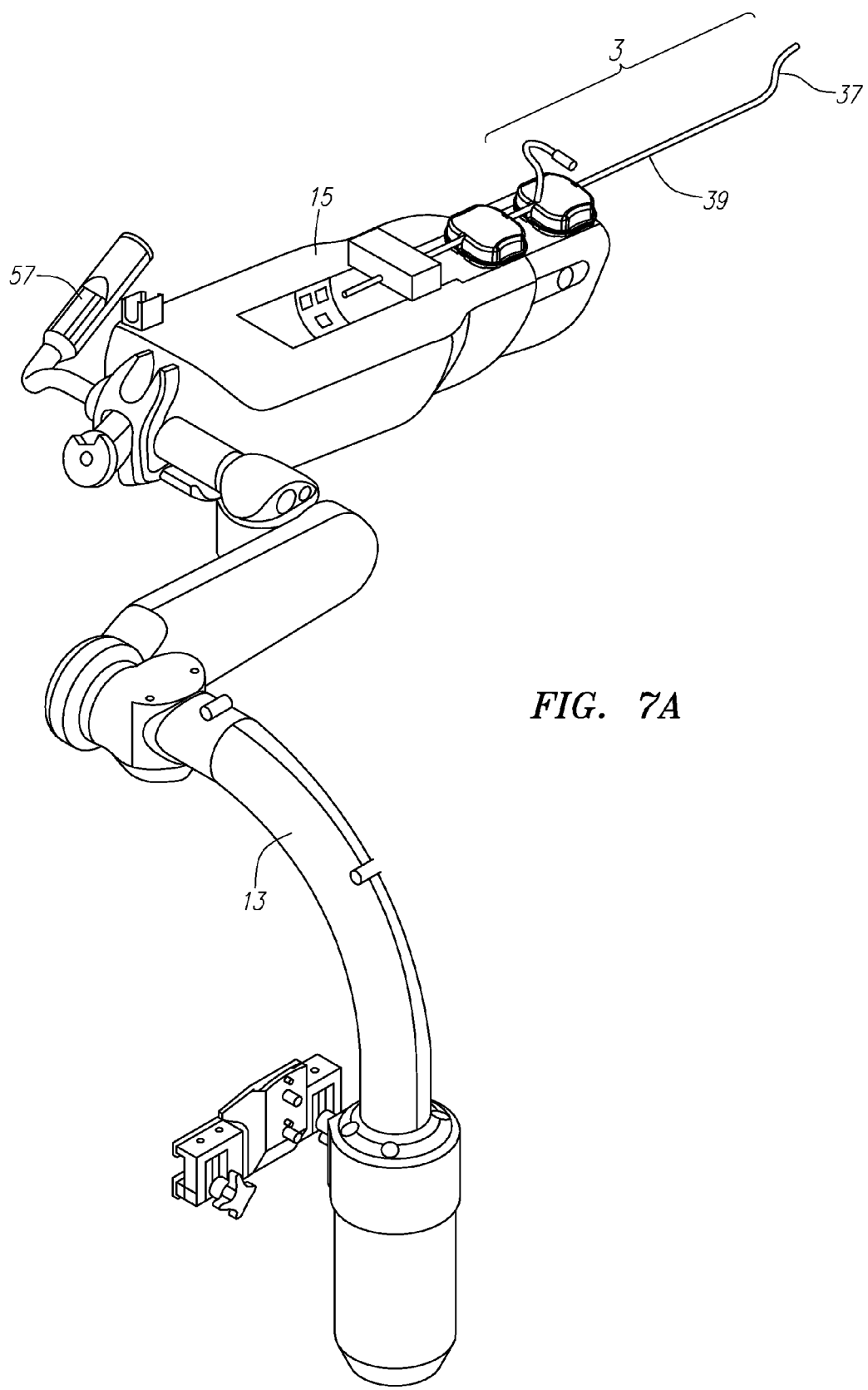
FIGS. 7A-E illustrate various aspects and components of a support assembly with which embodiments may be utilized, where
Figure 7B:
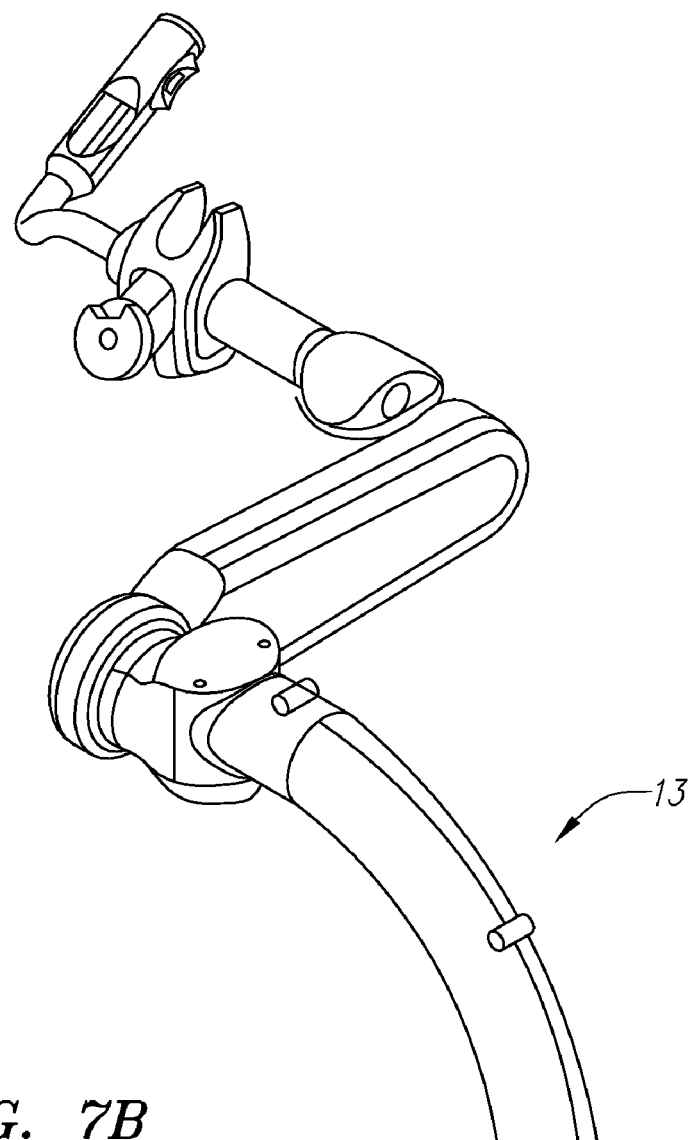
Figure 7C:
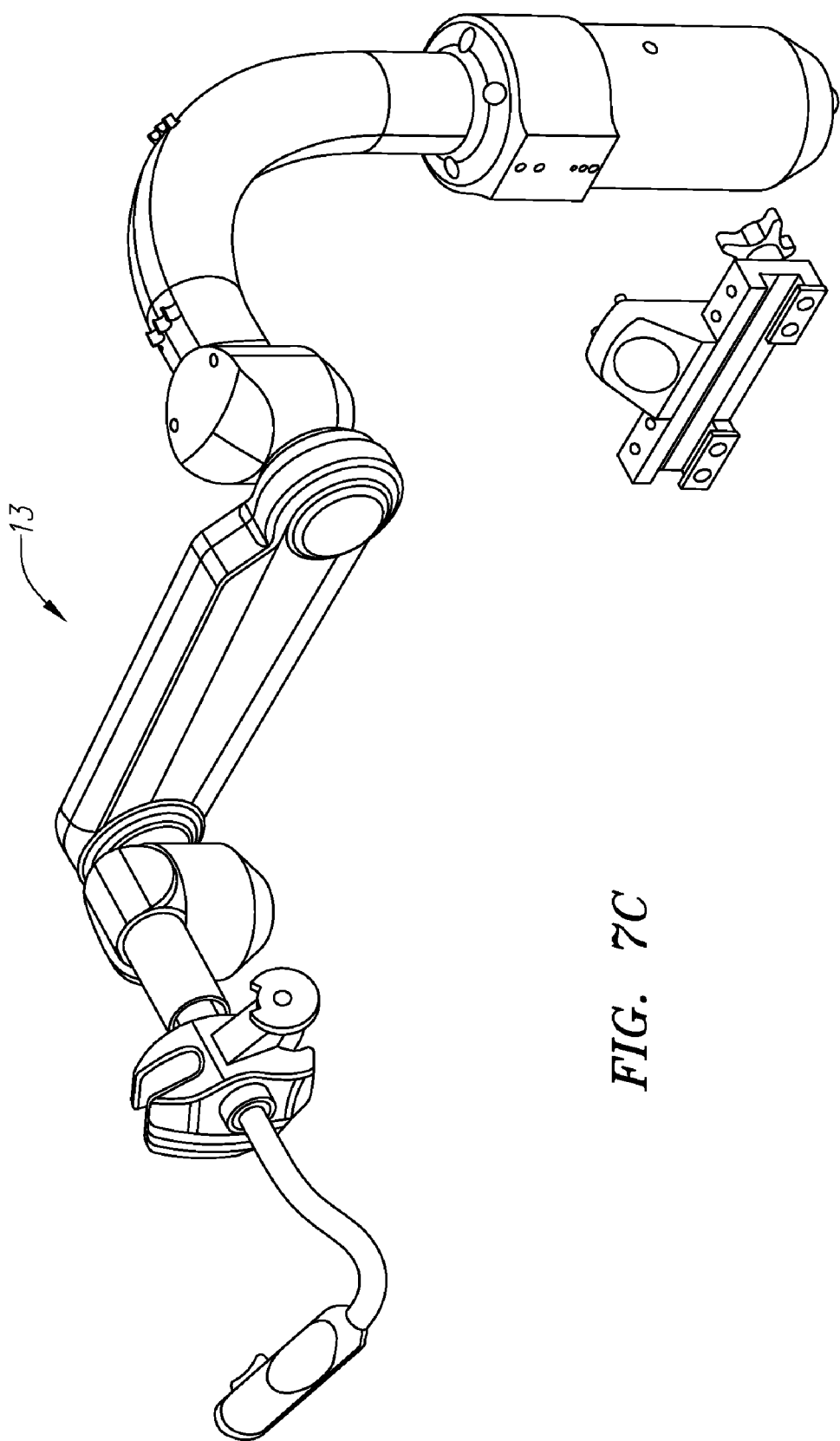
Figure 7D:
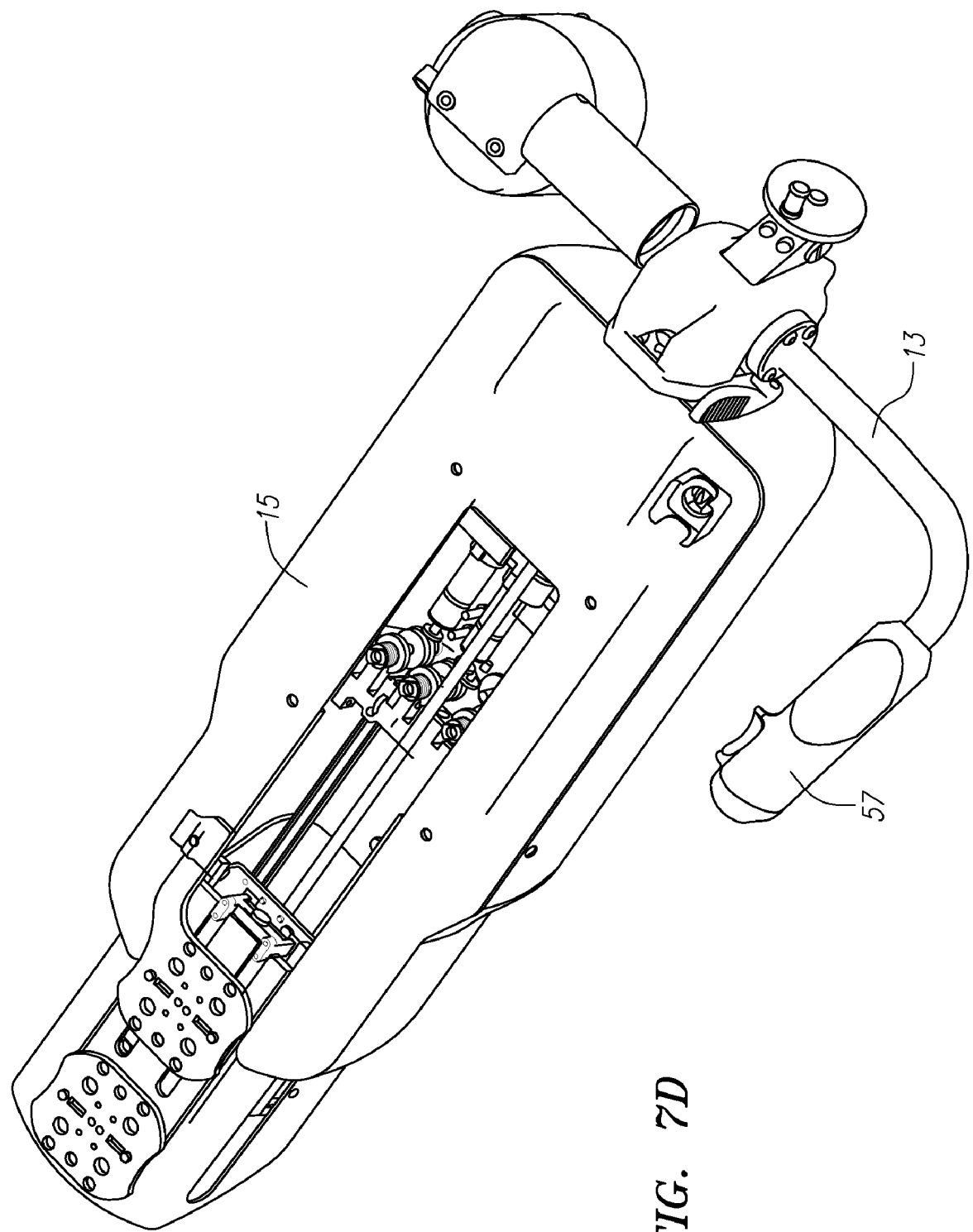
Figure 7E:
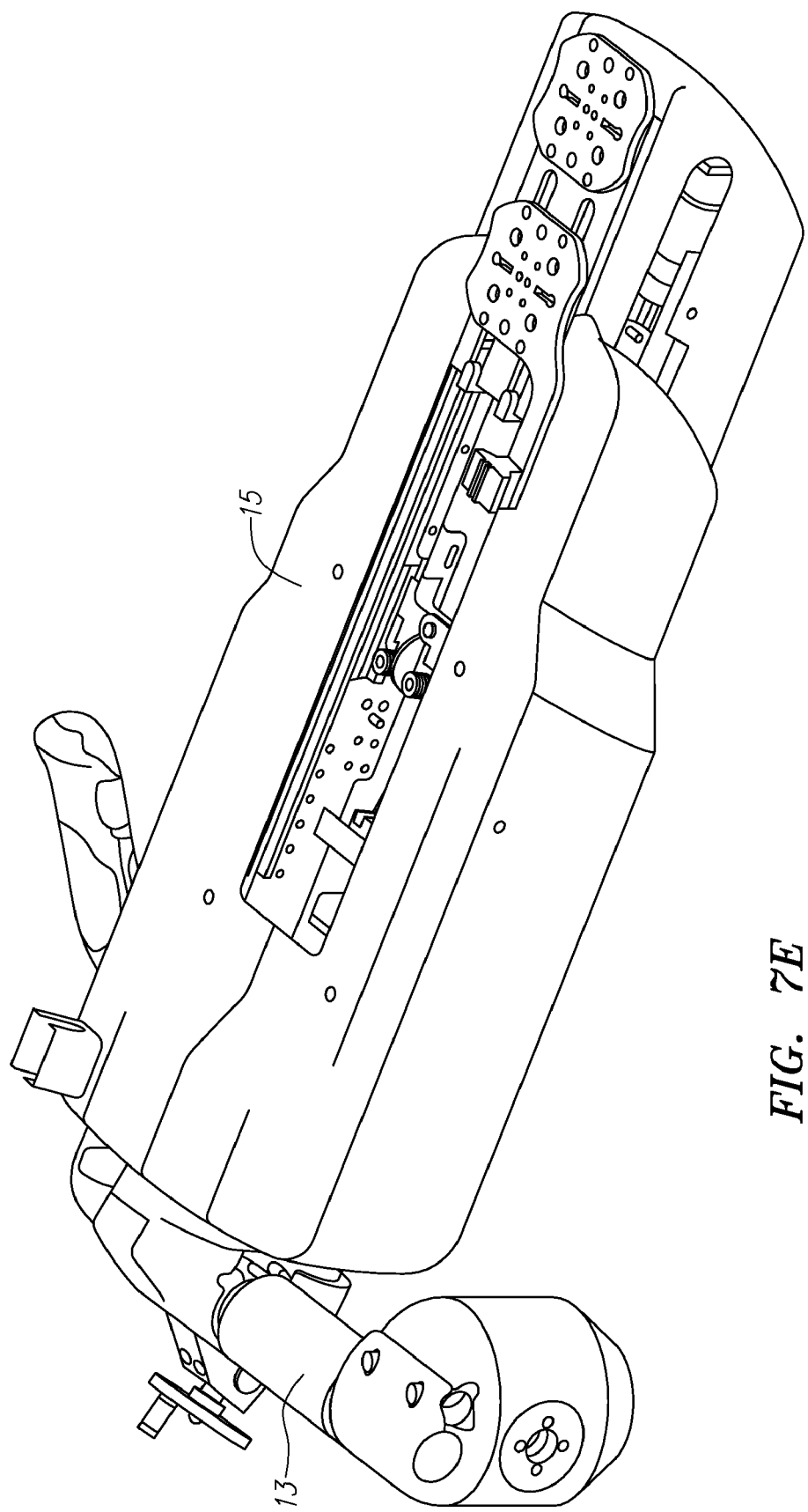
Figure 8B:
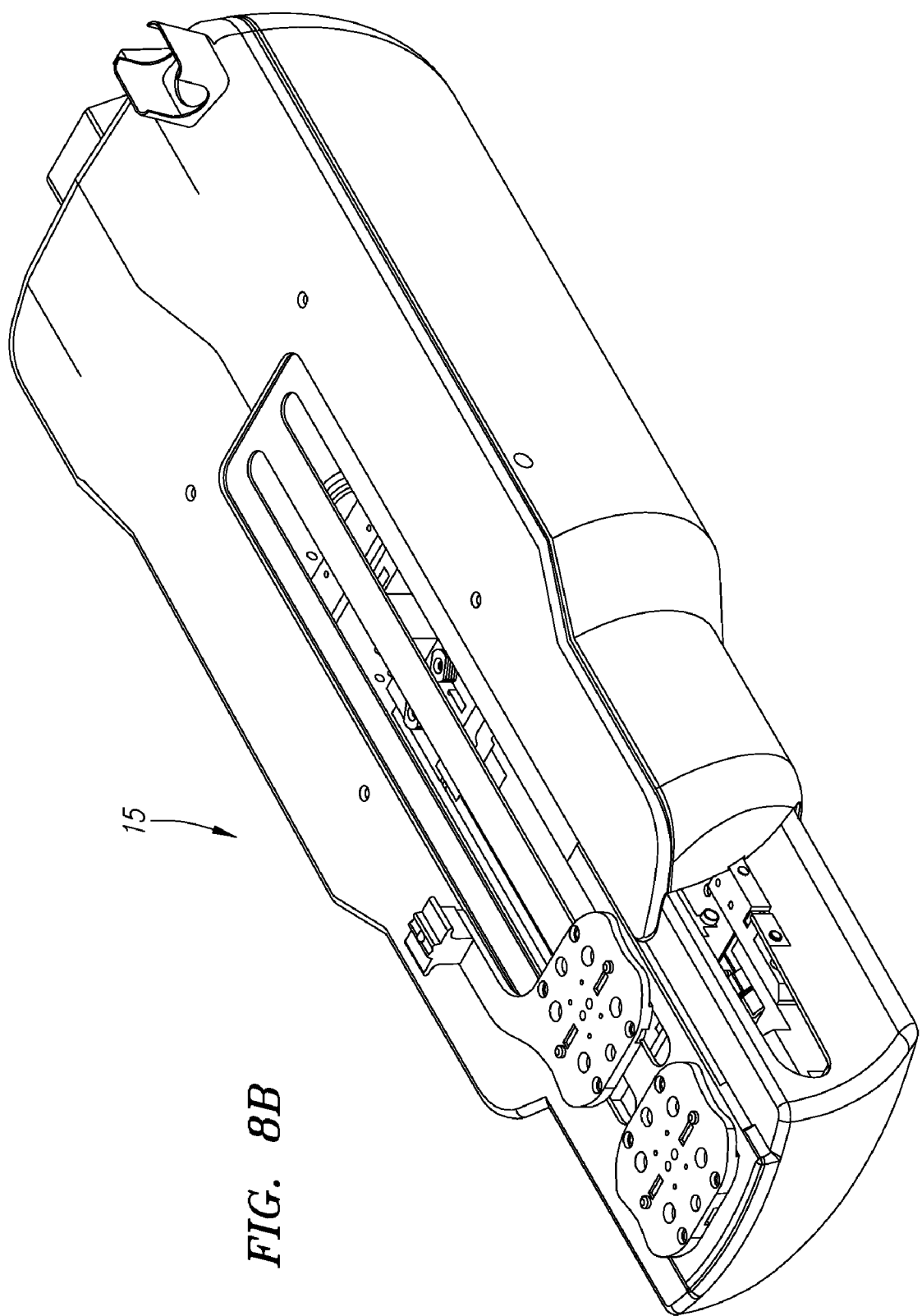
Figure 8C:
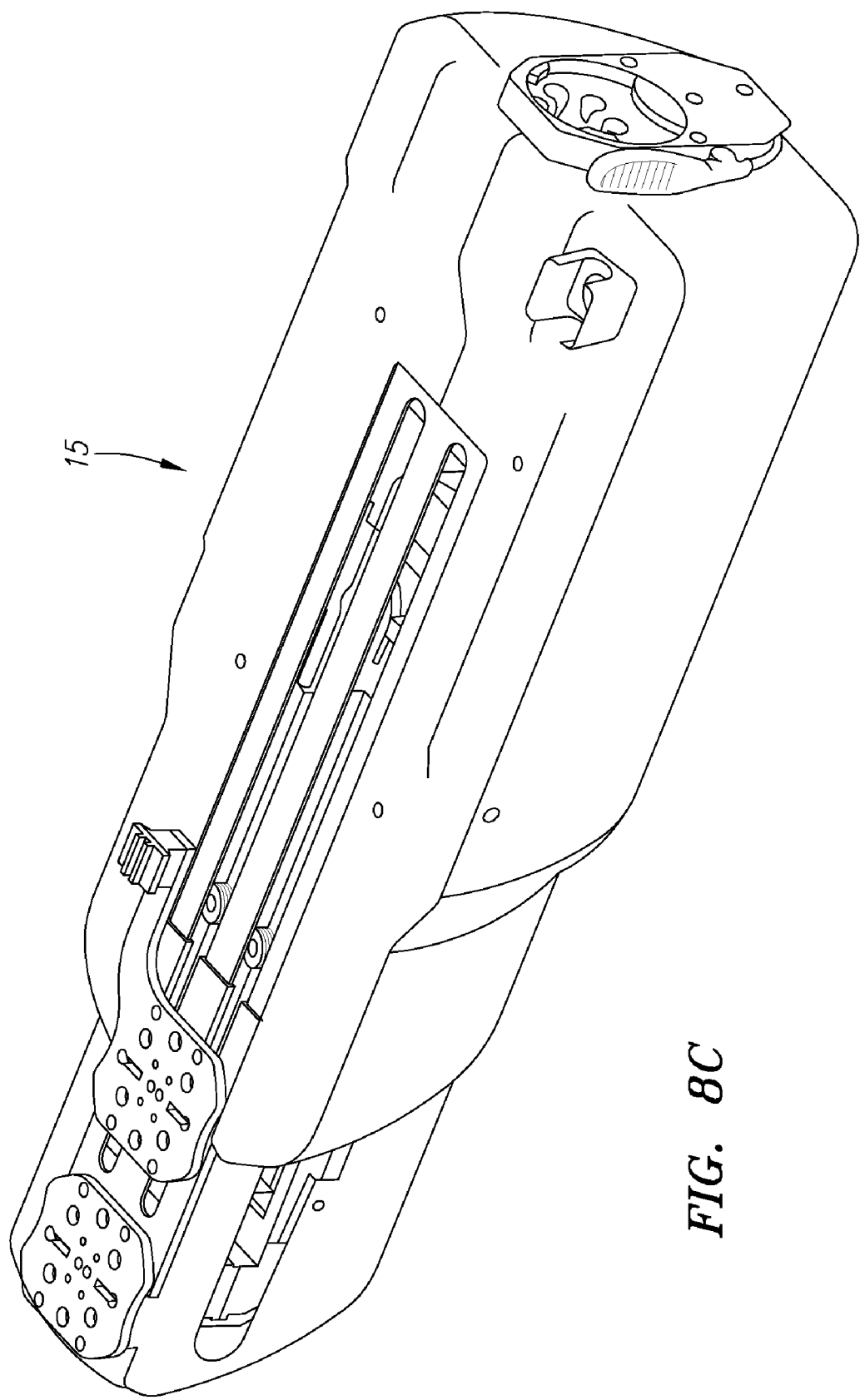
Figure 9A:
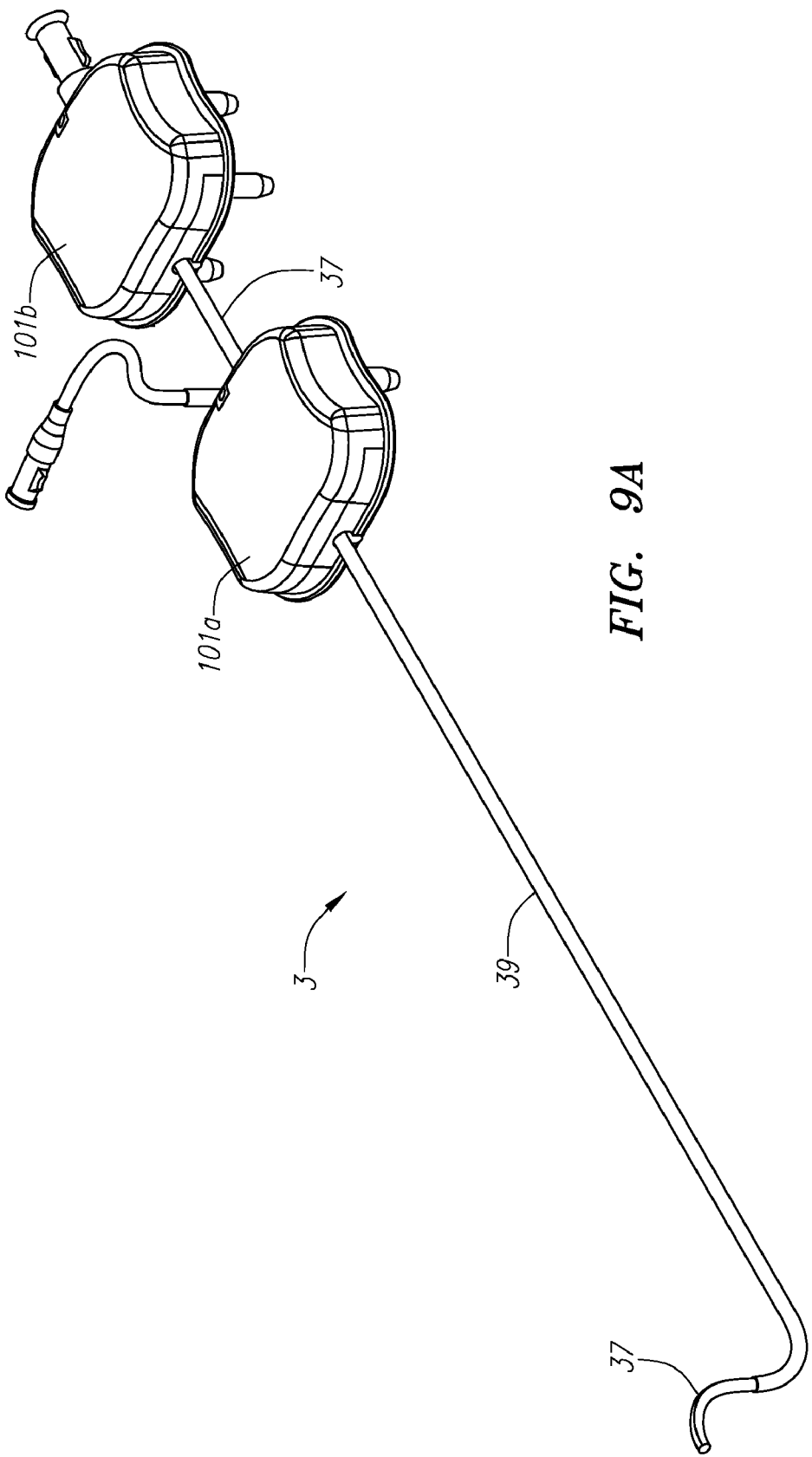
Figure 9B:
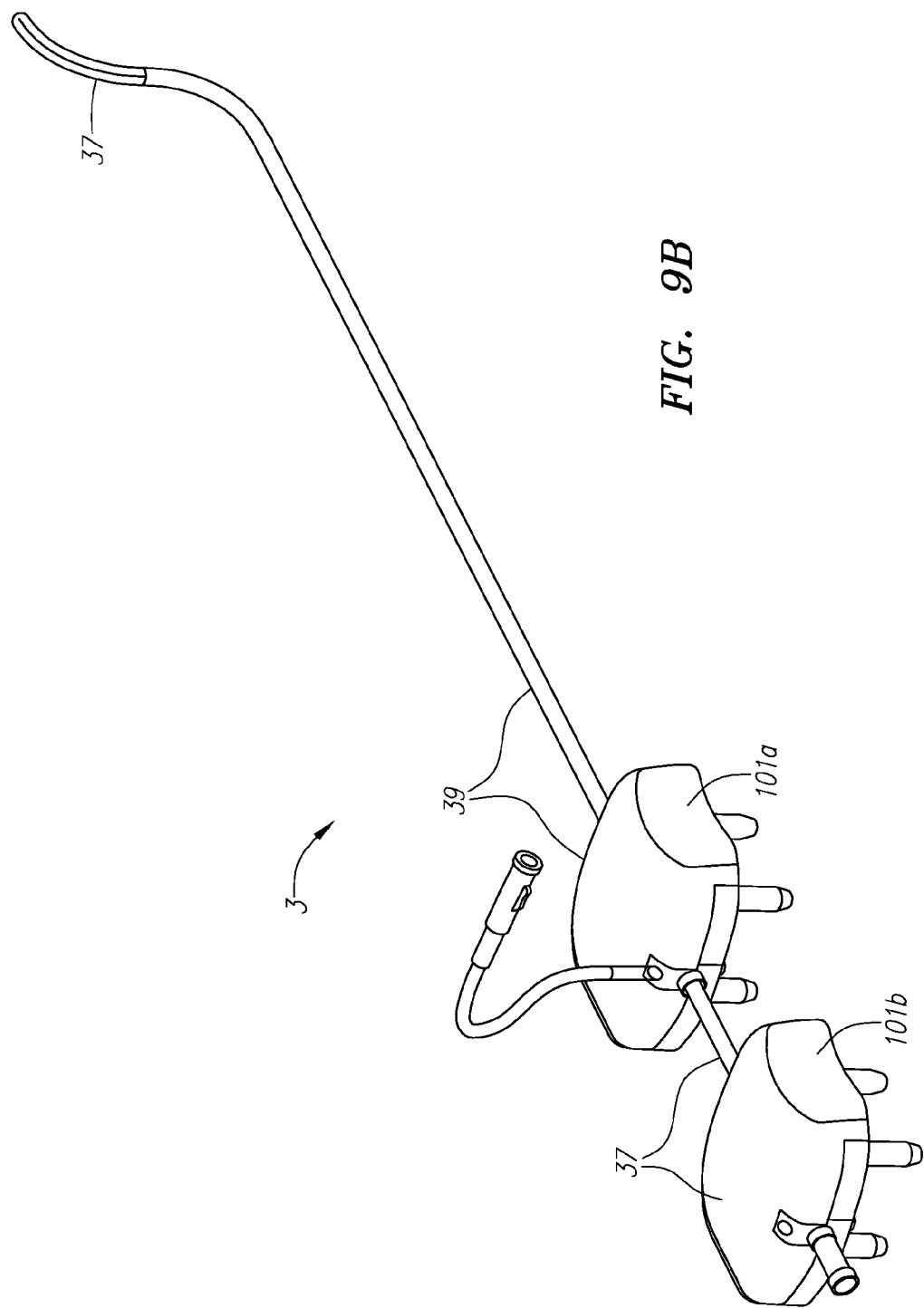

Referring to FIG. 5E, a system architecture 47 of a robotic catheter system 1 includes a master computer 49 that manages operation of the system 1. The master computer 49 is coupled to receive user input from hardware input devices such as a data glove input device 35 and a haptic MID 27. The master computer 49 may execute master input device software, data glove software, visualization software, instrument localization software, and software to interface with operator control station buttons and/or switches. Data glove software 53 processes data from the data glove input device 35, and master input device hardware and software 51 processes data from the haptic MID 27. In response to the processed inputs, the master computer 49 processes instructions to instrument driver computer 55 to activate the appropriate mechanical response from the associated motors and mechanical components to achieve the desired response from the flexible catheter assembly 3.

Referring to FIGS. 6, 7A-E and 8A-D, an example of a setup joint, instrument mounting brace or support assembly 13 (generally referred to as a support assembly 13) that supports the instrument driver 15 above the operating table 7 is an arcuate-shaped structure configured to position the instrument driver 15 above a patient lying on the table 7 for convenient access to desired locations relative to the patient. The support assembly 13 may also be configured to lock the instrument driver 15 into position. In this example, the support assembly 13 is mounted to the edge of a patient bed 7 such that a catheter assembly 3 mounted on the instrument driver 15 can be positioned for insertion into a patient and to allow for any necessary movement of the instrument driver 15 in order to maneuver the catheter assembly 3 during a surgical procedure. A distal portion of the support assembly 13 includes a control lever 57 that may be manipulated to maneuver or position the support assembly 13.

In the illustrated example, the support assembly 13 is configured for mounting of a single instrument driver 15 to a mounting plate on a support member at a distal portion of the setup joint 13. Other system configuration may be utilized, e.g., a plurality of instrument drivers 15 on which a plurality of flexible catheter assemblies 3 may be controlled. For example, a pair of flexible catheter assemblies 3 may be mounted on respective instrument drivers 15 and inserted into a patient for use together during a surgical procedure, e.g., utilizing an elongate master sheath 63 (as described in further detail with reference to FIG. 12). Other embodiments may involve the use of more than two instrument drivers 15, e.g., three instrument drivers 15, to simultaneously deploy three flexible catheter assemblies 3.

FIGS. 9A-E illustrate various flexible catheter assemblies 3 including a flexible catheter instrument or guide catheter 37 and a flexible sheath instrument 39. The sheath instrument 39 may include a splayer portion 101a (FIGS. 9B-C) having one or more control elements or pull wires and a flexible sheath member 105 having a central lumen. Similarly, the guide catheter instrument 37 may also include a splayer portion 101b (FIG. 9D) located proximally of the splayer 101a for the sheath 39, and has one or more control elements or pull wires and a catheter sheath or flexible catheter instrument member 103. Tubing 109 may be provided for insertion of another catheter device, and valves 111 may be provided for injection or removal of fluids. For example, the catheter instrument member 103 has a central lumen configured for passage of a working element or instrument 41, such as a tool, a scope, or another catheter, or a control cable for the same, which can be transported from the proximal end to the distal end of the guide catheter 37. The flexible catheter instrument member 103 may have a preconfigured working instrument 41 mounted on an orientation platform at its distal tip.

Prior to use of the catheter assembly 3 during a surgical procedure, a guide catheter 37 is positioned proximally relative to the sheath 39 and the flexible catheter instrument member 103 is inserted into the sheath splayer 101a, through the lumen of the sheath instrument member 105, such that the two instrument members 103, 105 are coaxially positioned. Both splayers 101a-b are mounted to respective mounting plates on the instrument driver 15. The splayers 101a-b can be controlled or adjusted using, e.g., control knobs 107 (FIG. 9E). Although each splayer 101a,b as illustrated includes four control knobs 107, other numbers of control knobs 107 may be utilized, and in some applications, they may be exposed for manual manipulation, and in others, they may be covered by a housing. Further, the guide catheter instrument 37 and sheath instrument 39 may have different numbers of control knobs 107 depending on the number of control elements or pull wires that are needed to control the particular instrument.

For example, a flexible catheter instrument having a distal orientation platform and an end-effector can require a larger number of control elements whereas a one degree of freedom (DOF) sheath may require fewer control elements. Similarly, a catheter instrument having numerous controllable portions or greater degrees of freedom may need to be wired with more control elements, each of which has to be robotically controlled by the instrument driver. When the splayer for a flexible instrument is mounted onto the mounting plate of an instrument driver 15, an identification chip on the splayer is accessed by the instrument driver. By deciphering that information, the instrument driver 15 may be able to configure and pretension the control elements to a known state.

FIGS. 10A-D illustrate various examples of flexible guide catheter instruments 37 that include different numbers of control knobs 107 and different flexibilities. Referring to FIG. 10A, one guide catheter instrument 37 such as a guide catheter has a splayer 101b coupled to an instrument member 103 having two sections of different flexibility. A proximal section 117 may be rigid, and a distal section may be flexible or bendable as shown in FIG. 10A. As shown in FIG. 10B, the instrument member 103 may have a rigid section 117, followed by a flexible or bendable section 119, followed by another rigid section 121, followed by a distal flexible or bendable section 123. Referring to FIG. 10C, there may be sections 119, 123 having different flexibility or bendability. For example, as shown in FIG. 10C, there may be a rigid section 117 followed by sections 119 and 123 that have different flexibilities, e.g., the section 123 may be more flexible than section 119.

FIGS. 11A-B illustrate flexible catheter instrument member and sheath instrument member 103, 105 without splayers for clarity. The flexible catheter member 103 is coaxially positioned within the flexible sheath member 105. As a result, certain sections of the catheter member 103 may mimic a similar curvature or path as that of the sheath member 105, especially the portions of the catheter member 103 that are located within the sheath member 105. A distal tip 123 of the catheter member 103 may include or be operably coupled to one or more orientation platforms to which one or more working instruments 41, tools or end-effectors may be mounted or attached. As shown in FIG. 11B, a section, e.g., section 117, may be operably coupled to the sheath member 105 using a keying arrangement, examples of which are shown in FIGS. 11C-H in the shape of a square, triangle, rectangle, star, cross and hexagon. Other shapes may also be utilized. A non-circular keying arrangement may facilitate rotation of the catheter instrument 117 in response to the sheath instrument distal tip 131 by reducing or eliminating slippage between components.

In one implementation, the distal tip 123 has a single degree of freedom relative to the catheter member 117 and can be controllably rotated about a central longitudinal axis 125 extending through the catheter member section 117. For example, the distal tip 123 and any attached working instrument or tool 41 may freely rotate 360° about the longitudinal axis 125. In another implementation, the distal tip 123 may be configured to rotate 180°. The degree of axial rotation may depend on the particular design and application. Thus, examples discussed here are provided to illustrate how embodiments can be implemented in a non-limiting manner. Further, the distal tip 123 may be implemented to rotate in a clockwise or counterclockwise manner, but may also be implemented to rotate in both a clockwise and counterclockwise manner.

The flexible catheter member 103 may include a distal tip 123 that is capable of controlled pitching such that it can rotate about a lateral or transverse axis that is perpendicular to the central longitudinal axis. The distal tip 123 may have a positive (+) pitch or a negative (−) pitch, or even capable of both positive and negative (+/−) pitch. The catheter member 103 may have a distal tip 123 capable of controlled yawing such that it can rotate about a transverse axis that is perpendicular to both the central longitudinal axis and the transverse axis of pitch. In some implementations, the distal tip 123 may have a positive (+) pitch or a negative (−) yaw, or even capable of both positive and negative (+/−) yaw. Further, a catheter member 103 may include a distal tip 123 having three degrees of freedom such that it can rotate about a longitudinal axis, pitch about a first transverse axis, and yaw about a second transverse axis, wherein each of the three axes are perpendicular to the other two. The degrees of movement can vary depending on the particular implementation.

As discussed above with reference to FIG. 1, one robotic instrument system is used to control the rigidity of a flexible catheter instrument 103, such as a multi-segment sheath catheter 102, which may be advanced through a flexible or rigid master sheath 63. The sheath catheter 102 can assume different rigidity states including a flexible state (F) that allows the sheath catheter 102 to be inserted through the master sheath 63 with desired flexibility and maneuverability (FIG. 1B) and a rigid or substantially rigid state (R) to form a platform (P) or portion thereof. As shown in FIG. 1, a guide catheter 37 may extend through the sheath catheter 102, and a working instrument 41 may be operably coupled to the guide catheter 37.

Figure 12:
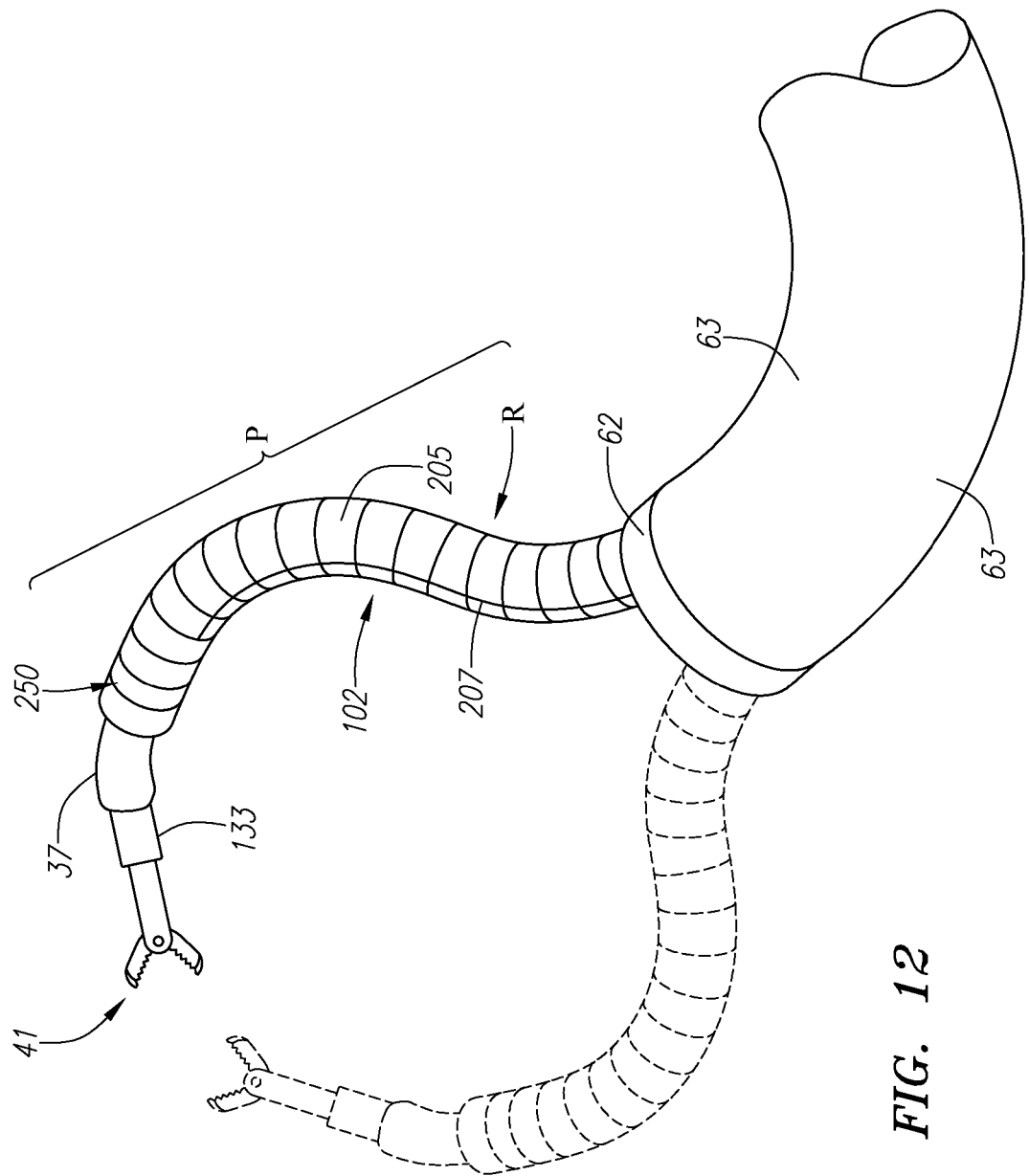
FIG. 12 illustrates a robotic instrument system in which embodiments of the invention may be implemented and that includes a substantially rigid platform extending from a distal end of a master sheath, a rotatable apparatus or tool, and an orientation platform.

FIG. 12 illustrates a robotic instrument system in which rotatable apparatus or tool 250 embodiments may be implemented. The system includes an elongate sheath, such as a master sheath 63, which may be a stand-alone component, coupled to its own instrument driver 15, and/or robotically controlled from a workstation 5 or manually maneuvered by a surgeon. The master sheath 63 has a sufficiently large lumen or defines a sufficient number of lumens through which one or more sheath catheters 102 may be advanced to extend out of, and be retracted or pulled back into, the master sheath 63. For example, the master sheath 63 may define a single lumen for multiple sheath catheters 102 or multiple smaller lumens for individual sheath catheters 102 (additional sheath catheters 102 are represented in phantom in FIG. 12). For ease of explanation, reference is made to a sheath catheter 102 generally, but it should be understood that an individual sheath catheter 102 or multiple sheath catheters 102 may be utilized and that the sheath catheters 102 may have the same or different curvature.

A working instrument or surgical tool 41 is operatively coupled to a platform 133, which may be operably coupled to a distal end of the guide catheter 37, which is operably coupled to an embodiment of a rotatable apparatus 250, which is operatively coupled to a sheath catheter 102. Components are advanced through the master sheath 63 or sheath catheter 103, and manipulated and controlled by the surgeon for performing minimally invasive diagnostic and/or interventional procedures at one or more operation or target sites.

In the illustrated embodiment, the effective lever arm (SLA) is substantially shorter than the lever arm (LA) or distance from the proximal portion of the catheters to the distal portion of the catheters (the proximal portions of the catheters may be located outside the body of a patient). In this manner, it is easier for the surgeon to manipulate and control the working instruments 41 from the intermediate or extension platform (P) formed by one or more sheath catheters 102 that are made substantially rigid (R) by manipulation of one or more control elements or pull wires 207.

Figure 13:
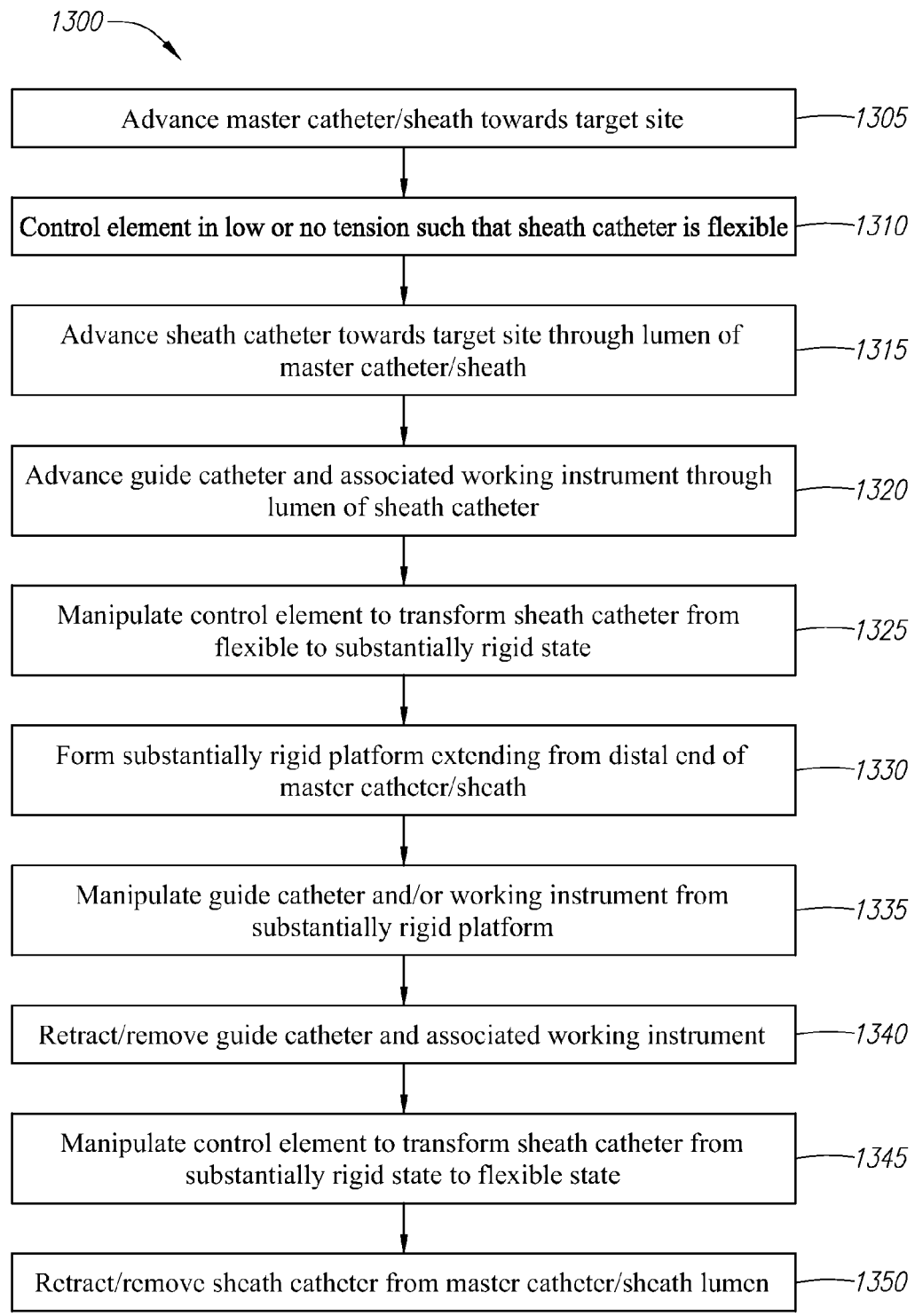
FIG. 13 is a flow chart of a method of controllably manipulating a sheath catheter to form a substantially rigid platform that extends from a distal end of a master sheath or catheter.

Referring to FIG. 13, a method 1300 of controlling components of a robotic instrument system using the system and apparatus embodiments described above forms a temporary, intermediate platform (P) that extends from a distal end 62 of an elongate master sheath 63. The method 1300 includes advancing the master sheath 63 towards target site or anatomical region of interest at step 1305. At step 1310, a control element, such as a pull wire 207, is manipulated or placed in a state of low or no tension such that a sheath catheter 102 is flexible (F) or has sufficient flexibility for advancement through a master sheath 63. In other words, the catheter sheath 102 may be in a naturally relaxed state or un-deployed state, substantially non-rigid state.

At step 1315, the sheath catheter 102 is advanced through a lumen of the elongate master sheath 63 towards the target site. At step 1320, a guide catheter 37 and a separate or operably coupled working instrument 41 is advanced through a lumen of the sheath catheter 102. At step 1325, the control element 207 is manipulated such that the sheath catheter 102 is transformed from a flexible state (F) to a substantially rigid or rigid state (R), e.g., by temporarily and controllably linking, joining, or compressing segments 205 of the sheath catheter 102.

As a result, at step 1330, the substantially rigid distal portion of the sheath catheter 102 that extends beyond a distal end 62 of the master sheath 63 forms at least a portion of a substantially rigid platform (P). In one embodiment, the substantially rigid platform (P) is formed by a single substantially rigid sheath catheter 102. Although FIG. 13 illustrates a method 1300 involving one sheath catheter 102, other sheath catheters 102 may also be inserted through the master sheath 63 in a similar manner such that multiple sheath catheters 102 are transformed from flexible (F) to substantially rigid (R) states to cooperatively form a substantially rigid platform (P) that extends beyond a distal end 62 of the elongate master sheath 63.

At stage 1335, one or more other system instruments, such as a guide catheter 37 and/or a working instrument 41 are controlled, used or manipulated from the substantially rigid platform (P) as point of reference or orientation. Such manipulation may involve controllable articulation and/or controllable rotation (e.g., using embodiments of a rotatable apparatus 250) The trajectory of the portion of the guide catheter 37 that extends outwardly from the distal end of the sheath catheter 102 may be defined at least in part by the bending section of the sheath catheter 102.

When the procedure or treatment at a given site has been completed, the guide catheter 37 and associated working instrument 41 can be retracted back into or removed from the catheter sheath 102 lumen at stage 1340. At stage 1345, the control element 207 is manipulated such that the sheath catheter 102 is transformed from a substantially rigid state (R) that forms the platform (P) or portion thereof to a flexible state (F) such that at stage 1350, the sheath catheter 102 can be retracted back into or removed from the lumen of the main catheter 63. Similar method steps are applicable to other apparatus and system embodiments described below.

Figure 14A:
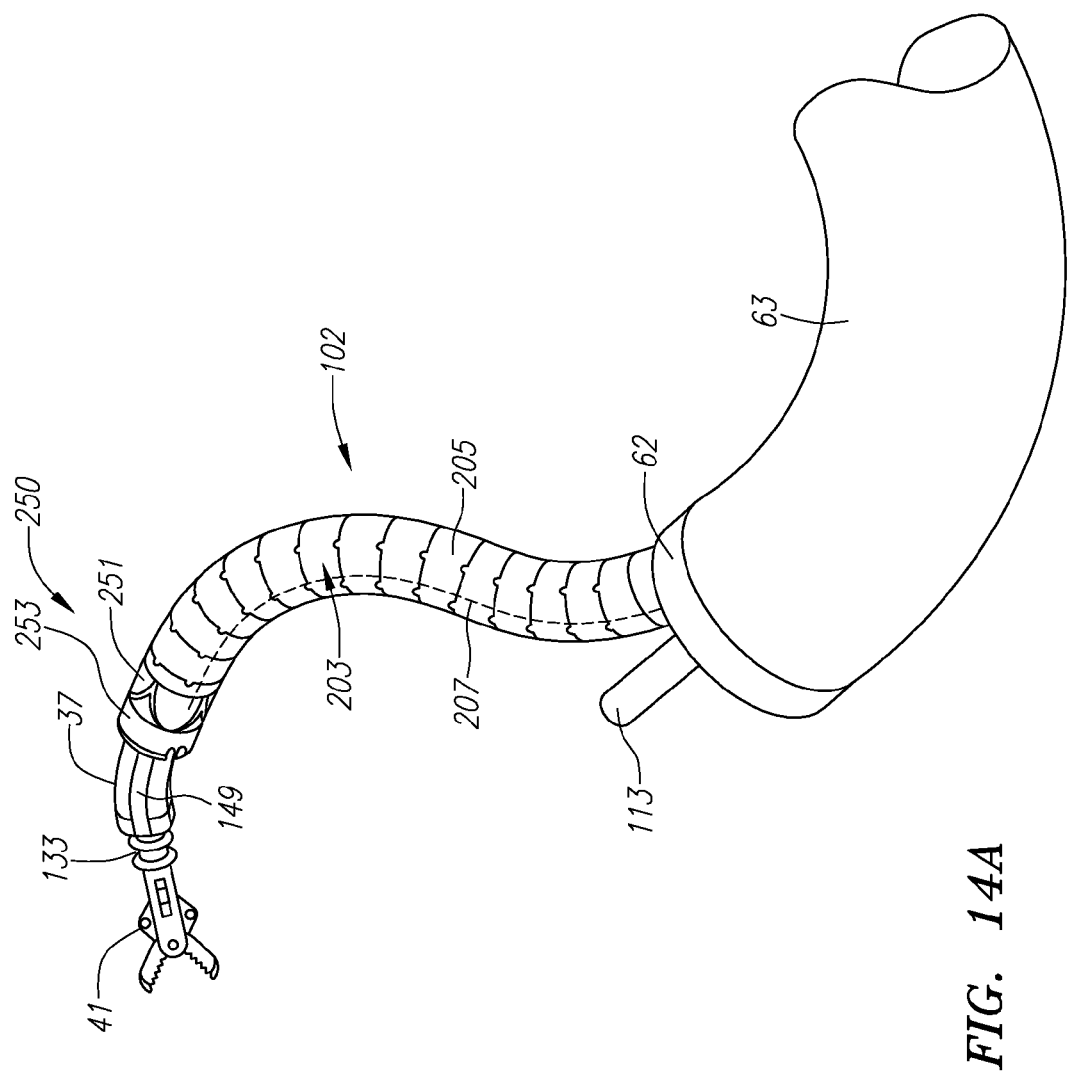
FIGS. 14A-E illustrate configurations of a robotic instrument system in which embodiments may be utilized and that includes a substantially rigid platform extending from a distal end of a master sheath, where

FIG. 14A illustrates an extension system in which rotational apparatus 250 embodiments may be implemented and one manner in which system components may be structurally configured and operably coupled together. In the illustrated embodiment, a sheath catheter 102 includes multiple segments 205 having shaped surfaces that interlock or matingly engage each other. The segments 205 can be placed in a compressed or rigid state (R) and in a relaxed or flexible state (F). One or more of the shape, size, number, arrangement and interlocking structure of the segments 205 determine how the shape and rigidity of the sheath catheter 102 changes when a control element 207 operably coupled to one or more segments 205 is subjected to different tensions. As shown in FIG. 14A, the trajectory of the portion of the guide catheter 37 that extends outwardly from the distal end of the sheath catheter 102 may be defined at least in part by the distal bending section of the sheath catheter 102.

Figure 14B:
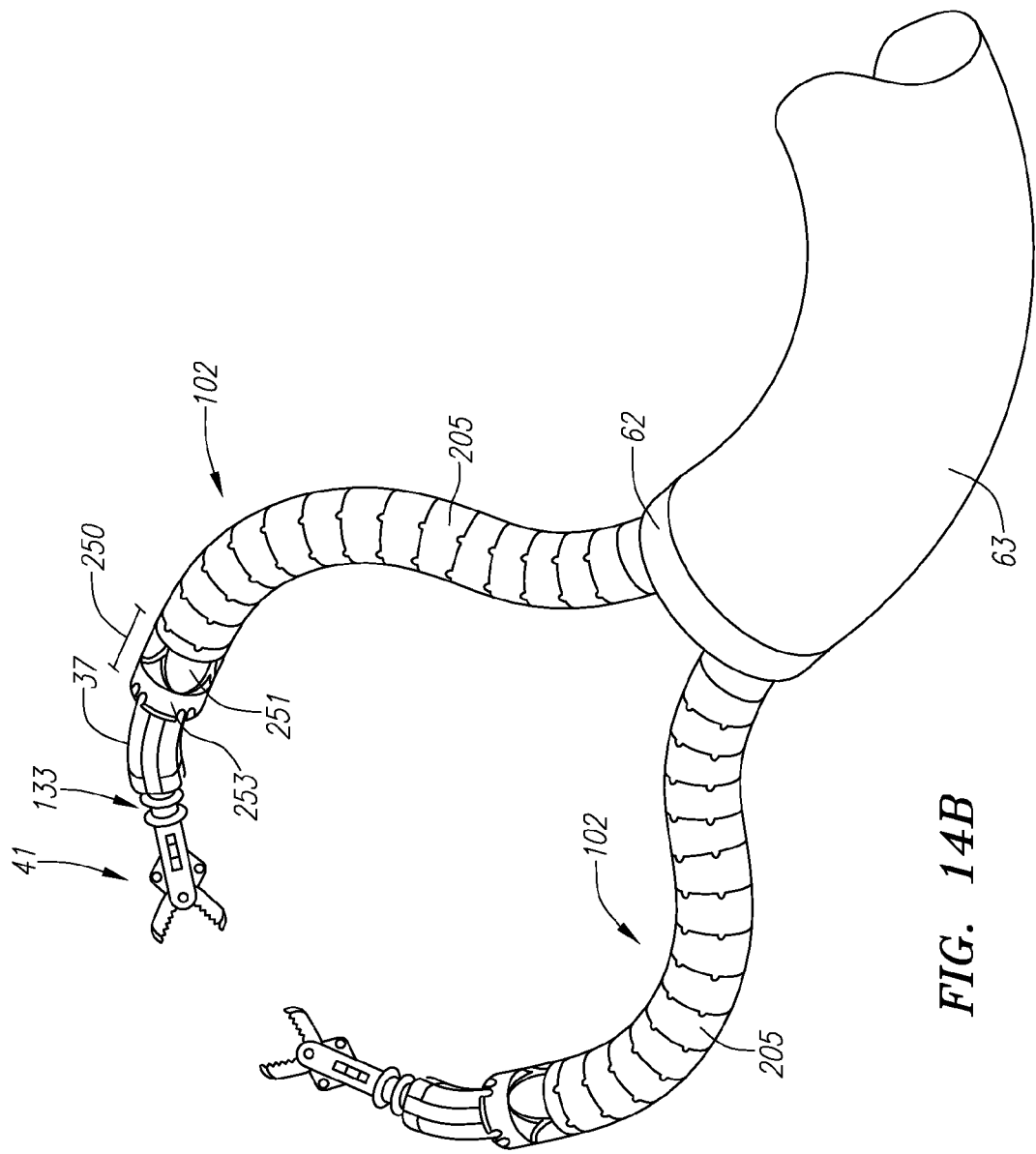
Figure 14C:
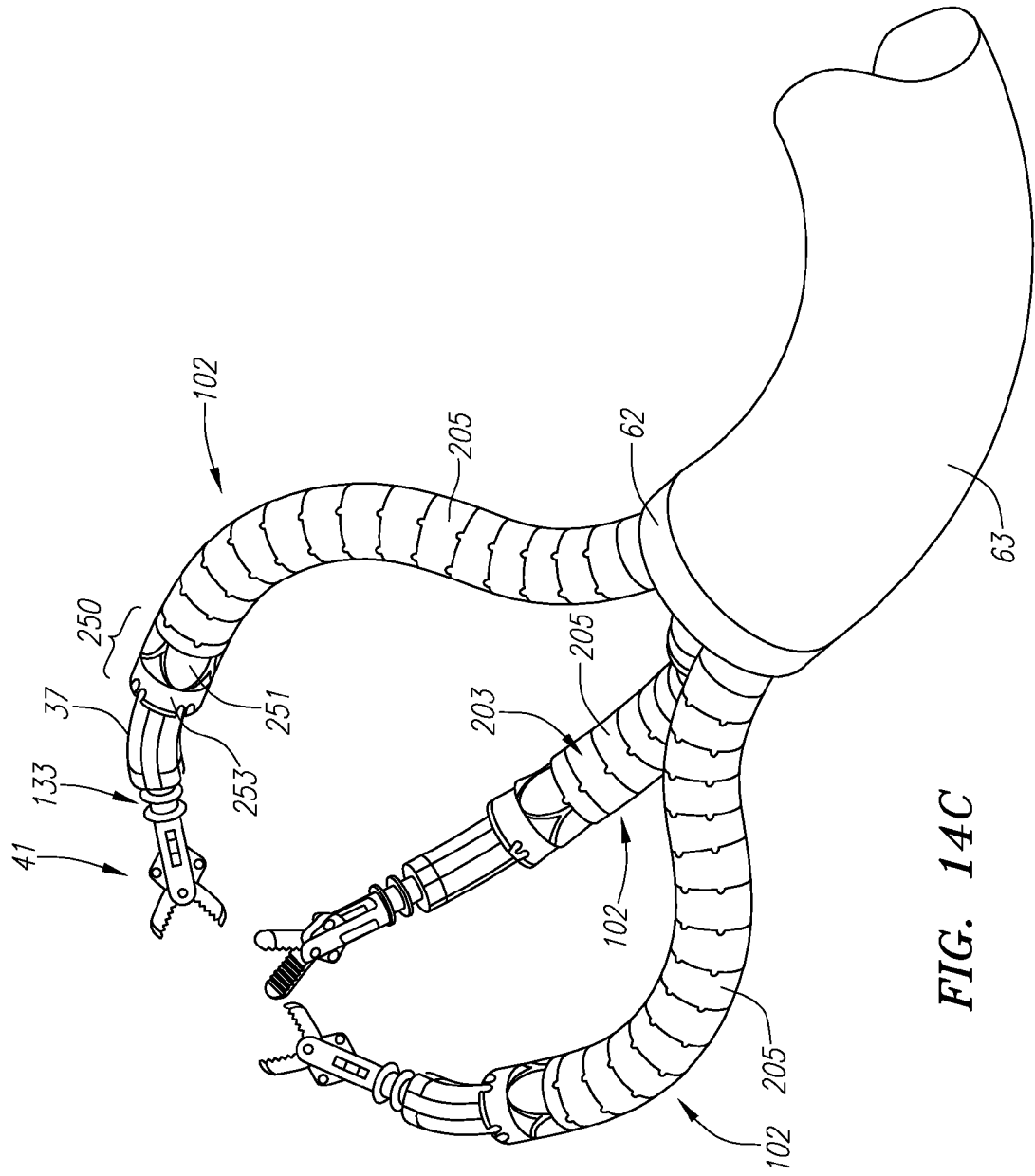
Figure 14D:
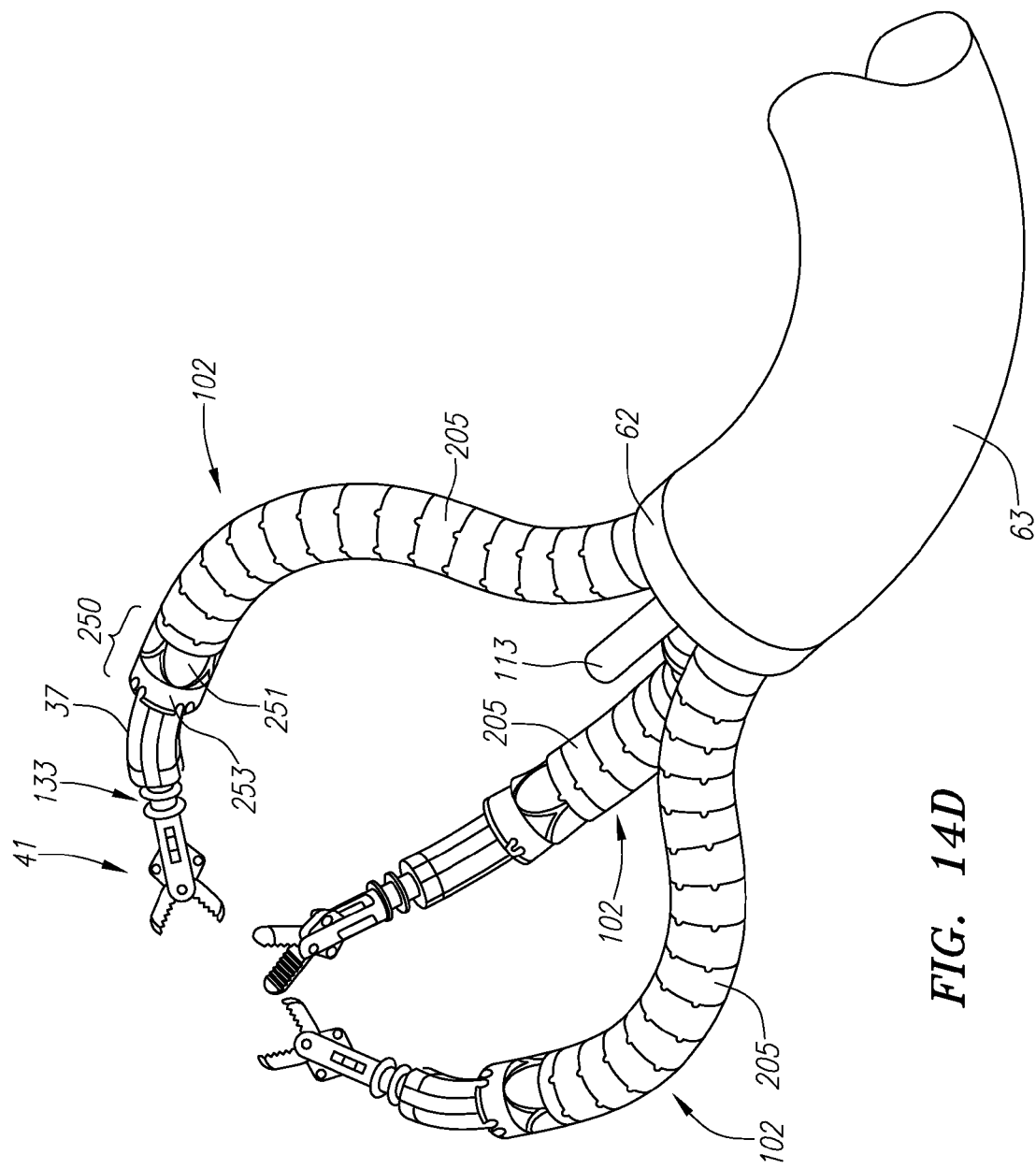

In the embodiment illustrated in 14A, a substantially rigid platform (P) is formed by and includes a single sheath catheter 102. Another system instrument, such as an endoscope 113, may also extend through the master sheath 63 if necessary. A scope may be used to provide optical and/or positional feedback of the surgical instruments and target site to the surgeon. FIG. 14B illustrates an embodiment that includes two sheath catheters 102 that cooperatively form a substantially rigid platform (P) or multiple substantially rigid platforms (P) when the distal portions thereof are placed in a substantially rigid state (R). FIG. 14C illustrates a further embodiment that includes three sheath catheters 102 that cooperatively form a substantially rigid platform (P) or multiple substantially rigid platforms (P), which may also include another system instrument, such as an endoscope 113, as shown in FIG. 14D.

Figure 14E:
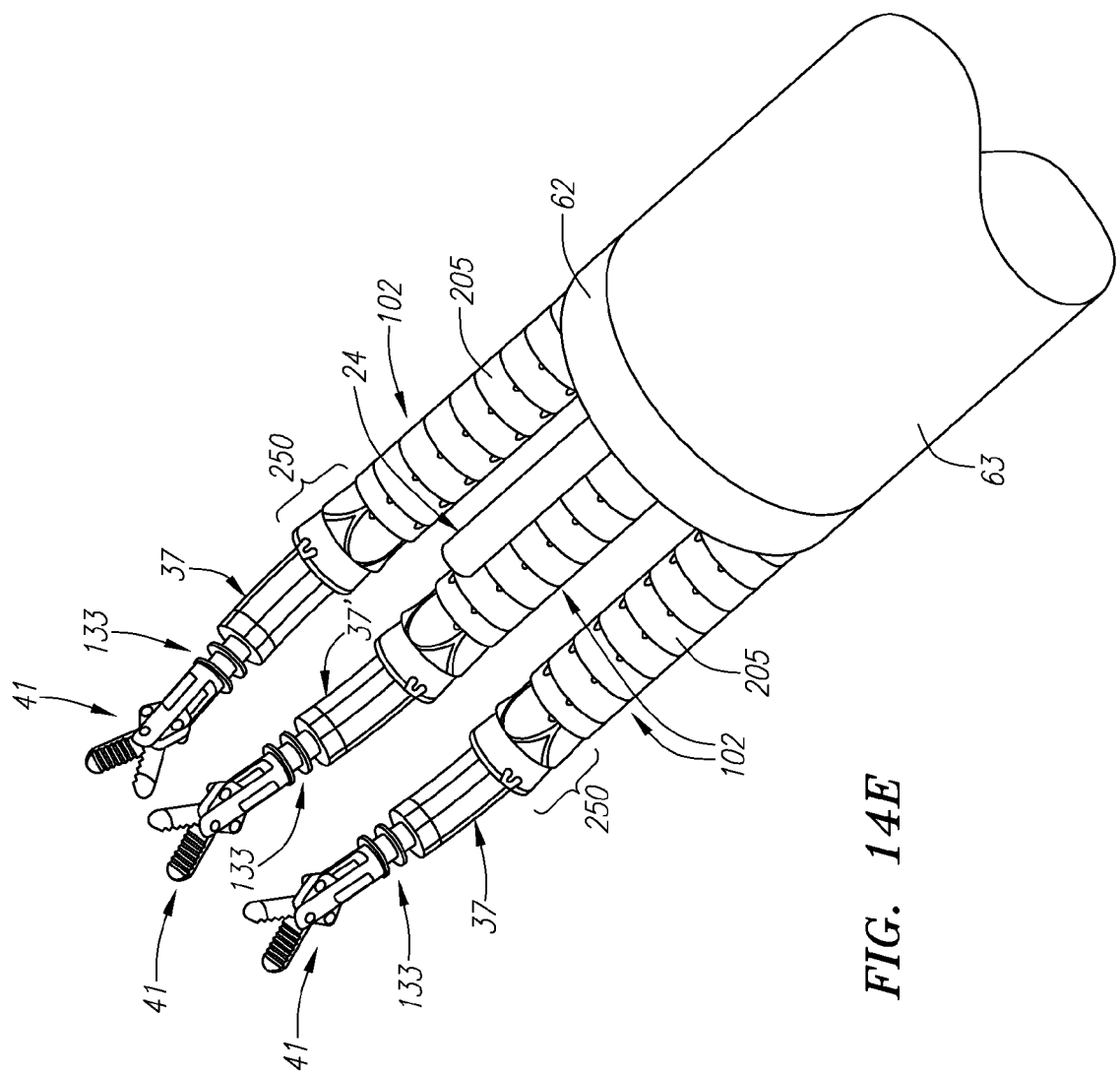

Thus, as shown in FIGS. 14A-D, systems may be implemented may include various numbers of extension systems and other related instruments and may provide controllable articulation and rotation of system components using one or more control elements and distal wrist control or rotatable apparatus 250 embodiments. While certain embodiments are described as forming a substantially rigid platform (P) including sheath catheters 102 that assume a curved shape when they are substantially rigid (R), other embodiments, as illustrated in FIG. 14E, may include various numbers of sheath catheters 102 that are substantially linear when they are substantially rigid (R), thus forming one or more platforms (P) including substantially linear and substantially rigid sheath catheters 102. For ease of explanation, reference is made to a sheath catheter 102 generally or a sheath catheter 102 that assumes a curved or arcuate shape when tension is applied to make the sheath catheter 102 rigid.

Figure 15:
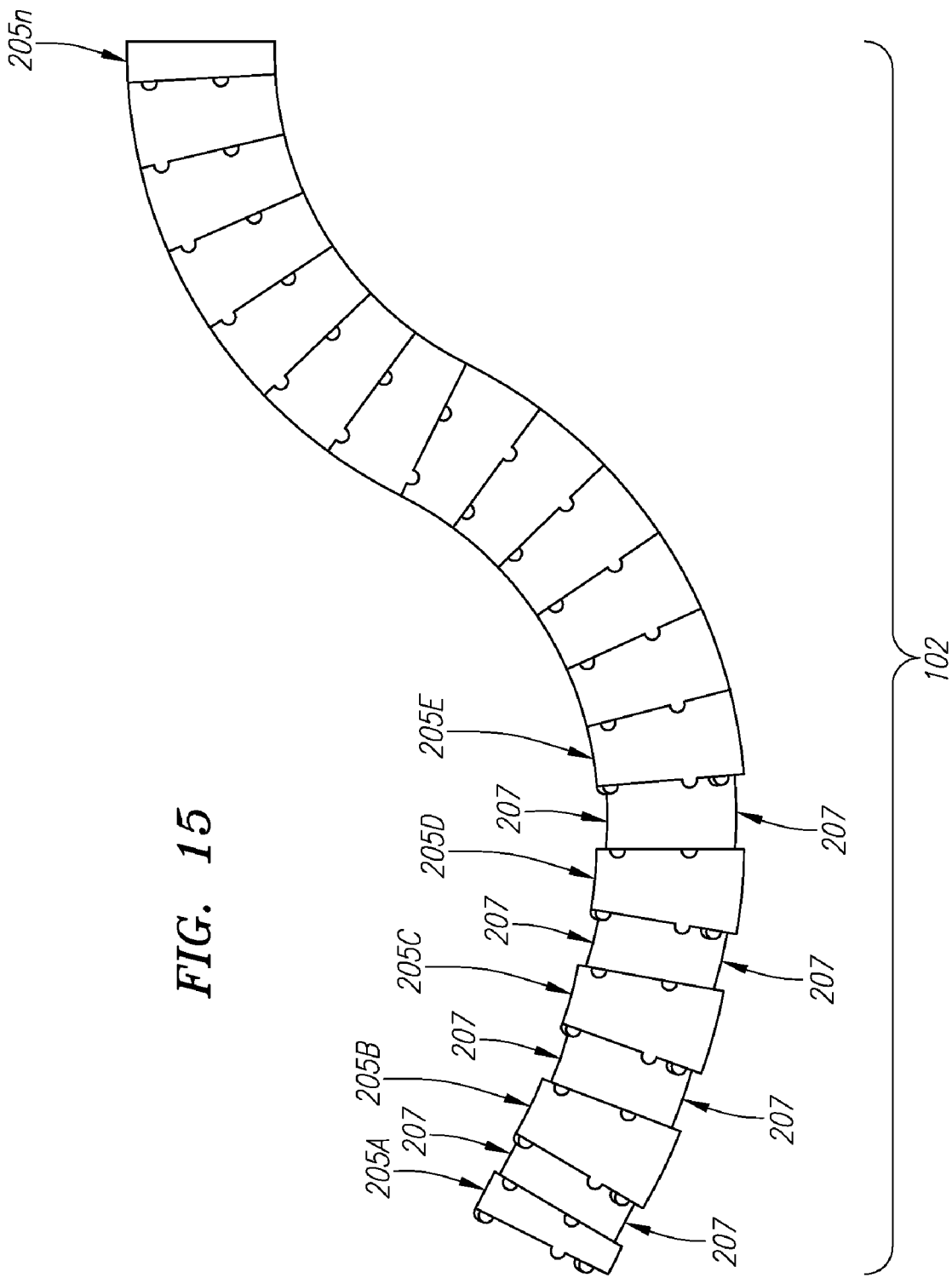
FIG. 15 is a side view of a multi-segment sheath catheter with which embodiments may be utilized and that includes interlocking segments of different shapes and/or sizes in order to achieve a desired curvature in a substantially rigid state.

Referring to FIG. 15, the sheath catheter 102 with which rotational apparatus or tool 250 embodiments of the invention may be utilized may include a plurality of interlocking segments 205 which, may be interconnected by one or more control elements 207. In the illustrated embodiment, the segments 205 are generally circular in shape and have top and bottom faces or surfaces that are configured to matingly engage or interlock with adjacent segments 205. As a result, one segment is not rotatable relative to another segment, thereby providing enhanced rigidity and advantageously decreasing compressive forces that are required to form a substantially rigid structure compared to other structures that are not so configured.

In the illustrated embodiment, interlocking segments 205 having different shapes and/or sizes (e.g., different diameters) relative to other segments 205. For example, the profile or shape or size of segment 205A is different than the profile or shape or size of the segment 205B, and the segment 205B is different than other segments in the chain of segments 205A, 205B, 205C, 205D ... 205n, while the different shaped or sized segments interlock or matingly engage adjacent segments 205. According to one embodiment, as a result of the different shapes of the chain of segments 205, the sheath catheter 102 assumes a certain curved, rigid shape (R) when placed under tension, e.g., by a pull wire 207, that is attached to one, some or all of the segments 205. The resulting rigid shape may be adjusted by changing the number, arrangement, order, shape, size and/or interlocking structures of the segments 205.

Figure 16:
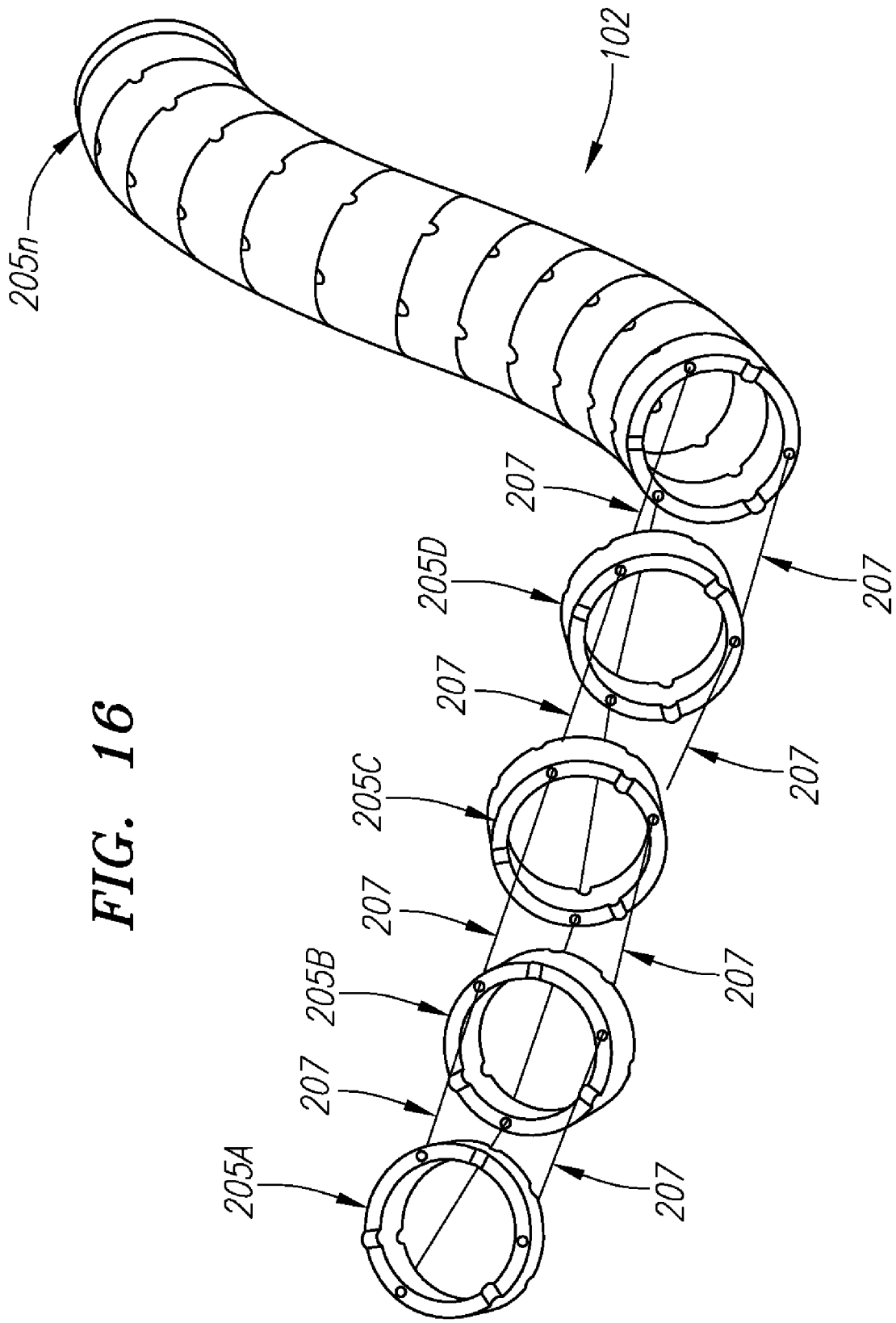
FIG. 16 further illustrates a sheath catheter with which embodiments may be utilized and that includes interlocking segments that define aligned passages or apertures through which a control element extends.
Figure 17A:
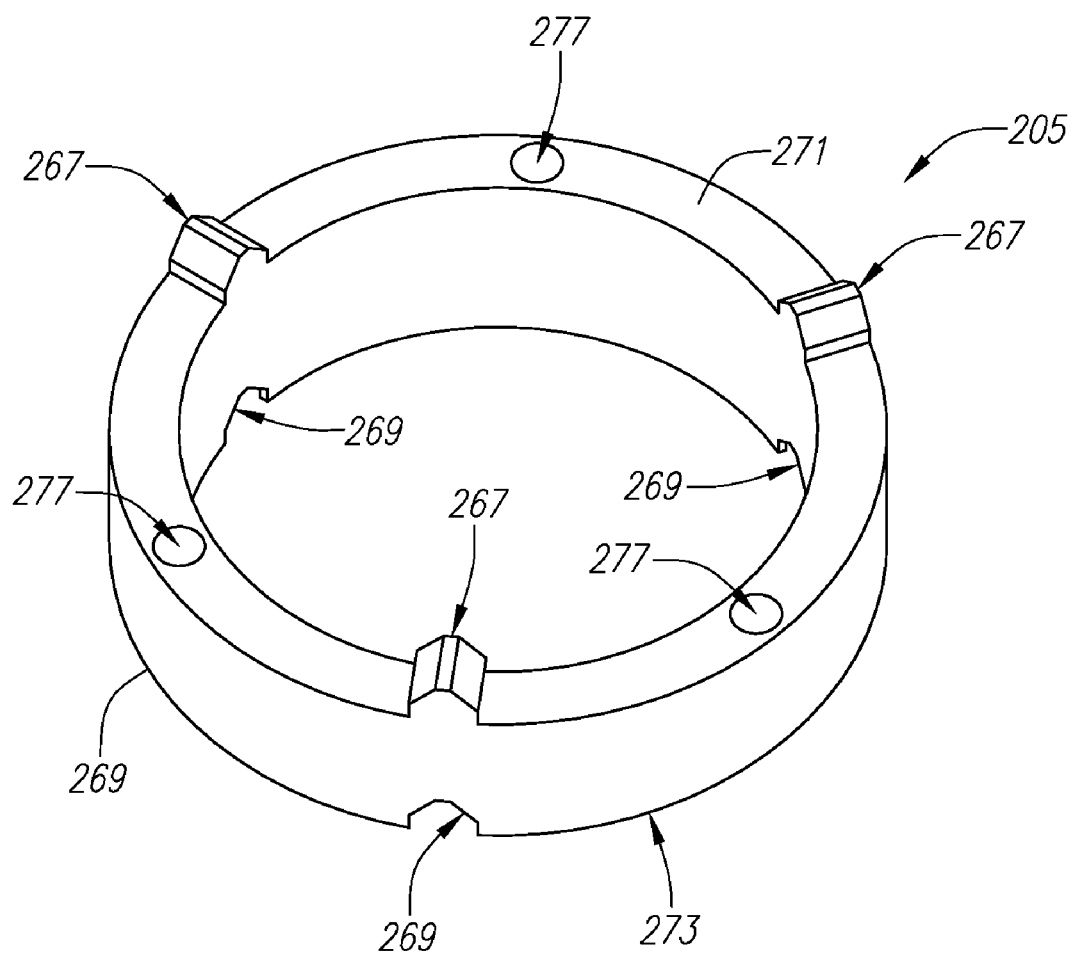
FIGS. 17A-D illustrate different views of a segment of a sheath catheter with which embodiments may be utilized and that includes shaped bottom and top surfaces for matingly engaging or interlocking with one or more adjacent segments.
Figure 17B:
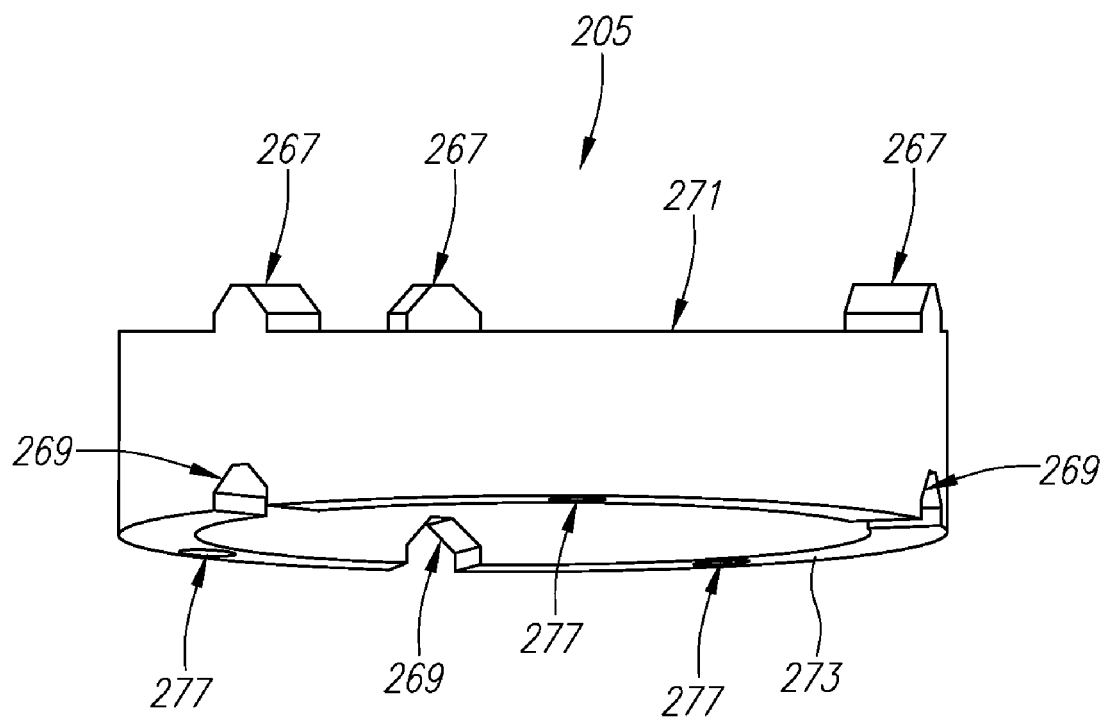
Figure 17C:
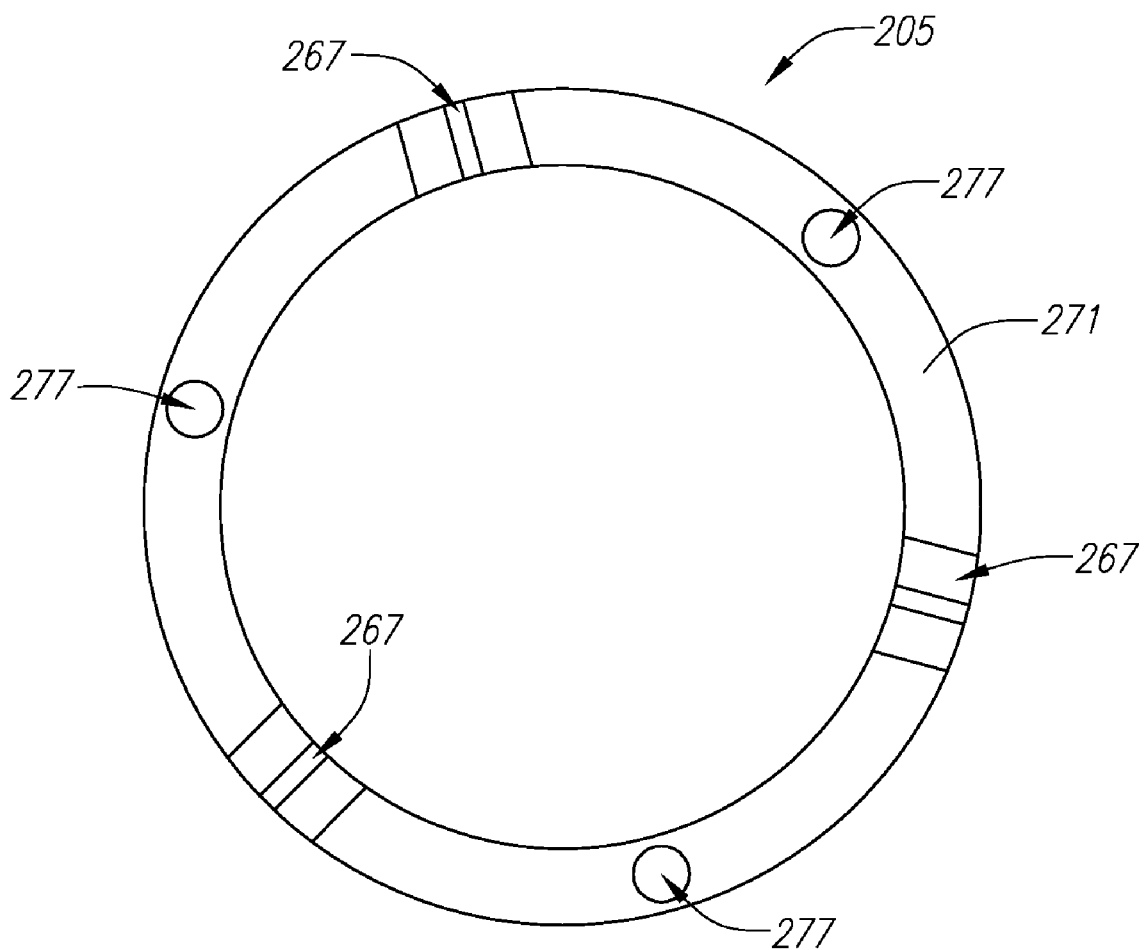
Figure 17D:
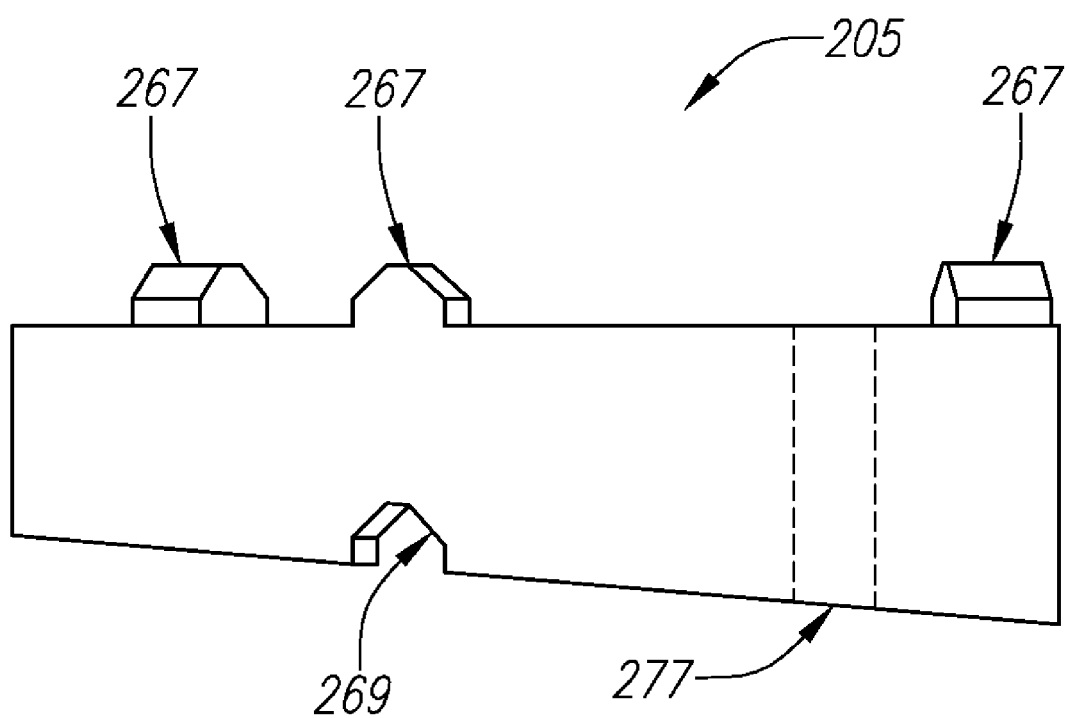
Figure 18A:
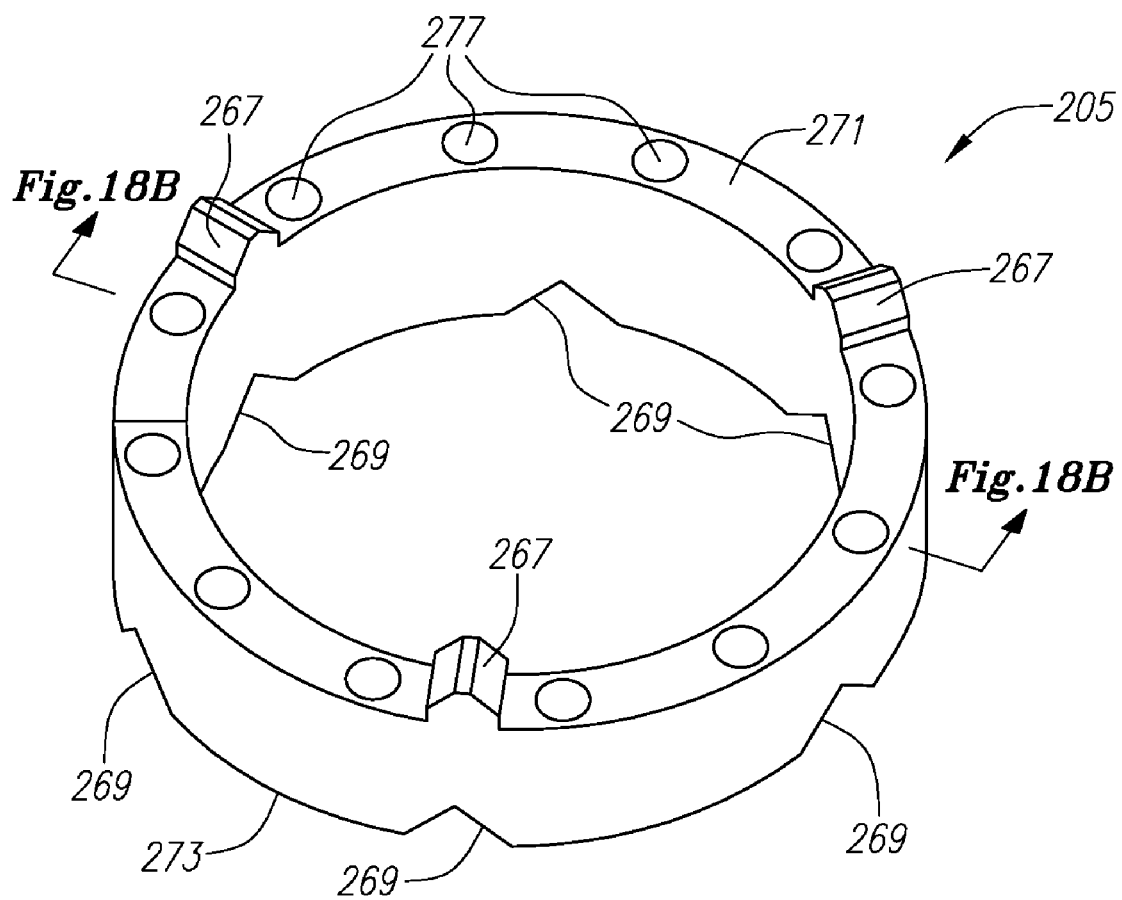
Figure 18B:
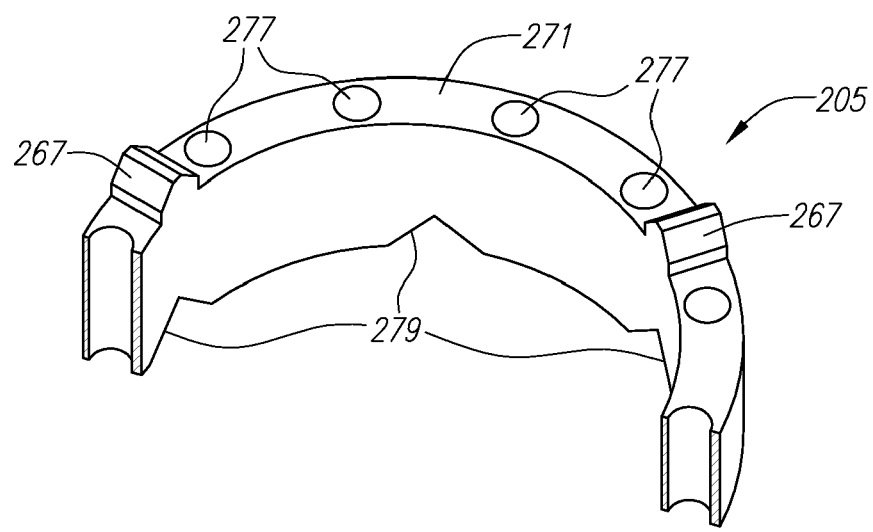

FIG. 16 illustrates a sheath catheter 205 apparatus constructed according to one embodiment. In the illustrated embodiment, each segment 205 is generally the same shape, e.g. round ring-like structures, but may differ to some degree, e.g., as shown in FIG. 15. The segments 205 can also be other shapes, e.g., square, rectangular, triangular, pentagonal, hexagonal, octagonal, circular, spherical, elliptical, star, etc. For ease of explanation, reference is made to generally round segments 205. The segments 205 may be constructed, fabricated, formed, etc., from various materials including stainless steel and other materials that are suitable for surgical procedures.

In the illustrated embodiment, pull wires 207 are operably coupled to each segment 205 and extend through aligned passages, apertures or channels 277 defined by a wall of each segment 205. For example, a pull wire 207 may be coupled to a distal most segment 205 such that placing the control element 207 in tension also places more proximal segments 205 in tension. In another embodiment, the pull wires 207 can be attached to some or all of the segments 205, e.g., attached to an exterior surface of a segment 205.

In the illustrated example of a segment 205, control elements 207 are advantageously routed through the body of a segment 205, i.e., through apertures 277 defined by a segment 205 wall, rather than through an inner or central lumen defined by a collection of segments 205. In this manner, embodiments advantageously reduce the components extending through the inner or central lumen, thereby providing more space through which other instruments and devices, such as a guide catheter 37 and/or working instrument 41 may be inserted. Instruments can also be advanced through the sheath catheter 102 more easily since the control elements 207 do not interfere with the instruments since the control elements 207 advantageously extend through apertures 277 defined through the segment 205 bodies instead.

FIGS. 17A-D illustrate in further detail one embodiment of an individual segment 205 of a sheath catheter 102 having shaped, interlocking top and bottom surfaces 271, 273 that allow the segment 205 to matingly engage adjacent segments 205. In the illustrated embodiment, each segment 205 includes mating teeth or protrusions 267 and notches or grooves 269. Teeth or protrusions 267 of a first segment 205 matingly engage notches or grooves 269 of a second, adjacent segment 205, and the notches or grooves 269 of the first segment 205 matingly engage teeth or protrusions 267 of a third, adjacent segment 205. As a result, interlocked segments 205 are not rotatable relative to each other.

Each segment 205 also defines one or more apertures 277. The interlocking teeth/notch structures 267, 269 are arranged such that when a plurality of segments 205 are matingly engaged or interlocked, the apertures 277 are aligned with each other to collectively define a lumen that extends through the plurality of segment 205 bodies and through which a control element 207 extends. For this purpose, in the illustrated embodiment, the interlocking structures can be symmetrical, but other interlocking structures can be utilized. Thus, in the illustrated embodiment, the control element 207 is advantageously contained within a segment 205 rather than extending through the inner or central lumen defined by each segment 205, thereby facilitating advancement of other instruments or components through the inner or central lumens of the stack or group of segments 205.

While FIGS. 17A-D illustrate a structural configuration of one embodiment of a segment 205, other numbers and arrangements of teeth or protrusions 267, notches or grooves 268 and apertures 277 that may be utilized, and other shapes and patterns may be utilized. Further, in other embodiments, individual segments 205 may have different numbers of teeth or protrusions 267 and notches 269 depending on the need to provide additional stability, support, and rigidity to the sheath catheter 102 when the sheath catheter 102 is deployed to form a platform (P).

For example, the sheath catheter segment 205 shown in FIGS. 18A-D includes three apertures 277 for control elements 207, three keys, teeth or protrusions 267, and three notches 269, which are symmetrically arranged such that a protrusion 267 of a certain segment 205 can matingly engage with a notch 269 of a first adjacent segment, and a notch 269 of the segment can matingly engage with a protrusion 267 of a second adjacent segment 205. In this manner, the apertures 277 of each segment 205 are aligned such that the control element 207 can extend through multiple segments 205 and be placed in tension to place the group of segments 205 in tension or a rigid state (R), or placed in a relaxed or low tension state to place the group of segments in a flexible state (F). Further, the inner lumens of the segments 205 are aligned to collectively define a platform lumen, free of control elements 207, that extends along a length of the catheter sheath 102 for delivering various instruments and components to a target site.

As another example, the sheath catheter segment 205 shown in FIGS. 18A-D includes a greater number of apertures 277, but the same number and arrangement of protrusions 267 and notches 269 as the segments 205 described above. FIG. 19 illustrates a sheath catheter segment 205 having a different teeth/notch arrangement that includes six teeth or protrusions 267 and six mating notches 269, and having a wall that defines six pairs of apertures 277 through which control elements 207 can be inserted. Additional interlocking segments may be used to provide greater rigidity and resistance to rotation.

Accordingly, the structural configuration of a segment 205 can vary, and FIGS. 15-19 are provided to illustrate different interlocking structures that may be utilized to prevent rotation, enhance rigidity of the sheath catheter utilizing reduced compressive forces relative to other systems that may utilize other structures. Further, interlocking segments 205 may also provide further rigidity and resistance to twisting or rotational loads on the sheath catheter 102. Alternatively, the force provided by the pull wires 207 may be sufficient for the deployed sheath catheter 102 to rotational movements.

Further, although sheath catheters 102 are described above with reference to a plurality of segments 205 that matingly engage or interface with each other, a sheath catheter 102 with which embodiments may be utilized may also include a plurality of segments 205 that are connected to each other but do not necessarily matingly engage or interface with each other using keys or teeth and corresponding notches as described above. For example, referring to FIGS. 20A-B, a sheath catheter 102 with which rotatable apparatus embodiments may be utilized may include a plurality of segments 205 in the form of wedges, e.g., trapezoidal-like wedges. The top and bottom surface of each wedge does not have interlocking or mating structures, however, the top and bottom surf aces of each segment 205 shown in FIGS. 20A-B may include an interlocking structure similar to the segments described with reference to FIGS. 17A-19.

In the illustrated example, segments 205 in the form of wedges have a trapezoid-like shape when viewed from one side and a rectangular shape when viewed from another side. The segments 205 are stacked together and arranged such that a control element 207 extends through the sheath catheter 102 and is coupled to the segment 205 that is located closest to the distal tip of the sheath catheter 102. With further reference to FIGS. 20C-E, a pivot point 209 exists where each segment 205 contacts an adjacent segment 205 along a single edge. When the control element 207 is pulled downwardly in this configuration, the segments 205 revolve about their respective pivot points 209, and the space between the trapezoidal segments 205 is gradually reduced as the catheter 102 bends to the left. As illustrated in FIG. 20B, when the space between the segments 205 is eliminated, a maximum bend radius has been reached, and the control element 207 is fully tensioned and substantially rigid. To unfurl or straighten the catheter 102, the control element 207 may be released and pushed back up to reduce the tension on the segments 205.

In this manner, the control element 207 can be manipulated to control the rigidity of the sheath catheter 102 since the catheter configured as shown in FIG. 20A can be sufficiently flexible (F) for insertion through a lumen of a master sheath 63, whereas the catheter 102 configured as shown in FIG. 20B resulting from application of tension on the control element 207 compresses the segments 205 which, in turn, results in a substantially rigid structure (R) that may form a platform (P) or portion thereof that extends from a distal end 62 of the master sheath 63, and from which a guide instrument 37 and/or working instrument 41 may be manipulated, e.g., controllably rotated utilizing rotatable apparatus 250 embodiments.

FIGS. 20C-E illustrate compression springs 211 that may be used to assist with control and flexing of the catheter 102. In the illustrated example, a spring 211 is coupled between each segment 205 on the edge opposite from the pivot point 209. As shown in FIG. 20C, the control element 207 is not being engaged such that the springs 211 are not under load. As a result, the springs 211 are shown as pushing the segments 205 open as they revolve about their respective pivot points 209. Referring to FIG. 20D, the sheath catheter 102 assumes the shape of a substantially straight line as the control element 207 is pulled downwardly to a specified tension. In one embodiment, the control element 207 may be automatically pre-tensioned to such a designated tension so that the sheath catheter 102 is in a known shape or configuration. Referring to FIG. 20E, the stack of segments 205 is bent to the left as the control element (207) is pulled downwardly to place greater tension on the distal segment 205, thereby causing further compression of springs 211. As a result, the space between the wedges 205 is reduced, thus increasing the rigidity of the structure and forming a temporary substantially rigid platform (P) from which another system instrument can be manipulated.

A sheath catheter 102 constructed using wedge segments 205 and one or more control elements 207 as shown in FIGS. 20A-E operates in a similar manner as described above. A master or main sheath or catheter 63 or other suitable sheath or catheter is advanced to a target site or another area of interest. The sheath catheter 102 is advanced through the master sheath 63. When the sheath catheter 102 is advanced through the master sheath 63, it can be in a low tension, substantially non-rigid, naturally relaxed state. Tension can be applied to one or more pull wires 207 (as shown in FIG. 20B) such that the segments 205 come together and/or are compressed, thereby forming a substantially rigid structure (R) that may serve as a platform (P) or portion thereof at a location beyond the distal end 62 of the master sheath 63.

As illustrated, the control element 207 extends along one side of the segments and is connected to an outer surface of the distal segment 205. The control element 207 may also be connected to multiple segments 205, e.g., every other segment or to each segment 205. The configurations that are illustrated are provided illustrate how these devices may be implemented. It should be understood, however, that other configurations may be utilized. Reference is made to a sheath catheter 102 including a plurality of segments 205 operably coupled by a control element, e.g., as shown in FIGS. 15-19 for ease of explanation.

FIGS. 21A-F include different views of a sheath catheter 102 components and related system components including sheath catheter segments 205, a rotatable apparatus or tool 250 constructed according to one embodiment, a guide catheter 37, an orientation platform or interface 133, control elements or pull wires 207, and a working instrument 41, and how these components are arranged relative to each other and assembled. In the illustrated embodiment, the catheter sheath 102 or flexible catheter member 103 is comprised of a plurality of segments 205 and form a spine-like structure 203. Each segment 205 includes three teeth or protrusions 267, notches 279 and apertures 277 through which control elements 207 may extend. In the illustrated embodiment, the rotatable apparatus or tool 250 including an interface component and a rotatable collar or tool base is operably coupled to a distal end of the sheath catheter 102. An inner catheter member, such as a guide catheter 37, is coaxially located within the central lumen of the sheath catheter 102. An orientation platform 133 operably coupled to a distal end of the guide catheter 37 and serves as an adjustable interface or connector for the working instrument 41.

Figure 21A:
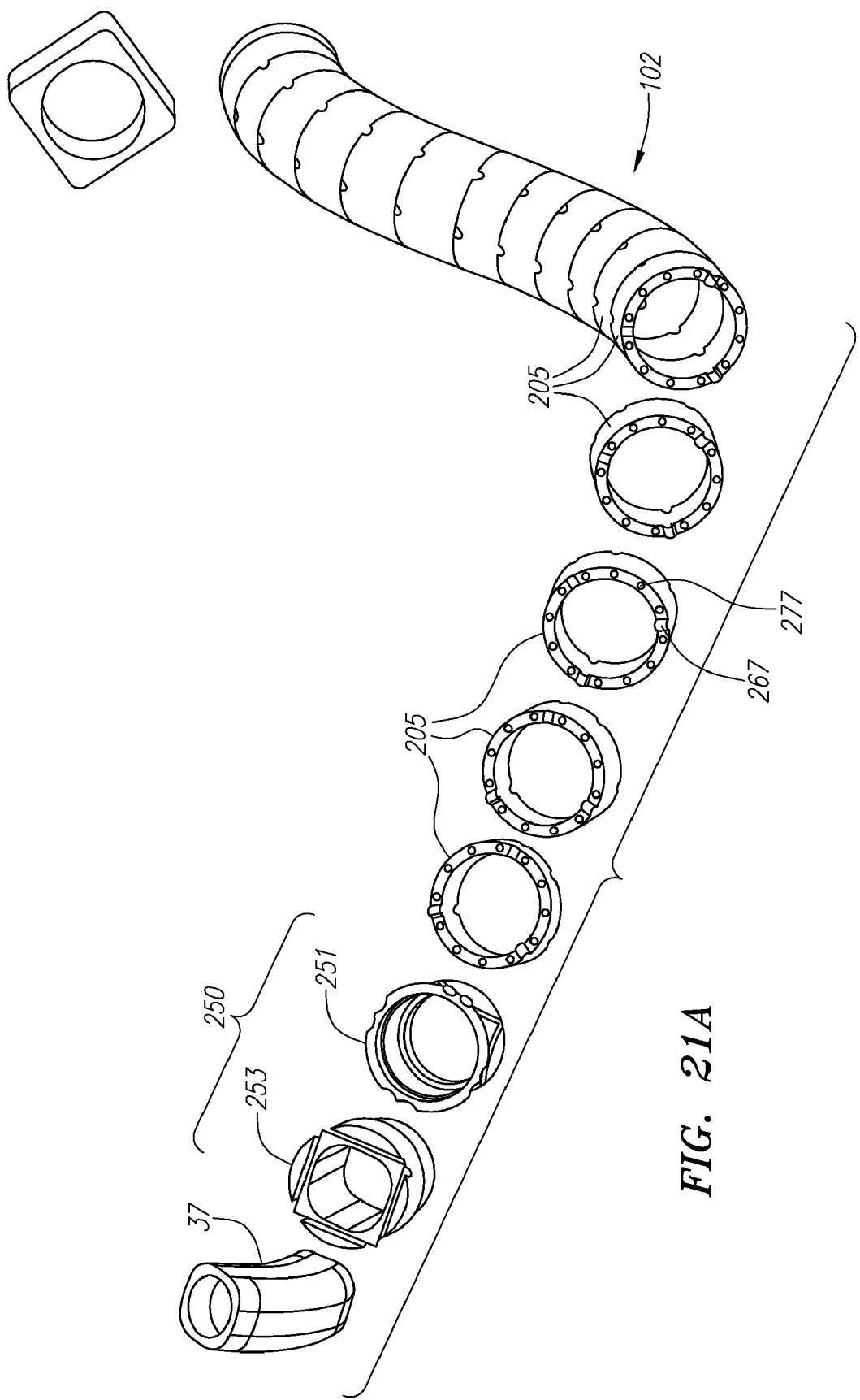
Figure 21B:
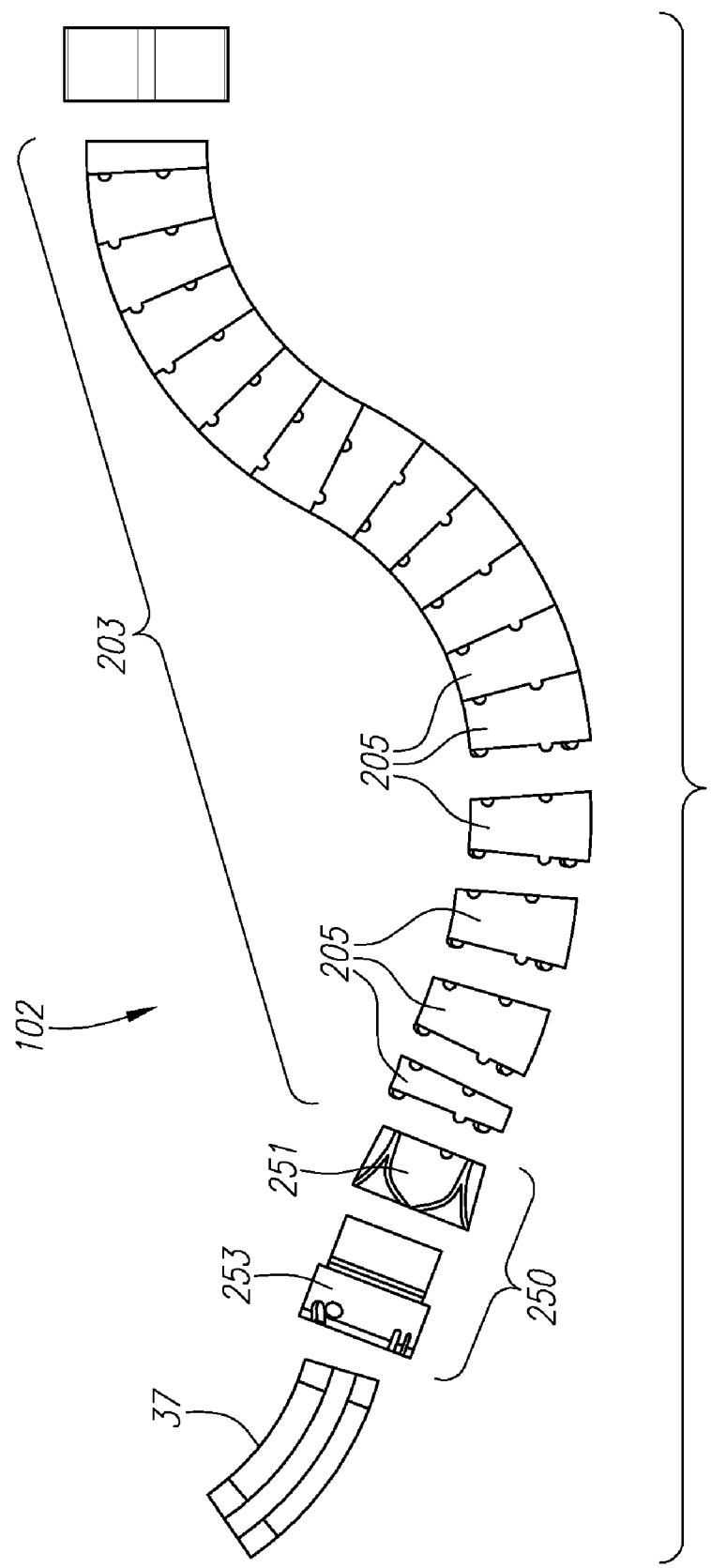
Figure 21C:
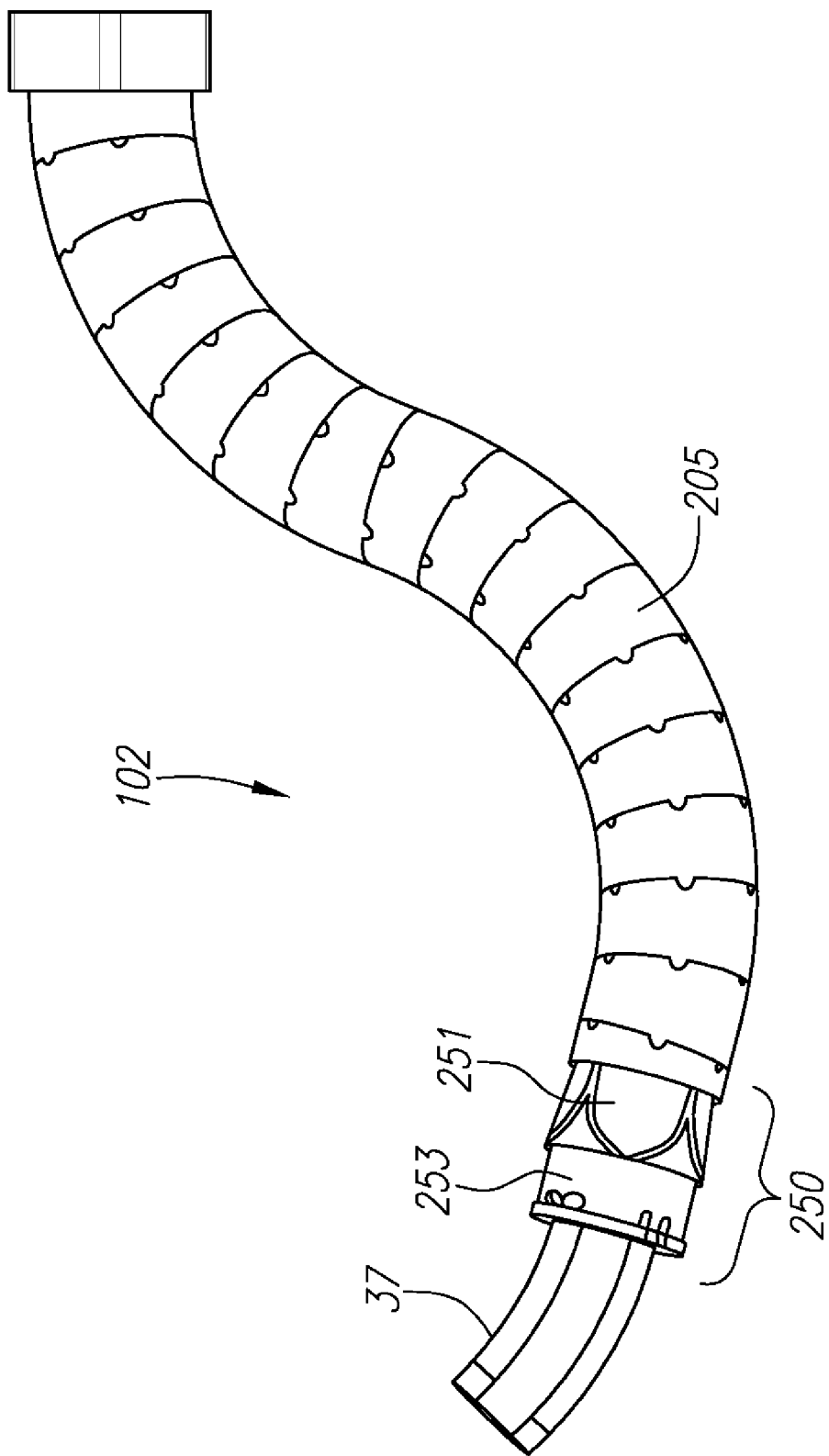
Figure 21D:
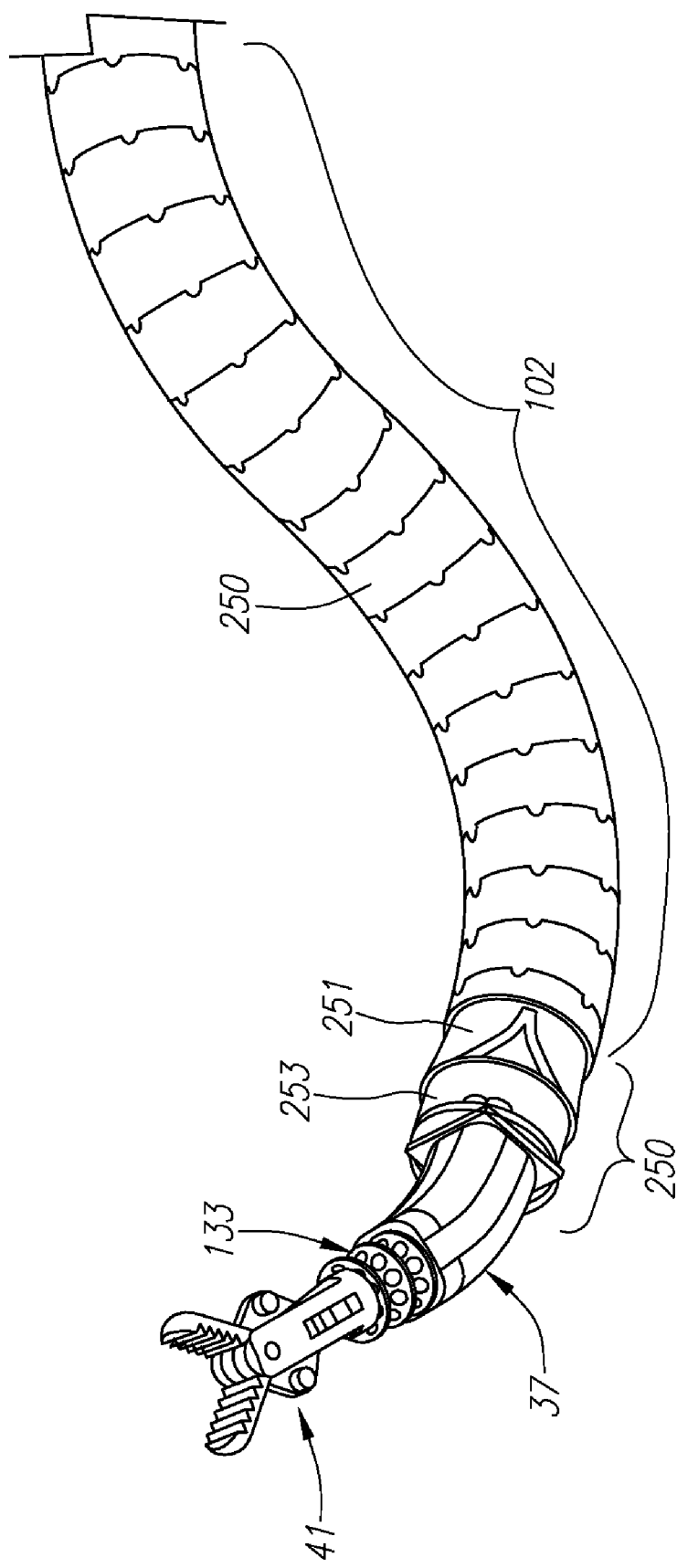
Figure 21E:
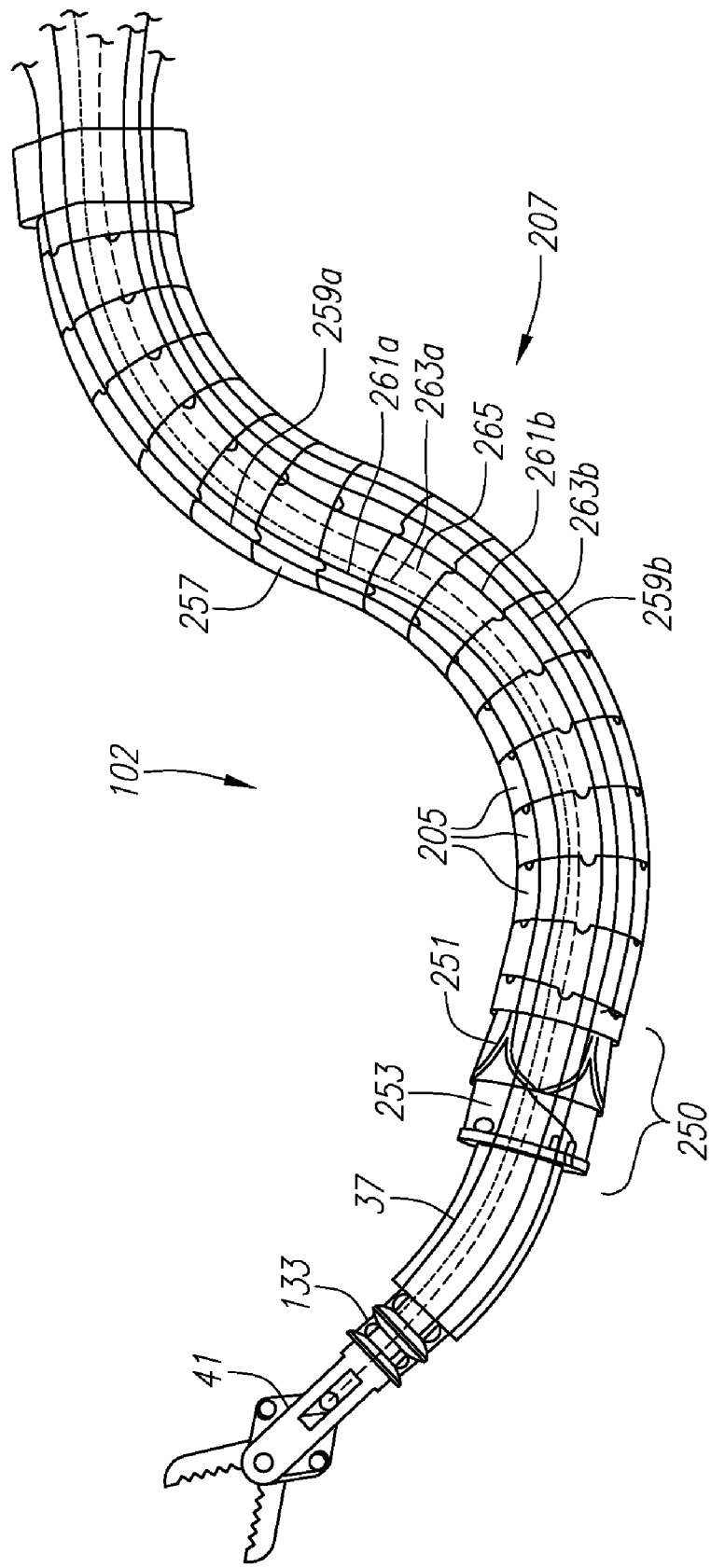
Figure 21F:
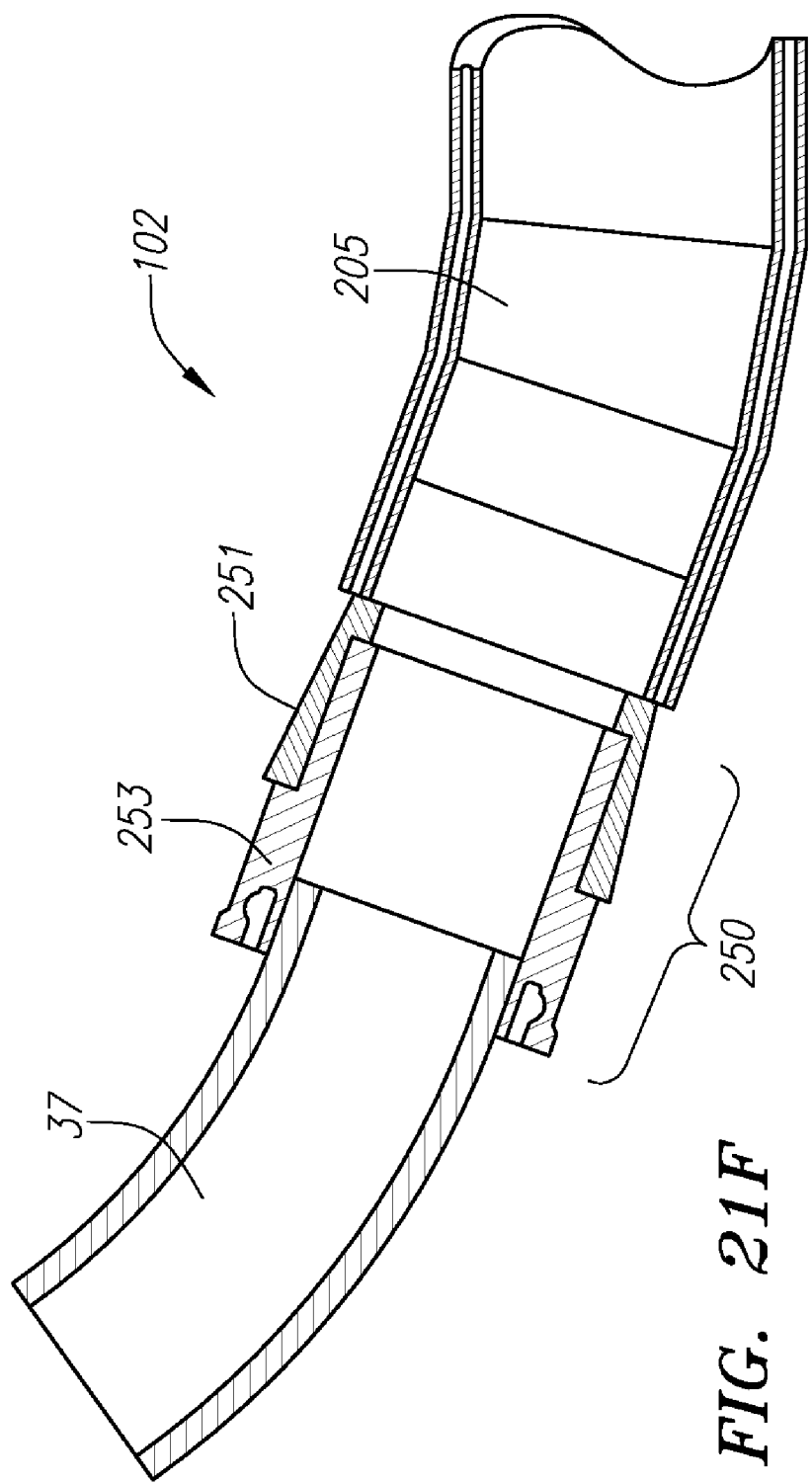

A more detailed view of how different control elements 207 may be used for implementing different controls is provided in FIG. 21E. A first pair of control elements or wires 259a,b extend from a splayer at proximal end of the sheath catheter 102 or flexible catheter assembly 103 to termination points on a rotatable component or collar 253 (generally referred to as rotatable collar 253). Second and third pairs 261, 263 of control elements extend from the splayer to termination points on the distal orientation platform 133. In some embodiments, the different pairs of control elements may be mounted to and controlled by different splayers, while a single splayer may control all the control elements of a flexible catheter in other embodiments. During a surgical procedure, an operator inputs commands to the system via the user interfaces on the workstation. The system processes the commands and communicates the control signals to activate the necessary motors and servos to cause the desired mechanical response on the catheter assembly. As the mechanical parts of the instrument driver 15 respond to the commands, various control elements are actuated at the splayers, causing the relevant portion of the flexible catheter to move or flex.

The first pair of control elements 259a,b may be manipulated to cause the rotatable collar or tool base 253 and items located within its lumen, the inner flexible catheter instrument member 149 or guide catheter 37 in this case, to controllably rotate either clockwise or counterclockwise. The second pair of control elements 261*a,b* may be manipulated to cause the distal orientation platform 133 to controllably pitch forward (+) or backward (−). A third pair of control elements 263*a,b* may be manipulated to cause the distal orientation platform 133 to yaw forward (+) or backward (−). In the illustrated embodiment, one or more control elements 265 for controlling the working instrument or tool 41 extend from the working instrument downwardly through a lumen of the inner flexible catheter to a splayer or servo at the proximal end of the catheter assembly 103. As these control elements 259, 261, 263, 265 are manipulated, the working instrument 41 may be actuated to perform the desired movements. Depending on the complexity of the particular flexible instrument embodiment and the degrees of freedom achievable, varying numbers of control elements may be implemented to control these movements.

Having described aspects robotic instrument systems and components thereof that may include or utilized rotatable apparatus 250 embodiments, further aspects of rotatable apparatus 250 embodiments, components thereof and their operation are described with reference to FIGS. 22A-30K.

FIGS. 22A-G illustrate embodiments of a rotatable apparatus or tool 250 that provide greater degrees of freedom and movement of a guide catheter 37, orientation platform 133 and/or working instrument 47 coupled thereto or associated therewith. A rotatable apparatus or tool 250 constructed according to one embodiment, as generally illustrated in FIGS. 14A-E and 21E, includes an interface or wire guide apparatus 251 (generally referred to as interface or interface component 251) and a rotatable collar, tool base or wire receive apparatus 253 (generally referred to as rotatable collar or tool base 253). The interface and rotatable collar components 251, 253 may be constructed, fabricated, or formed from various suitable materials including, for example, stainless steel and other materials that can be used at body temperature and are compatible with bodily fluids such as blood and enzymes.

The interface and rotatable collar 251, 253 are rotatably coupled together and may form a single unit or be parts of different system components. More particularly, in one embodiment, the interface 251 is operably coupled or fixed to a distal end of an elongate medical instrument such as a sheath catheter 102, and the collar 253 is rotatable relative to the interface 251. Thus, with embodiments, a "tool" that is rotatably coupled to a distal end portion of a medical instrument, such as a catheter, may be the rotatable collar or tool base 253, a working instrument or other component operably coupled to the collar or tool base 253, the collar or tool base 253 in combination with one or more of a guide catheter 37, an orientation platform 133 and a working instrument 41 that are operably coupled to the collar or tool base 253, and may be used for controlling rotation of components used in diagnostic, therapeutic and surgical procedures. In one embodiment, the interface 251 is an integral component of a distal end portion of a medical instrument such as a catheter, e.g., sheath catheter 102. In this embodiment, the rotatable collar or tool base 253 is operably coupled to, and rotatable relative to, the integral interface 251. In another embodiment, as generally illustrated in FIGS. 22G-O, the interface 251 is not integral with a medical instrument but may be operably coupled or attached to a distal end portion of a medical instrument, and the collar or tool base 253 is rotatable relative to the interface 251. In another embodiment, the interface 251 may be an integral component of a distal end portion of a medical instrument such as a catheter, and the collar or tool base 253 may be an integral part of another component, such as a platform 133 or working instrument 41, and these integral components can be rotatably coupled together. In a further embodiment, the interface 251 may be a separate component that is attached to a distal end portion of a medical instrument, and the collar or tool base 253 is an integral part of another component, such as a platform 133 or working instrument 41, which is rotatably coupled to the interface 251.

Thus, although FIGS. 22A-O illustrate a rotatable apparatus 250 as having a collar or tool base 253 that is rotatably coupled to an interface 251, it should be understood that the interface 251 and collar 253 can be made as a single unit, the interface 251 can be a separate component that is coupled to the collar 253 such that the collar 253 is rotatable relative to the interface, the interface 251 can be a separate component that can be coupled to a distal end portion of a medical instrument, the interface 251 can be an integral component of the distal end portion of a medical instrument, and the collar or tool base 253 can be an integral part of another system component such as an orientation platform 133 or working instrument 41. For ease of explanation, reference is made generally to a rotatable apparatus 250, which includes an interface 251 and a rotatable collar or tool base 253, but it should be understood that apparatus or adapter 250 components can form a single unit or be attached to, or integral with different and separate system components.

Referring to FIGS. 22A-B, similar to segments of the sheath catheter 102 described above, one embodiment of an interface component 251 of a rotatable apparatus 250 is a generally cylindrical body that includes notches 279 that are distributed about its bottom face. The notches 279 are configured and arranged to engage with corresponding teeth or keys 267 of a segment 205 of the sheath catheter 102 or other elongate instrument and may be configured to cap a stack or assembly of segments 205.

In the illustrated embodiment, the outer surface of the interface component 251 defines one or more guides, channels or grooves 281 (generally referred to as channels 281). The channels 281 serve to guide, direct or route a control element 207 (not shown in FIGS. 22A-G, and shown in FIGS. 21E and 22H-O), such as one or more of control elements 259*a,b* shown in FIG. 21E, across the interface 251 and to the rotatable collar 253. The control element 207 may be a control element that extends from a top segment 205 of the sheath catheter 102 or another control element depending on the configuration of the rotatable apparatus 250 and other system component. For example, the particular configuration employed may depend on whether the rotatable apparatus 250 is used with other system components or as a stand-alone device for attachment to a catheter to convert the distal end of the catheter into a rotatable distal end.

In the illustrated embodiment, multiple channels 281 extend between the bottom or proximal end and the top or distal end of the interface 251. The channels 281 may have various shapes and depths depending on the particular configuration employed, but in the illustrated embodiment, a channel 281 is defined by a proximal groove 283 that begins at the bottom or proximal end of the interface 251 and extends upwardly and splits or bifurcates into two arcuate or curved channels or channel segments. Although a generally symmetrical arrangement of channels 281 is illustrated, other embodiments may utilize asymmetrical channel 281 arrangements, e.g., to provide different rotation in different directions.

For example, an interface 251 may include four grooves 283*a-d* (generally referred to as a groove 283), each of which splits or bifurcates into a pair of arcuate or curved channel segments 281*a-b*, 281*c-d*, 281*e-f*, 281*g-h* (generally referred to as a channel or channel segment 281). As shown in FIG.

22A, the channel segments 281 may form a V-shaped or Y-shaped structure and sweep outwardly and distally from a groove 283 in opposite directions towards the top or distal edge of the interface component 251. In the illustrated embodiment, channel segments 281*b*, 281*c* originating from different grooves 283*a*, 283*b* merge together, or share a common channel portion, which is useful for providing fewer termination points. The channel segments 281*b*, 281*c* curve outwardly so as to extend in a substantially helical shape about the longitudinal axis of the interface 251.

Although FIG. 22A illustrates an interface component 251 that includes eight channel segments 281, other embodiments may include different numbers of grooves 283 and/or channel segments 281 and arrangements thereof. Further, although various figures show two channel segments 281 forming a V-shaped or Y-shaped structure, other numbers of channel segments 281 may stem and split from a groove 283. Further, although embodiments are shown as having channel segments 281 that merge, other embodiments may utilize other channel segment arrangements for other control element 207 routing. The particular configuration that is employed may depend on, for example, the desired degree of rotation, the number of control elements 207 to be guided, the size of the interface 251, etc. Thus, FIG. 22A illustrates one example of how embodiments can be implemented.

Referring to FIGS. 22B-C, the interface component 251 and the rotatable collar or tool base 253 are operably or rotatably coupled together. For this purpose, the illustrated embodiment of the interface 251 defines a recess 285 configured to receive a bottom, proximal or mating section 287 of the rotatable collar 253. An inner groove 289 extends circumferentially around an interior surface of the interface component 251 (FIG. 22B) proximate to the top edge of the interface component 251. The mating section 287 engages or mates with a circumferential ridge 295 that extends around an outer surface of the rotatable collar 253. When the rotatable collar 253 is fitted with the interface component 251, the ridge 295 of the rotatable collar 253 is allowed to rotatably glide within the inner groove 289 of the interface component about a central axis 297.

With reference to FIGS. 22C and 22G, in the illustrated embodiment, the top or distal surface or section 288 of the rotatable collar or tool base 253 includes one or more channels, grooves or slots through which control elements 207 guided by the interface 251 extend and may terminate. In the illustrated embodiment, the rotatable collar 253 includes four channels or slots 301*a-d* (generally referred to as a channel 301). The four channels 301*a-d* are arranged in a square shape, and each channel 301 has a rectangular shape and include three substantially flat surfaces and an open side or face that receives or provides access to a control element 207. Other arrangements and shapes of channels 301 may be utilized. Thus, FIGS. 22C and 22G are provided to illustrate one manner in which embodiments may be implemented.

FIG. 22G illustrates the interface 251 and rotatable collar 253 operably coupled together such that a guide or path for a control element 207 includes a groove 283 and a channel or channel segment 281 defined by the interface component 251 and a channel or slot 301 defined by the rotatable collar 253. Thus, the interface component 251 defines a "first guide" or channel or guide configuration G1, and the rotatable collar 253 defines a "second guide" or channel or guide configuration G2, which is different than the first configuration G1. The guide configurations G1, G2 may be different in that they have different channel shapes, numbers of channels, orientation of channels, channel arrangements and/or sizes.

For example, as shown in FIG. 22G, the first and second guide configurations G1 and G2 have different shapes since the first guide configuration G1 defined by grooves 283 and/or one or more channel segments 281 has an arcuate shape, e.g., a V-shape or Y-shape, whereas the second guide configuration G2 includes channels 301*a-d* having a linear shape, and which may define a square-like configuration. Further, in the illustrated embodiment, grooves 283 and channels 281 that define the first guide configuration G1 are physically separated and disconnected from the channels 301*a-d* defined within the top surface 288 of the rotatable collar 253. Further, as shown in FIG. 22G, the channels 281*a-d* are defined in a substantially vertical manner to define a substantially vertical, arcuate plane or portion thereof, whereas the channels 301*a-d* defined within a substantially horizontal top surface 288 of the rotatable collar 253, such that the channels 301 define a plane that is substantially parallel to the plane of rotation (represented by bi-directional arrows in FIG. 22G) of the rotatable collar 253 and substantially orthogonal to the channels 281.

Referring to FIG. 22H-I, in one embodiment utilizing a single control element 207, such as control element 259*a* or 259*b* shown in FIG. 21E, the control element 207 may be positioned within a channel 281 of the interface component 251, which is fixedly mounted to a distal end portion of a medical instrument. Although only one channel 281 may be needed in the illustrated embodiment, other channels are shown for purposes of illustration to show that control element routing 207 can be in different directions.

In this manner, the control element 207 extends through a guide having a first configuration G1, e.g., extends through or is positioned within the groove 283 and a channel or channel segment 281, around a bottom or distal portion of the rotatable collar 253 that does not define any channel or slot, and through a guide having a second configuration G2, e.g., extends through or is positioned within a channel or slot 301 defined by the top surface 288 of the rotatable collar 253. For this purpose, a circular notch 303 at an end of the channel 301 can be configured to receive a termination piece of the control element 207. The control element 207 may terminate with a metal solder ball or with a knot such that when the control element 207 is positioned into the channel 301, its termination piece may be seated into the circular notch 303 for that channel 301 and locked into place. In this manner, the distal end of the control element 207 can be secured within a channel 301 of a top portion of the rotatable collar 253.

In the illustrated embodiment, the control element 207 wraps around a substantial portion of the rotatable collar 253 between the guide channels 281 of the interface 251 and the guide channels 301 of the collar 253. As shown in the particular embodiment illustrated in FIGS. 22H-I, the control element 207 is guided through a channel 281 from a first side, e.g., a front (F) of the rotatable collar 253 (FIG. 22H), wraps upwardly around the front and a second or right side (R) (FIGS. 22H-I), around a third, rear or back side (B) (FIG. 22I), and terminating in the channel 301 defined in a fourth or left (L) side (FIGS. 22H-I), e.g. a circular notch 303 at an end of the channel 301 can be configured to receive a termination piece of a control element 207.

With this arrangement, the distal end of the control element 207 is secured to a top portion 288 of the rotatable collar 253 by wrapping around a substantial portion of the rotatable collar 253, e.g., more than one half of the outer circumference of the rotatable collar 253 and through guided (G1, G2) and unguided sections of the rotatable apparatus 250.

With further reference to FIG. 22J, when tension on the control element 207, e.g., the control element 259 that extends through the spine-like 203 collection of segments 205, is increased (represented by downward arrow) by axial movement of the control element 259, the tension is transferred along the length of the control element 207, thereby causing the rotatable collar 253 to rotatably slide about the interface piece 251. Thus, the curved grooves 281 translate axial forces on the control element 207 along the longitudinal axis of the catheter 102 into partially transverse forces that result in rotation of the rotatable collar 253. In the illustrated embodiment, the rotation is in a clockwise direction given the particular configuration and routing of the control element 207 shown in FIG. 22J. The collar 253 may be rotated substantially, e.g. about 225 degrees. The amount of rotation may depend on the size of the interface and collar components 251, 253, the arrangement of channels 181, 301 and control element 207, which may result in the control element extending around the rotatable collar 253 by different degrees.

Thus, pulling or placing tension on the control element 207 rotates the collar 253 and associated instruments such as a guide catheter 37 and working instrument 41, thereby advantageously providing rotational control as well as articulation control of system components. Embodiments that are utilized with a sheath catheter 102 that can assume flexible and rigid states are operable such that axial movement of a control element 259 relative to a medical instrument such as a catheter to rotate the collar 253 does not cause appreciable bending of the substantially rigid distal end portion of the catheter. Similarly, referring to FIG. 22K, when a control element 207 that is in tension is relaxed due to decreased tension (represented by upward arrow), the decreased tension results in counter-clockwise rotation of the rotatable collar 253 given the particular configuration and routing of the control element 207 shown in FIG. 22K.

Moving the control element 207 to increase or decrease control element 207 tension can result in rotation in a different directions depending on how the rotatable apparatus 250 is structured, e.g., depending on whether the control element 207 is routed from left to right, or from right to left. Further, it should be understood that the degree of circumferential wrapping of a control element 207 around the rotatable component, and how much a control element 207 wraps around a portion of the interface component 251 and rotatable collar 253 can vary depending on the particular structural configuration of rotatable apparatus 250 embodiments. Thus, FIGS. 22H-I are provided as one example of how embodiments may be implemented utilizing a single control element 207. In other embodiments, a rotatable apparatus 250 may guide or direct multiple control elements 207.

For example, in another embodiment illustrated in FIGS. 22L-O, a rotatable apparatus or tool or portion thereof 250 as described above guides or directs two or other numbers of control elements 207a, 207b (generally referred to as control element 207), which extend from an instrument such as a catheter at circumferentially offset locations. As shown in FIG. 22L, a first control element 207a is guided along a channel 281b that extends in a first direction, and a second control element 207b is guided along a channel 281c that extends in a second direction. With this arrangement, the control elements 207a, 207b cross each other, e.g., at a top surface of the interface component 251, and each control element 207a, 207b wraps around a portion of the rotatable collar 253 and is secured within respective channels 301 defined within the top surface 288 of the rotatable collar 253 as described above.

With the configuration illustrated in FIGS. 22L-M, when the control element 207a, e.g., control element 259 that extends through the spine-like 203 collection of segments 205 of the sheath catheter 102, is pulled to increase the tension of the control element 207a (represented by downward arrow), the tension causes the rotatable collar 253 to move in the direction of the pulled controlled element 207a. In the illustrated example, the increased tension results in clockwise rotation of the rotatable collar 253 as a result of the control element 207a traversing the arcuate channel 281b formed within the interface 251 and wrapping right to left to be secured to the left channel 301 formed within the top surface 288 of the rotatable collar 253. Similarly, when the control element 207b, e.g., a control element 259 that extends through the spine-like 203 collection of segments 205 of the sheath catheter 102, is pulled to increase the tension of the control element 207b (represented by downward arrow), the tension causes the rotatable collar 253 to move in a counter-clockwise direction. Thus, the curved grooves or channels 281a, 281b serve to translate axial forces on the control element 207a along a longitudinal axis of the catheter 102 into partially transverse forces to rotate the collar 253 in different directions. Embodiments that are utilized with a sheath catheter 102 that can assume flexible and rigid states are operable such that axial movement of a control element relative to the catheter instrument to rotate a collar 253 does not cause appreciable bending of the substantially rigid distal end portion of the catheter. Further, moving the control element 207 in the opposite direction to reduce the tension on a tensioned control element 207a, b would also result in rotation of the collar 253 in a manner that is the opposite of what is shown in FIGS. 22N-O.

The interface 251 and rotatable collar 253 may define similarly sized central lumens 291, 293 that extend along their respective longitudinal axes, and which may be joined with the central lumen 275 of the associated sheath catheter 102 or other elongate instrument. Although the lumen openings 291, 293 are shown as having a circular shape, other embodiments may have interface lumen openings of other shapes, e.g., as shown in FIGS. 22D-F, e.g., to accommodate guide catheters 37 of different shapes and sizes.

For example, the collar 253 may have a substantially rectangular inner lumen or space 293, and a guide catheter 37 may have an outer cross-sectional shape that is also substantially rectangular and matches with the cross-sectional shape of the inner space or lumen 293 of the collar 253 such that the guide catheter 37 may substantially mate with or fit in the inner space or lumen of the collar 253. At the same time, the guide catheter 37 may be able to slide in the inner space or lumen of the collar 253, such that the guide catheter 37 may be advanced or retracted through the lumen of the collar 253. The mating or fitting of the two, guide catheter 37 and the collar 253, enables both the guide catheter 37 and the collar 253, and an associated platform 133 and/or working instrument 47, to rotate substantially in unison as substantially a single unit.

Other embodiments of a rotatable apparatus 250 are described with reference to FIGS. 23A-30K. Examples of such devices include a helical drive, a BNC drive, a rotational devices that utilize a reciprocating pin/cam drive, a dual reciprocating pin/cam drive, a harmonic drive, a wobble plate utilizing cam or control element drive, and are described in detail in U.S. application Ser. Nos. 12/032,626; 12/032,634; 12/032,622 and 12/032,639, filed on Feb. 15, 2008, the contents of which were previously incorporated herein by reference.

Referring to FIGS. 23A-C, in one embodiment, a rotatable apparatus 250 includes an elongate outer body 316 and an inner body 305 positioned within the lumen of the outer body 316. The outer body 316 may be a groove extender apparatus or a sheath, and the inner body 305 may be a drive shaft, such as a catheter drive shaft, or a guide catheter. For example, in one embodiment, the outer body is operably coupled to or attached to a sheath, and the inner body or shaft 305 is operably coupled or attached to a guide catheter. For ease of explanation, embodiments are described with reference to an outer body or body 316 and a drive shaft or catheter drive shaft 305. An inner surface of the distal end of the outer body 316 and an outer surface of a distal end of the drive shaft 305 are operatively coupled or shaped such that axial displacement of the drive shaft 305 relative to the body 316 causes a corresponding rotation of one of the drive shaft 305 and body 316 relative to the other. An orientation platform 133 (e.g., as described with reference to FIGS. 31A-57) or a working instrument tool 41 (e.g., as shown in FIGS. 4A-Z) may be mounted to the distal tip of the rotatable apparatus 250 to controllably rotate these components.

According to one embodiment, the outer surface 305a of the distal end of the drive shaft 305 and the inner surface 103b of the distal end of the body 316 include complimentary threaded surfaces. In the embodiment illustrated in FIGS. 23A-B, the threaded surfaces are helical threads 311 and teeth 309. In FIG. 23A, the distal portion of the flexible catheter body 316 is shown with the lower portion cutaway to expose an interior drive shaft 305, and only the top surface of the drive shaft 305 is visible, and helical teeth 309 on the distal end of the drive shaft 305 are hidden inside of the body 316 and represented as phantom lines. The outer surface of the helical distal portion 311 matingly engage a corresponding helically threaded inner surface such that the distal tip of the drive shaft 305 may be controllably extended beyond the distal tip of the body 316 (as shown in FIG. 23B) and be controllably retracted into the body 316 (as shown in FIG. 23A).

More particularly, when the drive shaft 305 is positioned inside of the body 316, the helical teeth and threads 309, 311 may be fitted or mate together such that pushing the drive shaft 305 from its proximal end results in upward forces that move the shaft 305 upwardly. This axial motion also results in rotational motion about a central axis of the shaft 305 due to the helically threaded surface 311 and corresponding helical teeth 309 of the drive shaft 305, resulting in translation of an upward force into a rotational force along the inclined surface. In other words, because the helical threads 311 are distributed about the inner shaft of the body 316, traversing the helical threads 311 results in rotation of the drive shaft 305 about the longitudinal axis 125, while the drive shaft 305 translates upwardly.

In this manner, the drive shaft 305 may be translated upwardly such that its distal tip extends from the body 316, while being rotated in a counterclockwise direction (when viewed from the perspective of looking into the distal tip). Rotation in the opposite direction may also be utilized. The drive shaft distal tip 313 may also be retracted into the body 316 (as shown in FIG. 23A), by pulling the drive shaft 305 downwardly, which causes the drive shaft 305 to rotate clockwise and translate downwardly along the helical surfaces 311. With embodiments, a user can robotically actuate simultaneous rotational and translational motion of the distal tip of the body 316. Further, in certain embodiments, rotational interaction of the helical gear elements may also cause some rotational movement or twisting to occur on the drive shaft member below the helical gear arrangement.

The drive shaft 305 may also include a lumen 307 that extends from its distal end to its proximal end at the catheter splayer. The lumen 307 may be used to house or deliver a cable connected to a working instrument or a control element.

In the embodiment illustrated in FIGS. 23A-B, the lumen 307 has a circular or cylindrical shape. In other embodiments, e.g. as shown in FIGS. 23D-E, the lumen 307 may have different shapes, e.g., a rectangular shape, depending on an outer shape of a guide catheter 37 or other instrument that is inserted through the lumen 307 to allow the components to rotate substantially in unison, as discussed above. Other lumen 307 shapes may also be utilized, e.g., triangle, square, star and other shapes.

For example, a guide catheter 37 can be advanced towards the target site through the inner space or lumen 307 of the drive shaft or spline extender apparatus 305. Analogous to collar or wire receiver apparatus 253, the drive shaft 305 has an inner space or lumen 307 with a cross-sectional shape that may be substantially rectangular (e.g., as in FIGS. 23D-E) to match a guide catheter 37 having a substantially rectangular shape to match the lumen 307, such that guide catheter 37 may substantially mate with or fit in the inner space or lumen 307 of the shaft 305. Because of the mating or fitting of the two, guide catheter 37 and the drive shaft or spline extender apparatus 305 of rotational apparatus, the guide catheter 37 and the shaft 305 can rotate and be translated substantially in unison. As apparent to one skilled in the art, the cross-sectional shape of the inner space or lumen of spline extender apparatus (904) and the outer cross-sectional shape of guide catheter (18) may be of various geometrical shapes (e.g., triangular, square, star, etc.) such that the rotation of the spline extender apparatus (904) would cause the guide catheter to rotate in substantial unison.

FIGS. 24A-C illustrate a catheter assembly that operates in a similar manner as described with reference to FIGS. 23A-C except that the embodiment shown in FIGS. 24A-C includes a different type of translational/rotational drive element 250. In the embodiment illustrated in FIGS. 24A-B, the outer surface of the distal end of the catheter drive shaft 305 and the inner surface of the distal end of the body 316 form a connector that is in the form of a Bayonet Neill-Concelman (BNC) connector or drive element or slot extender/peg extender apparatus.

As shown in FIG. 24A, the distal portion of a body 316 is shown with the lower portion cutaway to expose and interior drive shaft 305. The drive shaft 305 of this embodiment is coaxially located in the central lumen of the body 316 along the longitudinal axis of the body 316. In one embodiment, the outer surface of the distal end of the drive shaft 305, which is in the form of a peg extender apparatus, includes an outwardly extending pin 315, and the inner surface of the distal end of the body 316, which is in the form of a slot extender apparatus, defines an arcuate groove 317 or female mating surface configured to receive the pin 315. The female mating surface 317 may include a spring that maintains a clamping force. More particularly, to couple the two surfaces, a pin 315 on the male surface is aligned with and inserted within a slot 317 on the female surface. Once the pin 315 reaches the bottom or end of the slots 317, the two surfaces may be turned in opposite directions to guide the pin 315 into a perpendicular slot that prevents or restricts removal of the pin 315 from the slot 317, e.g. utilizing one or more springs then hold the pin 315 in position within the slot 317 to prevent backing out of the pin 315. To disconnect the two surfaces, they are pushed together to overcome the springs, and the locking turn is reversed.

Thus, with such a BNC drive shaft or element 305, a user may be able to robotically actuate rotational and translational movements at the distal tip of the body 316. In alternative embodiments, the female receptor slots 317 on the inside surface of the 305 may be configured to cause a clockwise rotation. Furthermore, in some embodiments, the rotational interaction of the male pin elements may also cause some rotational movement or twisting to occur on the drive shaft member below the bayonet connector arrangement. The drive shaft distal tip 313 may be controllably extended from and controllably retracted into the catheter body 316 by pushing/pulling the drive shaft 305, thereby causing rotational and translational motion of the drive shaft 305 and associated orientation platform 133 and/or working instrument 41.

The drive shaft 305 may include a lumen 307 extending from its distal end to its proximal end at the catheter splayer e.g., for a cable to control a working instrument 41 or a guide catheter 37. The lumen 307 can have a circular or cylindrical shape (as shown in FIGS. 24A-B) or other shapes (e.g., as shown in FIGS. 24D-E), to match an outer surface of a guide catheter 37 to enable the guide catheter 37 and the shaft or peg extender apparatus 305 to rotate substantially in unison.

Referring to FIGS. 25A-H, another embodiment is directed to a rotational apparatus 250 of a robotic medical system includes an elongate catheter body or tubular body 321, an actuation element 319 coaxial with the tubular body 321 and positioned within the tubular body 321 lumen, and a control element 327, such as a pull wire, that extends through the tubular body 321. The actuation element 319 is coupled to an internal portion of the tubular body 321. Manipulation of the control element 327 causes the actuation element 319 and the catheter or tubular body 321 to rotate together.

According to one embodiment, as illustrated in FIGS. 25A-H, the actuation element 319 is in the form of a ratchet drive or reciprocating pin/cam drive that rotates a distal segment of a tubular body 321. In FIG. 25A, the outer portion of the distal tip of the tube 321 is removed to illustrate the actuation element 319 (as represented by phantom lines). According to one embodiment, the actuation element 319 includes a gear, such as a helical gear 319, having a plurality of teeth and defining a plurality of corresponding grooves, a guide or track 325 (generally referred to as guide 325) that is disposed on an inner surface of the distal end of the tube 321 adjacent to the gear, and a pin 335 that is movable along the guide 325, e.g., within a slot defined by the guide 325. A control element 327 is attached to the pin 335 such that manipulation of the control element 327 results in movement of the pin 335 along the guide 325 and within a groove defined by teeth of the gear 319, resulting in rotation of the actuation element 319 and the tubular body 321. In the illustrated embodiment, rotation is counterclockwise (represented by arrow), but components can be configured for clockwise rotation.

Referring to FIGS. 25A-D, in one embodiment, the helical gear 319 is affixed, attached or couple to a length of the catheter body or tube 321 having a ridge 331 that interfaces with a groove 333 inside of the body 316 at its first end. As the helical gear 319 and tube 321 rotate, the ridge 331 is allowed to move within the groove 333, thus allowing the tube 321 to also rotate coaxially within the body 316. In the illustrated embodiment, the centers of the helical gear 314 and the tube 321 include a hollow portion or lumen that allows access to a lumen 115 of the body 316. An orientation platform or tool (not illustrated in FIG. 25A) may be mounted to the tube of this instrument member and controlled by running one or more control elements through the lumen 307 to the proximal end.

FIGS. 25C-D are cross-sectional views illustrating the placement of a helical gear 319 and its associated pin 335. A pin 335 for actuating rotation of this helical gear 319 resides inside a slotted track 325 on the inside surface of the tube 321. The slotted track 325 in this embodiment has triangle shaped structure as illustrated in FIG. 25A. In this implementation, rotation of the helical gear 319 may be actuated by sequentially pulling and releasing a control element 327 coupled to the pin 323.

FIG. 25C shows the pin 335 at a first position on the slotted guide 325. As the pin 335 travels downwardly on the slotted guide 325 in response to the downward force on the control element 327, the helical gear 319 is caused to rotate counterclockwise (as viewed from the perspective of looking into the distal tip) as shown in FIG. 25D. However, the slotted guide 325, according to one embodiment, has a non-uniform thickness or depth.

More particularly, FIG. 25E is a cross-sectional, stretched out view of one embodiment a non-uniform surface 325a of a guide 325. The bottom edge 325b of the cross-sectional view of FIG. 25E represents the outer surface of the outer body or tube 321, e.g., a catheter body of the catheter instrument assembly 103, and the top edge 325a represents the uneven, non-uniform or undulating inner surface 325a. With this configuration, as the pin 335 traverses the surface 325a, e.g., within a slot formed in the guide 325 through which the pin 335 may extend, the pin 335 is caused to rise and drop in accordance to the undulating surface 325a.

FIG. 25B illustrates how the pin 335 extend outwardly to engage with threads of the helical gear 319 when the pin 335 is at a raised or thicker portion of the guide 325, and how the pin 335 withdraws into the sidewall of the catheter or tubular body 321 when the pin 335 is at a lowered or thinner portion of the guide 325.

Referring to FIGS. 25F-H, movement of the pin 335 along the guide 325, and how the helical gear 319 is moved to the right (i.e., rotated counterclockwise in the example illustrated in FIGS. 25A-D) as the pin 335 traverses along the slotted guide 325 is further illustrated. For reference, the lowercase letters identifying different portions of the surface 325a of the guide 325 in FIG. 25E are provided in FIGS. 25F-H to show how the pin 335 is extended and retracted relative to the helical gear 319.

In the illustrated embodiment, the pin 335 is configured to traverse or slide along the guide 325 in a single direction (as indicated by directional arrow in FIG. 25E). The taller or thicker the guide 325 surface, the more the pin 335 will extend outwardly from the sidewall of the catheter or tubular body 321 since the guide 325 is attached to, disposed on, or formed in an inner surface or side wall of the body 321 as shown in FIG. 25F.

Referring to FIG. 25F, assume, for example that the initial position of the pin 335 is position 'd' at which the pin 335 is forced outwardly and does not engage any teeth of the gear 319. In this example, force may be applied to a control element 327 to cause the pin 335 to move from position 'd' to position 'e', rounding the corner or vertex of the a guide that may have a triangular shape. As the pin 335 rounds the first vertex on the right side of the triangle approximately at position 'e', and with further reference to FIG. 25E, the pin 335 retracts into the sidewall and slides down the sloped track segment to position 'f'. More particularly, as shown in FIG. 25E, the height of the surface 325 at position 'd' is higher than position 'e' and, therefore, the pin follows the surface down to a lower level, thereby resulting in retraction of the pin 335. In one embodiment, movement of the pin 335 between positions 'e' and 'f' may be assisted by gravity. In another embodiment, the pin 335 may be biased with a spring force.

Downward force may be applied to the control element 327 to force the pin 335 outwardly from the sidewall when moving from position 'f' (which, in the illustrated embodiment, is at the same level as position 'e') to position 'a' at the second corner or vertex. More particularly, as the pin 335 traverse the surface 325a, the pin is extended outwardly as it approaches position 'a' at which point the pin 335 contacts a left side of a tooth, i.e. the third or middle tooth (identified by crosshatching) of the gear 319. By pulling the control element 327, the attached pin 335 is pulled along the guide 325 from position 'a' to position 'b'. In the embodiment illustrated in FIG. 25E, the level of the surface 325a between positions 'a' and 'b' remains the same, and the pin 335 continues to engage the left surface of the third gear tooth element. As such, downward force along the left inclined face or surface of this tooth is translated into a rightward or rotational force that causes the gear 319 to move towards the right, as illustrated in FIGS. 25G-H.

Referring to FIG. 25G, the gear 319 moves or rotates as the pin 335 traverses the guide 325 between positions 'a' and 'b'. But because the gear 319 is a wheel about the longitudinal axis of the catheter instrument, the gear 319 is caused to rotate towards the right (or counterclockwise) in this example. Referring to FIG. 25H, it can be observed that the second vertex of the slotted guide 325 is now positioned between the first and second gear teeth, whereas the second vertex was previously positioned between the second and third gear teeth before the gear rotation as shown in FIG. 25F. As the pin 335 moves past position 'b' and approaches the third vertex at position 'c', the pin 335 retracts into the sidewall and becomes disengaged from the gear 319 as a result of the change in the surface 325a of the guide 325, as shown in FIG. 25E.

By releasing or slacking the control element 327, the pin 335 is allowed to travel from position 'c' to position 'd' while the pin 335 remains in a retracted position and out of contact from the gear 319. Upward movement of the pin 335 from position 'c' to position 'd' may be facilitated with a spring urging the pin 335 upwardly and thus also pulling the control element 327 upwardly. In one implementation, the control element 327 is biased with an upward force so that the pin 335 may be actuated by applying downward force as the control element 327 is pulled.

Although one embodiment has been described with reference to specific physical attributes of a gear 319 and non-uniform, undulating guide surface 325a, other embodiments may be implemented with other actuation element or gear designs, and other surface 325a attributes. Further, in the illustrated embodiment, the guide 325 is triangular, but other shapes may also be utilized. Similarly, the particular surface 325a profile and height levels of different portions of the surface 325a may vary. For ease of explanation, however, one embodiment has been described with reference to an actuation element that includes a single pin 335, a guide 325 having a triangular shape, and a control element 327 in the form of a pull wire. Further, although embodiments are described with reference to the helical gear 319 rotating in a counterclockwise direction, the actuation element may also be configured such that the gear 319 rotates in a clockwise direction. Moreover, in other alternative embodiments, multiple actuation elements may be utilized. For example, two actuation elements may be utilized, as shown in further detail in FIGS. 26A-E.

Referring to FIGS. 26A-E, according to another embodiment, a rotational apparatus 250 of a robotic medical system constructed according to another embodiment includes an elongate catheter or tubular body 321, multiple actuation elements and multiple control elements 327. Portions of the actuation elements are coupled to internal portions of the body 321 such that rotation of the actuation element results in rotation of the body 316.

In the illustrated embodiment, a rotational apparatus 250 includes two actuation elements that are positioned within the catheter or tubular body 321 and positioned within the body 321 lumen, one actuation element being positioned at the distal end of the body. During use, one or both of the actuation elements are rotatable together, e.g., in response to manipulation of at least one of the first and second control elements 327, 340.

In the illustrated embodiment, a the rotational apparatus 250 includes the same components as described with reference to FIGS. 25A-H, except one actuation element includes a gear 319 configured to rotate in a first direction, and the other actuation element includes a gear 323 configured to rotate in a second direction, e.g., as a reversing or dual reciprocating pin/cam drive. During use, both gears 319, 323 may rotate independently of each other, one gear may be rotated at a time, or both gears may be rotated at the same time. In practice, meaningful movement at the distal tip may be obtained when one gear is rotated.

More particularly, referring to FIG. 26A, an outer portion of the distal tip is illustrated in phantom such that inner components of the apparatus are visible. In the illustrated embodiment, a first gear 323 is shown positioned coaxially inside of a central lumen of a flexible catheter or tubular body 123 just below the distal tip portion of the body 123. A second gear 319 is shown positioned coaxially inside of the tubular body 123, proximally of and coaxial with the first gear 323.

In the illustrated embodiment, the gears 319, 323 are helically threaded gears. Further, in the illustrated embodiment, the helical gears 319, 323 are attached or affixed to a length of tube 321 having a ridge 331 that interfaces with a groove 333 inside the instrument member at its first end and extends out of the distal tip at its second end. As the helical gears 319, 323 and tube 321 rotate, the ridge 331 is allowed to move within the groove 333, thus allowing the tube 321 to also rotate coaxially within an instrument member. In this embodiment, the centers of the helical gears 319, 323 and tube 321 include a hollow portion that allows access to instrument lumen 307 from the distal tip. Although not illustrated here, an orientation platform or tool may be mounted to the tube of this instrument member and controlled by running one or more control elements through the lumen 307 to the proximal end.

FIGS. 26B-C further illustrate the how first and second helical gears 329, 323 and their associated pins 335, 337 are configured. Actuation of a first pin 337 causes rotation of the first helical gear 323 in a counterclockwise direction (as viewed from the perspective of looking into the distal tip) as shown in FIG. 26B and indicated by a counterclockwise directional arrow. Actuation of the second pin 335 causes rotation of the second helical gear 319 in a clockwise direction as shown in FIG. 26C and indicated by a clockwise directional arrow. Because both gears 319, 323 are affixed or attached to the tube 321, rotation of one gear causes the tube 321 and the other gear to also rotate in the same manner.

In the illustrated embodiment, the first pin 337 resides inside a first slotted track or guide 339 dispose on or formed within the inside surface of the catheter or tubular member 123, and the second pin 335 resides inside a second slotted guide or track 325. In the illustrated embodiment, the guides 325, 339 have the same shape and are triangle-shaped guides that face opposite directions. Each guide may function in the manner described with reference to FIGS. 25A-H. In alternative embodiments, the slotted guides 325, 339 may have other shapes and orientation, and the guides may be the same or different shapes and sizes. For ease of explanation, the structure of the guides 325, 339 of the illustrated embodiment are similar to the guide 325 described in FIG. 25E.

During use, as pins 335, 337 traverse respective guides 325, 339, each pin rises and falls as it follows the non-uniform surface (e.g., surface 325a shown in FIG. 25E), of its guide. Rotation of a helical gear may be actuated by sequentially pulling and releasing a control element coupled to its pin. In the illustrated embodiment, control element or wire 340 is coupled to pin 337 carried by guide 339 and that engages gear 323, and control element or wire 327 is coupled to pin 335 carried by guide 325 and that engages gear 319.

FIG. 26B shows the first pin 337 driving the gear 323 in a counter-clockwise direction as the control element 340 is pulled downwardly, and the second pin 335 is disengaged from the second gear 319. FIG. 26C shows the second pin 335 driving the gear 319 in a clockwise direction as the control element 327 is pulled downwardly, and the first pin 337 is disengaged from the first gear 323. FIGS. 26D-E further illustrate how the gears 319, 323 may be moved depending on whether respective pins 335, 337 engage the gear based on the guide surface 325a.

More specifically, FIG. 26D illustrates how the first helical gear 323 is moved to the right (or rotated counter-clockwise in the context of FIGS. 26A-C) as a first pin 337 traverses the guide or track 339, and a second pin 335 is disengaged from the second gear 319. In the illustrated embodiment, the first pin 337 is configured to travel in a single direction along the first track 339 as is noted in FIG. 26D by a directional arrow. As discussed above with reference to the track of FIG. 25E, the taller or thicker the surface 325a of the guide 325, the more the pin will extend outwardly from the sidewall of the catheter or tubular member 321 to engage the gear 323.

With further reference to FIG. 25E, in the illustrated example, assuming the first pin 337 is initially positioned at 'd' (at which the first pin 337 is forced outwardly to engage the gear 323. Moving the pin 337 from position 'd' to 'e' results in the pin 337 rounding the first corner or vertex on the right side of the triangle-shaped guide 339. As a result, the first pin 337 slides down the sloped guide surface 325a to a lower level, resulting in retraction of the pin 337 from the gear 323 and remains at this level between positions 'e' and 'f'. Application of downward force to the first control element 340 forces the first pin 337 to move along the guide 339 from position 'f' to position 'a' thereby resulting in the pin 337 being extended outwardly from the sidewall of the catheter or tubular body 123. At position 'a', the pin 337 is extended to engage the gear 323. In the illustrated example, the pin 337 contacts the left hand surface of the fifth gear tooth element (shown with crosshatching) on the first gear 323. By pulling the first control element 340, the attached first pin 337 is pulled along the guide 339 from position 'a' to position 'b'. As the first pin 337 traverses the guide 339 between positions 'a' and 'b', the pin 337 engages with the left surface of the fifth gear tooth element and the downward force along the left surface is translated by the inclined, angled or helical tooth surface into a rightward that causes the first gear 323 to move towards the right and rotate.

Thus, because the first gear 323 is a wheel-like structure that is movable about the longitudinal axis of the catheter or tubular body 123, the first gear 323 rotates counterclockwise in this illustrated example. Upon the first pin 337 reaching position 'b' on its guide 339, the second vertex of the first guide 339 is now positioned between the third and fourth gear teeth, whereas the second vertex was previously positioned between the fourth and fifth gear teeth before gear 323 rotation. As the first pin 337 traverses the guide 339 and moves past position 'b' and approaches the third vertex at position 'c', the first pin 337 retracts into the sidewall of the catheter or tubular body 123 and disengages the first gear 323. By releasing or slacking the first control element 340, the first pin 337 is allowed to travel from position 'c' to position 'd' while the first pin 337 is out of contact from the first gear 323.

The second gear 319 is moved by a second slotted guide or track 325 in a similar manner, except that in this example, the teeth of the gear 319 and the guide 325 are oriented in a different manner such that the gear 319 rotates clockwise as the second pin 335 traverses the second guide 325, and the first pin 337 disengages from the first gear 323. Thus, the rotational direction of the catheter or tubular member 321 may be reversed relative to rotational motion resulting from the first gear 319 by the second gear 319. In this embodiment, the second pin 335 is also configured to travel in a single direction along the second guide 325 as shown by a directional arrow in FIG. 26E. For ease of explanation, and given the similar structural configurations shown in FIGS. 25A-H and FIGS. 26A-E, further details regarding the manner in which the second pin 335 traverses the guide 325 are not repeated.

In this manner, a distal tip of an instrument or component of a robotic instrument system may be controllably rotatable. Further, depending on which gear is rotated, a tool or orientation platform mounted to the distal tip of the instrument or component may also be controllably rotatable.

FIGS. 27A-D illustrate another embodiment of a rotational apparatus 250 of a robotic medical system that includes a harmonic drive element 341 that may be used to rotate a segment, such as the distal end of a catheter member 103 or catheter body or tube 123. In the illustrated embodiment, a harmonic drive element 341 includes a harmonic wave generator 343, a flexible spline or gear 345 and an outer circular spline or gear 347. The harmonic wave generator has an elliptical shape and is rotatable within a bore of the flexible spine 345 to impart an elliptical shape to the flexible spline 345, which is positioned within a bore of the outer or circular spline 347. Components of the harmonic drive element 341 may be made of stainless steel, plastic, polycarbonate, aluminum, copper, metal and other suitable materials. The manner in which the harmonic drive element functions may be based on principles involving high mechanical leverage being achieved by generating a traveling deflection wave in a flexing spline element.

In the illustrated embodiment, the wave generator 343 is an elliptical cam that is enclosed within an anti-friction ball bearing assembly and functions as a rotating input element. The drive shaft 343a of the wave generator 343 may, for example, have a diameter of about 1 mm to about 10 mm or another suitable diameter that is capable of providing the necessary input torque to drive the wave generator apparatus 343.

The wave generator 343 may be coupled to a primary power source or servomotor (not shown in FIGS. 27A-D). As the servomotor operates the wave generator 343 serves as a high efficiency torque converter. More particularly, when the wave generator 343 is inserted into the bore 349 of the flexspline 345, the wave generator 343 imparts its elliptical shape to the flexspline 345, thereby causing the external teeth 351 of the flexspline 345, e.g., on or near its outer circumference, to engage with the internal teeth 353 of the circular spline 347 at locations. In the illustrated embodiment, these locations are at opposite ends of the wave generator 343, i.e. separated by 180°, thus forming a positive gear mesh at these engagement points. In another embodiment, the wave generator 343 may be an assembly comprising a bearing and a steel disk known as a wave generator plug. The ball bearing is pressed around the carefully machined elliptical shape of the wave generator plug, causing the bearing to conform to the same elliptical shape of the wave generator plug. For ease of explanation, reference is made to the structural configuration shown in FIGS. 27A-D.

The flexspline 345 according to one embodiment is a flexible, thin-walled cylindrical cup with gear teeth that are machined into an outer surface of the flexspline 345 near the open end of the cup near the brim. This structural configuration allows the walls of the cup to be radially compliant, yet remain torsionally stiff as the cup has a larger diameter. In the illustrated embodiment, the flexspline 345 is slightly smaller in circumference and has two less teeth than the circular spline 347. The cup in FIG. 27A has a rigid boss at one end to provide a rugged mounting surface. For this example, a platform, such as an orientation platform on which a tool may be mounted, is coupled to the flexspline 345.

The circular spline 347 may be a thick-walled, rigid ring with internal spline teeth. The circular spline 347 is usually attached to the housing and often functions as the fixed or non-rotating member, but may be utilized as a rotating output element as well in certain applications. Although the flexspline 345 is often the rotating output element as in this implementation, it can also be utilized as a fixed, non-rotating member when output is through the circular spline 347.

During assembly of the harmonic drive element 341, the wave generator 343 is inserted inside the flexspline 345 such that the bearing is at the same axial location as the flexspline teeth 351. The flexspline 345 wall near the brim of the cup conforms to the same elliptical shape of the bearing, thus causing the teeth 351 on the outer surface of the flexspline 345 to conform to this elliptical shape. Effectively, the flexspline 345 now has an elliptical gear pitch diameter on its outer surface. The circular spline 347 is located such that its teeth 353 mesh with those of the flexspline 345. The now elliptical tooth pattern of the flexspline 345 engages the circular tooth profile of the circular spline 345 along the major axis of the ellipse, in a manner that is similar to an ellipse inscribed concentrically within a circle. FIGS. 27B-C illustrate cross-sectional views of the harmonic drive element 341 relative to cross section B-B. An inscribed ellipse will contact a circle at two points; however, as a practical matter, the gear teeth of this embodiment have a finite height so there may be two regions of teeth engagement instead of simply two points. Moreover, in other embodiments, approximately 30% of the teeth may be engaged at all times.

The pressure angle of the gear teeth transforms the tangential force of the output torque into a radial force that acts upon the wave generator 343 bearing. The teeth of the flexspline 345 and circular spline 347 are engaged near the major axis of the ellipse and disengaged at the minor axis of the ellipse. Referring to FIG. 27B, as the wave generator 343 begins to rotate in a clockwise direction in response to its servomotor, a continuously moving elliptical form or wave-like motion is imparted to the flexspline 345. An initial position 335 on the flexspline 345 is marked with a small arrow in FIG. 27B. This motion causes the meshing of the external teeth 351 of the flexspline 345 with the internal teeth 353 of the circular spline 347 at their two equidistant points of engagement and allows for a full tooth disengagement at the two points along the minor axis of the wave generator 343. Thus the zones of tooth engagement travel with the major elliptical axis of the wave generator 343.

When the wave generator 343 has rotated 180° clockwise, the flexspline 347 has regressed by one tooth relative to the circular spline 347. In this embodiment, each complete revolution of the wave generator 343 displaces the flexspline 345 two teeth counter-clockwise relative to the circular spline 347. FIG. 27C illustrates the displacement of the marked position 355 on the flexspline 345 relative to FIG. 27B in a counter-clockwise direction in response to clockwise revolutions of the wave generator 343. This displacement is in the opposite direction of the rotation of the wave generator 343 such that if the wave generator 343 of this example rotates in a counter-clockwise direction, then the two tooth per revolution displacement of the flexspline 345 will be in a clockwise direction.

A harmonic drive element 341 may also allow for finer rotational control of a distal platform coupled thereto since this type of drive element also functions as a speed reducer. In contrast to high speed input from a power source to the wave generator 343, the considerably slower flexspline 345 causes a two-tooth per revolution displacement. The resulting reduction ratio may be calculated by dividing the number of teeth on the flexspline 345 by the difference between the number of teeth on the circular spline 347 and the flexspline 345 as follows:

$$\text{Reduction Ratio} = \frac{\#\,teeth_{Flexspline}}{\#\,teeth_{Flexspline} - \#\,teeth_{Circular\,Spline}}$$

In this example, the reduction ratio is calculated as:

$$\text{Reduction Ratio} = \frac{\#\,teeth_{Flexspline}}{\#\,teeth_{Flexspline} - \#\,teeth_{Circular\,Spline}}$$
$$= \frac{98}{98 - 100}$$
$$= -49:1$$

The negative sign in the above expression indicates that the input and output are turning in opposite directions. It is contemplated that the reduction ratio in other embodiments will be different as the difference between the number of teeth of the flexspline 345 and the number of teeth of the circular spline 347 may vary.

FIGS. 28A-E illustrate another embodiment of a rotational apparatus 250 of a robotic instrument system that includes an elongate catheter or tubular body and a wobble plate drive element 357 that is coaxial with the catheter body and located at the distal end of the catheter body. The wobble plate drive element 357 is operable to rotate a segment, such as the distal end, of the catheter body. As with other embodiment discussed above, including the ratchet-type drive element, embodiments of a wobble plate drive element 357 may be positioned at a distal tip of a flexible catheter instrument member and utilized to controllably rotate a segment of the catheter.

According to one embodiment, a wobble plate drive element 357 includes a rotatable drive shaft 367, a first, stationary gear element 361, a second gear element 359 that is coaxial with the shaft 367 and rotatable about the first gear element 361 and around the shaft 367, a compression element, such as a spring 363, disposed between the first and second gear elements 361, 359 that urges the second gear element 359 away from the first gear element 361, and a cam drive member or element 365 configured to manipulate or rotate the second gear element 359 to urge a portion of the second gear element 359, against the force of the spring 363, to engage a portion of the first gear element 361, while an opposite portion of the second gear element 359 does not engage the first gear element 361. In the illustrated embodiment, the first and second gear elements 361, 359 may be in the form of gear plates, which may be made of stainless steel, plastic, polycarbonate, aluminum, metal, and other suitable materials.

The drive shaft 367 may have a diameter of about 1 mm to about 10 mm and extend downwardly into a central lumen of a catheter or other instrument member to a power source, such as a servomotor, at the proximal end of the catheter. In some embodiments, a micro-motor may be employed proximate to the wobble plate drive element 357 itself.

The cam drive element 365 shown in FIG. 28B, according to one embodiment, includes an angled arm or finger element 369 that is secured to the end of the drive shaft 367 such that when the drive shaft 367 rotates, the arm or finger element 369 also rotates together with the shaft 367 and in the same direction. The arm or finger element 369 is in contact with a portion of a top surface of an upper or distal gear element 359, which is coaxially located about the drive shaft 367 and includes a plurality of teeth or gear elements extending proximally towards the first, stationary gear element 361. According to one embodiment, the gear element 359 includes "n" teeth, e.g., 100 teeth, and includes more teeth than the other gear element 361, which may include, e.g., "n−1" teeth, or 99 teeth in this example. Although the drive shaft 367 passes through the center of the first gear element 359, the drive shaft 367 is configured to freely rotate without directly causing rotational movement of the first gear 359.

Also coaxially located about the drive shaft 367 and below the first gear element 359 is the second, bottom gear element 361 that is stationary and has a plurality of teeth. For example, the second gear 361 may be attached or affixed to a catheter or other instrument. According to one embodiment, the gear element 361 includes 99 teeth on a top surface thereof, i.e., less than the other gear element 359. The spring 363 coaxially located about the drive shaft 367 between the first gear 369 and the second gear 361 serves to urge the two gears apart.

FIGS. 28C-E illustrate how the wobble plate drive element 357 functions during use. To engage the drive element 357, a combination of tensional and rotational forces may be imparted onto the drive shaft 367. By pulling the drive shaft 367 in downward direction, the resulting tensional force causes the arm or finger element 369 to press down on a portion of a top surface of the first gear 359, which serves to compress the spring 363. As the requisite amount of downward force is supplied, a portion of the teeth on the first gear 359 positioned below the arm or finger element 369 engage and mesh with certain teeth on the second gear 361. In FIG. 28C, for example, the teeth on the left sides of the gear elements 361, 359 are engaged, whereas teeth on the other side are not engaged. During use, the shaft 367 is rotated in either a clockwise or counterclockwise direction which, in turn, causes the arm or finger element 369 to turn about the central axis of the drive element 357, as generally represented by a curved arrow in FIG. 28C. In the illustrated example, the drive shaft 367 rotates counter-clockwise (as viewed from the top of the device). The associated counter-clockwise rotation of the arm or finger element 369 causes a tip 371 to circle about and press down the top surface of the first gear 359. Because the first gear 359 is tilted relative to the second gear 361 (due to the spring 363 exerting upward force on other portions of the gear element 359), this motion causes the first gear 359 to "wobble" over the second gear 361. As the tip 371 continues to circle about the gear element 361, the wobbling action forces the different portions of teeth from the first gear 359 and the second gear 361 to temporarily engage or mesh as the incline on the first gear 359 changes as shown in FIGS. 28C-E.

Further, because the first and second gears 359, 361 have a different number of teeth and full tooth disengagement is achieved, each complete revolution of the tip 371 results in a predetermined displacement between the two gears 359, 361 in the opposite direction of the rotation. In one embodiment, the second gear 361 has two less teeth than the first gear 359 such that a two tooth displacement in a clockwise direction is obtained with each complete counter-clockwise revolution, resulting in rotational motion as the top gear element 359 wobbles over the bottom gear element 361. Although embodiments are described with reference to gear elements 361, 359 having 100 and 99 teeth, respectively, other embodiments may involve gear elements having different numbers of teeth. Further, the teeth number difference may also vary such that the wobble effects and reduction ratios can be adjusted.

The first gear element 359 may be coupled to a distal tip platform or orientation platform on which a tool may be deployed. In this manner, the rotational motion generated by the wobble plate element can be imparted to the platform or tool. Further, in another embodiment, a lumen may extend through the drive assembly to allow a cable to link to a working instrument or provide a passage of another catheter device or fiber.

Referring to FIGS. 29A-D, a wobble plate drive element 357 constructed according to another embodiment is similar to the embodiment shown in FIGS. 28A-E except that rather than using a cam drive 365 as shown in FIGS. 28A-E, this embodiment actuated through the sequencing of control elements or tension cables 373. Referring to FIG. 29A, and similar to the components discussed above, the wobble plate drive 357 includes a first gear plate 359, a compression spring 363, a second gear plate 361, and a central shaft 375. The first gear 359 has a set of teeth on its bottom surface and the second gear 361 has a set of teeth on its top surface. The number of teeth on the first gear 359 differs from the number of teeth on the second gear 361. The first gear 359 and the second gear 361 are each coaxially coupled with the central shaft 375, with the spring located on the coaxially on the shaft between the two gears 359, 361. The spring 363 serves to urge the two gears apart.

A set tension cables 373, e.g., six tension cables 373 labeled 'A' through 'F', are distributed about the circumferential edge of the first gear element 359. Each tension cable 373 is connected to the first gear element 359 at one end while the other end extends downwardly to a proximal end of a catheter through a catheter lumen. In one embodiment, each tension cable 373 is routed through its own individual lumen defined in a sidewall of a catheter or other instrument. In another embodiment, one or more tension cables may be grouped together and routed through a central lumen. For ease of explanation, reference is made to tension cables 373 that are attached to equidistantly spaced locations on the top gear element 359.

With this configuration, and as with the wobble drive element 357 shown in FIGS. 28A-E, a platform or working instrument coupled to the wobble drive element 357 shown in FIGS. 29A-D is rotated by wobbling the first gear 359 on top of the second gear 361. With this example, a user sequentially tensions each cable 373 by pulling each cable downward with enough force to overcome the spring 363 and to cause a portion of the gear teeth on the first gear 359 proximate to that particular cable to mesh with a portion of the teeth underneath on the second gear 361. During operation of the drive 357, the cables 373 are sequentially tensioned in either a clockwise or counterclockwise direction. FIG. 29A illustrates how the tension cables are sequenced in counterclockwise manner (when viewing the drive from above) with a pattern of "A-B-C-D-

E-F-A". In response to this counterclockwise sequencing of the cables 373, the first gear 359 gradually becomes displaced in a clockwise direction relative to the second gear 361. For a clockwise sequencing, the displacement would be in a counterclockwise direction.

FIGS. 29B-D illustrate the displacement of the first gear 359 in response to the sequential tension of the cables 373. As indicated by the arrows pointing down in FIG. 29B-D, cables 'A', 'B', and 'C' are each pulled downward to tilt the first gear 359 as it wobbles over the second gear 361. Because the first and second gears 359, 361 have a different number of teeth and full tooth disengagement is achieved, each complete revolution of the first gear 359 results in a predetermined displacement between the two gears 359, 361 in the opposite direction of the wobbling and cable sequencing, thereby resulting in rotational motion.

Referring to FIG. 30, a rotational apparatus 250 of a robotic instrument system constructed according to another embodiment includes an elongate body having a proximal end and a controllable and flexible distal end, the body having a longitudinal axis and defining a lumen, and a planetary gear drive element 377 that is coaxial with the catheter body and located at the distal end of the catheter body. The planetary gear drive element 377 is operable to rotate a segment, such as the distal end, of the catheter body and any platform or working instrument attached thereto.

A planetary gear element 377 constructed according to one embodiment includes at least three components: a central sun gear 379, one or more planet gears 381 of the same size and driven by shafts 381a that may have a diameter of about 1 mm to about 10 mm, and a ring gear 383. The various drive components may be made of stainless steel, plastic, polycarbonate, aluminum, metal, etc. or combinations thereof, but are not such restricted.

The sun 379 and planet gears 381 are located inside the ring gear 383, which may also be referred to as the annulus. Because the entire planetary gear element 377 is only as large as the largest gear, the system may be very compact. The teeth of the ring gear 383 are located on an inside surface such that they can mesh with the planet gears 381 within the ring gear 383. In this embodiment, gear teeth of all of the gears are clearly visible. In some embodiments, the gear teeth may be of smaller dimensions or knurls may be implemented in lieu of teeth.

The sun gear 379 is coaxially located in the center of the ring gear 383. Located between the sun gear 379 and the ring gear 383 are the one or more planet gears 381, whose gear teeth mesh with the teeth both the sun 379 and the ring 383. When a plurality of planet gears 381 are used in such a drive, there are several points of contact where the teeth on the planet gears 381 mesh simultaneously with those of the two coaxial gears 379, 383. The more teeth that are meshed, the stronger the arrangement is and the greater the ability to handle very high torques. In the illustrated embodiment, planet gears 381 are held into place by a disc or planet carrier, and are free to turn on pinions 382 that attach the planet gears 381 to the planet carrier. Although not shown in FIG. 31, the planet carrier is located coaxially with the sun gear 379 and the ring gear 383. In some instances, a planetary gearing system may also be referred to as an epicyclic gearing system.

A planetary gear drive element 377 may be implemented using a number of configurations. For example, each of the three components can be the input, the output, or held maintained as stationary. Thus, there are six possible combinations, although three of these provide velocity ratios that are reciprocals of the other three. Choosing which piece plays which role determines the gear ratio for the gearset. Locking any two of the three components together will lock up the whole device at a 1:1 gear reduction. The ratio of input rotation to output rotation is dependent upon the number of teeth in the ring gear 383 and the sun gear 379, and upon which component is held stationary. However, the ratios are independent of the number of planets 381 or the number of teeth on each planet 381.

During operation of the drive in one implementation, input power drives one member of the assembly, a second member is driven to provide the output, and the third member is fixed. If the third member is not fixed, no power is delivered. For one configuration, the sun gear 379 is used as the input, the planet carrier is locked in position so it cannot rotate but its planet gears 381 can rotate on their pinions 382, and the ring gear 383 is the output. In this case, the ring gear 383 will rotate in the opposite direction from the sun gear 379, and the gear ratio will be the ring gear over the sun gear 379:

$$\text{Gear Ratio} = -\frac{\# teeth_{Ring}}{\# teeth_{Sun}}$$

For another configuration, the sun gear 379 is used as the input, the ring gear 383 is held stationary, and the planet carrier is used as the output, with the planet carrier rotating in the same direction as the sun gear 379. The resulting ratio is:

$$\text{Gear Ratio} = 1 + \frac{\# teeth_{Ring}}{\# teeth_{Sun}}$$

because the planet carrier has to circle the sun one additional time in the same direction it is spinning. Furthermore, in other embodiments, planetary gear drive elements 377 may include different number of teeth, and the pitch of the various gear teeth may also vary in different embodiments.

Referring again to FIG. 30, the ring gear 383 or annulus may be mounted coaxially in the central lumen of a body such as a catheter instrument member 103. In one embodiment, the ring gear 383 may be fixedly coupled to the sidewall of the catheter instrument member 103 such that ring gear 383 and catheter instrument member 103 rotate or move together. In another embodiment, the ring gear 383 may be held into place in the catheter instrument member 103 with a set of retaining rings or grooves. In yet another embodiment, the ring gear 383 may be built into the sidewall such that the teeth of the ring gear 383 jut out of the sidewall. In this example, the sun gear 379 is illustrated with a counterclockwise rotation on its shaft whereas the three planets 381 rotate clockwise on their pinions 382. Because of these rotational movements, the ring gear 383 is caused to rotate in a clockwise direction. By reversing the direction of rotation at the input, the directions of all these components become reversed also.

Because of the varying gear ratios that can be achieved from the different combinations, it may be possible to achieve an output speed that is slower than the input speed, an output speed that is faster than the input speed, or an output direction that is reverse from the input direction. Although the planetary gear drive elements 377 disclosed are in the context of a single drive unit, in other embodiments, a planetary gear drive element 377 may include multiple stages. For example, multiple planet and sun gear units may be placed in series within the same ring gear housing such that the output shaft of the first stage becomes the input shaft of the next stage, thus providing a larger (or smaller) gear ratio. In the present implementation, any of the ring gear 383, planet carrier, or the sun gear 379 may be coupled to a distal tip platform or orientation platform on which working instrument or tool may be deployed. In another embodiment, a lumen may extend through the drive assembly to link with a catheter or instrument member central lumen to allow passage of another catheter device or fiber.

Whereas each of the components in FIG. 29 includes a set of teeth to mesh with other gears, the sun member 385 and the ring member 387 of the implementation illustrated in FIGS. 30A-K are tubular lengths of shafts without teeth. The four planet gears 381 illustrated in FIG. 30A are fabricated with knurled patterns. In the illustrated embodiment, the planet gears 381 have straight patterns as shown in FIG. 30C. In other embodiments, the knurled surface may have a pattern similar resembling diamond-shapes (crisscross), bumps, straight ridges, helices, or combinations thereof.

Furthermore, a planet gear 381 may also be manufactured with an irregular gripping surface. With this configuration, knurled surfaces 384 of the planet gears 381 grip or bite into the surfaces of the sun member 385 and the ring member 387 as the planet gears 381 rotate, thus causing the sun member 385 and the ring member 387 to also rotate. The components of this planetary gear drive element 377 are assembled together in a manner such that the planet gears 381 are sufficiently tight against both the sun member 385 and the ring member 387, but still allowing for rotational motion by the planet gears 381.

In this embodiment, the motor input is provided through the planet gears 381, the central shafts of which are flexible and extend downwardly through the catheter or instrument member to a motor block at the proximal end of the catheter instrument. Thus, by rotating these axles at a proximal location, the planet gears 381 may be driven to rotate at a distal location. These central shafts of one embodiment are flexible, sleeved cables such as speedometer cables. In another embodiment, the motor input may be provided through a planet carrier via the planet gears 381.

As shown in FIG. 30A, a first dot on the ring member 387 marks its starting position and a second dot on the sun member 385 marks its starting position. FIGS. 30C-D illustrate cross-sectional views of the drive assembly within a flexible instrument member. As the planet gears 381 begin to turn in a counterclockwise rotation as shown in FIGS. 30A and 30C, the sun member 385 beings to rotate in a counterclockwise direction and the ring member 387 turns in a clockwise direction. Referring now to FIG. 30B, the sun member 385 and ring member 387 can both be seen slightly rotated in response to the revolving planet gears 381 as the marks have shifted counterclockwise and clockwise, respectively.

As shown in FIG. 30D, a platform is attached to the sun member 385 in this example, but in alternative embodiments, any of the ring member 387, planet carrier, or the sun member 385 may be coupled to a distal tip platform or orientation platform on which a working instrument or tool may be deployed. In another embodiment, a lumen may extend through the drive assembly, as with the sun member 385 of FIG. 30D, to link with an instrument member central lumen to allow passage of another catheter device or fiber.

The planetary gear drive element 377 shown in FIG. 30D is built into its own flexible tube, sheath or catheter instrument member 103 and has been inserted into through the lumen 115 of the catheter member 103 and locked in position when the sun member 385 is installed. Thus, in this embodiment, the planetary gear drive element 377 may be removed from the distal tip of an instrument, if desired, by extracting the sun member 385 from the assembly.

Various planetary drive element components of different embodiments may be constructed out of stainless steel, plastic, polycarbonate, aluminum, metal, etc. or combinations thereof, but are not restricted as such. Component materials may be selected so that the knurled surfaces 384 of the planet gears 381 are able to firmly grip or bite into the surfaces of the gears 381 and the sun member 385. Further, although the planetary gear drive element 377 components in one embodiment may be designed with the same height dimensions at their contact surfaces, in other embodiments, the components may be fashioned with different heights so long as the desired rotational actions and drive functionality are achieved. For example, the various components of the drive assembly shown in FIGS. 30C-D may not necessarily have the height dimensions. The sun member 385, planet gears 381, and ring member 387 each have a different height in FIG. 30C. In FIG. 30D, the planet gears 381 and the ring member 387 are of one height while the sun member has a different height.

FIGS. 30E-K illustrate a planetary gear drive element 377 constructed according to another embodiment. FIGS. 30E-F are perspective views of this embodiment without a catheter instrument, but as with the various drive assemblies disclosed in this document, embodiments of the present invention may be installed into or at the distal tip of a flexible catheter instrument member in order to rotate a platform, tool, or segment of a catheter instrument. The planetary gear drive element 377 of this embodiment is also constructed with a sun band piece 389, four planet gears 381, and a ring band piece 391. More specifically, the sun piece 389 is coaxially located inside the ring piece 391 and the planet gears 381 are located between the sun piece 389 and the ring piece 391. Each of the planet gears 381 are in simultaneous contact with sun piece 389 and the ring piece 391. The planet gears 381 of this implementation are held into place with the drive assembly with a pair retention discs 393 and collars on the planet gear drive shafts 382.

As shown in FIG. 30K, a sun band piece 389 may include a through lumen and an offset lip about its circumferential edge. In other embodiments, the sun band piece 389 may or may not include one or more physical characteristics such as a lumen, ridges, grooves, etc. Two retention discs 393, which also serve as part of the planet carrier in this embodiment, are shown in FIG. 30G. FIG. 30J illustrates a closer view of a retention disc 393 with a plurality of circumferential holes 395 through which planet gears 381 may be positioned and a central through hole 397 that overlaps with the sun band through lumen. Depending on the particular design, one or more of the holes 395 may be left vacant if the number of planet gears needed is fewer than the number of holes. In one embodiment, a retention disc 393 may be fabricated to include only the needed number of holes. A first retention disc 393 fits over the top portion of the drive assembly 377 and the second disc 393 fits over the bottom portion of the drive assembly, thus sandwiching the sun piece 389, ring piece 391, and the planet gears 381. The present example includes four planet gears 381, but it is contemplated that more or less planet gears 381 may be used in other embodiments. FIG. 31L illustrates one embodiment of a planet gear component 381 constructed in this manner.

In this embodiment, each planet gear component 381 is comprised of shaft member 382 having a gear portion 384 knurled with a straight pattern about a first end and a hole to receive a dowel pin about a second end. The hole or aperture in FIG. 30L is transverse to the longitudinal axis of the shaft member and allows for the dowel pin to pass completely through the shaft. In one embodiment, a flexible cable such as a speedometer cable is coupled to the shaft member via the dowel pin. In another embodiment, the cable may be fastened to the shaft by a clamp collar. Alternatively, a cable may be threaded through the hole and held into place with a solder ball or a knot. Sandwiching the knurled gear portion 384 of the shaft member are ridged sleeves, both of which assist with keeping the retention discs together 393. The ridge sleeve in some embodiments may be a cap, clamp, collar clamp, lock washer, ring, or any fastener which may lock into position on the shaft member.

FIG. 30I illustrates one example of such a planetary gear drive element 377. In assembling the drive of one embodiment, the sun piece 389 has a lipped portion seated with a central hole or aperture of a retention disc 393. Planet gears 381 are inserted through the designated circumferential holes of that retention disc 393 and held into place with clamp pieces 399. A ring band is fitted onto the retention disc 393 around the planet gears 381 and sun piece 389. A second retention disc 393 is placed over this subassembly, with the planet gears 381 aligning with and fitted through circumferential holes of this second retention disc 393. Additional clamp pieces are fastened onto the planet gear pieces 382 to hold this retention disc 393 to the other pieces. The planet gear shaft members 382 may be coupled to a motor block for providing input via flexible drive cables. The drive may now be coupled with a flexible instrument member to provide rotational action.

FIGS. 31A-P illustrate an interface or orientation platform 133 of a robotic instrument system in which rotatable apparatus 250 embodiments may be utilized (e.g., as shown in FIGS. 12 and 14A-E). One embodiment of an orientation platform 133 is configured to control a working instrument 41 (one example of which is illustrated) coupled to a distal end of a catheter instrument 37 or other instrument assembly 3 of a robotic medical system, e.g., a sheath 39 covered catheter 37.

According to one embodiment, an interface or platform 133 includes a base member or socket plate 417 configured for coupling to a distal end of catheter instrument member 103, a spacer element 419 and another socket plate or platform member 415. The spacer element 419 is retained or interposed between, and separates, the base member 417 and the platform member 415. The platform member 415 is movable relative to the base member 417 about the spacer element 419. The interface or platform 133 also includes a control element 405, such as a pull wire, that extends through the catheter member 103, through an aperture defined by the base member 417, and terminating at the platform member 415.

Embodiments may be utilized to control an orientation of the platform member 415 and an orientation of the working instrument 41 are controllably adjustable by manipulation of the control member 405. For example, in the embodiment shown in FIGS. 31A-C, a catheter assembly 3 includes a first flexible catheter instrument 37 coaxially disposed in a flexible sheath instrument 39. A tool actuation cable 403 and a platform control element 405 are routed through one or more lumens inside the instruments 37 to a proximal portion of the assembly 3. An interface or platform 133 servers as a controllable interface between the distal end of the catheter 37 and the working instrument 41.

More particularly, in the illustrated embodiment, an interface or orientation platform 133 is shown coupled to the distal tip of the catheter instrument member 103. A mating ring 407 is provided for attaching a working instrument or tool 41 to the orientation platform 133, and the tool 41 may be coupled to the mating ring 407. In the illustrated embodiment, the mating ring 407 includes a pair receptors with female slots 409 to engage with a pair corresponding male pins 411 located on the tool 41, and in one embodiment, the fastening mechanism for removably connecting the tool 41 to the instrument member 103 in this example is a type of bayonet mount.

To install a tool 41, pins 411 on the male side are aligned with the slots 409 on the female receptor and the two surfaces are pushed together. Once the pins 411 reach the end of the slots 409, the two surfaces are turned in opposite directions to guide each pin 411 into a perpendicular portion of the slot 409 that prevents it from slipping. A spring in the mating ring 407 maintains a clamping force at the mating surfaces. To disconnect the tool 41, the two surfaces are pushed together to overcome the spring force and the locking turn is reversed. A tool actuation cable 403 with an eyehook at one end connects to the tool 41 in this implementation and is used to control the opening and closing action of the grasping tool. As shown in FIG. 31C, this actuation cable 403 passes through the mating ring 407, a lumen 413 in the orientation platform 133, and the catheter instrument member 103 to a control knob or motor at the proximal end of the catheter assembly 3.

According to one embodiment, as shown in, for example, FIGS. 31D-E, the interface or platform 133 includes a ball and socket assembly. According to one embodiment, a ball and socket assembly is formed by a spacer element 419 that is in the form of a spherical element or ball, which is secured within indentations of adjacent socket plates 417, 415. In this embodiment, controlled pitching action is accomplished by the application of force on one or more control elements 405 together with one or more connectors or springs 433.

An interface or orientation platform 133 that includes base and platform members 417, 415 in the form of socket plates, the spacer element 419 may be in the form of a ball-like, semi-spherical structure, or a spherical structure. The spacer element 417 may define a lumen 421 through which, for example, a control cable 403 for a working instrument 41 may be inserted. In one embodiment, the first and second socket plates 415, 417 are identical and may be inverted versions of each other, and each socket plate 415, 417 includes a concave cup cavity 431 configured to receive and interface with a spherical spacer unit 419. The socket plate 415, 417 also includes a larger center aperture 423 and a plurality of smaller apertures 425 distributed about its circumferential portion of the disc. In this illustration, four apertures 427 that are positioned at approximately 90° apart are slightly larger in size than each of the three apertures 429 located between adjacent 90° holes 427. However, other embodiments may include apertures of similar dimensions or of a variety of different dimensions.

Figures 32D, 32E:
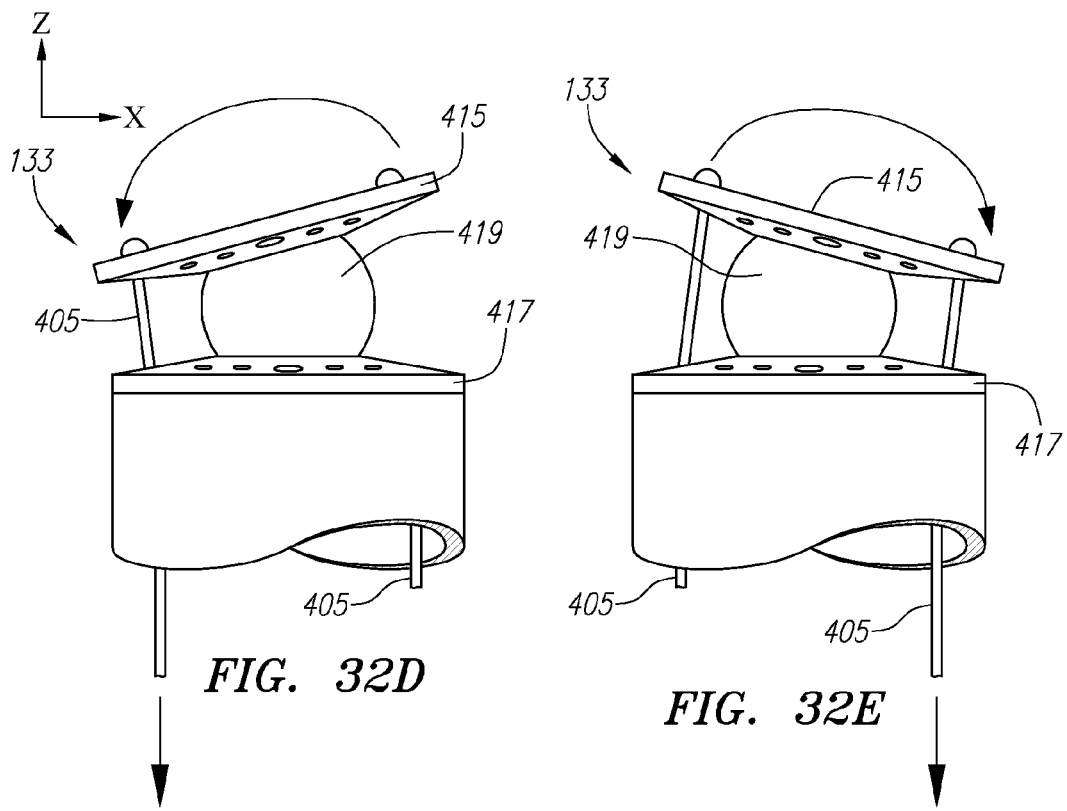

With the embodiment illustrated in FIGS. 31D-E, the interface or orientation platform 133 is assembled by inserting the spacer element or ball unit 419 into the concave cavities 431 of the base 417 and platform 415 members or socket plates. The ball unit 419 may be adjusted to ensure alignment of its lumen 421 with the center apertures or apertures 423 of the first and second socket plates 415, 417. Similarly, the plates 415, 417 may be adjusted to ensure that the 90° apertures 427 on the first plate 415 are aligned with the corresponding apertures 427 on the second plate 417. One end of a tension spring 433 is hooked into one of the large apertures 427 on the first socket plate 415 and a second end is hooked into the large aperture 427 on the second socket plate 417 directly below the first aperture. A control element 405 with a ball termination 406 that terminates at the platform member 415 is threaded through a 90° apertures 427 of the socket plates 417, 415, and through a lumen 115 in the instrument member 103 to a splayer at the proximal end of the catheter assembly. Although the control element 405 shown in FIG. 32E is located within a lumen of instrument, other embodiments of an instrument member may have one or more dedicated lumens for containing control elements and tool actuation cables.

Referring to FIGS. 31F-H, the orientation platform 133 is designed for a pitch degree of freedom. The XYZ orientation compass associated with FIG. 32D indicates that this orientation platform may perform a pitching motion by rotating about the Y axis in a XZ plane. In one embodiment, the spring 433 may be calibrated to provide a preset amount of tension force in its neutral state and the control element 405 also has to be pre-tensioned to counterbalance that force such that the orientation platform 133 may naturally assume a known state or position. For example, sufficient downward force may be applied to the control element 405 to cause the top or platform member 415 to have 0° of tilt relative to the longitudinal axis of the instrument or to be parallel to the second plate 417 (as shown in FIG. 31D).

Referring to FIGS. 31F and 31H, because this spring 433 is biased to compress, the first plate or platform member 415 of the orientation platform 133 is caused to tilt or pitch to the left in a pitch-direction when the control element 405 is slack or applies insufficient force. FIG. 32H shows that not only is the top plate or platform member 415 moving, but the spacer element 419 also rotates counter-clockwise as the orientation platform 133 tilts down on the left side. It can also be observed that the lumen 421 of the spacer element 419 may become slightly misaligned with the center holes 423 of the base and platform members 417, 415, but there is sufficient overlap such that a cable, an instrument, a tool, etc. may still pass from a catheter and through the orientation platform 133. Preferably, the center apertures 423 and lumen 421 are dimensioned such that when the orientation platform 133 is utilized, the central lumen or passage does not become unduly constricted or a situation wherein an instrument or cable in the passage may become undesirably crimped is not created. The center holes 423 and lumen 421 of different embodiments may have various shapes an sizes to allow for sufficient clearance as components traverse through this passage when the orientation platform 133 is pitching. The control element 405 may also flex or bend as the orientation platform 133 moves.

Referring to FIGS. 31G and 31I, pulling down on the platform control element 405 results in a downward force conveyed by the cable tension. The control element 405 flexes as the space between the plates 415, 417 narrow on the right side whereas the coils of the spring 433 are stretched apart due to the load caused the downward force on the control element 405. If the force is sufficient to counteract the spring 433 force, the right edge of the platform member 415 proximate to where the termination 406 of the control element 405 is engaged to tilt downward and pitch to the right in a pitch+ direction. Similar to the pitch- discussion above, the illustration in FIG. 32I shows that in addition to the platform member 415 moving, the spacer element 419 also rotates clockwise as the orientation platform 133 tilts downwardly on the right side. Here, the lumen 421 of the spacer element 419 may also become slightly misaligned with the center holes 423 of the base and platform members 417, 415, but there is sufficient overlap in these openings such that material may still pass from the catheter or instrument member lumen and through the orientation platform 133.

FIGS. 31J-M illustrate another embodiment of an interface or platform 133 that includes the same components discussed above except that the interface 401 does not include a tension spring 433. Certain aspects of this embodiment are not repeated since the configuration and operation of the embodiment shown in FIGS. 31D-I applies.

As shown in FIG. 31J, in the illustrated embodiment, a compression spring 435 replaces the tension spring 433 to provide known amount of compressive force in its neutral state. The control element 405 is also pre-tensioned to counter-balance that force such that the orientation platform 133 may naturally assume a known state or position. For example, sufficient downward force may be applied to the control element 405 to cause the platform member 415 of the orientation platform 133 to have a 0° of tilt to be parallel to the second plate 417. The compression spring 435 and the control element 405 are coaxially located on the same side of the orientation platform 133. One end of the spring 435 is coupled to the platform member 415 and the other end is coupled to the base member 417. A control element 405 with a termination 406 at one end is threaded through a 90° hole 427 of the platform member 415, through the spring 435, through a corresponding 90° hole 427 underneath on the second plate 417, and through a lumen 115 defined by the catheter or instrument to a splayer at the proximal end of the catheter assembly. The compression spring 435 of this embodiment is designed to provide a known amount force to push apart the first and second socket plates 415, 417 in its neutral state as illustrated in FIG. 31J.

Thus, when a sufficient amount of force is applied to control element 405 to pull the top plate 415 downward to compress the spring 435, the spring force may be counteracted and the orientation platform placed in a neutral position wherein the orientation platform may have a 0° of tilt relative to the longitudinal axis of the instrument. But because the spring 435 is biased to expand, the platform member 415 of the interface or platform 133 tilts or pitches to the left in a pitch- direction when tension on the control element 405 is slackened or if insufficient compression force is applied to the cable 405 to counteract the spring force. FIG. 2L shows that not only is the partition member 415 moves, but the spacer element 419 also rotates counter-clockwise as the platform 133 tilts down on the left side. The control element 405 may also flex or bend as the orientation platform 133 moves.

Referring to FIGS. 31K-M, when an amount of force sufficient to overcome the spring force is applied to the control element 405, the platform member 415 may be pulled downward beyond a 0° of tilt position to compress the compression spring 435 as illustrated in FIGS. 31K and 31M. Thus by pulling down on the control element 405, the overwhelming downward force conveyed by the cable tension causes the right edge of the platform member 415 proximate to the ball termination 406 to tilt downwardly and pitch to the right in a pitch+ direction when sufficient force has been exerted to counteract the spring force.

FIGS. 31N-P illustrate another embodiment of an interface or platform 133 that includes many of the same component as discussed above and that operate in the same or substantially similar manner, but the embodiment shown in FIGS. 31N-P includes two similar springs 437, and a control element 405 that extends through each spring 437. This embodiment is also designed for a pitch degree of freedom. In its neutral state, the two springs 437 are configured such that one spring 437 counteracts the spring force of the opposing spring 437. For example, if both springs are tension springs, then the force of the left spring 437 in FIG. 31N pushing upward to pivot the top plate 415 about the spherical element 419 towards the right side while the right spring 437 exerts an upward force to pivot the top plate 415 about the spherical element 419 towards the left side. However, because the forces are equal, the top plate or platform member 415 remains in an equilibrium state with a 0° of tilt. If either of the control elements 405 are manipulated, the platform member 415 can be caused to pitch in a predetermined direction, as shown in FIGS. 31O-P.

Figures 32F, 32G:
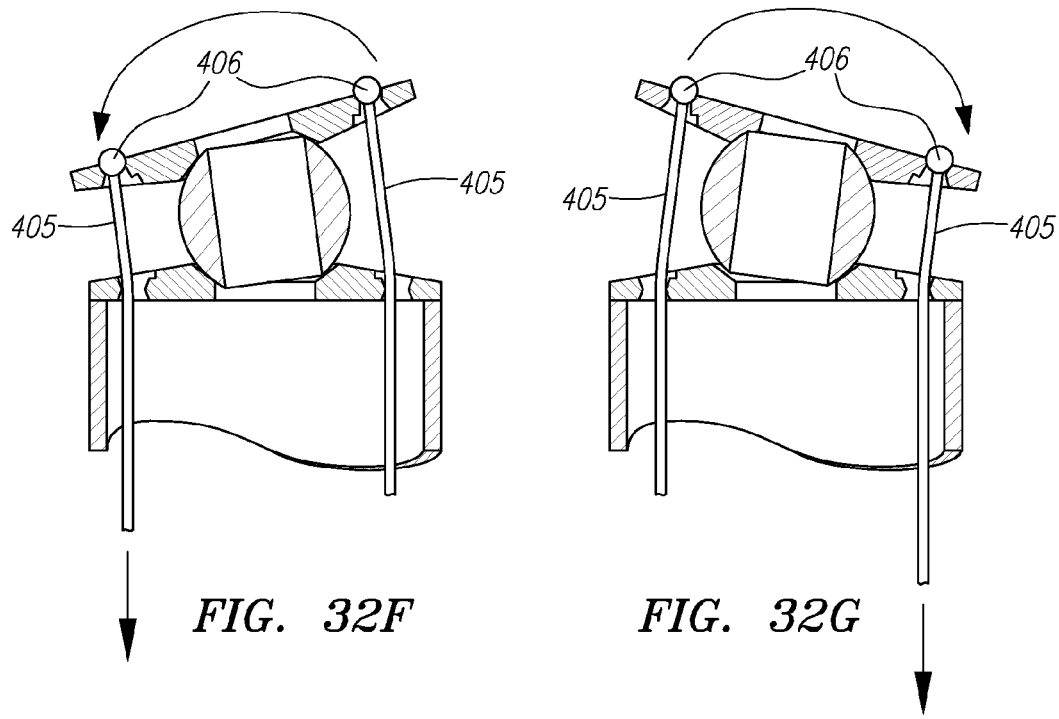

FIGS. 32A-G illustrate another embodiment of an orientation platform or interface 401 constructed with a ball and socket assembly as described above. Many of the components shown in FIGS. 32A-G are the same as components discussed above and function in the same manner and, therefore, are not repeated. In this embodiment, however, the platform or interface 401 does not include any springs (tension or compression) and instead includes multiple control elements 405. Thus, the illustrated embodiment is designed for a pitch degree of freedom, and the XYZ orientation compass associated with FIG. 32D indicates that this orientation platform may perform a pitching motion by rotating about the Y axis in a XZ plane. In one implementation, the control elements 405 are pre-tensioned to a predetermined setting during setup such that the orientation platform is in a known state (i.e., 0° of pitch). In one embodiment, the orientation platform 133 is maintained in a 0° pitch position while the forces on the control elements 405 are balanced. During a procedure, the control elements 405 may be tensioned or slackened to cause the orientation platform to controllably pitch as needed in a positive or negative direction. FIGS. 32D and 32F show a platform member 415 being controllably tilted or pitched about the Y axis toward the left in a pitch– direction when the left control element 405 is tensioned with a downward force that overcomes the downward force applied on the right control element 405, or if the right control element 405 is slackened. Because each control element 405 is coupled to the platform member 415 with a ball termination 406, a force pulling on the control element 405 may be transferred to the platform member 415 via the ball terminations 406. By tensioning the right control element 405, the pitching action may be stopped or reversed.

Further, if the right control element 405 is tensioned with a downward force sufficient to overcome the force on the left control element 405 or if the left control element 405 is slackened, the platform member 415 may be brought back to a 0° of pitch position. FIGS. 32E and 32G illustrate the right control element 405 tensioned by a downward force, causing the orientation platform 133 to pitch in a pitch+ direction.

FIGS. 33A-C illustrate yet another embodiment of an orientation platform 133. In this embodiment, controlled pitching action is accomplished by the application of force on two control elements 439, 441 and two tension springs 433. FIGS. 34A-C illustrate yet another embodiment of an orientation platform 133. In this embodiment, controlled pitching action is accomplished by the application of force on one control element 405 and three tension springs 433. Other numbers and combinations of tension springs 433 and control elements 405 may also be utilized. Further, embodiments that do not include any springs may include different numbers and arrangements of control elements.

For example, FIGS. 35A-C illustrate an embodiment of an interface or platform 133 including four control elements. A first control element 443 with a ball termination 406 at one end is threaded through an aperture 427 on the platform member 425, through a corresponding aperture 427 underneath on the base member 417, and through a first lumen 115 in a catheter instrument member 103 to a splayer 101 at a proximal end of the catheter 37. Second, third and fourth control elements 445, 447, 449 are arranged in a similar manner. Thus, in viewing the orientation platform from above in FIG. 35B, the first control element 443 may be view as being at the 0° position, the second control element 445 at the 90° position, the third control element 447 at the 180° position, and the fourth control element 449 at the 2700 position. However, it is contemplated that the control elements may be also located in other positions relative to each other. In one embodiment, the orientation platform 133 is maintained in a 0° tilt position while the forces on the four control elements are balanced. However, during a procedure, the control elements may be tensioned or slackened to cause the orientation platform to controllably tilt as needed.

For example, if the intention is to pitch the orientation platform 133, the platform 133 may be controllably pitched in the pitch– direction by tensioning the pitch– control element 449 with a downward force and slackening the tension on the pitch+ control element 445. Conversely, if the intention is to pitch in the pitch+ direction, the pitch+ control element 445 is tensioned and the pitch– control element 449 slackened. Similarly, if the intention is to yaw the orientation platform 133, the platform 133 may be controllably yawed in the yaw– direction by tensioning the yaw– control element 443 and slackening the yaw+ control element 447. For a tilt in the yaw+ direction, the yaw+ control element 447 is tensioned and the yaw– control element 443 slackened. Furthermore, by manipulating a combination of the pitch and yaw control elements 443, 445, 447, 449, it is possible to cause the orientation platform to both pitch and yaw to varying degrees. Further, although manipulation of the control elements have been described in the context of tensioning one element as another is slackened, it is contemplated that one or more slackening actions may be avoided if that amount of force being applied to the control element being tensioned is sufficient to overcome any tensioning force on the control elements formerly described as being slackened.

FIGS. 36A-C illustrate another embodiment of an orientation platform 133 that is similar to the embodiment shown in FIGS. 35A-C except that the embodiment shown in FIGS. 36A-C includes eight control elements. Other embodiments can include other numbers and arrangements of control elements. During a procedure, the eight control elements may be tensioned or slackened to cause the orientation platform 133 to controllably tilt as needed. For example, if the intention is to pitch the orientation platform 133, the platform 133 may be controllably pitched in the pitch– direction by tensioning the pitch– control element 449 with a downward force and slackening the tension on the pitch+ control element 445. Conversely, if the intention is to pitch in the pitch+ direction, the pitch+ control element 445 is tensioned and the pitch– control element 449 slackened. By manipulating a combination of the pitch and yaw control elements 443, 445, 447, 449, it is possible to cause the orientation platform to both pitch and yaw to varying degrees.

FIGS. 37A-E illustrate another embodiment of an interface or platform 133 for controlling an orientation of a working instrument coupled to a distal end of a flexible catheter of a robotic medical system. The interface or platform 133 includes a base member or first plate 417 configured for coupling to the distal end of the flexible catheter, a spacer element, e.g., a spherical element or ball 419, a platform member or second plate 415 arranged such that the spacer element 419 is retained between and separates the base member 417 and the platform member 415. Control elements 451, 453, 455, 457 (generally 451) extend through the catheter and through apertures 427 defined by the base member 417. The control elements 451 are arranged such that at least one control element extends between the base and platform members 417, 415 at an angle, i.e., not parallel to the longitudinal axis of the base member 417. In other words, an angle, e.g., at least 30 degrees, and other angles as appropriate, may be defined between the longitudinal axis of the base member 417 and a longitudinal axis of the control element.

Overlapping or crossing control elements are referred to as control cables 451. Thus, the term "control elements" as used in this specification is defined to include a control element that is not arranged in a criss-cross pattern (e.g., as shown in FIGS. 32B-C), and also control elements in the form of control cables 451 that cross or overlap with at least one other control cable 451 in an angular arrangement. Such control cables 451 are identified with heavier or dark lines compared to non-crossing or non-overlapping control elements, which may be illustrated as non-filled or lighter lines. Such control cables and their associated overlapping or crossing patterns provide different control characteristics compared to non-overlapping control elements when the control cables 451 are placed in tension or slackened.

More particularly, an embodiment of a platform 133 constructed according to one embodiment includes, for example, a spherical or semi-spherical spacer element 419, may be assembled by inserting the spacer element 419 into the concave cavities 431 of the base and platform members 417, 415. A first control element 405 with a ball termination 406 at one end is threaded through the platform member 415, through a corresponding hole 427 underneath on the base member 417, and through a first lumen 115 in the instrument or catheter member 103 to a splayer at the proximal end of the catheter assembly. A second control element 405 is similarly threaded through the first plate 415, the second plate 417, and through a second lumen 115 in the instrument member 103. In this example, the first and second control elements 405 are positioned oppositely from each other on the first plate 415, or offset by 180°.

Control elements in the form of four control cables 451, 453, 455, 457 (generally 451) are also threaded through apertures 427 defined by the platform member 415, apertures 427 defined by base member 417, and down through the catheter instrument member 103. Unlike the other control elements 405, however, the control elements in the form of control cables 451, 453, 455, 457 are, in one embodiment, arranged in an overlapping or crossing or criss-cross manner, as illustrated in FIG. 38A. In one embodiment, overlapping or crossing control cables 451 extend across a substantial width of the base member 417. Overlapping or crossing control cables 451 may or may not contact each other depending on, for example, the configuration of the base and platform members 417, 415 and the location of the misaligned apertures 427. For purposes of illustration, control cables 451 are illustrated with heavier lines compared to non-overlapping or non-crossing control elements.

These crossing patterns result from control cables 451 extending through misaligned apertures 427 of the base member 417 and the platform member 415. In other words, at least one control cable 451 extends through a base member 417 aperture and through a platform member 415 aperture that is not directly above, or in-line with, the base member 417 aperture. In this manner, all of the cables 451 may extend through misaligned apertures 427 of the base and platform members 417, 415, or some of the cables 451 may extend through misaligned apertures 427, whereas one or more other control elements 405 do not. Instead, control elements 405 and extend through aligned apertures 427 of the base and platform members 417, 415. Embodiments utilizing these arrangements may result in some type of overlapping or criss-cross cable configuration involving a control cable 451.

One manner in which embodiments may be implemented is illustrated in FIGS. 38A-B. A first control cable 451 extends through misaligned apertures 427 of the base and platform members 417, 415 and crosses the second control cable 453, and a second control cable 453 crosses the first control cable 451. In essence, the control cables 451, 453 have swapped second plate holes 427 compared to the routing scheme of the control elements 405, which extend through aligned apertures and are parallel to the longitudinal axis of the catheter instrument 103, i.e., perpendicular to surfaces of the base and platform members 417, 415.

As shown in FIGS. 37A-B, pulling or tensioning a first opposing pair 452 of control cables 453, 455 and slackening a second opposing pair 454 of control cables 455, 457 results in the platform member 415 rotating in a clockwise manner as illustrated in FIG. 38B (represented by directional arrow). On the other hand, pulling or tensioning the pair 454 of control cables 451, 457 and slackening the pair 452 of control cables 453, 455, the platform member 415 rotates in a counterclockwise manner, as illustrated in FIG. 37D.

Further, as shown in FIG. 37E, by performing a combination of pulling or tension a first opposing pair 452 of control cables 453, 455, slackening the second opposing pair 454 of control cables 451, 457, and tensioning the pitch+ control element 405, the platform member 415 may be caused to pitch and rotate in a clockwise manner. Thus, FIGS. 37A-E illustrate how control elements may be manipulated in various ways, by pulling and slackening various combinations of elements 405 and cables 451, for desired pitch and rotation.

FIGS. 38A-C illustrate another embodiment of an interface or platform 133 in which the platform 133 is controlled with control elements in the form of a set of four control elements in the form of cables 451, 453, 455, 457 (generally cable 451) that are also arranged in an overlapping or crossing manner, without non-crossing control/pitch elements 405. The control cables 451 can be manipulated in various ways to rotate and tilt the platform 133. For example, clockwise rotation can be achieved by pulling control cables 453, 455 (as shown in FIG. 38B), and clockwise rotation and positive pitch can be achieved by pulling one or more control cables (e.g., 453, 455) while stabilizing a counter rotation line so rotation is stopped.

FIG. 39A illustrate another embodiment of an interface or platform 133 in which the platform 133 is controlled with a set of control elements in the firm of four control cables 451, 453, 455, 457 (generally 451) that may cross or overlap, but no non-crossing control elements. Further, the control cables 451 are woven in a more complex criss-cross fashion and routed through larger apertures 427 and smaller apertures 429. Also, in the illustrated embodiment, multiple control cables may be threaded through a single aperture 427. Moreover, control cables may be threaded through an aperture 427 defined through a top or distal surface of the platform member 415, traverse or pass over the distal or top surface of the platform member 415, then be threaded back through the platform member 415 and the base member 417.

Referring to FIG. 39B, in another embodiment, the orientation platform 133 is controlled with four control elements—two non-crossing control elements 405 that terminate at 406 on the platform member 415, and two control cables 451, 453. The control elements 405 are controlled from the proximal end of the catheter instrument (as discussed above), and the two control cables 451, 453 are woven in a crossing or criss-cross manner in which both ends of each control cable 451, 453 extend through the base and platform members 417, 415, traverse a top surface of the platform member 415, then extend from the platform member 415 to the base member 417 such that each control cable extends along opposite sides of the intermediate spacer element 419. Each control cable 451, 453 terminate at the base member 417, e.g., on a bottom surface or underside of the base member 417.

In another embodiment, referring to FIGS. 40A-B, an interface or platform 133 may include a different crossing cable 451 arrangement in which the platform 133 may be controlled with a set of four control cables 451, 453, 455, 457 without the need for any control elements 405. In this embodiment, the control cables 451 may be woven in a crossing or overlapping manner, and one end of each control cable 451 may terminate on a top surface of the platform member 415. FIGS. 40A-B illustrate an example of omni-directional motion by pulling cable 453 and slackening cables 451, 455, 457, thereby resulting in rotation, pitch and yaw motion, positive yaw being slightly larger than positive pitch in this example.

Various embodiments described with reference to FIGS. 31A-40B include a spacer element in the form of a spherical element or ball 419, e.g., as part of a ball and socket assembly. Other embodiments, however, may utilize different types of spacer elements.

For example, referring to FIGS. 41A-B illustrate one embodiment of an orientation platform 133 employing a spacer element in the form of an elastomeric cylinder 459. An elastomeric cylinder 459 suitable for embodiments may be semi-flexible and may allow for bending as the orientation platform 133 if caused to move in response to manipulation of the control elements 405. Similar to the spherical spacer element 419, the elastomeric cylinder may also define a lumen 460 for passage of, e.g., a cable for a working instrument 41 or other component or a working substance. The manner in which control elements 405 may be manipulated to achieve desired rotation and orientation of the interface or platform 133 is described in detail with respect to a spherical spacer element 419, and the same principles generally apply to the embodiment shown in FIGS. 41A-B that utilizes an elastomeric cylinder 459 as a spacer element.

In a further alternative embodiment, the spacer element may be in the form of a flexure element 461, as shown in FIGS. 42A-B. A flexure 461 for use in embodiments may be semi-flexible and allow for bending as the orientation platform 133 if caused to move in response to the control elements 405. Similar to the spherical spacer element 419, the flexure 461 may also define a lumen 462 for passage of, e.g., a cable for a working instrument 41 or other component or a working substance. The manner in which control elements 405 may be manipulated to achieve desired rotation and orientation of the platform 133 is described in detail with respect to a spherical spacer element 419, and the same principles generally apply to the embodiment shown in FIGS. 42A-B having a flexure 461 as a spacer element.

Referring to FIGS. 43A-B, in yet another alternative embodiment, the spacer element may be in the form of a non-spherical element or ball 463 rather than a spherical ball or element 419. In the illustrated embodiment, surfaces of the non-spherical element have planar faces that interface with surfaces of the base and platform members 417, 415. Similar to the spherical spacer element 419, a non-spherical spacer element 463 may also define a lumen 464 for passage of, e.g., a cable for a working instrument 41 or other component or a working substance. The manner in which control elements 405 may be manipulated to achieve desired rotation and orientation of the interface or platform 133 is described in detail with respect to a spherical spacer element 419, and the same principles generally apply to the embodiment shown in FIGS. 42A-B that a non-spherical spacer element.

FIG. 44 illustrates another alternative embodiment of an orientation platform 133 employing a flexible coil 465 as a spacer element. The flexible coil 465 for use in embodiments may be semi-flexible and may allow for bending as the orientation platform 133 is caused to tilt in a variety of ways in response to the control elements 405. The discussion above regarding how control elements 405 may be manipulated to achieve desired rotation and orientation of the platform 133 is described in detail above, and the same principles generally apply to the embodiment shown in FIG. 45 that includes a flexible coil 465 spacer element.

While various spacer units are described and may be utilized within an interface or platform 133, the various spherical elements 419, 463, elastomeric cylinder 459, flexure 461, and flexible coil 465 may be fabricated from a variety of materials, preferably a material that is inert and suitable for medical procedures. Suitable materials for certain embodiments may include, for example, Buna-N (nitrile), propylene (EPDM), silicone, cast polyurethane, chloroprene (Neoprene), fluorocarbon (Viton, Fluorel), fluorosilicone, liquid silicone rubber, etc., but are not so limited.

Referring to FIG. 45, according to another embodiment, an orientation platform 133 includes a universal joint 467 as a spacer element. The universal joint 467 of this embodiment is controlled with a plurality of control elements 405 in a similar manner as discussed above and may be manipulated to tilt as the orientation platform 133 in response to manipulation of the control elements 405.

FIGS. 46A-C illustrate one embodiment of an orientation platform 133 employing a pin and groove arrangement 469 as a spacer element. The pin and groove 469 of the illustrated embodiment includes a platform member 415 in the form of a first plate 471 having a cylindrical pin element 473 on its bottom face. The base member 417 is in the form of a second plate 475 that includes a semi-circular structure 477 disposed on its top face. This semi-circular structure 477 may be fabricated as a half disc with a groove or channel 479 extending partway along its edge. The orientation platform 133 is constructed by mating the pin element of the first plate 471 into the half disc channel 477 of the second plate 475. Control elements 405 are threaded through the first and second plates 471, 475 on opposite sides of the orientation platform 133. In this embodiment, the pin element 473 may freely slide within the groove 479 on the disc surface, thus tilting the top plate 471. Control elements 405 can be manipulated to control tilting action of the proximal end of the instrument.

Embodiments described with reference to FIGS. 32A-47C include a "single-level" interface or platform 133. Alternative embodiments of an orientation interface or platform 133 may include multiple levels.

For example, referring to FIGS. 47A-O, a multi-level platform or interface 133 for coupling to a distal end of flexible catheter having a lower level or stage 487 and an upper level or stage 485. In the illustrated embodiment, each level 485, 487 is structured in a manner that is similar to the platform 133 shown in FIGS. 31D-I.

In the embodiment illustrated in FIGS. 47A-M, the multi-level platform 133 includes two "ball and socket" spacer elements 419a, 419b (generally 419). A first spherical spacer element is disposed between a base member 417 and a first platform member 415a, and a second spherical spacer element 419b is disposed between the first platform member 415a and a second, distal platform member 415b. In the illustrated embodiment, the first platform member 415a is constructed to include with multiple components to interface between the first and second levels 485, 487. In the illustrated embodiment, the first platform member 415a includes a first plate 489 that interfaces with a lower spacer element 419*a*, and a second, top plate 495 that interface with the upper spacer element 419*b*.

The lower stage 485 is controllably yawed in a positive or negative direction by tensioning or slackening a control element 405*a* that terminates at the first platform member 415*a* to counterbalance a tension spring 433*a* (shown in FIG. 48C). Similarly, the upper stage 487 of the orientation platform 133 is controllably pitched in a positive or negative direction by tensioning/slackening a control element 405*b* that terminates at the second platform member 415*b* to counterbalance a tension spring 433*b*. Because the lower stage 485 is rotated relative to the upper stage 487 by 90°, the pitch degree of freedom in the upper stage 487 has become a yaw degree of freedom for the lower stage 485. By manipulating the first and second control elements 405*a*, 405*b* in combination, the distal tip of this flexible catheter may be caused to controllably pitch and yaw in a variety of directions.

FIGS. 48A-G illustrate another embodiment of a flexible catheter having a multi-level interface or platform 133 that includes first and second stages 485, 487 in which the stages 485, 487 are constructed in a manner that is similar to the orientation platform 133 including compression springs 435 and control elements 405 that extend through respective compression springs 435 as described with reference to FIGS. 31N-P. The lower stage 485 of the platform 133 is controllably yawed in a positive or negative direction by tensioning or slackening of control elements 405*a* to counterbalance compression springs 435*a*. The upper stage 487 is controllably pitched in a positive or negative direction by tensioning or slackening control elements 405*b* to counterbalance compression springs 435*b*. Because the lower stage 485 is rotated relative to the upper stage 487 by 90°, the pitch degree of freedom of the upper stage 487 has become a yaw degree of freedom for the lower stage 485. By manipulating the first and second control elements 405*a*, 405*b*, the distal tip of this flexible catheter may be caused to pitch and yaw in a variety of directions.

FIGS. 49A-C illustrate another embodiment of a flexible catheter having a multi-level interface or platform 133 that includes spacer elements in the form of spherical elements or balls 419. Each level 485, 487 is constructed in a manner that is similar to the platform 133 structure described with reference to FIGS. 32A-G, in which control elements 405, but not any springs, are used to manipulate the platform. In the illustrated embodiment, the lower stage 485 of the orientation platform 133 is controllably yawed in a positive or negative direction by tensioning or slackening of control elements opposing control elements 405*a* that terminate at the first platform member 415*a*. The upper stage 487 is controllably pitched in positive or negative directions by tensioning or slackening control elements 405*b* that terminate at the second or distal platform member 415*b*. Because the lower stage 485 is rotated relative to the upper stage 487 by 90°, the pitch degree of freedom of the upper stage 487 has become a yaw degree of freedom for the lower stage 513. By manipulating the control elements 405*a,b*, the distal tip of this flexible catheter may be caused to pitch and yaw in various directions.

Referring to FIGS. 50A-B, a further alternative embodiment of a multi-level orientation interface or platform 133 including multiple elastomeric cylinders 459*a,b*. The stages 485, 487 of this embodiment are structured in a manner that is similar to the orientation platform 133 described with reference to FIGS. 41A-B. The lower stage 485 of the orientation platform 133 is controllably yawed in a positive or negative direction by tensioning or slackening control elements 405*a*. The upper stage 487 of the orientation platform 133 is controllably pitched in a positive or negative direction by tensioning or slackening control elements 405*b*. Because the lower stage 485 is rotated relative to the upper stage 487 by 90°, the pitch degree of freedom of the upper stage 487 has become a yaw degree of freedom for the lower stage 513. The distal tip of this flexible catheter may be caused to pitch and yaw in a variety of directions by manipulating control elements 405*a,b*.

Referring to FIGS. 51A-B, another alternative embodiment of a multi-level orientation interface or platform 133 including multiple stages 485, 487 includes flexures 461*a,b*. The stages 485, 487 of this embodiment are structured in a manner that is similar to the orientation platform 133 described with reference to FIGS. 42A-B. The lower stage 485 of the orientation platform 133 is controllably yawed in a positive or negative direction by tensioning or slackening of control elements 405*a*, and the upper stage 487 is controllably pitched in a positive or negative direction by tensioning or slackening of control elements 405*b*. Because the lower stage 485 is rotated relative to the upper stage 487 by 90°, the pitch degree of freedom of the upper stage 487 has become a yaw degree of freedom for the lower stage 485. The control elements 405*a,b* can be manipulated to cause pitch and yaw motions of the distal tip of this flexible catheter in various directions.

FIGS. 52A-B illustrate a further alternative embodiment of a multi-level orientation interface or platform 133 for a flexible catheter and that includes non-spherical elements or balls 463*a,b*. The lower and upper stages 485, 487 of this embodiment are structured in a manner that is similar to the orientation platform 133 described with reference to FIGS. 44A-B. The lower stage of the platform 133 is controllably yawed in a positive or negative direction by tensioning or slackening control elements 405*a*, and the upper stage 487 is controllably pitched in a positive or negative direction by tensioning or slackening control elements 405*b*. Because the lower stage 485 is rotated relative to the upper stage 487 by 90°, the pitch degree of freedom of the upper stage 487 has become a yaw degree of freedom for the lower stage 485. The control elements 405*a,b* can be manipulated to cause the distal tip of a flexible catheter to pitch and yaw in various ways.

FIG. 53 illustrates another alternative embodiment of a multi-level orientation interface or platform 133 for a flexible catheter and that includes flexible coils 465*a,b*. The lower and upper stages 485, 487 of this embodiment are structured in a manner that is similar to the orientation platform 133 descried with reference to FIG. 45. The lower stage 485 of the orientation platform 133 is controllably yawed in a positive or negative direction by tensioning or slackening of control elements 405*a*, and the upper stage 487 is controllably pitched in a positive or negative direction by tensioning or slackening control elements 405*b*. Because the lower stage 485 is rotated relative to the upper stage 487 by 90°, the pitch degree of freedom of the upper stage 487 has become a yaw degree of freedom for the lower stage 485. By manipulating the control elements 405*a,b*, the distal tip of this flexible catheter may be caused to pitch and yaw in a variety of directions.

FIG. 54 illustrates another embodiment of a multi-level orientation interface or platform 133 for a flexible catheter and that includes multiple universal joints 467*a,b*. The lower and upper stages or levels 485, 487 of this embodiment are structured in a manner that is similar to the orientation platform 133 described with reference to FIG. 45. The lower stage 485 of the orientation platform 133 is controllably yawed in a positive or negative direction by tensioning or slackening control elements 405*a*, and the upper stage 487 is controllably pitched in a positive or negative direction by tensioning or slackening control elements 405b. Because the lower stage 485 is rotated relative to the upper stage 487 by 90°, the pitch degree of freedom in the upper stage 487 has become a yaw degree of freedom for the lower stage 485. By manipulating the control elements 405a,b the distal tip of this flexible catheter may be caused to pitch and yaw in a variety of directions.

FIGS. 55A-G illustrate a further embodiment of a multi-level orientation platform or interface 133 and components thereof. The first and second stages 485, 487 may be constructed such that they include only crossing control cables (generally 451), or a combination of crossing control cables 451 and non-crossing control elements 405 similar to various embodiments previously described, e.g. as in FIG. 39B. Spacer elements, e.g., in the form of a spherical element 419 or other element described in other embodiments, may include an eyelet or loop 530 or other tying structure 532 for facilitating crossing or overlapping control cables 451 within a multi-level structure as necessary. Manipulation of motion and positioning of distal tip of a flexible catheter may be achieved by manipulation of control elements 405a,b and control cables 451.

Other crossing patterns within a multi-level platform 133 that may be implemented with embodiments are illustrated in FIGS. 56A-D. As shown in these figures, control cables 451 may cross within one level, e.g., the lower level 485, but not cross in another level, e.g., the upper level 487. Other control cable 451 patterns may be utilized. Alternatively, control cables 451 may cross within each level 485, 487. Further, as shown in FIG. 57, cams 527 maybe provided to assist with the routing of the various control cables 529.

Although embodiments are described as having single- or bi-level orientation platforms, embodiments may also be implemented with additional levels and additional ball and socket elements as necessary. Thus, the orientation platforms described above are provided as examples of how embodiments may be implemented.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Many combinations and permutations of the disclosed embodiments are useful in minimally invasive surgery, and the system is configured to be flexible for use with other system components and in other applications. Thus, various changes and modifications may be made without departing from the scope of the claims.

For example, although embodiments are described with reference to a two-piece rotatable apparatus 250 including an interface 251 and rotatable collar 253, other rotatable apparatus 250 embodiments may include other numbers of components, which may be assembled or formed as a single component. Further, rotatable apparatus 250 embodiments can be configured for one or multiple control elements 207. The degree of rotation that can be achieved with a rotatable apparatus 250 may depend on, for example, the number and arrangement of channels 283, 281 and/or 301, and the how far a control element 207 wraps around a component of a rotatable apparatus 250 to control to what degree the rotatable apparatus 250 rotates.

Further, although embodiments are described with reference to an interface 251 having channels 281 that merge together, other embodiments may utilize different configurations, which may or may not merge, or which may merge at different locations. Additionally, although embodiments are described with reference to channels 283, 281, 301 that are defined within an outer surface of an interface 251 or collar 253, channels for routing control elements 207 may also be defined through a wall or body of the interface 251 and/or collar 253 such that they are hidden within the interface 251 or collar 253. Further, in embodiments involving a single control element 207, the interface 151 may define a single channel or slot 181, and the collar 253 may define a single channel or slot 301. Thus, figures showing multiple channels or slots or pairs thereof are provided as illustrative examples of how embodiments can be implemented.

Additionally, although embodiments are described with reference to a collar 253 having a bottom or proximal section that does not define any channels or slots such that channels 181 of the interface 251 are not in communication with or are disconnected from channels 301 of the collar 253, other embodiments may be implemented utilizing longer channels that extend across this space, or intermediate channels that extend across the bottom or proximal section of the collar 253 that join the channels 181 and 301. Additionally, although certain embodiments are described with respect to symmetrical channels 281 and 301, other embodiments may involve different numbers, arrangements and shapes of channels 281, 301, which may be symmetrical or asymmetrical.

Further, embodiments of a rotational apparatus 250 can be adapted for attachment to a known catheter, e.g., to convert the catheter into a catheter having a rotatably controllably distal end. For example, the outer body 316 can be attached to a sheath, and the inner body 305 can be attached to a guide catheter such that the distal end of the resulting structure can be controllably rotated with pull wires or control elements 207. Accordingly, figures showing embodiments in the context of various system configurations are provided as illustrative examples of how a rotational apparatus 250 may be utilized, but it should be understood that embodiments and their applications are not so limited and can be operably coupled to various components and catheters of a robotic instrument system.

Additionally, a substantially rigid platform (P) can be formed from one, two, three and other numbers of sheath catheters 102, which may assume curved and/or linear configurations, and may be used with another instrument, such as an endoscope. Further, multiple sheath catheters 102 may form one or multiple platforms (P). Multiple sheath catheters 102 may be advanced through a common lumen, or through individual lumens defined by a master sheath 63. Further, in certain embodiments, certain substantially rigid sheath catheters 102 may have a linear or straight shape, and other substantially rigid sheath catheters 102 may have a curved or arcuate shape. For this purpose, segments 205 of a sheath catheter 102 may have the same or similar shapes and sizes, or different shapes and/or sizes in order to implement the desired curved or straight shape when the sheath catheter 102 is transitioned from a flexible state (F) and deployed to have a substantially rigid state (R) to form a platform (P) or a part thereof. Segment 205 shapes other than those shapes described and illustrated may be utilized, and a control element or pull wire 207 may extend through walls of one or more segments 205, or be coupled to an outer surface of one or more segments 205. Further, segments 205 may have various other interlocking surfaces or faces that prevent rotation and contribute to a substantially rigid structure.

Moreover, although embodiment are described with reference to a telemanipulation system or robotic control system, embodiments may also be manually controlled by a surgeon, e.g., near the proximal section of the sheath catheter 102. Further, although embodiments of a rotational apparatus 250 are described with reference to a system that may include, for example, an instrument 41, an orientation platform 133, a sheath catheter or extension system 102 having controllable rigidity and a master sheath 63, embodiments of a rotational apparatus 250 can be utilized with systems that include other components. Embodiments are advantageously suited for minimally invasive procedures, they may also be utilized in other, more invasive procedures that utilize extension tools and may be used in surgical procedures other than treatment of arrhythmias such as atrial fibrillation.

While rotational apparatus 250 embodiments are described with reference to a robotic instrument system, such as a robotic catheter system available from Hansen Medical of Mountain View, Calif., certain embodiments may also be used with other types of computer or robotically controlled surgical systems such as, for example, the da Vinci® surgical system available from Intuitive Surgical Inc. of Sunnyvale, Calif., the NIOBE Magnetic Navigation System and associated Magnetic GentleTouch Catheters, available from Stereotaxis, Inc. of St. Louis, Mo.; the Mako Haptic Guidance System available from Mako Surgical, Inc. of Ft. Lauderdale, Fla.; and the surgical platform available from NeoGuide Systems Inc. of Los Gatos, Calif.

Because one or more components of embodiments may be used in minimally invasive surgical procedures, the distal portions of these instruments may not be easily visible to the naked eye. As such, embodiments of the invention may be utilized with various imaging modalities such as magnetic resonance (MR), ultrasound, computer tomography (CT), X-ray, fluoroscopy, etc. may be used to visualize the surgical procedure and progress of these instruments. It may also be desirable to know the precise location of any given catheter instrument and/or tool device at any given moment to avoid undesirable contacts or movements. Thus, embodiments may be utilized with localization techniques that are presently available may be applied to any of the apparatuses and methods disclosed above. For example, one or more localization coils may be built into a flexible catheter instrument or sheath catheter. In other implementations, a localization technique using radio-opaque markers may be used with embodiments of the present invention. Similarly, a fiber optic Bragg sensing fiber may be built into the sidewall of a catheter instrument or sheath catheter to sense position and temperature. Further, a plurality of sensors, including those for sensing patient vitals, temperature, pressure, fluid flow, force, etc., may be combined with the various embodiments of flexible catheters and distal orientation platforms.

Various system components including catheter components may be made with materials and techniques similar to those described in detail in U.S. patent application Ser. No. 11/176,598, incorporated by reference herein in its entirety. Further, various materials may be used to fabricate and manufacture sheath catheter segment, rotatable apparatus and orientation platform devices. For example, it is contemplated that in addition to that disclosed above, materials including, but not limited to, stainless steel, copper, aluminum, nickel-titanium alloy (Nitinol), Flexinol® (available from Toki of Japan), titanium, platinum, iridium, tungsten, nickel-chromium, silver, gold, and combinations thereof, may be used to manufacture components such as control elements, control cables, segments, gears, plates, ball units, wires, springs, electrodes, thermocouples, etc. Similarly, non-metallic materials including, but not limited to, polypropylene, polyurethane (Pebax®), nylon, polyethylene, polycarbonate, Delrin®, polyester, Kevlar®, carbon, ceramic, silicone, Kapton® polyimide, Teflon® coating, polytetrafluoroethylene (PTFE), plastic (non-porous or porous), latex, polymer, etc. may be used to make the various parts of a catheter, orientation platform, tool, etc.

Additionally, certain system components are described as having lumens that are configured for carrying or passage of control elements, control cables, wires, and other catheter instruments. Such lumens may also be used to deliver fluids such as saline, water, carbon dioxide, nitrogen, helium, for example, in a gaseous or liquid state, to the distal tip. Further, some embodiments may be implemented with a open loop or closed loop cooling system wherein a fluid is passed through one or more lumens in the sidewall of the catheter instrument to cool the catheter or a tool at the distal tip.

Further, although certain system components are described with reference to examples of working instruments 41 such as end effectors shown in FIGS. 4A-Z, embodiments may be utilized with other types of tools and end-effectors including, for example, a Kittner dissector, a multi-fire coil tacker, a clip applier, a cautery probe, a shovel cautery instrument, serrated graspers, tethered graspers, helical retraction probe, scalpel, basket capture device, irrigation tool, needle holders, fixation device, transducer, and various other graspers. A number of other catheter type instruments may also be utilized together with certain embodiments including, but not limited to, a mapping catheter, an ablation catheter, an ultrasound catheter, a laser fiber, an illumination fiber, a wire, transmission line, antenna, a dilator, an electrode, a microwave catheter, a cryo-ablation catheter, a balloon catheter, a stent delivery catheter, a fluid/drug delivery tube, a suction tube, an optical fiber, an image capture device, an endoscope, a Foley catheter, Swan-Ganz catheter, fiberscope, etc. Thus, it is contemplated that one or more catheter instruments may be inserted through one or more lumens of a flexible catheter instrument, flexible sheath instrument, or any catheter instrument to reach a surgical site at the distal tip. Similarly, it is contemplated that one or more catheter instruments may be passed through an orientation platform to a region of interest.

Accordingly, embodiments are intended to cover alternatives, modifications, and equivalents that may fall within the scope of the claims.

What is claimed is:

1. A medical instrument system, comprising:
   an instrument defining a longitudinal axis;
   a tool rotatably coupled to a distal end portion of the instrument;
   a control element extending from the instrument and coupled to the tool such that the tool is controllably rotatable about the instrument axis by axial movement of the control element relative to the instrument; and
   a guide channel through which the control element passes, said guide channel having a first portion extending axially along said longitudinal axis, and a second portion distal to said first portion, said second portion not rotatable with said tool relative to said instrument, wherein the second portion of the guide channel curves so as to extend in a substantially helical shape about said longitudinal axis.

2. The system of claim 1, the instrument having a fixed tool interface, and the tool having a base rotatably coupled to the interface, wherein said guide channel extends along said interface and said tool base.

3. The system of claim 1, wherein the instrument distal end portion is flexible, and wherein the control element is coupled to the tool in a manner such that axial movement of the control element relative to the instrument does not cause appreciable bending of the instrument distal end portion.

4. The system of claim 1, wherein the control element comprises a first control element, the system further comprising a second control element extending from the instrument and coupled to the tool, such that the tool is controllably rotatable about the instrument axis in a first direction by axial movement of the first control element relative to the instrument, and the tool is controllably rotatable about the instrument axis in a second direction opposite to the first direction by axial movement of the second control element relative to the instrument.

5. The system of claim 4, the instrument having a fixed tool interface, and the tool having a base rotatably coupled to the interface, wherein the first control element passes through first respective guide channels in the interface and the tool base, and the second control element passes through second respective guide channels in the interface and the tool base.

6. The system of claim 5, wherein the guide channels in the interface and the guide channels in the tool base lie within different planes.

7. The system of claim 5, wherein respective ends of the first and second control elements are secured to the tool base within the respective first and second guide channels in the tool base.

8. The system of claim 5, wherein the first and second control elements extend from the instrument at circumferentially offset locations, the first and second guide channels in the interface having arcuate shapes and being arranged to direct the respective first and second control elements to cross one another.

9. The system of claim 8, wherein the first and second control elements cross each other multiple times.

10. The system of claim 8, wherein the respective first and second guide channels in the tool base have substantially linear shapes.

11. The system of claim 8, wherein arcuate shaped first and second guide channels of the interface form a V-shaped or Y-shaped channel.

12. The system of claim 8, wherein the first and second control elements each wraps around a respective portion of the tool base in between the respective guide channels of the instrument interface and tool base.

13. The system of claim 8, wherein the respective first and second guide channels in the instrument interface have a common channel portion.

14. The system of claim 4, wherein the instrument comprises a plurality of interlocking segments that are drawn together by at least one of the first and second control elements being placed in tension.

15. The system of claim 4, wherein the instrument distal end portion is bendable, and wherein the control element is coupled to the tool in a manner such that axial movement of the first or second controls element relative to the instrument does not cause appreciable bending of the instrument distal end portion.

16. The system of claim 1, wherein said tool comprises a distal surface having at least one tool guide channel through which said control element passes.

17. The system of claim 16, wherein said at least one tool guide channel comprises four channels orthogonally arranged on said distal surface and defining a plane that is substantially parallel to a plane of rotation of said tool.

18. A medical instrument system, comprising:
an elongate instrument;
a rotatable apparatus coupled to the elongate instrument, the rotatable apparatus defining a lumen therethrough and a longitudinal axis;
a guide catheter disposed within the lumen of the rotatable apparatus;
a working instrument operatively coupled to the guide catheter;
a control element operatively coupled to the rotatable apparatus, wherein respective rotation of the rotatable apparatus and working instrument are controllable by manipulation of the control element; and
a guide channel through which the control element passes, said guide channel having a first portion extending axially along said longitudinal axis, and a second portion distal to said first portion, said second portion not rotatable with said rotatable apparatus, wherein the second portion of the guide channel extends in a substantially helical shape about said longitudinal axis.

19. The system of claim 18, the rotatable apparatus having an interface for coupling the rotatable apparatus to the elongate instrument, and a collar that is controllably rotatable relative to the interface, the working instrument being coupled to and controllably rotatable with the collar.

20. The system of claim 19, wherein the interface is integral with the elongate instrument.

21. The system of claim 19, wherein the collar and the interface are operably coupled together as a single unit.

22. The system of claim 19, wherein the collar is integral with the working instrument.

23. The system of claim 18, wherein said guide channel has an interface portion extending along said interface and a collar portion extending along said collar.

24. The system of claim 23, wherein the interface portion of the guide channel has an arcuate shape, and the collar portion of the guide channel has a substantially linear shape.

25. The system of claim 23, wherein the interface portion and the collar portion of the guide channel lie within different planes.

26. A medical instrument system, comprising:
an instrument defining a longitudinal axis;
an adapter rotatably coupled to a distal end portion of the instrument;
a control element extending from the instrument and coupled to the adapter such that the adapter is controllably rotatable about the longitudinal axis by axial movement of the control element relative to the instrument; and
a guide channel through which the control element passes, said guide channel having a first portion extending axially along said longitudinal axis, and a second portion distal to said first portion, said second portion not rotatable with said adapter, wherein the second portion of the guide channel curves so to extend in a substantially helical shape about said longitudinal axis.

27. The system of claim 26, the adapter having an interface and a collar rotatably coupled to the interface, wherein said guide channel extends along said interface and said collar.

28. The system of claim 26, further comprising a working instrument operably coupled to the adapter, the working instrument being configured for a minimally invasive procedure.

29. The system of claim 28, wherein the working instrument is a clasper, a clamp, a scissors, an electrode, or an endoscope.

30. A medical instrument system, comprising:
an instrument defining a longitudinal axis;
a tool rotatably coupled to a distal end portion of the instrument;
a control element extending from the instrument and coupled to the tool such that the tool is controllably rotatable about the instrument axis by axial movement of the control element relative to the instrument; and a guide channel through which the control element passes, said guide channel having a first portion extending axially along said longitudinal axis, and a second portion distal to said first portion, said second portion not rotatable with said tool relative to said instrument, wherein the second portion of the guide channel curves so as to extend at least partially transverse to said longitudinal axis;

said tool comprising a distal surface having at least one tool guide channel through which said control element passes; and said at least one tool guide channel comprising four channels orthogonally arranged on said distal surface and defining a plane that is substantially parallel to a plane of rotation of said tool.

* * * * *